US005807875A

United States Patent [19]

Rudolf et al.

[11] Patent Number: 5,807,875

[45] Date of Patent: Sep. 15, 1998

[54] AMINO ACID DERIVATIVES, PHARMACEUTICAL COMPOSITIONS CONTAINING THESE COMPOUNDS AND PROCESSES FOR PREPARING THEM

[75] Inventors: Klaus Rudolf; Wolfgang Eberlein; Wolfhard Engel; Gerhard Mihm, all of Biberach; Henri Doods, Warthausen; Heike Andrea Wieland, Biberach; Klaus-Dieter Willim, Schweinhausen/Hochdorf; Jürgen Krause, Ummendorf; Horst Dollinger; Franz Esser, both of Ingelheim; Gerd Schnorrenberg, Gau-Algesheim; Michael Entzeroth, Warthausen; Wolfgang Wienen, Äpfingen, all of Germany

[73] Assignee: Dr. Karl Thomae GmbH, Biberach, Germany

[21] Appl. No.: 763,504

[22] Filed: Dec. 11, 1996

Related U.S. Application Data

[62] Division of Ser. No. 458,093, Jun. 1, 1995, Pat. No. 5,616,620, which is a division of Ser. No. 184,160, Jan. 21, 1994, abandoned.

[30] Foreign Application Priority Data

| | | | |
|---|---|---|---|
| Jan. 20, 1993 | [DE] | Germany | 43 01 452.6 |
| Aug. 6, 1993 | [DE] | Germany | 43 26 465.4 |

[51] Int. Cl.[6] ...................... A61K 31/445; A61K 31/165; C07D 233/66; C07C 273/00; C07C 275/00

[52] U.S. Cl. .......................... 514/364; 514/397; 514/398; 514/399; 514/401; 514/620; 514/364; 514/383; 514/384; 514/400; 548/336.1; 548/338.1; 548/133; 548/263.4; 548/265.4; 564/56; 564/155; 564/158; 564/157

[58] Field of Search .................................... 564/155, 158, 564/56, 157; 548/338.1, 336.1, 133, 265.4, 263.4; 514/650, 397, 398, 400, 401, 620, 399, 364, 384, 383

[56] References Cited

U.S. PATENT DOCUMENTS

| | | | |
|---|---|---|---|
| 2,376,424 | 3/1945 | Fell | 548/338.1 X |
| 2,496,882 | 2/1950 | Martin et al. | 564/155 |
| 3,412,150 | 11/1968 | Erlanger | 548/338.1 |
| 3,856,848 | 12/1974 | Smithwick | 548/338.1 |
| 4,251,132 | 2/1981 | Kramer et al. | 548/338.1 X |
| 4,529,713 | 7/1985 | Jouquey et al. | 548/338.1 X |
| 4,692,455 | 9/1987 | Gordon | 548/338.1 |
| 4,841,067 | 6/1989 | Iizuka et al. | 548/338.1 X |
| 4,851,387 | 7/1989 | Koike et al. | 548/338.1 X |
| 4,857,650 | 8/1989 | Iizuka et al. | 548/338.1 X |
| 4,870,183 | 9/1989 | Iizuka et al. | 548/338.1 X |
| 5,180,744 | 1/1993 | Hanson et al. | 514/616 |
| 5,223,529 | 6/1993 | Bourzat et al. | 514/414 |
| 5,229,369 | 7/1993 | Hanson et al. | 548/338.1 X |
| 5,346,907 | 9/1994 | Kerwin et al. | 548/338.1 X |
| 5,585,358 | 12/1996 | Bialer et al. | 514/19 |
| 5,616,620 | 4/1997 | Rudolf et al. | 514/620 |

FOREIGN PATENT DOCUMENTS

| | | | |
|---|---|---|---|
| 0152872 | 8/1985 | European Pat. Off. | 548/338.1 |
| 0383690 | 8/1990 | European Pat. Off. | 548/338.1 |
| 1538207 | 1/1979 | United Kingdom | 548/338.1 |
| 2007663 | 5/1979 | United Kingdom | 548/338.1 |
| 90-08709 | 5/1992 | WIPO | 548/338.1 |
| 94-17035 | 8/1994 | WIPO | 564/155 |

*Primary Examiner*—Floyd D. Higel
*Attorney, Agent, or Firm*—Robert P. Raymond; Alan R. Stempel; Mary-Ellen Devlin

[57] ABSTRACT

Amino acid derivatives, suitable for the treatment of obesity. The following compound is exemplary of the class: (R,S)-$N^2$-(diphenylacetyl)-N-[(4-hydroxyphenyl)methyl]-$N^5$-(1H-imidazol-2-yl)-ornithinamide.

8 Claims, No Drawings

AMINO ACID DERIVATIVES, PHARMACEUTICAL COMPOSITIONS CONTAINING THESE COMPOUNDS AND PROCESSES FOR PREPARING THEM

This is a division of application Ser. No. 08/458,093, filed Jun. 01, 1995, now U.S. Pat. No. 5,616,620, which is a division of application Ser. No. 08/184,160, filed Jan. 21, 1994, now abandoned.

The present invention relates to new amino acid derivatives of general formula

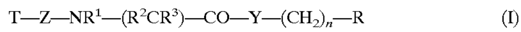

$$T—Z—NR^1—(R^2CR^3)—CO—Y—(CH_2)_n—R \quad (I)$$

the tautomers, diastereomers and elantiomers thereof, mixtures thereof and salts thereof, more particularly the physiologically acceptable salts thereof with inorganic or organic acids or bases, and processes for preparing them.

In general formula I above:

n denotes the number 0, 1, 2, 3, 4 or 5,

R denotes a hydrogen atom, a phenyl or naphthyl group optionally mono- or disubstituted by fluorine, chlorine, bromine or iodine atoms, or by cyano, alkyl, phenyl, hydroxy, alkoxy, dialkylaminoalkoxy, hydroxyphenyl, phenylalkoxy, alkylcarbonyl, amino, alkylamino, dialkylamino, alkylsulphonylamino, alkylcarbonylamino, alkoxycarbonylamino, alkoxycarbonyloxy, carboxy, alkoxycarbonyl, aminocarbonyl, alkylaminocarbonyl, dialkylaminocarbonyl, alkylcarbonyloxy, alkylsulphonyloxy, hydroxymethyl, hydroxyethyl, hydroxypropyl, hydroxybutyl, trifluoromethyl, trifluoromethoxy, trifluoromethylthio, aminoalkyl, alkylaminoalkyl, aminocarbonylaminoalkyl, benzoylamino, alkanoylaminoalkyl, alkoxycarbonylaminoalkyl, benzyloxycarbonylaminoalkyl, aminosulphonyl, alkylaminosulphonyl, dialkylaminosulphonyl, aminosulphonylamino, alkylaminosulphonylamino, dialkylaminosulphonylamino, cyanamino, aminocarbonylamino, alkylaminocarbonylamino, dialkylaminocarbonylanino, aminosulphonylaminoalkyl, alkylaminosulphonylaminoalkyl, carboxyalkyl, alkoxycarbonylalkyl, aminocarbonylalkyl, alkylaminocarbonylalkyl, aminosulphonylalkyl, alkylaminosulphonylalkyl, alkylsulphonyl, aminosulphonyloxy, alkylaminosulphonyloxy, dialkylaminosulphonyloxy or cyanoguanidino groups wherein the substituents may be identical or different, an aminophenyl or aminonaphthyl group additionally disubstituted by chlorine or bromine atoms wherein the substituents may be identical or different, or a hydroxyphenyl or hydroxynaphthyl group, additionally disubstituted by chlorine or bromine atoms or alkyl or alkoxy groups, wherein the substituents may be identical or different, a diphenylmethyl group, an aminocarbonylalkyl group substituted in the alkyl moiety by a hydroxyphenylalkyl group, or a (2,2-diphenylethyl)aminocarbonylaminophenyl group, a 5-membered heteroaryl group bound via a carbon or nitrogen atom, which contains one or two imino groups each optionally substituted by a $C_{1-6}$-alkyl group or by a phenyl or phenylalkyl group, or contains an oxygen or sulphur atom, or contains an imino group optionally substituted by a $C_{1-6}$-alkyl group or by a phenylalkyl group, and an oxygen, sulphur or nitrogen atom, or a 6-membered heteroaryl group bound via a carbon atom, which contains 1 or 2 nitrogen atoms, wherein a 1,4-butadienyl group may be attached to two adjacent carbon atoms of the above-mentioned 5-membered and 6-membered heteroaromatic rings and the bicyclic heteroaromatic rings thus formed may also be bound via a carbon atom of the 1,4-butadienyl group and additionally all the above-mentioned mono- or bicyclic heteroaryl groups may be monosubstituted in the carbon skeleton by a fluorine, chlorine or bromine atom or by an alkyl, alkoxy, hydroxy, phenyl, nitro, amino, alkylamino, dialkylamino, alkanoylamino, cyano, carboxy, alkoxycarbonyl, aminocarbonyl, alkylaminocarbonyl, dialkylaminocarbonyl, fluoromethyl, difluoromethyl, trifluoromethyl, alkanoyl, aminosulphonyl, alkylaminosulphonyl or dialkylaminosulphonyl group or disubstituted by fluorine, bromine or chlorine atoms or by methyl, methoxy or hydroxy groups, whilst the substituents may be identical or different, a phenyl group substituted by a [1,5-dihydro-2,4(3H)-dioxo-imidazol-3-yl]alkyl or [1,2-dihydro-3,5(4H)-dioxo-3H-1,2,4-triazol-4-yl]alkyl group, wherein the imidazole and triazole moiety may additionally be substituted by 1 or 2 phenyl groups, a $C_{4-8}$-cycloalkyl group optionally substituted by a hydroxy, amino, alkylamino or dialkylamino group, wherein the above-mentioned substituents, if Y denotes an oxygen atom, are not bound in the 1-position of the cycloalkyl group, a 1-[[[5,11-dihydro-6(6H)-oxo-pyrido[2,3-b][1,4]-benzodiazepin-11-yl]carbonyl]methyl]-4-piperidinyl or 3-hydroxy-1-propyn-1-yl group, or a 2,3-dihydro-1H-isoindol- 2-yl group optionally substituted by a diphenylaminocarbonyl group at the nitrogen atom, or if Y denotes an oxygen atom or an $NR^4$ group and n denotes one of the numbers 2 to 5, R may also denote a hydroxy group;

$R^1$ denotes a hydrogen atom, a branched or straight-chained $C_{1-10}$-alkyl group, a $C_{3-7}$-cycloalkyl group, a phenyl group optionally substituted by a hydroxy or hydroxyalkyl group or a phenylmethyl group optionally substituted in the phenyl moiety by a hydroxy or hydroxyalkyl group, $R^2$ denotes an unbranched $C_{1-5}$-alkyl group which may be substituted in the ω-position by an amino or alkylamino group (optionally protected by a protecting group for an amino group), by a dialkylamino, N-alkyl-benzylamino, aminocarbonyl, aminocarbonylamino, aminomethylimino, aminoiminomethyl, [amino (hydroxyimino)methyl], [amino(alkoxyimino)methyl], guanidino, hydrazinoiminomethyl, [amino(nitroimino) methyl], [amino(nitroimino)methyl]amino, [amino (cyanimino)-methyl], [amino (cyanimino)methyl]-amino, [(alkylamino)iminomethyl]amino, [(alkylamino)-(alkylimino)methyl]amino, [amino (alkylimino)methyl]-amino, 2-amino-imidazol-1-yl, (5-amino-4H-1,2,4-triazol-3-yl)amino, (5-amino-4H-1,2,4-triazol-3-yl)methylamino, (3-amino-1,2,4-oxadiazol-5-yl)amino or (5-amino-1,2,4-oxadiazol-3-yl)-amino group or by an imidazol-4-yl, imidazol-2-yl, 1-methyl-imidazol-2-yl, imidazol-2-yl-amino, imidazol-2-yl-methylamino or (4,5-dihydro-1H-imidazol-2-yl)amino group optionally substituted at a carbon by one or two methyl groups, or a phenyl or phenylmethyl group optionally substituted in the aromatic ring by a cyano, iminomethylamino, cyaniminomethylamino, (methylamino) methylideneamino, aminoiminomethyl, [amino (hydroxyimino)methyl], [amino-(alkoxyimino) methyl], hydrazinoiminomethyl, [amino(cyanimino) methyl] or guanidino group or by an imidazol-2-yl, 1-methyl-imidazol-2-yl or 4,5-dihydro-1H-imidazol-2-yl group optionally substituted at a carbon atom by one or two methyl groups, wherein in the aminoiminomethyl, [amino (hydroxyimino)-methyl] and guanidino groups mentioned above in the definition of $R^2$, one or more hydrogen atoms bound to nitrogen atoms may independently be replaced by alkyl groups, or two hydrogen atoms bound to different nitrogen atoms may be replaced by a $C_{2-4}$-alkylene bridge and additionally a hydrogen atom in an HN<, HN═ or $H_2N$— group present in the group $R^2$ may additionally be replaced by an alkoxycarbonyl group having a total of 2 to 7 carbon atoms, by a phenylalkyloxycarbonyl group having 1 to 6 carbon atoms in the alkyl moiety, by a phenyloxycarbonyl group, or by an $R^{15}$—CO—O—($R^{16}CR^{17}$)—O—CO— or ($R^{18}$O)PO($OR^{19}$)— group, wherein $R^{15}$ denotes a $C_{1-5}$-alkyl group, a $C_{3-7}$-cycloalkyl group, a phenyl group or a phenylalkyl groups having 1 to 3 carbon atoms in the alkyl moiety, $R^{16}$ and $R^{17}$, which may be identical or different, denote hydrogen atoms or ($C_{1-6}$-alkyl groups and one of the groups $R^{16}$ or $R^{17}$ may additionally denote a $C_{3-7}$-cycloalkyl group or a phenyl group, $R^{18}$ and $R^{19}$, which may be identical or different, denote hydrogen atoms, $C_{1-4}$-alkyl groups, or benzyl or phenyl groups;

$R^3$ denotes a hydrogen atom, a $C_{1-7}$-alkyl group or a $C_{4-7}$-cycloalkyl group, T denotes a hydrogen atom, a phenyl group or a 5-membered heteroaryl group bound via a carbon or nitrogen atom, said heteroaryl group containing an optionally alkyl-substituted nitrogen atom or an oxygen or sulphur atom or an optionally alkyl-substituted nitrogen atom as well as an additional oxygen, sulphur or nitrogen atom, or, if Z denotes a bond, T may also represent a protecting group for an amino group, or the groups ($T^1T^2$U)—($CH_2$)$_m$— or $T^3$O—, wherein $T^1$ to $T^3$, which may be identical or different, denote phenyl groups or 6-membered heteroaryl groups bound via carbon atoms and which each contain one or two nitrogen atoms.

or 5-membered heteroaryl groups bound via carbon or nitrogen atoms and which contain an optionally alkyl-substituted nitrogen atom, an oxygen atom or a sulphur atom, or an optionally alkyl-substituted nitrogen atom and an additional oxygen, sulphur or nitrogen atom, whilst additionally a 1,4-butadienyl bridge may be attached to two adjacent carbon atoms of the 5- and 6-membered heteroaryl groups mentioned above in the definition of group T, $T^1$, $T^2$ and $T^3$ and the bicyclic aromatic and heteroaromatic rings thus formed may also be bound via a carbon atom of the 1,4-butadienyl group and additionally the phenyl groups, the 5- and 6-membered heteroaryl groups and also the bicyclic aromatic and heteroaromatic rings may in the carbon skeleton by mono- or disubstituted by fluorine, chlorine, bromine or iodine atoms or by cyano, hydroxy, amino, dimethylamino, diethylamino, N-ethyl-methylamino, trifluoromethyl, trifluoromethoxy, trifluoromethylthio, acetylamino, propionylamino, methanesulphonylamino, methanesulphonyloxy, phenyl, phenylmethoxy, 2-phenylethoxy, alkyl or alkoxy groups, or trisubstituted by an amino or hydroxy group together with two chlorine or bromine atoms or by a hydroxy group together with two alkyl or alkoxy groups, and the substituents may be identical or different and the above-mentioned alkyl and alkoxy moieties may each contain 1 to 4 carbon atoms, or $T_1$ to $T_3$ denote hydrogen atoms, $C_{1-12}$-alkyl groups, $C_{3-10}$-cycloalkyl groups, or bicyclo- or tricycloalkyl groups each having 6 to 12 carbon atoms, and $T^1$ and $T^2$ may together denote a straight-chained $C_{3-7}$-alkylene group, U denotes a >CH— group wherein the hydrogen atom may be replaced by an alkyl, phenyl, hydroxy, alkoxy, alkanoyloxy, alkoxycarbonyl or alkanoylamino group, whilst the above-mentioned alkyl and alkoxy moieties may each contain 1 to 3 carbon atoms and the above-mentioned alkanoyl moiety may contain 2 or 3 carbon atoms, or U denotes a >$CHCH_2$— group or a nitrogen atom, and m denotes the number 0, 1, 2 or 3, or T denotes a ($T^1T^2$U)—($CH_2$)$_m$— group wherein $T^1$, $T^2$, U and m are as hereinbefore defined, with the proviso that the mono- or bicyclic aromatic or heteroaromatic rings mentioned above for $T^1$ and $T^2$ are linked together via a bond or via a —$CH_2$—, —$C(CH_3)_2$—, —$CH_2CH_2$—, —CH═CH— or —NHCO— bridge;

Y denotes an oxygen atom or an —$NR^4$— group, wherein $R^4$ has the meanings given above for $R^1$ and the groups $R^1$ and $R^4$ are identical or different, and Z denotes a single bond, or a —CO—, —$CH_2$—, —SO— or —$SO_2$— group, and unless otherwise specified the above-mentioned alkyl and alkoxy moieties may each contain 1 to 3 carbon atoms.

As examples of the definitions given hereinbefore for the groups:

$T^1$ and $T^2$, which may be identical or different, may denote a phenyl, 2-pyridinyl, 3-pyridinyl, 4-pyridinyl, 2-thienyl, 3-thienyl, 2-furyl, 3-furyl, 1H-pyrrol-2-yl, 1H-pyrrol-3-yl, 1-methyl-1H-pyrrol-2-yl, 1-methyl-1H-pyrrol-3-yl, 1-naphthyl, 2-naphthyl, 1H-indol-2-yl, 1H-indol-3-yl, benzo[b]furan-2-yl, benzo[b]furan-3-yl, benzo[b]thiophen-2-yl, benzo[b]thiophen-3-yl, 2-quinolinyl, 3-quinolinyl, 4-quinolinyl, benzo[c] thiophen-1-yl, 1-isoquinolinyl, 3-isoquinolinyl, 4-isoquinolinyl, pyrazinyl, 2-pyrimidinyl, 4-pyrimidinyl, 5-pyrimidinyl, 3-pyridazinyl, 4-pyridazinyl, 2-imidazolyl, 4-imidazolyl, 3-pyrazolyl, 4-pyrazolyl, 1,3-oxazol-2-yl, 1,3-oxazol-4-yl, 1,3-oxazol-5-yl, 3-pyrazolyl, 4-pyrazolyl, 3-isoxazolyl, 4-isoxazolyl, 5-isoxazolyl, 2-quinazolinyl, 4-quinazolinyl or 2-quinoxalinyl group, whilst these may additionally be substituted by the groups mentioned hereinbefore, $T^1$ and $T^2$ may together denote a 1,3-propandiyl, 1,4-butandiyl, 1,5-pentandiyl or 1,6-hexandiyl group, a ($T^1T^2U$)- group may denote a 9H-fluoren-9-yl, 5,11-dihydro-6(6H)-oxo-dibenz[b,e]azepin-11-yl, 5H-dibenzo[a,d]cyclohepten-5-yl, 10H-phenothiazin-10-yl, 2-chloro-10H-phenothiazin-10-yl, 5H-dibenzo[b,f]azepin-5-yl, 10,11-dihydro-5H-dibenzo[b,f]azepin-5-yl, 10H-phenoxazin-10-yl, 10H-pyrido[3,2-b][1,4]benzothiazin-10-yl, 9H-xanthen-9-yl, 9H-thioxanthen-9-yl, 5,11-dihydro-6(6H)-oxo-pyrido[2,3-b][1,4]benzodiazepin-11-yl, 5,10-dihydro-11(11H)-oxo-dibenzo[b,e][1,4]diazepin-5-yl, 4,9-dihydro-3-methyl-10(10H)-oxo-thieno[3,4-b][1,5]benzodiazepin-4-yl, 1,3-dimethyl-10-oxo-1,4,9,10-tetrahydropyrrolo[3,2-b][1,5]benzodiazepin-4-yl or 6,11-dihydro-5(5H)-oxo-pyrido[2,3-b][1,5]-benzodiazepin-11-yl group and R may denote a phenyl, 2-pyridinyl, 3-pyridinyl, 4-pyridinyl, 2-thienyl, 3-thienyl, 2-furyl, 3-furyl, 1H-pyrrol-2-yl, 1H-pyrrol-3-yl, 1-methyl-1H-pyrrol-2-yl, 1-methyl-1H-pyrrol-3-yl, 1-naphthyl, 2-naphthyl, 1H-indol-2-yl, 1H-indol-3-yl, 2,3-dihydro-1H-isoindol-2-yl, 2,3-dihydro-1H-isoindol-3-yl, 2,3-dihydro-1H-isoindol-4-yl, 2,3-dihydro-1H-isoindol-5-yl, 1H-benzimidazol-2-yl, 1H-benzimidazol-4-yl, 1H-benzimidazol-5-yl, benzo[b]furan-2-yl, benzo[b]furan-3-yl, benzo[b]furan-5-yl, benzo[b]-thiophen-2-yl, benzo[b]thiophen-3-yl, benzo[b]thiophen-5-yl, 2-quinolinyl, 3-quinolinyl, 4-quinolinyl, 6-quinolinyl, benzo[c]thiophen-1-yl, 1-isoquinolinyl, 3-isoquinolinyl, 4-isoquinolinyl, pyrazinyl, 2-pyrimidinyl, 4-pyrimidinyl, 5-pyrimidinyl, 3-pyridazinyl, 4-pyridazinyl, 2-imidazolyl, 4-imidazolyl, 3-pyrazolyl, 4-pyrazolyl, 1,3-oxazol-2-yl, 1,3-oxazol-4-yl, 1,3-oxazol-5-yl, 3-pyrazolyl, 4-pyrazolyl, 3-isoxazolyl, 4-isoxazolyl, 5-isoxazolyl, 2-quinazolinyl, 4-quinazolinyl or 2-quinoxalinyl group, whilst these may additionally be substituted by the groups mentioned hereinbefore, the protecting groups for an amino or imino group mentioned in the definition of groups T and $R^2$ may be the usual protecting groups for an amino or imino group (see for example Houben-Weyl, "Methoden der organischen Chemie" Vol. 15/1) such as the p-toluenesulphonyl, phenylmethoxycarbonyl, tert.butyloxycarbonyl, (4-methoxyphenyl)methoxycarbonyl, adamantyloxycarbonyl, biphenylylisopropyloxycarbonyl, isonicotinoyloxycarbonyl, o-nitrophenylsulphenyl, formyl, o-nitrophenylsulphenyl, biphenylylisopropyloxycarbonyl, 9-fluorenylmethoxycarbonyl, acetyl, trifluoroacetyl, (2-chlorophenyl)methoxycarbonyl, (4-chlorophenyl)methoxycarbonyl, (4-nitrophenyl)methoxycarbonyl or phthaloyl group.

The present invention relates to the racemates, provided that, in compounds of general formula I, the asymmetric carbon atom of the central amino acid is the sole chirality element. However, the application also includes the individual diastereomers or mixtures thereof which occur when a compound covered by general formula I contains two or more chirality elements. Particularly preferred are the compounds which fall within general formula I and which are in D- or (R)-configuration with regard to the partial amino acid structure $$—NR^1—(R^2CR^3)—CO—.$$

The compounds of general formula I have valuable properties. Thus, the compounds of general formula I wherein T denotes a hydrogen atom and at the same time Z denotes a bond are valuable intermediate products for preparing the other compounds of general formula I which have useful pharmacological properties, particularly the effect of lowering blood pressure on the basis of their NPY-antagonistic properties. The invention further relates to pharmaceutical compositions containing these compounds, the use thereof and the preparation thereof.

Preferred compounds of general formula I above are those wherein the R—$(CH_2)_n$— group denotes a $C_{1-3}$-alkyl group which may be substituted by 2 phenyl groups in the ω-position, a straight-chained $C_{2-5}$-alkylene group terminally substituted by a hydroxy group, a phenyl or phenylalkyl group having 1 to 4 carbon atoms in the alkyl moiety, in which the phenyl group is optionally substituted in each case by a fluorine, chlorine or bromine atom, by an alkylaminocarbonyl group having 1 to 4 carbon atoms in the alkyl moiety, by an ethylaminocarbonylamino group (in which the ethyl moiety is substituted by one or two phenyl groups), or by a methyl, hydroxymethyl, phenyl, hydroxyphenyl, hydroxy, methoxy, ethoxy, dimethylaminosulphonyloxy, cyano, carboxy, methoxycarbonyl, acetyl, aminocarbonyl, dimethylaminocarbonyl, amino, methylamino, dimethylamino, acetylamino, methoxycarbonylamino, ethoxycarbonylamino, aminocarbonylamino, methylaminocarbonylamino, dimethylaminocarbonylamino, methylsulphonylamino, aminosulphonyl, [amino(imino)-methyl]-, [amino(imino)methyl]amino, [1,2-dihydro-3,5(4H)-dioxo-1,2-diphenyl-3H-1,2,4-triazol-4-yl]methyl, [1,5-dihydro-2,4(3H)-dioxo-5,5-diphenyl-imidazol-3-yl]methyl, aminomethyl, aminosulphonylamino, hydroxyethyl, hydroxypropyl, hydroxybutyl, 3-(dimethylamino)propoxy or ethoxycarbonyloxy group, a methyl group which is substituted by a hydroxycyclohexyl, 4-hydroxy-3-methyl-phenyl, 3,4-dimethoxyphenyl, 3-hydroxy-4-methoxyphenyl, 3-methoxy-4-hydroxyphenyl, 4-amino-3,5-dibromophenyl, 4-amino-3,5-dichlorophenyl, 4-hydroxy-3,5-dibromophenyl, 4-hydroxy-3,5-dichlorophenyl, 4-amino-3-fluorophenyl, 4-hydroxy-3,5-dimethylphenyl, thienyl, pyridinyl, indolyl, benzimidazolyl, quinolinyl- or 2-(diphenylaminocarbonyl)-2,3-dihydro-1H-isoindolyl group, an ethyl group substituted by an indolyl, 5-methoxyindolyl, 1,2-diphenyl-3,5(4H)-dioxo-1,2,4-triazol-4-yl or imidazolyl group, a 2-(2-hydroxyphenyl)ethyl group substituted in the α-position by an aminocarbonyl group, a 3-[1-[2-[5,11-dihydro-6(6H)-oxopyrido[2,3-b][1,4]-benzodiazepin-5-yl]-2-oxoethyl]-4-piperidinyl]propyl or 3-hydroxy-1-propyn-1-yl group, the T—Z— group denotes a hydrogen atom, a carbonyl group which may be substituted by a $C_{1-4}$-alkyl group which itself may be substituted in the α- or β-position by a $C_{1-3}$-alkyl group or by one or two phenyl groups optionally mono- or disubstituted by methoxy groups, hydroxy groups or chlorine or bromine atoms, a carbonyl group which is substituted by an indolyl group (itself substituted by a benzyloxy or phenylethoxy group), or by a methyl, tricyclo[3.3.1.1$^{3.7}$]dec-1-yl, benzyl, (hydroxyphenyl)methyl, (methylphenyl) methyl, (biphenylyl)methyl, (dichlorophenyl)methyl, phenyl, 3,5-dichlorophenyl, 3,4-dichlorophenyl, naphthyl, naphthylmethyl, α-cyclopentyl-benzyl, diphenylamino, naphthylamino, hexamethyleneimino, 5-phenylethoxy-indolyl, 1,2,3,4-tetrahydro-2-quinolinyl, 2-quinolinyl, 1,2,3,4-tetrahydro-3-quinolinyl, (dichlorophenoxy)-methyl, 9-fluorenyl, triphenylmethyl, 1-piperidinyl, (diphenylmethyl)amino or 5,10-dihydro-11(11H)-oxo-dibenzo[b,e][1,4] diazepin-5-yl group, or a 4-amino-3,5-dichloro-phenylsulphonyl or naphthylsulphonylamino group, $R^1$ denotes a hydrogen atom, $R^2$ denotes an unbranched $C_{1-5}$-alkyl group which is substituted in the ω-position by a guanidino group (wherein the hydrogen atoms at the nitrogen atoms may each be replaced by $C_{1-3}$-alkyl groups), by an amino, tert.butoxycarbonylamino, dimethylamino, N-methyl-benzylamino, methylamino, aminocarbonyl, aminocarbonylamino, aminomethylideneimino, methylaminomethylideneimino, [amino(nitroimino) methyl]-amino, 1H-imidazol-2-yl-amino, 4,5-dihydro-1H-imidazol-2-yl-amino, (5-amino-4H-1,2,4-triazol-3-yl)amino, (3-amino-1,2,4-oxadiazol-5-yl)amino or (5-amino-1,2,4-oxadiazol-3-yl)amino group, a methyl group which is substituted by a phenyl, cyanophenyl, aminomethylphenyl, amidinophenyl, methylaminomethylideneiminophenyl, cyanoiminomethylaminophenyl, methyliminomethylaminophenyl, (4,5-dihydro-1H-imidazol-2-yl)phenyl or imidazolyl group, $R^3$ denotes a hydrogen atom or a methyl group and Y denotes an imino group optionally substituted by a methyl or ethyl group, the tautomers, the diastereomers and enantiomers thereof, mixtures thereof and the salts thereof.

Particularly preferred compounds of general formula I above are those wherein the R—$(CH_2)_n$— group denotes a $C_{1-3}$-alkyl group which may be substituted in the ω-position by two phenyl groups, a straight-chained $C_{2-5}$-alkylene group terminally substituted by a hydroxy group, a phenyl or phenylalkyl group having 1 to 3 carbon atoms in the alkyl moiety, in which the phenyl group in each case is substituted by a fluorine, chlorine or bromine atom or by a methyl, hydroxymethyl, hydroxyethyl, hydroxypropyl, hydroxy, methoxy, ethoxy, dimethylaminosulphonyloxy, acetyl, methoxycarbonyl, aminocarbonyl, aminocarbonylamino, methylaminocarbonylamino, aminosulphonyl, dimethylamino, [1,2-dihydro-3,5 (4H)-dioxo-1,2-diphenyl-3H-1,2,4-triazol-4-yl] methyl, [1,5-dihydro-2,4(3H)-dioxo-5,5-diphenyl-imidazol-3-yl3methyl or ethoxycarbonyloxy group, a methyl group which is substituted by a 3,4-dimethoxyphenyl, 3-hydroxy-4-methoxyphenyl, 3-methoxy-4-hydroxyphenyl, 4-amino-3,5-dibromophenyl, 4-amino-3,5-dichlorophenyl, 4-hydroxy-3,5-dimethylphenyl, 4'-hydroxy-4-biphenylyl, thienyl, pyridinyl, benzimidazolyl or 1-[2-[5,11-dihydro-6(6H)-oxo-pyrido[2,3-b][1,4]-benzodiazepin-5-yl]-2-oxoethyl]-4-piperidinyl] or 4-amino-3-fluorophenyl group, the T—Z— group denotes a diphenylacetyl group in which the phenyl nucleus may be substituted by a chlorine or bromine atom, a carbonyl group which is substituted by an indolyl group (itself substituted by a benzyloxy or phenylethoxy group), or by a benzyl, (dichlorophenyl) methyl, dichlorophenyl, naphthyl, naphthylmethyl, α-cyclopentylbenzyl, 9-fluorenyl or (diphenylmethyl)amino group, $R^1$ denotes a hydrogen atom, $R^2$ denotes a straight-chained $C_{2-5}$-alkylene chain terminally substituted by an amino, amidino, guanidino, aminocarbonyl, aminocarbonylamino or (1H-imidazol-2-yl)-amino group, or a methyl group which is substituted by an (aminomethyl)-phenyl, amidinophenyl or (4,5-dihydro-1H-imidazol-2-yl)-phenyl group, $R^3$ denotes a hydrogen atom or methyl group and Y denotes an imino group optionally substituted by a methyl group, the tautomers, the diastereomers and enantiomers thereof, mixtures thereof and the salts thereof.

Most particularly preferred compounds of general formula I above are those wherein the $R(CH_2)_n$ group denotes a phenylmethyl group, wherein the phenyl group is substituted by a fluorine, chlorine or bromine atom, or by a methyl, hydroxymethyl, hydroxyethyl, hydroxypropyl, hydroxy, methoxy, ethoxy, dimethylaminosulphonyloxy, ethoxycarbonyloxy, acetyl, methoxycarbonyl, aminocarbonyl, aminocarbonylamino, methylaminocarbonylamino, aminosulphonyl, dimethylamino, [1,2-dihydro-3,5(4H) -dioxo-1,2-diphenyl-3H-1,2,4-triazol-4-yl]methyl or [1,5-dihydro-2,4(3H)-dioxo-5,5-diphenyl-imidazol-3-yl]methyl group, a methyl group which is substituted by a 3,4-dimethoxyphenyl, 3-hydroxy-4-methoxyphenyl, 3-methoxy-4-hydroxyphenyl, 4-amino-3,5-dibromophenyl, 4-amino-3,5-dichlorophenyl, 4-hydroxy-3,5-dimethylphenyl, 4'-hydroxy-4-biphenylyl, thienyl, pyridinyl, benzimidazolyl, 1-[2-[5, 11-dihydro-6(6H)-oxo-pyrido[2,3-b][1,4]-benzodiazepin-5-yl]-2-oxoethyl]-4-piperidinyl or 4-amino-3-fluorophenyl group, the T—Z— group denotes a diphenylacetyl group in which each phenyl ring may be substituted by a chlorine or bromine atom, a carbonyl group which is substituted by an indolyl group (itself substituted by a benzyloxy or phenylethoxy group) or by a benzyl, (dichlorophenyl)methyl, dichlorophenyl, naphthyl, naphthylmethyl, α-cyclopentylbenzyl, 9-fluorenyl or (diphenylmethyl) amino group, $R^1$ denotes a hydrogen atom, $R^2$ denotes a straight-chained $C_{2-5}$-alkylene chain which is terminally substituted by an amino, amidino, guanidino, aminocarbonyl, aminocarbonylamino or (1H-imidazol-2-yl)amino group or a methyl group which is substituted by an (aminomethyl) phenyl, amidinophenyl or (4,5-dihydro-1H-imidazol-2-yl)phenyl group, $R^3$ denotes a hydrogen atom or a methyl group and Y denotes an optionally methyl-substituted imino group, the tautomers, the diastereomers, and the enantiomers thereof, mixtures thereof and the salts thereof.

Of special interest are those compounds of general formula I above wherein the $R(CH_2)_n$— group is a phenylmethyl group in which the phenyl group is substituted by a fluorine, chlorine or bromine atom, or by a methyl, hydroxymethyl, hydroxyethyl, hydroxypropyl, hydroxy, methoxy, ethoxy, dimethylaminosulphonyloxy, ethoxycarbonyloxy, acetyl, methoxycarbonyl, aminocarbonyl, aminocarbonylamino, methylaminocarbonylamino, aminosulphonyl, dimethylamino, [1,2-dihydro-3,5(4H)-dioxo-1,2-diphenyl-3H-1,2,4-triazol-4-yl]methyl or [1,5-dihydro-2,4(3H)-dioxo-5,5-diphenyl-imidazol-3-yl]methyl group, a methyl group which is substituted by a 3,4-dimethoxyphenyl, 3-hydroxy-4-methoxyphenyl, 3-methoxy-4-hydroxyphenyl, 4-amino-3,5-dibromophenyl, 4-amino-3,5-dichlorophenyl, 4-hydroxy-3,5-dimethylphenyl, 4'-hydroxy-4-biphenylyl, thienyl, pyridinyl, benzimidazolyl, 1-[2-[5,11-dihydro-6(6H)-oxo-pyrido[2,3-b][1,4]-benzodiazepin-5-yl]-2-oxoethyl]-4-piperidinyl or 4-amino-3-fluorophenyl group, the T—Z— group denotes a diphenylacetyl group in which each phenyl ring may be substituted by a chlorine or bromine atom, a carbonyl group which is substituted by an indolyl group (itself substituted by a benzyloxy or phenylethoxy group) or by a benzyl, (dichlorophenyl)methyl, dichlorophenyl, naphthyl, naphthylmethyl, α-cyclopentylbenzyl, 9-fluorenyl or (diphenylmethyl) amino group, $R^1$ denotes a hydrogen atom, $R^2$ denotes a straight-chained $C_{2-5}$-alkylene chain terminally substituted by an amino, amidino, guanidino, aminocarbonyl, aminocarbonylamino or (1H-imidazol-2-yl)-amino group, or a methyl group which is substituted by an (aminomethyl)-phenyl, amidinophenyl or (4,5-dihydro-1H-imidazol-2-yl)phenyl group, $R^3$ denotes a hydrogen atom and Y denotes an optionally methyl-substituted imino group, the tautomers, diastereomers and enantiomers thereof, mixtures thereof and the salts thereof.

The following are examples of particularly preferred compounds:

(R)-$N^2$-(diphenylacetyl)-N-(phenylmethyl)-argininamide, (R)-$N^2$-(diphenylacetyl)-N-[(4-methylphenyl)methyl]-argininamide, (R)-N-[2-(4-hydroxyphenyl)ethyl]-$N^2$-[[5-(2-phenylethoxy)-1H-indol-2-yl]carbonyl]-argininamide, N-[(4-aminocarbonylaminophenyl)methyl]-$N^2$-(diphenylacetyl)-argininamide, (R)-N-[(4-hydroxyphenyl)methyl]-$N^2$-[[5-(2-phenylethoxy)-1H-indol-2-yl]carbonyl]-argininamide, (R)-$N^2$-(diphenylacetyl)-N-[(4-fluorophenyl)methyl]-argininamide, (R)-N-[(4-bromophenyl)methyl]-$N^2$-(diphenylacetyl)-argininamide, (R)-$N^2$-(diphenylacetyl)-N-(2-phenylethyl)-argininamide, optically active diastereomeric mixtures of $N^2$-(α-cyclopentyl-phenylacetyl)-N-[(4-hydroxyphenyl)methyl]-D-argininamide, N-[[4-(dimethylamino)phenyl]methyl]-$N^2$-(diphenylacetyl)-argininamide, (R)-$N^2$-(diphenylacetyl)-N-[[4-(hydroxymethyl)phenyl]-methyl]argininamide, (R)-$N^2$-(diphenylacetyl)-N-[[4-(1-oxoethyl)phenyl]methyl]-argininamide, (R)-N-[(4-chlorophenyl)methyl]-$N^2$-(diphenylacetyl)-argininamide, (R)-$N^2$-(diphenylacetyl)-N-[[4-[(methylaminocarbonyl)-amino]phenyl]methyl]-argininamide, (R)-N-[(4-amino-3,5-dichlorophenyl)methyl]-$N^2$-(diphenylacetyl)-argininamide, (R)-N-[(4-amino-3,5-dichlorophenyl)methyl]-$N^2$-(3,3-diphenyl-1-oxopropyl)-argininamide, (R)-N-[(4-amino-3,5-dichlorophenyl)methyl]-$N^2$-(3,4-dichlorobenzoyl)-argininamide, $N^2$-(diphenylacetyl)-N-[3-[1-[2-[5,11-dihydro-6(6H)-oxopyrido[2,3-b][1,4]benzodiazepin-5-yl]-2-oxoethyl]-4-piperidinyl]-propyl]-argininamide, $N^2$-(diphenylacetyl)-N-[(4-hydroxy-3-methoxyphenyl)-methyl]-argininamide, $N^2$-(diphenylacetyl)-N-[(3-hydroxy-4-methoxyphenyl)-methyl]-argininamide, (R,S)-N-[(4-amino-3,5-dibromophenyl)methyl]-$N^6$-(aminoiminomethyl)-$N^2$-(diphenylacetyl)-lysinamide, N-[(3,5-dimethyl-4-hydroxyphenyl)methyl]-$N^2$-(diphenylacetyl)-argininamide, N-[(1H-benzimidazol-5-yl)methyl]-$N^2$-(diphenylacetyl)-argininamide $N^2$-(diphenylacetyl)-N-[(4-hydroxy-3-methylphenyl)methyl]-argininamide N-[[4-(aminocarbonyl)phenyl]methyl]-$N^2$-(diphenylacetyl)-argininamide (R,S)-$N^6$-(aminoiminomethyl)-$N^2$-(diphenylacetyl)-N-[(4-hydroxyphenyl)methyl]-lysinamide, (R)-N-[(4-hydroxyphenyl)methyl]-$N^2$-(phenylacetyl)-argininamide $N^2$-(diphenylacetyl)-N-[(1H-indol-5-yl)methyl]-argininamide, (R)-N-[[4-(aminosulphonyl)phenyl]methyl]-$N^2$-(diphenylacetyl)-argininamide, (R)-$N^2$-(diphenylacetyl)-N-[[4-(methoxycarbonyl)phenyl]-methyl]-argininamide, (R)-$N^2$-(diphenylacetyl)-N-[(4-pyridinyl)methyl]-argininamide, (R)-N-[(4-amino-3,5-dibromophenyl)methyl]-$N^2$-(diphenylacetyl)-argininamide, (R)-$N^2$-(diphenylacetyl)-N-[(2-thienyl)methyl]-argininamide, (R)-N-[(4-amino-3,5-dichlorophenyl)methyl]-$N^2$-(2-naphthoyl)-argininamide, (R,S)-$N^5$-(4,5-dihydro-1H-imidazol-2-yl)-$N^2$-(diphenylacetyl)-N-[(4-hydroxyphenyl)methyl]-ornithinamide, (R,S)-$N^2$-(diphenylacetyl)-N-[(4-hydroxyphenyl)methyl]-$N^5$-(1H-imidazol-2-yl)-ornithinamide, (R)-N-[[3-[(1,2-dihydro-3,5(4H)-dioxo-1,2-diphenyl-3H-1,2,4-triazol-4-yl)methyl]phenyl]methyl]-$N^2$-(diphenylacetyl)-argininamide, $N^2$-(diphenylacetyl)-N-[(3-hydroxyphenyl)methyl]-argininamide, (R)-N-[[3-[(4,5-dihydro-2,4(3H)-dioxo-5,5-diphenyl-1H-imidazol-3-yl)methyl]phenyl]methyl]-$N^2$-(diphenylacetyl)-argininamide, (R)-$N^2$-(diphenylacetyl)-N-[(4-hydroxyphenyl)methyl]-argininamide, $N^2$-(diphenylacetyl)-N-[2-(4-hydroxyphenyl)ethyl]-argininamide, $N^2$-(diphenylacetyl)-N-[(4'-hydroxy-[1,1'-biphenyl]-4-yl)methyl]-argininamide, N-[[4-[(1,2-dihydro-3,5(4H)-dioxo-1,2-diphenyl-3H-1,2,4-triazol-4-yl)methyl]phenyl]methyl]-$N^2$-(diphenylacetyl)-argininamide, $N^2$-(diphenylacetyl)-N-[(4-methoxyphenyl)methyl]-argininamide, $N^2$-(diphenylacetyl)-N-[2-(4-methoxyphenyl)ethyl]-argininamide, $N^2$-(diphenylacetyl)-N-[2-(3-methoxyphenyl)ethyl]-argininamide, $N^2$-(diphenylacetyl)-N-[(3-methoxyphenyl)methyl]-argininamide, (R,S)-3-[4-(aminoiminomethyl)phenyl]-$N^2$-(diphenylacetyl)-N-[(4-hydroxyphenyl)methyl]-alaninamide, (R,S)-3-[3-(aminoiminomethyl)phenyl]-$N^2$-(diphenylacetyl)-N-[(4-methoxyphenyl)methyl]-alaninamide, (R,S)-3-[3-(aminoiminomethyl)phenyl]-$N^2$-(diphenylacetyl)-N-[(4-hydroxyphenyl)methyl]-alaninamide, (R)-$N^2$-[bis-(4-bromophenyl)acetyl]-N-[(4-hydroxyphenyl) methyl]-argininamide, (R)-$N^2$-(diphenylacetyl)-N-[(4-ethoxyphenyl)methyl]-argininamide, (R)-$N^2$-(diphenylacetyl)-N-[(4-hydroxyphenyl)methyl]-N-methyl-argininamide, (R,S)-N-[(4-amino-3,5-dibromophenyl)methyl]-3-[3-(aminoiminomethyl)phenyl]-$N^2$-(diphenylacetyl)-alaninamide, (R)-N-[[4-[(dimethylamino)sulphonyloxy]phenyl]methyl]-$N^2$-(diphenylacetyl)-argininamide, (R)-N-[(4-hydroxyphenyl)methyl]-$N^2$-(1-naphthoyl)-argininamide, (R)-N-[(4-hydroxyphenyl)methyl]-$N^2$-(2-naphthoyl)-argininamide, (R)-$N^2$-(2,2-diphenyl-2-hydroxyacetyl)-N-[(4-hydroxyphenyl)-methyl]-argininamide, (R,S)-$N^2$-(diphenylacetyl)-$N^5$-(1H-imidazol-2-yl)-N-[(4-methoxyphenyl)methyl]-ornithinamide, (R,S)-3-(3-(aminoiminomethyl)phenyl]-$N^2$-[[(diphenylmethyl)-amino]carbonyl]-N-[(4-hydroxyphenyl)methyl]-alaninamide, (R,S)-$N^2$-(diphenylacetyl)-$N^5$-(1H-imidazol-2-yl)-N-(phenylmethyl)-ornithinamide, (R,S)-N-[(4-amino-3,5-dichlorophenyl)methyl]-$N^2$-(diphenylacetyl)-$N^5$-(1H-imidazol-2-yl)-ornithinamide, (R,S)-N-[(4-hydroxyphenyl)methyl]-$N^5$-(1H-imidazol-2-yl) -$N^2$-(2-naphthoyl)-ornithinamide, (R,S)-$N^2$-[[(diphenylmethyl)amino]carbonyl]-N-[(4-hydroxyphenyl)methyl]-$N^5$-(1H-imidazol-2-yl)-ornithinamide, (R,S)-N-[(4-hydroxyphenyl)methyl]-$N^5$-(1H-imidazol-2-yl) -$N^2$-[(2-naphthyl)acetyl]-ornithinamide, (R,S)-N-[(4-hydroxyphenyl)methyl]-$N^5$-(1H-imidazol-2-yl) -$N^2$-[[(2-naphthyl)amino]carbonyl]-ornithinamide, (R,S)-N-[(4-hydroxyphenyl)methyl]-$N^5$-(1H-imidazol-2-yl) -$N^2$-[(1,2,3,4-tetrahydroquinolin-3-yl)carbonyl]-ornithinamide, (R,S)-N-[(4-hydroxyphenyl)methyl]-$N^5$-(1H-imidazol-2-yl) -$N^2$-[(1,2,3,4-tetrahydroquinolin-2-yl)carbonyl]-ornithinamide, (R)-N-[(4-aminosulphonylaminophenyl)methyl]-$N^2$-(diphenylacetyl)-argininamide, (R)-N-[(4-aminophenyl)methyl]-$N^2$-(diphenylacetyl)-argininamide, (R)-N-[(6-quinolinyl)methyl]-$N^2$-(diphenylacetyl)-argininamide, (R)-$N^2$-[(3,4-dichlorophenyl)acetyl]-N-[(4-hydroxyphenyl) methyl]-argininamide, (R)-$N^2$-(diphenylacetyl)-N-[[4-(2-hydroxyethyl)phenyl]-methyl]-argininamide, (R,S)-$N^5$-(3-amino-1,2,4-oxadiazol-5-yl)-$N^2$-(diphenylacetyl)-N-[(4-hydroxyphenyl)methyl]-ornithinamide, (R)-$N^2$-[(9-fluorenyl)carbonyl]-N-[(4-hydroxyphenyl)-methyl]-argininamide, (R,S)-6-(aminoiminomethyl)-$N^2$-(diphenylacetyl)-N-[(4-hydroxyphenyl)methyl]-norleucinamide (R,S)-3-[4-(4,5-dihydro-1H-imidazol-2-yl)phenyl]-$N^2$-(diphenylacetyl)-N-[(4-hydroxyphenyl)methyl]-alaninamide, (R,S)-3-[3-(aminoiminomethyl)phenyl]-$N^2$-(diphenylacetyl)-N-[(4-ethoxycarbonyloxyphenyl) methyl]-alaninamide, (R,S)-N-[2-(1,2-dihydro-1,2-diphenyl-3,5(4H)-dioxo- 1,2,4-triazol-4-yl)ethyl]-$N^2$-(diphenylacetyl)-argininamide, (R,S)-$N^2$-(diphenylacetyl)-N-[4-hydroxyphenyl)methyl]-2-methyl-argininamide, (R)-$N^2$-(diphenylacetyl)-N-[[4-(3-hydroxypropyl)phenyl]-methyl]-argininamide (R)-N-[[4-[(4,5-dihydro-5,5-dimethyl-2,4(3H)-dioxo-1H-imidazol-3-yl)methyl]phenyl]methyl]-$N^2$-(diphenylacetyl)-argininamide and the salts thereof.

The compounds of general formula I are prepared by methods which are known in principle, using in particular methods derived from peptide chemistry (see for example Houben-Weyl, "Methoden der Organischen Chemie", Vol. 15/2). The amino-protecting groups used may be those described In Houben-Weyl, "Methoden der Organischen Chemie", Vol. 15/1, whilst urethane-protecting groups such as the fluorenylmethoxycarbonyl, phenylmethoxycarbonyl or tert.butyloxycarbonyl group are preferred. Any functional groups present in the group $R^2$ of the compounds of general formula I may additionally be protected by means of suitable protecting groups in order to prevent side reactions (see, for example, G. B. Fields et al., Int. J. Peptide Protein Res. 35: 161 (1990); T. W. Greene, "Protective Groups in Organic Synthesis"). Examples of side chain-protected amino acids of this kind include, in particular, Arg $(NO_2)$, Arg(Mtr), Arg(di-Z), Arg(Pmc), Lys(Boc), Lys(Z), Orn(Boc), Orn(Z), Lys(Cl-Z), which are generally available, possibly in the form of derivatives. The side chain of [(aminomethyl) phenyl]alanine can theoretically be protected in the same way as those of ornithine or lysine (see also: M. Bodanszky, "Principles of Peptide Synthesis", Springer-Verlag 1984, pages 122–126), whilst particular attention should be paid to using so-called orthogonal combinations of protecting groups in order to protect the α-amino and side chain-amino groups, for example:

| Protection of the N (side chain) | $N^\alpha$-protection |
|---|---|
| p-toluenesulphonyl | phenylmethoxycarbonyl |
| | tert.butyloxycarbonyl |
| phenylmethoxycarbonyl | (4-methoxyphenyl)methoxycarbonyl |
| | tert.butoxycarbonyl |
| | adamantyloxycarbonyl |
| | biphenylylisopropyloxycarbonyl |
| | isonicotinoyloxycarbonyl |
| | o-nitrophenylsulphenyl |
| | formyl |
| tert.butoxycarbonyl | phenylmethoxycarbonyl |
| | p-toluenesulphonyl |
| | o-nitrophenylsulphenyl |
| | biphenylylisopropyloxycarbonyl |
| | 9-fluorenylmethoxycarbonyl |
| acetyl, trifluoroacetyl, formyl, (2-chlorophenyl)methoxycarbonyl, | tert.butyloxycarbonyl |

-continued

| Protection of the N (side chain) | $N^{\alpha}$-protection |
|---|---|
| (4-chloro-phenyl)methoxycarbonyl, 4-(nitrophenyl)methoxycarbonyl, phthaloyl | |

Instead of protecting amino groups in the group $R^2$, it is also possible to use amino acids or derivatives thereof which carry precursor functions and which are substituted in the side chain particularly by nitro or cyano, e.g. 6-cyano-norleucine, 2-(5-nitro-pentyl)-glycine or 3-(3-cyanophenyl)-alanine.

The basic functions present in the side chain of non-commercially available α-amino acids, characterised for example by aminoiminomethyl groups, may be protected in the same way as is already known for the side chain protection of arginine and its derivatives (see also: M. Bodanszky, "Peptide Chemistry", springer-Verlag, 1988, pages 94–97); groups which are particularly suitable as protecting groups for the aminoiminomethyl group are the p-toluenesulphonyl-, mesitylenesulphonyl(Mts), methoxytrimethylphenylsulphonyl(Mtr), 2,2,5,7,8-pentamethylchromane-6-sulphonyl(Pmc), pentachlorophenoxycarbonyl and nitro protecting groups.

The actual coupling is carried out using known methods from peptide chemistry (see for example Houben-Weyl, "Methoden der Organischen Chemie", Vol. 15/2). It is preferable to use carbodiimides, such as dicyclohexylcarbodiimide (DCC), diisopropylcarbodiimide (DIC) or ethyl-(3-dimethylaminopropyl)-carbodiimide, O-(1H-benzotriazol-1-yl)-N,N-N',N'-tetramethyluronium-hexafluorophosphate (HBTU) or -tetrafluoroborate (TBTU) or 1H-benzotriazol-1-yl-oxy-tris-(dimethylamino)-phosphoniumhexafluorophosphate (BOP). By the addition of 1-hydroxybenzotriazole (HOBt) or 3-hydroxy-4-oxo-3,4-dihydro-1,2,3-benzotriazine (HOObt) it is also possible to suppress racemisation if desired or to increase the reaction rate. The couplings are normally carried out with equimolar amounts of the coupling components and the coupling reagent in solvents such as dichloromethane, tetrahydrofuran, acetonitrile, dimethylformamide (DMF), dimethylacetamide (DMA), N-methyl-pyrrolidone (NMP) or mixtures thereof at temperatures between −30° and +30° C., preferably between −20° and +20° C. If necessary N-ethyl-diisopropylamine (DIEA) (Hünig base) is preferred as an additional auxiliary base.

Another coupling method used for synthesising compounds of general formula I is the so-called "anhydride method" (see also: M. Bodanszky, "Peptide Chemistry", Springer-Verlag 1988, pages 58–59; M. Bodanszky, "Principles of Peptide Synthesis", Springer-Verlag 1984, pages 21–27). Preferably the "mixed anhydride method" is used in the alternative proposed by Vaughan (J. R. Vaughan Jr., J. Amer. Chem. Soc. 73, 3547 (1951)), in which the mixed anhydride is obtained from the optionally $N^2$-protected α-amino acid which is to be coupled and the monoisobutylcarbonate, using isobutylcarbonate in the presence of bases such as 4-methylmorpholine or 4-ethylmorpholine. The preparation of this mixed anhydride and coupling with amines are carried out in the one-pot method, using the above-mentioned solvents and at temperatures between −20° and +20° C., preferably between 0° and +20° C.

Any protecting groups present in the α-amino acid side chain are finally cleaved with suitable reagents known from the literature, after the synthesis of the N- and C-terminally substituted amino acid derivative, specifically arylsulphonyl and hetarylsulphonyl protecting groups are preferably cleaved by acidolytic methods, i.e. by the action of strong acids, preferably trifluoroacetic acid, and nitro and arylmethoxycarbonyl protecting groups are cleaved by hydrogenolysis, e.g. with water in the presence of palladium black and using glacial acetic acid as solvent. If the substrate contains functions which are sensitive to hydrogenolysis, e.g. halogen atoms such as chlorine, bromine or iodine, or a phenylmethanol or heteroarylmethanol function or some other benzylheteroatom bond, particularly a benzyl-oxygen bond, the nitro group may also be cleaved non-hydrogenolytically, e.g. with zinc/2N trifluoroacetic acid (see also: A. Turan, A. Patthy and S. Bajusz, Acta Chim. Acad. Sci. Hung, Tom. 85 (3): 327–332 [1975]; C.A. 83, 206526h [1975]), with tin(II)-chloride in 60% aqueous formic acid (see also: SUNSTAR KK, JA-A-3271-299), with zinc in the presence of acetic acid (see also: A. Malabarba, P. Ferrari, G. Cietto, R. Pallanza and M. Berti, J. Antibiot. 42 (12): 1800–1816 (1989)) or excess aqueous 20% titanium(III)-chloride in aqueous methanol and in the presence of aqueous ammonium acetate buffer at 24° C. (see also: R. M. Freidinger, R. Hirschmann and D. F. Veber, J. Org. Chem. 43 (25), 4800–4803 [1978]).

Any precursor functions present in the side chain of the amino acid may also subsequently be converted into the desired amino functions by hydrogenolysis; nitroalkyl groups yield aminoalkyl groups under conditions which are familiar to chemists, whilst the cyano group changes into the aminomethyl group.

Nitrile functions may instead be selectively reduced with complex hydrides in the presence of other reactive groups, particularly amide groups (see also: J. Seyden-Penne, "Reductions by the Alumino- and Borohydrides in Organic Synthesis", VCH Publishers Inc., 1991, page 132 et seq.), e.g. with sodium borohydride in methanol and in the presence of cobalt(II)-chloride, with sodium borohydride in tetrahydrofuran in the presence of trifluoroacetic acid or with tetrakis-(n-butyl)-ammonium borohydride in dichloromethane; it is also possible to reduce aliphatic nitro functions to the primary amino function using sodium borohydride in the presence of tin(II)-chloride or copper(II)-acetylacetonate, without attacking the carboxamide groups present in compounds of formula I (see also: J. Seyden-Penne, ibid. page 137 et seq.).

The following processes are particularly suitable for preparing the compounds of general formula I according to the invention:

a) In order to prepare compounds of general formula I wherein T has the meanings given hereinbefore with the exception of a hydrogen atom:

Coupling of compounds of general formula II $$T^A—Z—X \quad (II)$$

(wherein

Z is as hereinbefore defined, $T^A$ has the meanings given for T with the exception of a hydrogen atom and X denotes a hydroxy group, a halogen atom such as chlorine, bromine or iodine, a $C_{1-10}$-alkylsulphonyloxy group, or a phenylsulphonyloxy or naphthylsulphonyloxy group optionally mono-, di- or tri-substituted by chlorine or bromine atoms or by methyl or nitro groups, wherein the substituents may be identical or different) with α-amino acid derivatives of general formula III

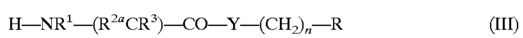

$$H—NR^1—(R^{2a}CR^3)—CO—Y—(CH_2)_n—R \quad (III)$$

wherein n, R, $R^1$, $R^3$ and Y are as hereinbefore defined and $R^{2a}$ has the meanings given for $R^2$ hereinbefore or denotes a group $R^2$ substituted by the above-mentioned protecting groups, or a precursor group for the group $R^2$, e.g. a nitroalkyl or cyanoalkyl group, and if necessary subsequent cleaving of protecting groups or modification of precursor functions according to the methods described hereinbefore.

If, in general formula II, X denotes a hydroxy group, then the coupling methods discussed in detail hereinbefore and known from peptide chemistry are used, particularly using the above-mentioned coupling reagents DCC, DIC, HBTU, TBTU or BOP, or the mixed anhydride method is used.

If, in general formula II, X is a halogen atom or an alkyl or arylsulphonyloxy group, the reaction is carried out under Schotten-Baumann or Einhorn conditions, i.e. the components are reacted in the presence of at least one equivalent of an auxiliary base at temperatures between −50° C. and +120° C., preferably −10° C. and +30° C., and optionally in the presence of solvents. Preferred auxiliary bases are alkali and alkaline earth metal hydroxides, e.g. sodium hydroxide, potassium hydroxide or barium hydroxide, alkali metal carbonates such as sodium carbonate, potassium carbonate or cesium carbonate, alkali metal acetates, e.g. sodium or potassium acetate, and tertiary amines, e.g. pyridine, 2,4,6-trimethylpyridine, quinoline, triethylamine, N-ethyl-diisopropylamine, N-ethyl-dicyclohexylamine, 1,4-diazabicyclo[2,2,2]octane or 1,8-diazabicyclo[5,4,0]-undec-7-ene, whilst the solvents used may be for example dichloromethane, tetrahydrofuran, 1,4-dioxane, acetonitrile, dimethylformamide, dimethylacetamide, N-methyl-pyrrolidone or mixtures thereof; where the auxiliary bases used are alkali or alkaline earth metal hydroxides, alkali metal carbonates or acetates, water may also be added to the reaction mixture as a co-solvent.

b) In order to prepare compounds of general formula I wherein T has the meanings given hereinbefore with the exception of a hydrogen atom:

Coupling of compounds of general formula IV $$T^A—Z—NR^1—(R^{2a}CR^3)—COOH \quad (IV)$$

wherein $R^1$, $R^{2a}$, $R^3$, $T^A$ and Z are as hereinbefore defined, with compounds of general formula V $$H—Y(CH_2)_n—R \quad (V)$$

wherein n, R and Y has the meanings given hereinbefore and, if necessary, subsequent cleaving of protecting groups or modification of precursor functions using the methods described above.

The coupling is carried out using the methods known from peptide chemistry and described hereinbefore, more particularly using DCC, DIC, HBTU, TBTU or BOP as reagents or using the mixed anhydride method.

If the starting compound IV used is enantiomerically pure, provided that Z denotes a carbonyl group which is not flanked by an oxygen atom, the coupling step must be expected to involve partial racemisation if triethylamine is used as the auxiliary base, and if dimethylformamide, dimethylacetamide or N-methylpyrrolidone is used as solvent quantitative racemisation may occur.

c) In order to prepare compounds of general formula I wherein Y denotes an oxygen atom:

Transesterification of amino acid esters of general formula VI, $$T—Z—NR^1—(R^2CR^3)—CO—OR^5 \quad (VI)$$

wherein $R^1$ to $R^3$, T and Z are as hereinbefore defined and $R^5$ denotes a $C_{1-4}$-alkyl group, with an alcohol of general formula VII $$HO—(CH_2)_n—R \quad (VII)$$

wherein

R and n are as hereinbefore defined.

The transesterification may be catalysed by acid or alkali (see also: J. March, "Advanced Organic Chemistry", John Wiley & Sons, Third Edition, 1985, page 351–352). Preferred alkaline catalysts are the corresponding alkali metal alkoxides which can easily be obtained from the alcohols of general formula VII or $R^5OH$, e.g. lithium, sodium or potassium alkoxides; examples of acid catalysts include, as well as anhydrous hydrochloric acid, especially sulphuric acid, p-toluenesulphonic acid, naphthalen-1- or -2-sulphonic acid or acid ion exchanger freshly charged with hydrogen ions, e.g. Wofatit KPS z.A. The equilibrium between the two esters is shifted in the desired direction in this process by distilling off the more volatile alcohol $R^5OH$.

With alkaline catalysis, the end product of general formula I is obtained as a racemate even if the starting compound VI is used in enantiomerically pure form.

d) In order to prepare compounds of general formula I wherein T has the meanings given for T hereinbefore with the exception of a hydrogen atom and $R^2$ denotes a straight-chained $C_{1-5}$-alkyl group or a phenyl or phenylmethyl group, wherein the alkyl group in the ω-position and the above-mentioned aromatic groups are each substituted by an $R^8R^9N—C(=NR^7)—NR^6—$ group and $R^6$ to $R^9$, which may be identical or different, denote hydrogen atoms or $C_{1-3}$-alkyl groups or $R^7$ and $R^8$ together denote a $C_{2-4}$-n-alkylene group:

Reacting compounds of general formula VIII

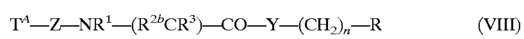

$$T^A—Z—NR^1—(R^{2b}CR^3)—CO—Y—(CH_2)_n—R \quad (VIII)$$

(wherein n, R, $R^1$, $R^3$, $T^A$, Y and Z are as hereinbefore defined and $R^{2b}$ denotes a straight-chained $C_{1-5}$-alkyl group or a phenyl or phenylmethyl group, wherein the alkyl group in the ω-position and the above-mentioned aromatic groups are each substituted by an $R^6NH—$ group and $R^6$ denotes a hydrogen atom or a $C_{1-3}$-alkyl group)

with carbonic acid derivatives of general formula IX $$X^1—(C=NR^7)—(R^8NR^9) \quad (IX)$$

wherein $R^7$, $R^8$ and $R^9$, which may be identical or different, denote hydrogen atoms or $C_{1-3}$-alkyl groups and $R^7$ and $R^8$ together may also denote a $C_{2-4}$-n-alkylene group and $X^1$ denotes a leaving group such as an alkoxy, alkylthio, alkylsulphinyl or alkylsulphonyl group each having 1 to 10 carbon atoms in the alkyl moiety, e.g. a methoxy, ethoxy, methylthio, ethylthio, methylsulphinyl, ethylsulphinyl, propylsulphinyl, isopropylsulphinyl, methylsulphonyl or ethylsulphonyl group, a chlorine atom, an $SO_2H$, $SO_3H$ or $OPOCl_2$ group or a group of general formula X

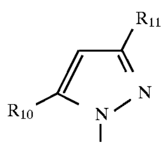

(x)

wherein $R^{10}$ and $R^{11}$, which may be identical or different, denote hydrogen atoms or $C_{1-3}$-alkyl groups.

The reactions are carried out using methods known from the literature (see G. B. L. Smith, J. Amer. Chem. Soc. 51: 476 [1929]; B. Rathke, Chem. Ber. 17: 297 [1884]; R. Phillips and H. T. Clarke, J. Amer. Chem. Soc. 45: 1755 [1923]; S. J. Angyal and W. K. Warburton, J. Amer. Chem. Soc. 73: 2492 [1951]; H. Lecher and F. Graf, Chem. Ber. 56: 1326 [1923]; J. Wityak, S. J. Gould, S. J. Hein and D. A. Keszler, J. Org. Chem. 52: 2179 [1987]; T. Teraji, Y. Nakai, G. J. Durant, WO-A-81/00109, Chem. Abstr. 94, 192336z [1981]; C. A. Maryanoff, R. C. Stanzione, J. N. Plampin and J. E. Mills, J. Org. Chem. 51: 1882–1884 [1986]; A. E. Miller and J. J. Bischoff, Synthesis 1986, 777; R. A. B. Bannard, A. A. Casselman, W. F. Cockburn and G. M. Brown, Can. J. Chem. 36: 1541 [1958]; Aktieselskabet Grea, Copenhagen, DE-C2-28 26 452; K. Kim. Y-T. Lin and H. S. Mosher, Tetrah. Letters, 29: 3183–3186 [1988]; H. B. Arzeno et al., Synth. Commun. 20: 3433–3437 [1990]; H. Bredereck and K. Bredereck, Chem. Ber. 94: 2278 [1961]; H. Eilingsfeld, G. Neubauer, M. Seefelder and H. Weidinger, Chem. Ber. 97: 1232 [1964]; P. Pruszynski, Can. J. Chem. 65: 626 [1987]; D. F. Gavin, W. J. Schnabel, E. Kober and M. A. Robinson, J. Org. Chem. 32: 2511 [1967]; N. K. Hart, S. R. Johns, J. A. Lamberton 32: 2511 [1967]; N. K. Hart, S. R. Johns, J. A. Lamberton and R. I. Willing, Aust. J. Chem. 23, 1679 [1970]; CIBA Ltd., Belgian Patent 655 403; Chem. Abstr. 64, 17481 [1966]; R. A. B. Bannard, A. A. Casselman, W. F. Cockburn and G. M. Brown, Can. J. Chem. 36: 1541 [1958]; J. P. Greenstein, J. Org. Chem. 2: 480 [1937]; F. L. Scott and J. Reilly, J. Amer. Chem. Soc. 74: 4562 [1952]; W. R. Roush and A. E. Walts, J. Amer. Chem. Soc. 106: 721 [1984]; M. S. Bernatowicz, Y. Wu and G. R. Matsueda, J. Org. Chem. 57: 2497–2502 [1992], and H. Tsunematsu, T.Imamura and S. Makisumi, J. Biochem. 94: 123–128 [1983]) at temperatures between 0° C. and +100° C., preferably +40° C. and +80° C., and using inert solvents, such as dichloromethane, tetrahydrofuran, 1,4-dioxane, acetonitrile, dimethylformamide, dimethylacetamide, N-methyl-pyrrolidone or mixtures thereof and generally in the presence of auxiliary bases, particularly alkali metal carbonates such as sodium or potassium carbonate, or tertiary amines, preferably N-ethyl-diisopropylamine or triethylamine.

e) In order to prepare compounds of general formula I wherein T has the meanings given for T hereinbefore with the exception of the hydrogen atom and $R^2$ denotes a straight-chained $C_{1-5}$-alkyl group or a phenyl or phenylmethyl group, whilst the alkyl group in the ω-position and the above-mentioned aromatic groups are each be substituted by an $R^{8a}R^9N—C(═NH)—NR^6—$ group and $R^6$, $R^{8a}$and $R^9$, which may be identical or different, denote hydrogen atoms or $C_{1-3}$-alkyl groups:

Reacting compounds of general formula VIII $$T^A—Z—NR^1—(R^{2b}CR^3)—CO—Y—(CH_2)_n—R \quad \text{(VIII)}$$

wherein n, R, $R^1$, $R^3$, $T^A$, Y and Z are as hereinbefore defined and $R^{2b}$ denotes a straight-chained $C_{1-5}$-alkyl group or a phenyl or phenylmethyl group, whilst the alkyl group in the ω-position and the above-mentioned aromatic groups are each substituted by an $R^6NH—$ group and $R^6$ denotes a hydrogen atom or a $C_{1-3}$-alkyl group, with cyanamides of general formula XI $$R^{8a}R^9N—CN \quad \text{(XI)}$$

wherein $R^{8a}$and $R^9$, which may be identical or different, each denote hydrogen atoms or $C_{1-3}$-alkyl groups.

The reactions are carried out at temperatures between ambient temperature and the boiling temperature of the solvent or solvent mixture used. Preferred solvents are alcohols such as methanol, ethanol or n-propanol, ethers such as dioxane or esters such as ethyl acetate. Water may be used as an additional cosolvent. Although the reaction will work without the addition of acids, it is preferable to carry out the reaction in the presence of organic acids such as acetic acid and particularly in the presence of strong acids such as methanesulphonic acid, sulphuric acid, hydrogen bromide, hydrogen chloride or hydrochloric acid. The compounds of general formula I then occur in the form of the corresponding salts (see also: Houben-Weyl, "Methoden der Organischen Chemie", 4th Edition, Georg-Thieme-Verlag, Stuttgart, from 1952, Volume VIII, pages 98 and 180; Ullmanns Encyclopädie der Technischen Chemie, Verlag Chemie, Weinheim, 1972–1977, Volume VIII, page 328; E. H. Sheers, Kirk-Othmer Encycl. Chem. Technol., 2nd ed., 10: 734 [1966]; A. Kämpf, Chem. Ber. 37: 1681 [1904]; and R. A. Corral, O. O. Orazi and M. F. de Petruccelli, Chem. Commun. 1970, 556).

f) In order to prepare compounds of general formula I wherein T has the meanings given for T hereinbefore with the exception of the hydrogen atom and $R^2$ denotes a straight-chained $C_{1-5}$-alkyl group or a phenyl or phenylmethyl group, wherein the alkyl group in the ω-position and the above-mentioned aromatic groups are each substituted by an $HR^8N—C(═NR^7)—NR^6—$ group and $R^6$, $R^7$ and $R^8$, which may be identical or different, denote hydrogen atoms or $C_{1-3}$-alkyl groups:

Reacting compounds of general formula VIII $$T^A—Z—NR^1—(R^{2b}CR^3)—CO—Y—(CH_2)_n—R \quad \text{(VIII)}$$

wherein n, R, $R^1$, $R^3$, $T^A$, Y and Z are as hereinbefore defined and $R^{2a}$ denotes a straight-chained $C_{1-5}$-alkyl group or a phenyl or phenylmethyl group, wherein the alkyl group in the ω-position and the above-mentioned aromatics are each substituted by an $R^6NH—$ group and $R^6$ denotes a hydrogen atom or a $C_{1-3}$-alkyl group, with carbodiimides of general formula XII $$R^7—N═C═N—R^8 \quad \text{(XII)}$$

wherein $R^7$ and $R^8$ are as hereinbefore defined.

The reactions are carried out by methods known from the literature (see S. J. C. Snedker, J. Soc. Chem. Ind. (London) 45, 353T [1927]; and F. Kurzer and K. Dourgahi-Zadeh, Chem. Rev. 67: 119 [1967]). If the starting compounds of general formula VIII are used in the form of their salts, the guanidinium salts of general formula I are also obtained in the form of the corresponding salts.

g) In order to prepare compounds of general formula I wherein T has the meanings given for T hereinbefore with the exception of the hydrogen atom and $R^2$ denotes a straight-chained $C_{1-5}$-alkyl group or a phenyl or phenylmethyl group, wherein the alkyl group in the ω-position and the above-mentioned aromatic groups are each substituted by an $R^{8a}R^9N—C(=NCN)—NR^6—$ group and $R^6$, $R^{8a}$ and $R^9$, which may be identical or different, denote hydrogen atoms or $C_{1-3}$alkyl groups:

Reacting compounds of general formula VIII

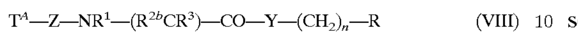

wherein

N, R, $R^1$, $R^3$, $T^A$, Y and Z are as hereinbefore defined and $R^{2b}$ denotes a straight-chained $C_{1-5}$-alkyl group or a phenyl or phenylmethyl group, wherein the alkyl group in the ω-position and the above-mentioned aromatic groups are each substituted by an $R^6NH—$ group and $R^6$ denotes a hydrogen atom or a $C_{1-3}$-allyl group, with cyano-isothioureas of general formula XIII

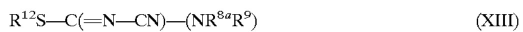

wherein $R^{8a}$ and $R^9$ are as hereinbefore defined and $R^{12}$ denotes a $C_{1-5}$-alkyl group, e.g. a methyl or ethyl group.

The reactions are carried out using methods known from the literature (see E. L. May, J. Org. Chem. 12: 437 [1947], and F. H. S. Curd, J. A. Hendry, T. S. Kenny, A. G. Murray and F. L. Rose, J. Chem. Soc. 1948, 1630) at temperatures between +20° C. and 140° C., optionally using a pressure autoclave, and preferably at the boiling point of the solvent or mixture of solvents used. Preferred solvents are alcohols, e.g. methanol, ethanol, n-butanol or isobutanol, and ethers, e.g. dioxane.

h) In order to prepare compounds of general formula I, wherein T has the meanings given for T hereinbefore with the exception of the hydrogen atom and $R^2$ denotes a straight-chained $C_{1-5}$-alkyl group or a phenyl or phenylmethyl group, wherein the alkyl group in the ω-position and the above-mentioned aromatic groups are each substituted by an $R^{8a}R^9N—C(=NCN)—NR^6—$ group and $R^6$, $R^7$, $R^{8a}$ and $R^9$, which may be identical or different, denote hydrogen atoms or $C_{1-3}$-alkyl groups:

Reacting compounds of general formula VIII

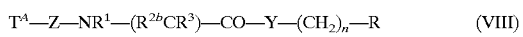

wherein n, R, $R^1$, $R^3$, $T^A$, Y and Z are as hereinbefore defined and $R^{2b}$ denotes a straight-chained $C_{1-5}$-alkyl group or a phenyl or phenylmethyl group, wherein the alkyl group in the ω-position and the above-mentioned aromatic groups are each substituted by an $R^6NH—$ group and $R^6$ denotes a hydrogen atom or a $C_{1-3}$-alkyl group, with equimolar quantities of cyanoiminodiphenylcarbonate and subsequently with an amine of general formula XIV $H—NR^{8a}R^9$ (XIV)

wherein $R^{8a}$ and $R^9$ are as hereinbefore defined.

The reaction is carried out according to methods known from the literature, the reaction proceeding via intermediate products of general formula VIII wherein $R^2$ denotes a straight-chained $C_{1-5}$-alkyl group or a phenyl or phenylmethyl group, wherein the alkyl group in the ω-position and the above-mentioned aromatic groups are each substituted by a phenoxy-$C(=N—CN)—NR^6—$ group, wherein $R^6$ denotes a hydrogen atom or a $C_{1-3}$-alkyl group, which may in theory be isolated (see also: R. L. Webb and C. S. Labaw, J. Het. Chem. 19: 1205 [1982]; R. L. Webb, D. S. Eggleston, C. S. Labaw, J. J. Lewis and K. Wert, J. Het. Chem. 24, 275 [1987]; P. Theobald, J. Porter, C. Rivier, A. Corrigan, W. Hook, R. Siraganian, M. Perrin, W. Vale and J. Rivier, J. Med. Chem. 34, 2395–2402 [1991]; and J. Hirschfeld, A. Buschauer, S. Elz. W. Schunack, M. Ruat, E. Traiffort and J. -C. Schwartz, J. Med. Chem. 35, 2231–2238 [1992]), in solvents such as dichloromethane, tetrahydrofuran, 1,4-dioxane, acetonitrile, but preferably in dimethylformamide, dimethylacetamide or N-methylpyrrolidone, and at temperatures between 0° C. and 60° C., preferably at ambient temperature.

i) In order to prepare compounds of general formula I wherein T has the meanings given for T hereinbefore with the exception of the hydrogen atom and $R^2$ denotes a straight-chained $C_{1-5}$-alkyl group or a phenyl or phenylmethyl group, wherein the alkyl group in the ω-position and the above-mentioned aromatic groups are each substituted by an $H_2N—C(=NCN)—NR^6—$ group and $R^6$ denotes a hydrogen atom or a $C_{1-3}$-alkyl group:

Reacting compounds of general formula VIII

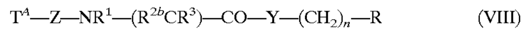

wherein n, R, $R^1$, $R^3$, $T^A$, Y and Z are as hereinbefore defined and $R^{2b}$ denotes a straight-chained $C_{1-5}$-alkyl group or a phenyl or phenylmethyl group, wherein the alkyl group in the ω-position and the above-mentioned aromatic groups are each substituted by an $R^6NH—$ group and $R^6$ denotes a hydrogen atom or a $C_{1-3}$-alkyl group, with alkali metal dicyanamides.

The reaction is carried out using methods known from the literature, preferably with sodium, lithium or potassium dicyanamide (see also: R. W. Turner, Synthesis 1975, 332; and F. H. S. Curd, J. A. Hendry, T. S. Kenny, A. G. Murray and F. L. Rose, J. Chem. Soc. 1948, 1630–1636) in alcohols, e.g. in ethanol, n-butanol, n-pentanol or isoamyl alcohol, and at elevated temperatures between +50° C. and +120° C. and in the presence of inorganic acids, e.g. hydrochloric or hydrobromic acid.

j) In order to prepare compounds of general formula I wherein T has the meanings given for T hereinbefore with the exception of the hydrogen atom and $R^2$ denotes a straight-chained $C_{1-5}$-alkyl group or a phenyl or phenylmethyl group, wherein the alkyl group in the ω-position and the above-mentioned aromatic groups are each substituted by an $R^{8a}R^9N—C(=NH)—$ group and $R^{8a}$ and $R^9$, which may be identical or different, denote hydrogen atoms or $C_{1-3}$-alkyl groups:

Reacting compounds of general formula XV

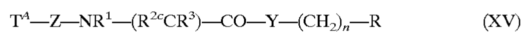

wherein n, R, $R^1$, $R^3$, $T^A$, Y and Z are as hereinbefore defined and $R^{2c}$ denotes a straight-chained $C_{1-5}$-alkyl group or a phenyl or phenylmethyl group, wherein the alkyl group in the ω-position and the above-mentioned aromatic groups are each substituted by a cyano group, with alcohols of general formula XVI, $R^5—OH$ (XVI)

wherein $R^5$ is as hereinbefore defined, and subsequent treatment with amines of general formula XIV $$H—NR^{8a}R^9 \quad (XIV)$$

wherein $R^{8a}$ and $R^9$ are as hereinbefore defined.

The first stage of the reaction is preferably carried out in an alcohol of general formula XVI as solvent, e.g. in methanol or ethanol, in the presence of dry hydrogen chloride and in the absence of water, at temperatures between −30° C. and +40° C., preferably at a temperature between 0° C. to +20° C., and the iminoesters which are obtained in the form of their hydrochlorides in this acid variant are generally not purified but are converted directly in the second step, by treatment with an amine of general formula XIV, at temperatures between −20° C. and the boiling temperature of the solvent, into the desired compounds of general formula I (see also: A. Pinner and F. Klein, Chem. Ber. 10: 1889 [1877]; A. Pinner, "Die Iminoäther und ihre Derivate", Oppenheim, Berlin, 1892; R. Roger and D. G. Neilson, Chem. Rev. 61: 179 [1961]; G. Wagner and J. Wunderlich, Pharmazie 31: 766 [1976]; G. Wagner, B. Voigt, D. Danicke and T. Liebermann, Pharmazie 31: 528 [1976]; R. R. Tidwell, L. L. Fox and J. D. Geratz, Biochim. Biophys. Acta 445: 729 [1976]; and T. Pantev and R. Georgieva, Farmatsiya (Sofia) 29: 1 [1979]). The iminoesters are also obtained in the form of their free bases during the base-catalysed addition of alcohols of general formula XVI to the nitriles of formula XV. Preferably, the alkali metal alkoxides corresponding to the alcohols used serve as the basic catalysts; particularly preferred is a combination of sodium methoxide and methanol (see also: C. Soula, A. Marsura and C. Luu-Duc, J. Pharm. Belg. 42: 293 [1987); and W. J. Haggerty and W. J. Rost, J. Pharm. Sci. 58: 50 [1969]).

In the acid variant of the synthesis of amidines of general formula I, instead of dry hydrogen chloride other anhydrous acid agents, such as hydrogen bromide, p-toluenesulphonic acid or sulphuric acid may be used in the first step. In the second step, the reaction of the resulting iminoesters with the amines of general formula XVI, instead of the free amines XIV the salts thereof with weak organic acids, e.g. the corresponding ammonium carbonates or acetates, are frequently used.

In the alkaline variant, as a rule the amines of formula XIV are used in the second step in the form of their organic acid salts, e.g. as the hydrochlorides; glacial acetic acid may also be used to advantage as the solvent in the second step.

k) In order to prepare compounds of general formula I wherein T has the meanings given for T hereinbefore with the exception of a hydrogen atom and $R^2$ denotes a straight-chained $C_{1-5}$-alkyl group or a phenyl or phenylmethyl group, wherein the alkyl group in the ω-position and the above-mentioned aromatic groups are each substituted by an $H_2N—C(=NOH)—$ group:

Addition of hydroxylamine to nitriles of general formula XV

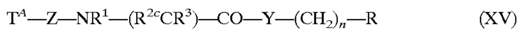

wherein n, R, $R^1$, $R^3$, $T^A$, Y and Z are as hereinbefore defined and $R^{2c}$ denotes a straight-chained $C_{1-5}$-alkyl group or a phenyl or phenylmethyl group, wherein the alkyl group in the ω-position and the above-mentioned aromatic groups are each substituted by a cyano group.

The reaction is carried out in suitable solvents, e.g. in dioxane, dimethylformamide, dimethylacetamide, N-methyl-pyrrolidone, 1,3-dimethyl-2-imidazolidinone, methanol, n-propanol, but preferably in ethanol, using small amounts of water as co-solvent and at temperatures between +30° and +100° C., preferably +60° C. to +80° C. However, it is particularly advantageous during the reaction to liberate the hydroxylamine in situ from its salts, e.g. its hydrochloride or sulphate, by means of weak bases, preferably alkali metal carbonates and most preferably sodium carbonate.

1) In order to prepare compounds of general formula I wherein T has the meanings given for T hereinbefore with the exception of the hydrogen atom and $R^2$ denotes a straight-chained $C_{1-5}$-alkyl group or a phenyl or phenylmethyl group, wherein the alkyl group in the ω-position and the above-mentioned aromatic groups are each substituted by an amidino group:

Hydrogenolysis of a compound of general formula XVII $$T^A—Z—NR^1—(R^{2d}CR^3)—CO—Y—(CH_2)_n—R \quad (XVII)$$

wherein n, R, $R^1$, $R^3$, $T^A$, Y and Z are as hereinbefore defined and $R^{2d}$ denotes a straight-chained $C_{1-5}$-alkyl group or a phenyl or phenylmethyl group, wherein the alkyl group in the ω-position and the above-mentioned aromatic groups are each substituted by an $H_2N—C(=NOH)—$ group.

The hydrogenolysis is carried out using palladium or nickel catalysts, e.g. palladium/animal charcoal, palladium black, palladium/barium sulphate or Raney nickel, in suitable solvents such as ethanol, methanol, glacial acetic acid, 1,4-dioxane or ethyl acetate, at temperatures between 0° and +100° C., preferably +50° C. and +70° C., under a hydrogen pressure of 0.5 to 200 bar, preferably 1 to 5 bar.

m) In order to prepare compounds of general formula I wherein T has the meanings given for T hereinbefore with the exception of the hydrogen atom and $R^2$ denotes a straight-chained $C_{1-5}$-alkyl group or a phenyl or phenylmethyl group, wherein the alkyl group in the ω-position and the above-mentioned aromatic groups are each substituted by an $R^{8a}R^9N—C(=NH)—$ group and $R^{8a}$ and $R^9$, which may be identical or different, denote hydrogen atoms or $C_{1-3}$-alkyl groups:

Converting nitrites of general formula XV $$T^A—Z—NR^1—(R^{2c}CR^3)—CO—Y—(CH_2)_n—R \quad (XV)$$

wherein n, R, $R^1$, $R^3$, $T^A$, Y and Z are as hereinbefore defined and $R^{2c}$ denotes a straight-chained $C_{1-5}$-alkyl group or a phenyl or phenylmethyl group, wherein the alkyl group in the ω-position and the above-mentioned aromatic groups are each substituted by a cyano group, into thioamides of general formula XVIII

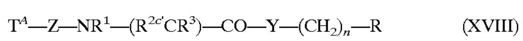

wherein n, R, $R^1$, $R^3$, $T^A$, Y and Z are as hereinbefore defined and $R^{2c'}$ denotes a straight-chained $C_{1-5}$alkyl group or a phenyl or phenylmethyl group, wherein the alkyl group in the ω-position and the above-mentioned aromatic groups are each substituted by an aminothiocarbonyl group, and subsequently alkylating with compounds of general formula XIX $$R^5—X^2 \quad (XIX)$$

wherein $R^5$ is as hereinbefore defined and $X^2$ denotes a leaving group such as a halogen atom, an alkylsulphonyloxy, alkoxysulphonyloxy or arylsulphonyloxy group, e.g. a chlorine, bromine or iodine atom, a methanesulphonyloxy, methoxysulphonyloxy or toluenesulphonyloxy group, or with a trialkyloxoniumtetrafluoroborate of general formula XX $$(R^5)_3OBF_4 \quad \text{(XX)}$$

wherein $R^5$ is as hereinbefore defined, and with subsequent aminolysis with compounds of general formula XIV $$H—NR^{8a}R^9 \quad \text{(XIV)}$$

wherein $R^{8a}$ and $R^9$ are as hereinbefore defined.

The reactions are carried out using methods known from the literature (see also: P. Chabrier and S. H. Renard, C. R. Acad. Sci. Paris 230: 1673 [1950]; Y. Nii, K. Okano, S. Kobayashi and M. Ohto, Tetrah. Lett. 1979, 2517; and Hoffmann-La Roche, EP-A-0381033).

In order to prepare the thiocarboxylic acid amides of general formula XVIII from the nitriles of general formula XV, it is preferable to carry out the reaction with hydrogen sulphide in pyridine and in the presence of gaseous ammonia or triethylamine, optionally in a pressurised autoclave. Suitable reaction temperatures range from 0° C. to +100° C., preferably from +50° to +60° C. (see also: Houben-Weyl, "Methoden der Organischen Chemie", 4th Edition, Georg-Thieme Verlag, Stuttgart, from 1952, Volume IX, page 762). It is also appropriate to carry out the reaction with thioacetamide in dimethylformamide saturated with dry hydrogen chloride at temperatures between 80° and 100° C. (see also: E. C. Taylor and J. A. Zoltewicz, J. Amer. Chem. Soc. 82: 2656 [1960]).

In order to prepare the thioimidic acid esters or the salts thereof from the thioamides of general formula XVIII it is preferred to carry out the reaction with methyliodide. Suitable solvents include ketones such as acetone or cyclohexanone and dipolar aprotic solvents of the type dimethylformamide, dimethylacetamide, N-methylpyrrolidone or 1,3-dimethyl-2-imidazolidinone type or mixtures thereof. Suitable reaction temperatures range from −20° C. to +100° C., preferably ambient temperature.

The aminolysis is carried out at temperatures between 0° C. and +100° C., preferably between +40° C. and +80° C., using inert solvents, e.g. dichloromethane, tetrahydrofuran, 1,4-dioxane, acetonitrile, dimethylformamide, dimethylacetamide, N-methyl-pyrrolidone or mixtures thereof, and generally in the presence of auxiliary bases, particularly alkali metal carbonates such as sodium or potassium carbonate, or tertiary amines, preferably N-ethyldiisopropylamine or triethylamine.

n) In order to prepare compounds of general formula I, wherein T has the meanings given for T hereinbefore with the exception of the hydrogen atom and $R^2$ denotes a straight-chained $C_{1-5}$-alkyl group or a phenyl or phenylmethyl group, wherein the alkyl group in the ω-position and the above-mentioned aromatic groups are each substituted by an NC—N═CH—$NR^6$— group and $R^6$ denotes a hydrogen atom or a $C_{1-3}$-alkyl group:

Reacting compounds of general formula VIII $$T^A—Z—NR^1—(R^{2b}CR^3)—CO—Y—(CH_2)_n—R \quad \text{(VIII)}$$

wherein n, R, $R^1$, $R^3$, $T^A$, Y and Z are as hereinbefore defined and $R^{2b}$ denotes a straight-chained $C_{1-5}$-alkyl group or a phenyl or phenylmethyl group, wherein the alkyl group in the ω-position and the above-mentioned aromatic groups are each substituted by an $HNR^6$— group and $R^6$ denotes a hydrogen atom or a $C_{1-3}$-alkyl group, with N-cyano-formimidic acid esters of general formula XXI $$R^{13}O—CH═N—CN \quad \text{(XXI)}$$

wherein $R^{13}$ denotes a $C_{1-10}$-alkyl group, but preferably a methyl or ethyl group.

The reaction is preferably carried out in the presence of polar solvents, e.g. acetone, ethanol, dimethylformamide, 1,4-dioxane, dimethylacetamide or N-methyl-pyrrolidone, and at temperatures between 0° C. and +50° C., but preferably at ambient temperature (see also: C. Bazzano, C. P. Vanoni, M. Mondoni, A. Gallazzi, E. Cereda and A. Donetti, Eur. J. Med. Chem. 21: 27–33 [1986]).

o) In order to prepare compounds of general formula I wherein T has the meanings given for T hereinbefore with the exception of the hydrogen atom and $R^2$ denotes a straight-chained $C_{1-5}$-alkyl group or a phenyl or phenylmethyl group, wherein the alkyl group in the ω-position and the above-mentioned aromatic groups are each substituted by an $R^{8a}R^9$N—CH═N— group and $R^{8a}$ and $R^9$, which may be identical or different, denote hydrogen atoms or $C_{1-3}$-alkyl groups:

Reacting compounds of general formula XXII $$T^A—Z—NR^1—(R^{2d'}CR^3)—CO—Y—(CH_2)_n—R \quad \text{(XXII)}$$

wherein n, R, $R^1$, $R^3$, $T^A$, Y and Z are as hereinbefore defined and $R^{2d'}$ denotes a straight-chained $C_{1-5}$-alkyl group or a phenyl or phenylmethyl group, wherein the alkyl group in the ω-position and the above-mentioned aromatic groups are each substituted by an NC—N═CH—NH— group, with amines of general formula XIV $$H—NR^{8a}R^9 \quad \text{(XIV)}$$

wherein $R^{8a}$ and $R^9$ are as hereinbefore defined.

The reaction is preferably carried out using polar solvents, e.g. alcohols such as methanol or ethanol, ethers such as tetrahydrofuran or 1,4-dioxane, or dimethylformamide, dimethylacetamide, N-methyl-pyrrolidone, dimethylsulphoxide, water or mixtures thereof, and at temperatures between 0° C. and +70° C., preferably at ambient temperature (see also: C. Bazzano, P. C. Vanoni, M. Mondani, A. Gallazzi, E. Cereda and A. Donetti Eur. J. Med. Chem. 21: 27–33 [1986]; and A. Donetti, E. Cereda, E. Bellora, A. Gallazzi, C. Bazzano, P. C. Vanoni, P. del Soldato, R. Micheletti, F. Pagani and A. Giachetti, J. Med. Chem. 27: 380 [1984]).

p) In order to prepare compounds of general formula I wherein T denotes a $T^1T^2$N— group:

Reacting isocyanates of general formula XXIII $$O═C═N—(R^{2a}CR^3)—CO—NR^4—(CH_2)_n—R \quad \text{(XXIII)}$$

wherein $R^{2a}$, $R^3$, $R^4$, R and n are as hereinbefore defined, with amines of general formula XXIV $$T^1T^2N—H \quad (XXIV)$$

wherein $T^1$ and $T^2$ are as hereinbefore defined.

The reaction is carried out at temperatures between 0° C. and 150° C., preferably +20° C. and 100° C., and optionally in the presence of anhydrous solvents, e.g. tetrahydrofuran, 1,4-dioxane, dimethylformamide, dimethylacetamide, N-methyl-2-pyrrolidone or 1,3-dimethyl-2-imidazolidinone.

q) In order to prepare compounds of general formula I wherein $R^2$ has the meanings given for $R^{2a}$ hereinbefore, T denotes a hydrogen atom and Z denotes a bond:

Cleaving the Boc group from compounds of general formula XXV $$(H_3C)_3C—O—CO—NR^1—(R^{2a}CR^3)—CO—Y—(CH_2)_n—R \quad (XXV)$$

wherein n, R, $R^1$, $R^{2a}$, $R^3$ and Y are as hereinbefore defined, with trifluoroacetic acid in dichloromethane (see also: M. Bodanszky, "Principles of Peptide Synthesis", Springer-Verlag, 1984, page 64) or the 9-fluorenylmethoxycarbonyl group from compounds of general formula XXVI $$R^{14}—O—CO—NR^1—(R^{2a}CR^3)—CO—Y—(CH_2)_n—R \quad (XXVI)$$

wherein n, R, $R^1$, $R^{2a}$, $R^3$ and Y are as hereinbefore defined and $R^{14}$ denotes a fluoren-9-yl-methyl group, with a 20 to 50% solution of piperidine in dimethylformamide (see also: M. Bodanszky, "Principles of Peptide Synthesis", Springer-Verlag, 1984, page 66).

r) In order to prepare compounds of general formula I wherein a hydrogen atom of an HN<, HN═ or $H_2N$— group present in the group $R^2$ is replaced by an alkoxycarbonyl group having a total of 2 to 7 carbon atoms or by a phenylalkoxycarbonyl group having 1 to 6 carbon atoms in the alkyl moiety or by a phenyloxycarbonyl, $R^{15}$—CO—O—($R^{16}CR^{17}$)—O—CO— or ($R^{18}$O)PO($OR^{19}$)— group:

Reacting a compound of general formula I $$T—Z—NR^1—(R^2CR^3)—CO—Y—(CH_2)_n—R \quad (I)$$

wherein

R, $R^1$ to $R^3$, T, Z, Y and n are as hereinbefore defined, with the proviso that $R^2$ must contain at least one free HN<, HN═ or $H_2N$— group, with a compound of general formula XXVII $$X^3—W \quad (XXVII)$$

wherein

W denotes an alkoxycarbonyl group having a total of 2 to 7 carbon atoms, a phenylalkoxycarbonyl group having 1 to 6 carbon atoms in the alkyl moiety, a phenyloxycarbonyl group, or an $R^{15}$—CO—O—($R^{16}CR^{17}$)—O—CO— or ($R^{18}$O)PO($OR^{19}$)— group, wherein $R^{15}$ to $R^{19}$ are as hereinbefore defined, and $X^3$ denotes a leaving group such as a halogen atom or an aryloxy group e.g. a chlorine or bromine atom or a p-nitrophenoxy group.

The reaction is conveniently carried out in a solvent such as tetrahydrofuran, methylene chloride, chloroform, ethyl acetate or dimethylformamide, appropriately in the presence of a base such as sodium carbonate, potassium carbonate or sodium hydroxide solution or in the presence of a tertiary organic base such as triethylamine, N-ethyl-diisopropylamine, N-methyl-morpholine or pyridine, which may simultaneously be used as solvent, at temperatures between −30° and 100° C., but preferably at temperatures between −10° and 60° C.

s) In order to prepare compounds of general formula I wherein T denotes a T'NH— group and Z denotes a CO— group:

Reacting isocyanates of general formula XXVIII $$T'N═C═O \quad (XXVIII)$$

wherein T' is as hereinbefore defined, with compounds of general formula III $$H—NR^1—(R^{2a}CR^3)—CO—Y—(CH_2)_n—R \quad (III)$$

wherein n, R, $R^1$, $R^{2a}$, $R^3$ and Y are as hereinbefore defined.

The reaction is carried out at temperatures between 0° and 150° C., preferably at temperatures between 20° and 100° C., and optionally in the presence of anhydrous solvents, e.g. tetrahydrofuran, 1,4-dioxane, dimethylformamide, dimethylacetamide, N-methyl-2-pyrrolidone or 1,3-dimethyl-2-imidazolidinone.

The amino acid derivatives of general formula I according to the invention contain at least one chiral centre. If, in addition, the group T is chiral, the compounds may occur in the form of two diastereomeric pairs of antipodes. The invention includes the individual isomers as well as the mixtures thereof.

The diastereomers are separated on the basis of their different physico-chemical properties, e.g. by fractionatal crystallisation from suitable solvents, by high-pressure liquid or column chromatography using chiral or preferably achiral stationary phases.

The racemates covered by general formula I are separated, for example, by HPLC on suitable chiral stationary phases (e.g. Chiral AGP, Chiralpak AD). Racemates which contain a basic function can also be separated by means of their diastereomeric, optically active salts which are formed on reacting with an optically active acid, e.g. (+)- or (−)-tartaric acid, (+)- or (−)-diacetyltartaric acid, (+)- or (−)-monomethyltartrate or (+)-camphorsulphonic acid.

According to a conventional method of isomer separation, the racemate of a compound of general formula I is reacted with one of the above-mentioned optically active acids in equimolar quantities in a solvent and the crystalline, diastereomeric, optically active salts obtained are separated using their different solubilities. This reaction may be carried out in any kind of solvent provided that it has a sufficient difference as regards the solubility of the salts. Preferably, methanol, ethanol or mixtures thereof, for example in a ratio by volume of 50:50, are used. Then each of the optically active salts is dissolved in water, neutralised with a base such as sodium carbonate or potassium carbonate and in this way the corresponding free compound is obtained in the (+)- or (−)- form.

By carrying out the methods of synthesis described above with a reagent containing the corresponding amino acid in the (R)-configuration, only the (R)-enantiomer or a mixture of two optically active diastereomeric compounds covered by general formula I is obtained.

The starting materials of general formulae II, V, VII, IX, X, XI, XII, XIII, XIV, XVI, XX, XXI, XXIV, and XXVIII required to synthesise the compounds of general formula I as well as the amino acids used are commercially available or are prepared by methods known from the literature. Acids of formula IV are obtained, for example, under the conditions of a Schotten-Baumann reaction from the corresponding α-amino acids and compounds of general formula II (see also: M. Bodanszky and A. Bodanszky, "The Practice of Peptide Synthesis", Springer-Verlag, 1984, pages 9–30). Esters of general formula VI may be synthesised analogously under the conditions of a peptide coupling reaction, i.e. using TBTU for example, from corresponding α-amino acid esters and compounds of general formula T—Z—OH. Isocyanates of general formula XXIII can readily be prepared from α-amino acid derivatives of general formula III wherein $R_1$ denotes a hydrogen atom and the other groups are as hereinbefore defined, or from the hydrochlorides thereof, by reacting with phosgene, diphosgene or triphosgene in the presence of pyridine (see also: J. S. Nowick, N. A. Powell, T. M. Nguyen and G. Noronha, J. Org. Chem. 57, 7364–7366 [1992]).

The compounds of general formula I obtained may be converted into the physiologically acceptable salts thereof with inorganic or organic acids, particularly for pharmaceutical applications. Examples of suitable acids include hydrochloric acid, hydrobromic acid, phosphoric acid, nitric acid, sulphuric acid, methanesulphonic acid, p-toluenesulphonic acid, acetic acid, fumaric acid, succinic acid, lactic acid, mandelic acid, malic acid, citric acid, tartaric acid or maleic acid.

Moreover, the new compounds of formula I thus obtained, if they contain a carboxy group, may if desired be converted subsequently into the addition salts thereof with inorganic or organic bases, and more especially for pharmaceutical uses into the physiologically acceptable addition salts thereof. Examples of suitable bases include sodium hydroxide, potassium hydroxide, ammonia, cyclohexylamine, dicyclohexylamine, ethanolamine, diethanolamine and triethanolamine.

The new compounds of general formula I, with the exception of those compounds wherein T denotes a hydrogen atom and at the same time Z denotes a bond, and the physiologically acceptable salts thereof, have NPY-antagonistic properties and show good affinity in NPY-receptor binding studies. The compounds exhibit NPY-antagonistic properties both in vivo and in vitro in the pharmacological test systems described hereinafter.

In order to demonstrate the affinity of compounds of general formula I for human NPY-receptors and their antagonistic properties the following tests were carried out:

A. Studies of binding with SK-N-MC cells (expressing the human $Y_1$-receptor)

The cells are detached using a mixture of 0.02% EDTA in PBS and resuspended in 10 ml of incubation medium (MEM/25 mM Hepes+0.5% BSA, 50 μM PMSF, 0.1% bacitracin, 3.75 mM $CaCl_2$) per 40 million cells approx. After 5 minutes' centrifuging (150×g) the pellet is resuspended in the same volume and, after a further washing step in 10 ml of incubation medium, counted and diluted to 1.25 million cells/ml. Then 200 μl of a suspension of 1.25 million cells/ml is incubated for 3 hours at ambient temperature with 25 μl of a 300 pM solution of [$^{125}$I]-Bolton-Hunter-NPY and increasing concentrations ($10^{-11}$ to $10^{-6}$M) of the test substances, whilst maintaining a total volume of 250 μl. Incubation is ended by centrifuging (10 minutes at 3000×g and 4° C.). After washing once with PBS, the radioactivity of the pellet is measured in a gamma counter. The radioactivity thus obtained represents the sum of specific and non-specific binding of [$^{125}$I]-Bolton-Hunter-NPY. The proportion of non-specific binding is defined as that radioactivity which is bound in the presence of 1 μM NPY. The $IC_{50}$ values of the unlabelled test substances are determined graphically. They represent the concentration of the test substance in question at which the specific binding of [$^{125}$I]-Bolton-Hunter-NPY to the NPY-$Y_1$ receptor is inhibited by 50%.

A=(R)-N$^2$-[(Bis(4-bromphenyl)acetyl]-N-[(4-hydroxyphenyl)-methyl]-argininamide-formiate,
B=(R)-N$^2$-(Diphenylacetyl)-N-[[4-(2-hydroxyethyl)phenyl]-methyl]argininamide,
C=(R)-N$^2$-(Diphenylacetyl)-N-[(4-hydroxyphenyl)methyl] argininamide-acetate,
D=(R)-N$^2$-(Diphenylacetyl)-N-[[(4-(hydroxymethyl) phenyl]-methyl]-argininamide-hydrate,
E=N$^2$-(Diphenylacetyl)-N-[(4-hydroxy-3-methylphenyl]-methyl]-argininamide-acetate,
F=(R,S)-3-[3-(aminoiminomethyl)phenyl]-N$^2$-(diphenylacetyl)-N-[(4-hydroxyphenyl)methyl]-alaninamide-hydrochloride,
G=(R)-N$^2$-(Diphenylacetyl-N-[(4-hydroxyphenyl)methyl]-N-methyl-argininamide,
H=(R,S)-N$^2$-(Diphenylacetyl)-N-[(4-hydroxyphenyl) methyl]-N$^5$-(1H-imidazol-2-yl)-ornithinamide,
I=N-[(3,5-Dimethyl-4-hydroxyphenyl)methyl]-N$^2$-(diphenylacetyl)-argininamide-acetate,
K=N$^2$-(Diphenylacetyl)-N-[(4-methoxyphenyl)methyl]-argininamide-acetate,
L=(R)-N-[[4-[(4,5-Dihydro-5,5-dimethyl-2,4(3H)-dioxo-1H-imidazol-3-yl)methyl]phenyl]methyl]-N$^2$-(diphenylacetyl)-argininamide-diacetate,
M=(R,S)-N-[(4-Hydroxyphenyl)methyl]-N$^5$-(1H-imidazol-2-yl)-N$^2$-(2-naphthoyl)-ornithinamide-hydrochloride,
N=(R,S)-N-[(4-Hydroxyphenyl)methyl]-N$^5$-(1H-imidazol-2-yl)-N$^2$-[[2-naphthyl)amino]carbonyl]-ornithinamide,
O=(R,S)-3-[4-(4,5-Dihydro-1H-imidazol-2-yl)phenyl]-N$^2$-(diphenylacetyl)-N-[4-hydroxyphenyl)methyl]-alaninamide-hydrochloride and
P=(R,S)-6-(Aminoiminomethyl)-N$^2$-(diphenylacetyl)-N-[(4-hydroxyphenyl)methyl-norleucinamide-hydrochloride.

The obtained values are shown below in Table 1.

TABLE 1

| Substance | $IC_{50}$ [nM] |
|---|---|
| A | 1.8 |
| B | 7.7 |
| C | 7.5 |
| D | 13.5 |
| E | 10.0 |
| F | 11.3 |
| G | 25.3 |
| H | 18.0 |
| I | 26.0 |
| K | 32.0 |
| L | 26.8 |
| M | 80.5 |
| N | 85.5 |
| O | 207.0 |
| P | 39.0 |

B. NPY-antagonism in vitro

Male rats (CHbb: THOM, 300 to 350 g) are given heparin (100 IU, i.v.) and the animals are then killed by a blow to the back of the neck. The abdomen is opened along the centre of the body and the left kidney is removed after the insertion of catheters in the renal artery, renal vein and ureter. The isolated kidney is immediately perfused with a modified Krebs-Ringer solution having the following composition (4 ml/minute):

NaCl 118.0 mmol/l $KH_2PO_4$ 1.2 mmol/l
KCl 4.8 mmol/l
$HgSO_4$ 1.2 mmol/l
$CaCl_2$ 2.5 mmol/l
$NaHCO_3$ 25.0 mmol/l
Glucose 6.5 mmol/l A mixture of 95% $O_2$/5% $CO_2$ is passed through the solution which is kept at a temperature of 37° C. The perfusion pressure is measured continuously using a pressure gauge. After a 60 minute stabilisation period the perfusion rate is adjusted so as to obtain a perfusion pressure of approximately 100 mm Hg. After a further 30 minutes the experiment is started and NPY (1 μM) is administered as a bolus (0.1 ml) at 15 minute intervals until the pressure increase observed reaches a constant value. The compounds to be tested are given in the form of a continuous infusion over a period of 5 minutes and then NPY is injected. After a 30 minute wash-out period the next highest concentration of test substance is investigated. 3 to 5 different concentrations of the particular compound are tested on each occasion. Concentration/activity curves can be obtained by plotting the percentage inhibition of the NPY activity against the logarithm of the concentration (mol/l) of the compound.

The obtained values are shown in Table 2.

TABLE 2

| Substance | $pIC_{50}$ (mol/l) |
|---|---|
| C | 7.15 |
| F | 7.70 |
| K | 6.70 |

C. In vivo NPY-antagonism

Male rats of normal blood pressure (Chbb:THOM, 300 to 350 g) are anaesthetised with sodium hexobarbital (150 mg/kg, i.p.). After intubation of the trachea the animals are pithed by introducing a blunt needle through the eye into the spinal bone marrow channel. The animals are ventilated with oxygen-rich ambient air using a respiratory pump (20 strokes/minute). A cannula is inserted in the left carotid artery and the arterial blood pressure is measured using a pressure gauge (Braun Melsungen Combitrans) connected to a recording device. For injection purposes a catheter is placed in the left jugular vein through which heparin is administered (200 IU/kg, i.v.). After the blood pressure has been stabilised, the animals are given 2 bolus injections of NPY (10 μg/kg, i.v.) at intervals of 15 minutes. The average increase in diastolic blood pressure is taken as the reference value (=100%). The test substances are injected in increasing doses (4 to 6 doses) at intervals of 15 minutes. One minute after administration of the test substance, NPY is administered.

The antagonistic effect of the test substances is determined by plotting the percentage inhibition of the NPY-induced blood pressure effects against the logarithm of the concentration of active substance.

The obtained values are shown in Table 3.

TABLE 3

| Substance | $pID_{50}$ (mol/kg) |
|---|---|
| C | 6.73 |
| F | 6.82 |
| K | 6.48 |

In view of their pharmacological properties, the compounds of general formula I (with the exception of those compounds where T denotes a hydrogen atom and Z simultaneously denotes a bond), and the physiologically acceptable salts thereof are suitable for treating cardiovascular diseases, e.g. for treating high blood pressure, chronic cardiac insufficiency, coronary heart disease, such as Angina pectoris, myocardial infarction and syndrome X, and also for treating subarachnoidal bleeding, chronic kidney failure, tumour diseases such as phaeochromocytoma, under-active thyroid and obesity and diabetes.

The dosage required to achieve this activity is expediently, by intravenous route, 0.01 to 3 mg/kg of body weight, preferably 0.1 to 1 mg/kg of body weight, and by oral route 0.1 to 10 mg/kg of body weight, preferably 1 to 10 mg/kg of body weight, given 1 to 3 times a day.

For this purpose, the compounds of general formula I prepared according to the invention may be incorporated, optionally together with other active substances such as agents for lowering blood pressure, ACE-inhibitors, diuretics and/or calcium antagonists, together with one or more inert conventional carriers and/or diluents, e.g. with corn starch, lactose, glucose, microcrystalline cellulose, magnesium stearate, polyvinylpyrrolidone, citric acid, tartaric acid, water, water/ethanol, water/glycerol, water/sorbitol, water/polyethyleneglycol, propyleneglycol, cetylstearyl alcohol, carboxymethylcellulose or fatty substances such as hard fat or suitable mixtures thereof, in conventional galenic preparations such as plain or coated tablets, capsules, powders, suspensions or suppositories.

Thus, for the combinations mentioned above, other active substances which may be used include for example bendroflumethiazide, chlorothiazide, hydrochlorothiazide, spironolactone, benzthiazide, cyclothiazide, ethacrinic acid, furosemide, metoprolol, prazosine, atenolol, propranolol, (di)hydralazine-hydrochloride, diltiazem, felodipine, nicardipine, nifedipine, nisoldipine, nitrendipin, captopril, enalapril, lisinopril, cilazapril, quinapril, fosinopril and ramipril. The dosage for these active substances is appropriately ⅕ of the lowest dose normally recommended up to 1/1 of the normally recommended dose, i.e. for example 15 to 200 mg of hydrochlorothiazide, 125 to 2000 mg of chlorothiazide, 15 to 200 mg of ethacrinic acid, 5 to 80 mg of furosemide, 20 to 480 mg of propranolol, 5 to 60 mg of felodipine, 5 to 60 mg of nifedipine or 5 to 60 mg of nitrendipine.

The invention further relates to the use of the compounds of general formula I (with the exception of those compounds wherein T denotes a hydrogen atom and Z at the same time denotes a bond), as useful adjuvants for the production and purification (affinity chromatography) of antibodies and, after appropriate radioactive labelling, e.g. by direct labelling with $^{125}I$ or $^{131}I$ or by tritiation of suitable precursors, for example by replacing halogen atoms with tritium, in RIA and ELISA assays and as diagnostic or analytical aids in neurotransmitter research.

The Examples which follow are intended to illustrate the invention:

Preliminary remarks

"Mp" denotes "melting point", "Decomp." denotes "decomposition". Satisfactory elementary analysis, IR, UV, $^{1}H$-NMR and generally mass spectra as well have been obtained for all the compounds. Unless otherwise specified, $R_f$ values were determined using TLC ready-made silica gel plates 60 $F_{254}$ (E. Merck, Darmstadt, Article No. 5729) and an eluant consisting of n-butanol/glacial acetic acid/water=4/1/1 (v/v/v), without chamber saturation. If there is no detailed information on the configuration, it is left open whether it is the (R)-enantiomer or whether partial or even total racemisation has occurred.

EXAMPLE 1

(R)-N-[[4-(Acetylamino)phenyl]methyl]-$N^2$-(diphenylacetyl)-argininamide-acetate a) (R)-$N^5$-[Amino(nitroimino)methyl]-$N^2$-(diphenylacetyl)-ornithine To a suspension of 50 g (0.228 mol) H-D-Arg($NO_2$)-OH in 400 ml of tetrahydrofuran was added a solution of 9.12 g (0.228 mol) sodium hydroxide in 100 ml of water. Then, within 30 minutes, a solution of 52.6 g (0.228 mol) diphenylacetyl chloride in 400 ml of tetrahydrofuran and a solution of 9.12 g (0.228 mol) of sodium hydroxide in water were simultaneously added dropwise to the mixture without any external cooling. The mixture was stirred for a further 12 hours at ambient temperature and then the solvents were distilled off under a water jet vacuum. The oily residue remaining was dissolved in 600 ml of water and the aqueous solution obtained was then acidified with 230 ml of 1N aqueous hydrochloric acid. The precipitate obtained was taken up in 500 ml of ethyl acetate, then the ethyl acetate solution was thoroughly washed with water, dried over sodium sulphate and freed from solvent in vacuo. After recrystallisation from acetone, 80.0 g (85% of theory) of colourless crystals were obtained, m.p. 80° C.

IR (KBr): 1710 (C═O), 1655 (C═O) $cm^{-1}$

ESI-MS: $(M-H)^-$=412 (calculated: 412)

b) (R)-N-[[4-(Acetylamino)phenyl]methyl]-$N^5$-[amino(nitroimino)methyl]-$N^2$-(diphenylacetyl)-ornithinamide To a solution of 0.82 g (1.98 mMol) (R)-$N^5$-[amino(nitroimino)methyl]-$N^2$-(diphenylacetyl)ornithine in 10 ml of tetrahydrofuran, cooled with crushed ice and ethanol, were added successively 0.202 g (2.0 mMol) of N-methylmorpholine and 0.273 g (2.0 mMol) of isobutylchlorocarbonate and, after 15 minutes' stirring with external cooling, 0.328 g (2.0 mMol) of 4-(amino-methyl)-acetanilide (m.p.: 126°–127° C., prepared in 77% yield by catalytic hydrogenation of 4-cyano-acetanilide in the presence of ammonia and Raney nickel). The mixture was allowed to come up to ambient temperature, suction filtered to remove the precipitate, the filtrate was evaporated down in vacuo, the residue was taken up in warm ethyl acetate/methanol, filtered and the colourless crystals obtained were thoroughly washed with methanol.

Yield 700 mg (63% of theory).

IR (KBr): 1640, 1665, 1690 $cm^{-1}$ (C═O)

EI-MS:

$(M+H)^+$=560

$(M+Na)^+$=582 c) (R)-N-[[4-(Acetylamino)phenyl]methyl]-$N^2$-(diphenylacetyl)-argininamide-acetate A solution of 0.59 g ($1.054_5$ mol) of (R)-N-[[4-acetylamino)-phenyl]methyl]-N-[amino(nitroimino)methyl]-N $^2$-(diphenylacetyl)-ornithinamide in 150 ml of 80% aqueous acetic acid was hydrogenated in the presence of 0.25 g of palladium black at 40° C. under 5 bar of hydrogen pressure until the uptake of hydrogen had ceased. The catalyst was filtered off, the filtrate was evaporated down in vacuo, mixed twice with 10 ml of water and evaporated down once again. The residue was decocted with ether and then with acetone and finally digested with a mixture of 95% acetone and 5% EtOH (v/v), the above compound being obtained in the form of colourless crystals.

M.p.: 175°–177° C.

Yield: 0.4 g (66% of theory), $R_f$=0.60.

IR (KBr): 1650–1680 $cm^{-1}$ (C═O)

ESI-MS: $(M+H)^+$=515

EXAMPLE 2

(R)-$N^2$-(Diphenylacetyl)-N-[[4-(ethoxycarbonylamino)phenyl]-methyl]-argininamide-acetate a) (R)-$N^5$-[Amino(nitroimino)methyl]-$N^2$-(diphenylacetyl)-N-[[4-(ethoxycarbonylamino)phenyl]methyl]-ornithinamide Prepared analogously to Example 1b) from (R)-$N^5$-[amino(nitroimino)methyl]-$N^2$-(diphenylacetyl)-ornithine, [4-(ethoxycarbonylamino)phenyl]methylamine (Mp.: 96°–98° C., prepared in a 64% yield from 4-(ethoxycarbonylamino)benzonitrile by catalytic hydrogenation in the presence of 1N HCl and 5% palladium/animal charcoal as catalyst) and isobutylchlorocarbonate in a yield of 70% of theory.

Mp.: 154°–156° C. (diisopropylether).

IR (KBr): 1700, 1678, 1640–1660 $cm^{-1}$ (C═O, C═N)

ESI-MS:

$(M+H)^+$=590

$(M+Na)^+$=612

$(M+K)^+$=628 b) (R)-$N^2$-(Diphenylacetyl)-N-[[4-(ethoxycarbonylamino)phenyl]methyl]-argininamide-acetate Prepared analogously to Example 1c) from (R)-$N^5$-[amino(nitroimino)methyl)-$N^2$-(diphenylacetyl)-N-[[4-(ethoxycarbonyl-amino)phenyl]methyl]-ornithinamide by catalytic hydrogenation in the presence of palladium black and 80% aqueous acetic acid in a yield of 74% of theory. Colourless crystals, mp. 152°–154° C. $R_f$=0.71.

IR (KBr): 1640, 1680, 1710, 1730 $cm^{-1}$ (C═O, C═N)

ESI-MS: $(M+H)^+$=545

EXAMPLE 3

(R)-$N^2$-(Diphenylacetyl)-N-(phenylmethyl)argininamide-acetate a) (R)-$N^5$-[Amino(nitroimino)methyl]-$N^2$-(diphenylacetyl)-N-(phenylmethyl)-ornithinamide Prepared analogously to Example 1b) from (R)-$N^5$-[amino(nitroimino)methyl]-$N^2$-(diphenylacetyl)-ornithine, benzylamine and isobutylchlorocarbonate in a yield of 89% of theory.

Mp.: 195°–197° C. (ethyl acetate).

IR (KBr): 1640 $cm^{-1}$ (C═O, C═N)

ESI-MS:

$(M+Na)^+$=525

$(M+K)^+$=541 b) (R)-$N^2$-(Diphenylacetyl)-N-(phenylmethyl)-argininamide acetate

Prepared analogously to Example 1c) from (R)-$N^5$-[amino(nitroimino)methyl]-$N^2$-(diphenylacetyl)-N-(phenylmethyl)-ornithinamide by catalytic hydrogenation in the presence of palladium black and 80% aqueous acetic acid in a yield of 97% of theory. Colourless amorphous substance, $R_f$=0.75.

IR (KBr): 1665 $cm^{-1}$ (C═O)

ESI-MS: $(M+H)^+$=458

EXAMPLE 4

(R)-$N^2$-(Diphenylacetyl)-N-[(4-methylphenyl)methyl]-argininamide-acetate a) (R)-$N^5$-(Amino(nitroimino)methyl]-$N^2$-(diphenylacetyl)-N-[(4-methylphenyl)methyl]-ornithinamide Prepared analogously to Example 1b) from (R)-$N^5$-[amino(nitroimino)methyl]-$N^2$-(diphenylacetyl)-ornithine, (4-methylphenyl)methylamine and isobutylchlorocarbonate in a yield of 77% of theory.

Mp.: 202°–204° C. (ethyl acetate).

IR (KBr): 1640 $cm^{-1}$ (C═O)

ESI-MS:

$(M+H)^+$=517

$(M+Na)^+$=539

$(M+K)^+$=555 b) (R)-$N^2$-(Diphenylacetyl)-N-[(4-methylphenyl)methyl]-argininamide-acetate

Prepared analogously to Example 1c) from (R)-$N^5$-[amino(nitroimino)methyl]-$N^2$-(diphenylacetyl)-N-[(4-methylphenyl)-methyl]-ornithinamide by catalytic hydrogenation in the presence of palladium black and 80% aqueous acetic acid in a yield of 77% of theory.

Colourless amorphous substance, $R_f$=0.76.

IR (KBr): 1655 $cm^{-1}$ (C═O)

ESI-MS: $(M+H)^+$=472

EXAMPLE 5

(R)-N-[2-(4-Hydroxyphenyl)ethyl]-$N^2$-[[5-(2-phenylethoxy)-1H-indol-2-yl]carbonyl]-argininamide-acetate a) 2-Nitro-5-(2-phenylethoxy)-toluene To a sodium ethoxide solution prepared from 15 g (0.652 Mol) of sodium and 500 ml of anhydrous ethanol were added, successively, 100 g (0.653 Mol) of 5-hydroxy-2-nitrotoluene and 90 ml (121.95 g=0.659 Mol) of 2-phenylethylbromide and the mixture was refluxed for 5 hours. A further 50 ml (0.366 Mol) of 2-phenylethylbromide were added and again the mixture was refluxed for 10 hours. The solvent was distilled off in vacuo, the residue was taken up in ether and extracted several times with dilute sodium hydroxide solution. The ethereal phase was evaporated down, the residue was stirred thoroughly with 400 ml of petroleum ether 35/60. The crystals obtained were suction filtered and washed with petroleum ether.

Yield: 95.2 g (57% of theory) of pale yellow crystals m.p. 70°–72° C.

IR ($CH_2Cl_2$): 1340, 1515 $cm^1$ ($NO_2$)

b) [2-Nitro-5-(2-phenylethoxy)phenyl]pyroracemic acid

To the clear solution obtained by adding 43.7 g (0.389 Mol) of potassium tert.butoxide to a mixture of 420 ml of anhydrous ether and 162 ml of anhydrous ethanol were added 50.6 ml (54.4 g=0.373 Mol) of diethyloxalate (whereupon a cloudy ochre-coloured mixture was formed) and, 30 minutes later, a solution of 95 g (0.369 Mol) of 2-nitro-5-(2-phenylethoxy)-toluene in 100 ml of anhydrous ether. The mixture was then refluxed for 4 hours and kept at ambient temperature for 36 hours. The black/violet precipitate was filtered off, washed thoroughly with dry ether and dried in the air. Yield of potassium salt of ethyl [2-nitro-5-(2-phenylethoxy)phenyl]pyroracemate: 101.5 g (70% of theory).

98.0 g (0.248 Mol) of this potassium salt were stirred with 800 ml of water, adjusted to pH 8–9 with dilute sodium hydroxide solution and stirred overnight at ambient temperature. The solution was filtered, the filtrate was carefully mixed with concentrated hydrochloric acid until the precipitation reaction had ended. The bright yellow acid precipitated was taken up in dichloromethane, the solution was washed with water, dried over sodium sulphate and evaporated down in vacuo. 87.0 g (74% of theory) of pale yellow crystals were obtained, m.p. 100°–105° C.

IR ($CH_2Cl_2$): 1738, 1790 $cm^{-1}$ (C═O)

ESI-MS: $M^+$=329 c) 5-(2-Phenylethoxy)-1H-indol-2-carboxylic acid 15.0 g (0.0456 Mol) of [2-nitro-5-(2-phenylethoxy)-phenyl]pyroracemic acid were dissolved in a solution of 65 ml of conc. ammonia and 28 ml of water. A solution of 85 g (0.306 Mol) of iron(II)-sulphate-heptahydrate in 93 ml of water was rapidly added thereto, the mixture was heated over a steam bath for 1 hour and refluxed for 30 minutes. The mixture was filtered while hot and the precipitate was washed thoroughly with 75 ml of 5% aqueous ammonia. The combined filtrates, still hot, were acidified with conc. hydrochloric acid against congo red. After cooling, they were extracted exhaustively with ethyl acetate and further processed in the usual way. 9.0 g (70% of theory) of colourless crystals were obtained, m.p. 184°–187° C. (aqueous ethanol).

IR (KBr): 1685 $cm^{-1}$ (C═O)

MS: $M^+$=281 d) (R)-$N^2$-(tert.Butoxycarbonyl)-N-[2-(4-hydroxyphenyl)-ethyl]-$N^5$-[amino(nitroimino)methyl]-ornithinamide To a mixture of 1.0 g (3.13 Mol) of Boc-D-Arg($NO_2$)-OH, 0.57 g (3.28 mMol) of tyramine-hydrochloride, 0.91 ml (0.66 g=6.53 mMol) of triethylamine and 20 ml of anhydrous acetonitrile were added 1.05 g (3.27 mMol) of TBTU, with stirring and external cooling with ice water. The mixture was allowed to come up to ambient temperature and stirring was continued overnight under these conditions. The precipitate was filtered off, the filtrate was evaporated down in vacuo, the residue was distributed between water and ethyl acetate. The ethyl acetate phase was then purified by column chromatography on silica gel (Macherey-Nagel, 35–70 mesh ASTM) using dichloromethane/methanol/cyclohexane/conc. aqueous ammonia=68/15/15/2 (v/v/v/v). 0.8 g (58% of theory) of the title compound were obtained in the form of an amorphous foam, $R_f$0.49 (Macherey-Nagel Polygram® SIL G/$UV_{254}$, ready-made films for TLC; eluant: dichloromethane/methanol/cyclohexane/conc. aqueous ammonia=68/15/15/2 (v/v/v/v)).

ESI-MS:

$(M+H)^+$=439

$(M+Na)^+$=461 e) (R)-$N^5$-[Amino(nitroimino)methyl]-N-[2-(4-hydroxyphenyl)-ethyl]-ornithinamide-trifluoroacetate To a solution of 0.8 g (1.82 mMol) of (R)-$N^5$-[amino (nitroimino)methyl]-$N^2$-(tert.-butoxycarbonyl)-N-[2-(4-hydroxyphenyl)ethyl]-ornithinamide in 20 ml of dichloromethane, externally cooled with crushed ice/ethanol, were added 2.5 ml of trifluoroacetic acid, then the mixture was allowed to come up to ambient temperature and stirred for a further 4 hours at this temperature. The clear solution obtained was evaporated down in a water jet vacuum and combined twice with 10 ml of water and once with 10 ml of toluene and then dried once more. The amorphous (R)-$N^5$-[amino(nitroimino)-methyl]-N-[2-(4-hydroxyphenyl)ethyl]-ornithinamide-trifluoroacetate obtained (0.61 g, 74% of theory), $R_f$0.33 (test conditions as in Example 5d) was further processed without any more purification.

EI-MS: $(M+H)^+$=339; $(2M+H)^+$=677 f) (R)-$N^5$-[Amino(nitroimino)methyl]-N-[2-(4-hydroxyphenyl)-ethyl]-$N^2$-[[5-(2-phenylethoxy)-1H-indol-2-yl]carbonyl]-ornithinamide To a mixture of 0.61 g (1.35 mMol) of (R)-$N^5$-[amino (nitroimino)methyl]-N-[2-(4-hydroxyphenyl)ethyl]-ornithinamide-trifluoroacetate, 0.52 g (1.85 mMol) of 5-(2-phenylethoxy)-1H-indole-2-carboxylic acid, 0.56 ml (0.407 g=4.02 mMol) of triethylamine and 9 ml of anhydrous acetonitrile were added, with stirring and external cooling in ice water, 0.65 g (2.024 mMol) of TBTU. The mixture was allowed to come up to ambient temperature and stirred overnight at the same temperature. It was evaporated down in vacuo, after the addition of a little methanol the residue was distributed between dichloromethane and water and the dichloromethane phase was column-chromatographed on silica gel (Macherey-Nagel, 35–70 mesh ASTM; dichloromethane/ethyl acetate/methanol/cyclohexane/conc. aqueous ammonia=59/25/7.5/7.5/1 (v/v/v/v)).

IR (KBr): 1630 $cm^{-1}$ (C═O)

ESI-MS: $(M-H)^-$=680 g) (R)-N-[2-(4-Hydroxyphenyl)ethyl]-$N^2$-[[5-(2-phenylethoxy)-1H-indol-2-yl]carbonyl]-argininamide-acetate Prepared analogously to Example 1c) from (R)-$N^5$-[amino(nitroimino)methyl]-N-[2-(4-hydroxyphenyl)ethyl]-$N^2$-[[5-(2-phenyl-ethoxy)-1H-indol-2-yl]carbonyl]-ornithinamide by catalytic hydrogenation in the presence of palladium black and 80% aqueous acetic acid in a yield of 53% of theory. Colourless foam, $R_f$ 0.73.

IR (KBr): 1620–1670 $cm^{-1}$ (C═O, C═N)

ESI-MS: $(M+H)^+$=557

EXAMPLE 6

(R)-$N^2$-(Diphenylacetyl)-N-(3-hydroxypropyl)-argininamide-acetate a) (R)-$N^5$-[Amino(nitroimino)methyl]-$N^2$-(diphenylacetyl)-N-(3-hydroxypropyl)-ornithinamide Prepared analogously to Example 5d) from (R)-$N^5$-[amino (nitroimino)methyl]-$N^2$-(diphenylacetyl)-ornithine and 3-amino-propanol in the presence of TBTU in a yield of 46% of theory.

Mp.: 178°–181° C. (dichloromethane/methanol/water).

IR (KBr): 1640, 1660 $cm^{-1}$ (C═O, C═N)

EI-MS: $(M-H)^-$=649 b) (R)-$N^2$-(Diphenylacetyl)-N-(3-hydroxypropyl)-argininamide-acetate

Prepared analogously to Example 1c) from (R)-$N^5$-[amino(nitroimino)methyl]-$N^2$-(diphenylacetyl)-N-(3-hydroxypropyl)-ornithinamide by catalytic hydrogenation in the presence of palladium black and 80% aqueous acetic acid in a yield of 73% of theory. Colourless amorphous substance, $R_f$ 0.44; soluble in water.

IR (KBr): 1635–1690 $cm^{-1}$ (C═O, C═N)

ESI-MS: $(M+H)^+$=426

EXAMPLE 7

(R)-N-[[4-[[(Dimethylamino)carbonyl]amino] phenyl]-methyl]-$N^2$-(diphenylacetyl)-argininamide-acetate a) (R)-$N^5$-[Amino(nitroimino)methyl]-N-[[4-[[(dimethylamino)carbonyl]amino]phenyl]methyl]-$N^2$-(diphenylacetyl)-ornithinamide Prepared analogously to Example 1b) from (R)-$N^5$-[amino(nitroimino)methyl]-$N^2$-(diphenylacetyl)-ornithine and N,N-dimethyl-N'-[4-(aminomethyl)phenyl]urea (mp.: 114°–115° C., prepared in a yield of 83% of theory from N,N-dimethyl-N'-(4-cyanophenyl)-urea by catalytic hydrogenation in the presence of ammonia and Raney-nickel) and isobutylchlorocarbonate in a yield of 70% of theory.

Colourless crystals m.p. 128°–130° C.

IR (KBr): 1630–1690 $cm^{-1}$ (C═O, C═N)

ESI-MS:

$(M+H)^+$=589

$(M+Na)^+$=611 b) (R)-N-[[4-[[(Dimethylamino)carbonyl]amino]phenyl]-methyl]-$N^2$-(diphenylacetyl)-argininamide-acetate Prepared analogously to Example 1c) from (R)-$N^5$-[amino(nitroimino)methyl]-N-[[4-[[(dimethylamino)-carbonyl]amino]phenyl]methyl]-$N^2$-(diphenylacetyl)-ornithinamide by catalytic hydrogenation in the presence of palladium black and 80% aqueous acetic acid in a yield of 68% of theory. Colourless crystals m.p. 162°–164° C. (acetone/ethanol=10/1 (v/v)) and $R_f$ 0.53.

IR (KBr): 1640, 1660 $cm^{-1}$ (C═N, C═O)

ESI-MS: $(M+H)^+$=544

EXAMPLE 8

N-[(4-Aminocarbonylaminophenyl)methyl]-$N^2$-(diphenylacetyl)-argininamide-acetate a) $N^5$-[Amino(nitroimino)methyl]-N-[(4-aminocarbonyl-aminophenyl)methyl]-$N^2$-(diphenylacetyl)-ornithinamide To a solution of 702 mg (1.698 mMol) of (R)-$N^5$-[amino (nitroimino)methyl]-$N^2$-(diphenylacetyl)-ornithine, 280 mg (1.695 mMol) of [4-(aminomethyl)phenyl]urea (mp.: 151°–153° C., prepared from 4-cyanophenyl-urea by catalytic hydrogenation in the presence of ammonia and Raney-nickel) and 0.17 g (1.68 mMol) of triethylamine in 20 ml of anhydrous dimethylformamide was added 0.55 g (1.713 mMol) of TBTU and the mixture was stirred for 1 hour at ambient temperature. The solvent was distilled off in a water jet vacuum, the residue was washed thoroughly with water and finally recrystallised from hot ethyl acetate. 0.5 g (53% of theory) of colourless crystals were obtained, m.p. 182°–183° C.

IR (KBr): 1650, 1670 $cm^{-1}$ (C═O, C═N)

b) N-[(4-Aminocarbonylaminophenyl)methyl]-$N^2$-(diphenyl-acetyl)-argininamide-acetate Prepared analogously to Example 1c) from $N^5$-[amino (nitroimino)-methyl]-N-[(4-aminocarbonylamino-phenyl) methyl]-$N^2$-(diphenylacetyl)-ornithinamide by catalytic hydrogenation in the presence of palladium black and 80% aqueous acetic acid in a yield of 77% of theory. Colourless, amorphous substance, $R_f$ 0.57.

IR (KBr): 1630–1690 $cm^{-1}$ (C═O, C═N)

ESI-MS: $(M+H)^+$=516

EXAMPLE 9

(R)-N-[(4-Hydroxyphenyl)methyl]-$N^2$-[[5-(2-phenylethoxy)-1H-indol-2-yl]carbonyl]-argininamide-acetate a) (R)-$N^2$-(tert.-Butoxycarbonyl)-N-[(4-hydroxyphenyl)-methyl]-$N^5$-[amino(nitroimino)methyl]-ornithinamide Prepared analogously to Example 5d) from Boc-D-Arg $(NO_2)$-OH, (4-hydroxyphenyl)methanamine and TBTU in a yield of 63% of theory. Colourless amorphous substance, $R_f$ 0.54 (Macherey-Nagel, Polygram® SIL G/$UV_{254}$, ready-made films for TLC; eluant: dichloromethane/methanol/cyclohexane/conc. aqueous ammonia=68/15/15/2 (v/v/v/v)).

IR (KBr): 1620, 1640, 1690, 1725 $cm^{-1}$ (C═N, C═O)

ESI-MS:

$(M+H)^+$425

$(M+NH_4)^+$=442

$(M+Na)^+$447

$(2M+H)^+$=849

$(2M+Na)^+$871.

b) (R)-$N^5$-[Amino(nitroimino)methyl]-N-[(4-hydroxyphenyl)-methyl]-ornithinamide-trifluoroacetate Prepared analogously to Example 5e) from (R)-$N^5$-[amino(nitroimino)methyl]-$N^2$-(tert.-butoxycarbonyl)-N-[(4-hydroxyphenyl)methyl]-ornithinamide and trifluoroacetic acid in a yield of 70% of theory. Colourless amorphous substance $R_f$ 0.3 (test conditions as in Example 9a).

EI-MS: $(M+H)^+$=325 c) (R)-$N^5$-[Amino(nitroimino)methyl]-N-[(4-hydroxyphenyl)-methyl]-$N^2$-[[5-(2-phenylethoxy)-1H-indol-2-yl]carbonyl]ornithinamide Prepared analogously to Example 5f) from 5-(2-phenylethoxy)-1H-indole-2-carboxylic acid, (R)-$N^5$-[amino (nitroimino)methyl]-N-[(4-hydroxyphenyl)methyl]-ornithinamide-trifluoroacetate and TBTU in a yield of 70% of theory. Colourless amorphous foam.

IR (KBr): 1630–1690 $cm^{-1}$ (C═N, C═O)

EI-MS: $(M-H)^-$=586 d) (R)-N-[(4-Hydroxyphenyl)methyl]-$N^2$-[[5-(2-phenylethoxy)-1H-indol-2-yl]carbonyl]-argininamide-acetate Prepared analogously to Example 1c) from (R)-$N^5$-[amino(nitroimino)methyl]-N-[(4-hydroxyphenyl)methyl]-$N^2$-[[5-(2-phenylethoxy)-1H-indol-2-yl]carbonyl]-ornithinamide by catalytic hydrogenation in the presence of palladium black and 80% aqueous acetic acid in a yield of 92% of theory. Colourless crystals, mp. 106°–109° C. (ethanol and diisopropylether) and $R_f$ 0.70.

IR (KBr): 1630–1690 $cm^{-1}$ (C═N, C═O)

ESI-MS: $(M+H)^+$=543

EXAMPLE 10

(R)-$N^2$-(Diphenylacetyl)-N-(4-hydroxybutyl)-argininamide-acetate a) (R)-$N^5$-[Amino(nitroimino)methyl]-$N^2$-(diphenylacetyl)-N-(4-hydroxybutyl)-ornithinamide Prepared analogously to Example 1b) from (R)-$N^5$-[amino(nitroimino)methyl]-$N^2$-(diphenylacetyl)-ornithine, 4-amino-1-butanol and isobutylchlorocarbonate in a yield of 80% of theory. Colourless crystals, mp. 136°–138° C. (dichloromethane).

IR (KBr): 1640 $cm^{-1}$ (C═O, C═N)

ESI-MS:

$(M+H)^+$=485

$(M+Na)^+$=507

$(M+K)^+$=523

$(2M+Na)^+$=991 b) (R)-$N^2$-(Diphenylacetyl)-N-(4-hydroxybutyl)-argininamide-acetate

Prepared analogously to Example 1c) from (R)-$N^5$-[amino(nitroimino)methyl]-$N^2$-(diphenylacetyl)-N-(4-hydroxybutyl)-ornithinamide by catalytic hydrogenation in the presence of palladium black and 80% aqueous acetic acid in a yield of 75% of theory.

Colourless amorphous substance $R_f$ 0.47.

IR (KBr): 1630–1690 $cm^{-1}$ (C═N, C═O)

ESI-MS: $(M+H)^+$=440

EXAMPLE 11

(R)-$N^2$-(Diphenylacetyl)-N-(5-hydroxypentyl)-argininamide-acetate a) (R)-$N^5$-[Amino(nitroimino)methyl]-$N^2$-(diphenylacetyl)-N-(5-hydroxypentyl)-ornithinamide Prepared analogously to Example 1b) from (R)-$N^5$-[amino(nitroimino)methyl]-$N^2$-(diphenylacetyl)-ornithine, 5-amino-1-pentanol and isobutylchlorocarbonate in a yield of 67% of theory.

Colourless crystals mp. 168°–170° C.

IR (KBr): 1640 $cm^{-1}$ (C═N, C═O)

ESI-MS:

$(M+H)^+$=499

$(M+Na)^+$=521

$(M+K)^+$=537 b) (R)-$N^2$-(Diphenylacetyl)-N-(5-hydroxypentyl)-argininamide-acetate

Prepared analogously to Example 1c) from (R)-$N^5$-[amino(nitroimino)methyl]-$N^2$-(diphenylacetyl)-N-(5-hydroxypentyl)-ornithinamide by catalytic hydrogenation in the presence of palladium black and 80% aqueous acetic acid in a yield of 100% of theory.

Colourless amorphous substance, $R_f$ 0.52.

IR (KBr): 1640, 1690 $cm^{-1}$ (C═N, C═O)

ESI-MS: $(M+H)^+$=454

EXAMPLE 12

(R)-$N^2$-(Diphenylacetyl)-N-[(4-fluorophenyl)-methyl]-argininamide-acetate a) (R)-$N^5$-(Amino(nitroimino)methyl]-$N^2$-(diphenylacetyl)-N-[(4-fluorophenyl)methyl]-ornithinamide Prepared analogously to Example 1b), but using acetonitrile as solvent instead of tetrahydrofuran, from (R)-$N^5$-[amino(nitroimino)methyl]-$N^2$-(diphenylacetyl)-ornithine, (4-fluorophenyl)methylamine and isobutylchlorocarbonate in a yield of 68% of theory.

Colourless crystals, mp. 124°–126° C. (ethyl acetate/tert.butyl-methylether).

IR (KBr): 1635–1690 $cm^{-1}$ (C═N, C═O)

ESI-MS:

$(M+H)^+$=521

$(M+Na)^+$=543

$(M+K)^+$=559 b) (R)-$N^2$-(Diphenylacetyl)-N-[(4-fluorophenyl)methyl]-argininamide-acetate

Prepared analogously to Example 1c) from (R)-$N^5$-[amino(nitroimino)methyl]-$N^2$-(diphenylacetyl)-N-[(4-fluorophenyl)-methyl]-ornithinamide by catalytic hydrogenation in the presence of palladium black and 80% aqueous acetic acid in a yield of 90% of theory.

Colourless amorphous substance, $R_f$ 0.73.

IR ($CH_2Cl_2$): 1630–1690 $cm^{-1}$ (C═N, C═O)

ESI-MS: $(M+H)^+$=476

EXAMPLE 13

$N^2$-(Diphenylacetyl)-N-[2-(1H-indol-3-yl)ethyl]-argininamide-acetate a) $N^5$-[Amino(nitroimino)methyl]-$N^2$-(diphenylacetyl)-N-[2-(1H-indol-3-yl)ethyl]-ornithinamide To an ice cooled mixture of 0.82 g (1.983 mMol) of (R)-$N^5$[amino(nitroimino)methyl]-$N^2$-(diphenylacetyl)-ornithine, 0.39 g (1.993 mMol) of tryptamine hydrochloride, 0.20 g (1.976 mMol) of triethylamine and 20 ml of anhydrous tetrahydrofuran, were added 0.41 g (1.987 mMol) of N,N'-dicyclohexylcarbodiimide and 0.27 g (1.998 mMol) of HOBt and the mixture was then maintained for 14 hours at a temperature from 0° C. to +5° C. The crystalline precipitate was filtered off with suction, the filtrate was freed from solvent in vacuo, the residue remaining was distributed between water and 10 ml of ethyl acetate and the ethyl acetate phase was washed with water once more and dried with sodium sulphate and then left for 8 hours at ambient temperature. The crystalline precipitate formed was suction filtered, washed with a little ethyl acetate, then decocted with 10 ml of methanol, finally suction filtered and washed with a little diethylether. 0.40 g (36% of theory) of colourless crystals were obtained, m.p. 176°–178° C.

IR (KBr): 1640 $cm^{-1}$ (C═O, C═N)

ESI-MS:

$(M+H)^+$556

$(M+Na)^+$=578 b) $N^2$-(Diphenylacetyl)-N-[2-(1H-indol-3-yl)ethyl]-argininamide-acetate

Prepared analogously to Example 1c) from $N^5$-[amino (nitroimino)-methyl]-$N^2$-(diphenylacetyl)-N-[2-(1H-indol- 3-yl)ethyl]ornithinamide by catalytic hydrogenation in the presence of palladium black and 80% aqueous acetic acid in a yield of 67% of theory.

Colourless amorphous substance $R_f$ 0.78.

IR (KBr): 1630–1690 $cm^{-1}$ (C═N, C═O)

ESI-MS: $(M+H)^+$=511

EXAMPLE 14

(R)-N-[(4-Bromophenyl)methyl]-$N^2$-(diphenylacetyl)-argininamide-hydrochloride a) (R)-$N^5$-[Amino(nitroimino)methyl]-N-[(4-bromophenyl)-methyl]-$N^2$-(diphenylacetyl)-ornithinamide Prepared analogously to Example 12a) from (R)-$N^5$-[amino(nitroimino)methyl]-$N^2$-(diphenylacetyl)-ornithine, 4-bromophenyl-methylamine and isobutylchlorocarbonate in a yield of 73% of theory.

Colourless crystals, m.p. 226°–228° C.

IR (KBr): 1645 $cm^{-1}$ (amide-C═O)

ESI-MS:

$(M+H)^+$=581/583 (Br)

$(M+Na)^+$=603/605 (Br)

b) (R)-N-[(4-Bromophenyl)methyl]-$N^2$-(diphenylacetyl)-argininamide-hydrochloride 0.76 g (1.307 mMol) of (R)-$N^5$-[amino(nitroimino) methyl]-N-[(4-bromophenyl)methyl]-$N^2$-(diphenylacetyl)-ornithinamide were dissolved in 23 ml of 60% aqueous formic acid, combined with 2.0 g (8.864 mMol) of tin(II)-chloride-dihydrate and heated to +50° C. for 10 minutes. 20 ml of formic acid were added, the mixture was kept at 50° C. for 3 hours, a further 1.0 g (4.432 mMol) of tin(II)-chloride-dihydrate were added and heating was continued for a further 5 hours to +50° C. Then water and formic acid were distilled off in vacuo at a bath temperature of not more than +50° C. The remaining viscous residue was carefully digested with water, then suction filtered and washed with water once more, then dried in the air. The solid material obtained was exhaustively decocted with acetonitrile. After evaporation, the combined acetonitrile extracts left behind 0.8 g of a porous virtually colourless substance which was taken up in 3 ml of a mixture of butanol/glacial acetic acid/water (4/1/1 (v/v/v)). The slurry obtained after standing for 1 hour at ambient temperature was cooled to 0° C. and then suction filtered and washed carefully first with 1 ml of ice cold butanol/glacial acetic acid/water (4/1/1 (v/v/v)) mixture, then with 2 ml of water, and finally dried over diphosphorus pentoxide in vacuo. 0.28 g (37% of theory) of colourless crystals were obtained, m.p. 135°–138° C. and $R_f$ 0.73.

IR (KBr): 1680 $cm^{-1}$ (amidine-C═N) 1635 $cm^{-1}$, 1655 $cm^{-1}$ (amide-C═O)

ESI-MS: $(M+H)^+$=536/538 (Br)

EXAMPLE 15

(R)-$N^2$-(Diphenylacetyl)-N-(2-phenylethyl)-argininamide-acetate a) (R)-$N^5$-[Amino(nitroimino)methyl]-$N^2$-(diphenylacetyl)-N-(2-phenylethyl)-ornithinamide Prepared analogously to Example 12a) from (R)-$N^5$-[amino(nitroimino)methyl]-$N^2$-(diphenylacetyl)-ornithine, 2-phenylethylamine and isobutylchlorocarbonate in a yield of 84% of theory.

Colourless crystals, m.p. 178°–181° C. (ethyl acetate).

IR (KBr): 1675 (amidine-C═N), 1660, 1625 $cm^{-1}$ (amide-C═O)

ESI-MS:

$(M+H)^+$=517

$(M+Na)^+$=539

$(M+K)^+$=555 b) (R)-$N^2$-(Diphenylacetyl)-N-(2-phenylethyl)-argininamide-acetate

Prepared analogously to Example 1c) from (R)-$N^5$-[amino(nitroimino)methyl]-$N^2$-(diphenylacetyl)-N-(2-phenylethyl)-ornithinamide by catalytic hydrogenation in the presence of palladium black and 80% aqueous acetic acid in a yield of 100% of theory.

Colourless amorphous substance, $R_f$ 0.75.

IR ($CH_2Cl_2$): 1630–1690 $cm^{-1}$ (C═O, C═N)

ESI-MS: $(M+H)^+$=472

EXAMPLE 16

(R)-$N^2$-([1,1'-Biphenyl]-4-yl-acetyl)-N-[(4-hydroxyphenyl)-methyl]-argininamide-acetate a) (R)-$N^5$-[Amino(nitroimino)methyl]-$N^2$-([1,1'-biphenyl]-4-yl-acetyl)-N-[(4-hydroxyphenyl)methyl]-ornithinamide Prepared analogously to Example 13a) from [1,1'-biphenyl]-4-acetic acid and (R)-$N^5$-[amino(nitroimino) methyl]-N-[(4-hydroxyphenyl)methyl]-ornithinamide in the presence of N,N'-dicyclohexylcarbodiimide and HOBt in a yield of 50% of theory.

Colourless crystals, m.p. 205°–210° C. (decomp.).

IR (KBr): 1615, 1635, 1625 $cm^{-1}$ (amide-C═O)

ESI-MS:

$(M+H)^+$=519

$(M+Na)^+$=541

$(M+K)^{+}$=557 b) (R)-$N^2$-([1,1'-Biphenyl]-4-yl-acetyl)-N-[(4-hydroxyphenyl)methyl]-argininamide-acetate Prepared analogously to Example 1c) from (R)-$N^5$-[amino(nitroimino)methyl]-$N^2$-([1,1'-biphenyl]-4-yl-acetyl)-N-[(4-hydroxyphenyl)methyl)-ornithinamide by catalytic hydrogenation in the presence of palladium black and 80% aqueous acetic acid in a yield of 46% of theory.

Colourless crystals, m.p. 159°–163° C. (isopropanol) and $R_f$ 0.70.

IR (KBr): 1640 $cm^{-1}$ (C═O)

ESI-MS: $(M+H)^+$=474

EXAMPLE 17

$N^2$-(Diphenylacetyl)-N-[(4-methanesulphonylaminophenyl)-methyl]-argininamide-acetate a) $N^5$-[Amino(nitroimino)methyl]-$N^2$-(diphenylacetyl)-N-[(4-methanesulphonylaminophenyl)methyl]-ornithinamide Prepared analogously to Example 8a) from (R)-$N^5$-[amino(nitroimino)methyl]-$N^2$-(diphenylacetyl)-ornithine and (4-methanesulphonylaminophenyl)methylamine (m.p.: 258° C. (decomp.), prepared from 4-aminobenzonitrile via 4-cyano-methanesulphonanilide m.p. 195°–196° C.) and in the presence of TBTU in a yield of 44% of theory. M.p.: 178°–180° C. (ethanol).

IR (KBr): 1642 $cm^{-1}$ (amide-C═O)

ESI-MS:

$(M+H)^+$=596

$(M+Na)^+$=618

$(M+K)^+$=534 b) $N^2$-(Diphenylacetyl)-N-[(4-methanesulphonylaminophenyl)-methyl]-argininamide-acetate Prepared analogously to Example 1c) from $N^5$-[amino (nitroimino)-methyl]-$N^2$-(diphenylacetyl)-N-[(4- methanesulphonylaminophenyl)methyl]-ornithinamide by catalytic hydrogenation in the presence of palladium black and 80% aqueous acetic acid in a yield of 54% of theory.

Colourless amorphous substance, $R_f$ 0.60.

IR (KBr): 1630–1690 $cm^{-1}$ (C=O, C=N)

ESI-MS: $(M+H)^+$=551

EXAMPLE 18

Optically active diastereomer mixture of $N^2$-(α-cyclopentyl-phenylacetyl)-N-[(4-hydroxyphenyl) methyl]-D-argininamide-acetate a) $N^5$-(Amino(nitroimino)methyl]-$N^2$-(α-cyclopentyl-phenylacetyl)-N-[(4-hydroxyphenyl)methyl]-D-ornithinamide (mixture of diastereomers)

Prepared analogously to Example 8a) from (R)-N-[(4-hydroxyphenyl)-methyl)-$N^5$-[amino(nitroimino)methyl]-ornithinamide and racemic α-cyclopentyl-phenylacetic acid and in the presence of TBTU in a yield of 69% of theory.

Colourless amorphous substance.

IR (KBr): 1630–1690 $cm^{-1}$ (C=O, C=N)

ESI-MS:

$(M+H)^+$=511

$(M+Na)^+$=533 b) $N^2$-(α-Cyclopentyl-phenylacetyl)-N-[(4-hydroxyphenyl) -methyl]-D-argininamide-acetate (mixture of diastereomers)

Prepared analogously to Example 1c) from $N^5$-[amino (nitroimino)-methyl]$N^2$-(α-cyclopentyl-phenylacetyl)-N[ (4-hydroxyphenyl)methyl]-D-ornithinamide (mixture of diastereomers) by catalytic hydrogenation in the presence of palladium black and 80% aqueous acetic acid in a yield of 100% of theory.

Colourless amorphous substance, $R_f$ 0.76.

IR (KBr): 1630–1690 $cm^{-1}$ (C=O, C=N)

ESI-MS: $(M+H)^+$=466

EXAMPLE 19

(R)-N-[(4-Hydroxyphenyl)methyl]-$N^2$-(tricyclo [3.3.1.1$^{3.7}$]-dec-1-ylacetyl)-argininamide-acetate a) (R)-$N^5$-[Amino(nitroimino)methyl]-N-[(4-hydroxyphenyl)-methyl]-$N^2$-(tricyclo[3.3.1.1$^{3.7}$]dec-1-ylacetyl)-ornithinamide Prepared analogously to Example 8a) from (R)-N-[(4-hydroxyphenyl)-methyl]-$N^5$-[amino(nitroimino)methyl]-ornithinamide, tricyclo[3.3.1.1$^{3.7}$]decane-1-acetic acid and TBTU in a yield of 85% of theory.

Colourless crystals, m.p. 100°–106° C.

IR (KBr): 1620–1690 $cm^{-1}$ (C=O, C=N)

ESI-MS:

$(M+Na)^+$=509

$(M+K)^+$=525 b) (R)-N-[(4-Hydroxyphenyl)methyl]-$N^2$-(tricyclo [3.3.1.1$^{3.7}$]-dec-1-ylacetyl)-argininamide-acetate Prepared analogously to Example 1c) from (R)-$N^5$-[amino(nitroimino)methyl]-N-[(4-hydroxyphenyl)methyl]-$N^2$-(tricyclo[3.3.1.1$^{3.7}$]dec-1-ylacetyl)-ornithinamide by catalytic hydrogenation in the presence of palladium black and 80% aqueous acetic acid in a yield of 90% of theory.

Colourless amorphous substance, $R_f$ 0.72.

IR (KBr): 1620–1690 $cm^{-1}$ (C=O, C=N)

ESI-MS: $(M+H)^+$=456

EXAMPLE 20

N-[[4-(Dimethylamino)phenyl]methyl]-$N^2$-(diphenylacetyl)-argininamide-diacetate and $N^2$-(diphenylacetyl)-N-[(4-(methylamino) cyclohexyl]-methyl]-argininamide-diacetate (mixture of diastereomers)

a) $N^5$-[Amino(nitroimino)methyl]-$N^2$-(diphenylacetyl)-N-[ [4-(dimethylamino)phenyl]methyl]-ornithinamide Prepared analogously to Example 13a) from (R)-$N^5$-[amino(nitroimino)methyl]-$N^2$-(diphenylacetyl)-ornithine, [4-(dimethylamino)phenyl]methylamine, N,N'-dicyclohexylcarbodiimide and HOBt in a yield of 76% of theory.

Colourless crystals, m.p. 221°–223° C.

IR (KBr): 1640 $cm^{-1}$ (amide-C=O)

ESI-MS:

$(M+H)^+$=546

$(M+Na)^+$=568

$(2M+Na)^+$=1113 b) N-[[4-(Dimethylamino)phenyl]methyl]-$N^2$-(diphenylacetyl)-argininamide-diacetate and $N^2$-(diphenylacetyl)-N-[[4-(methylamino)cyclohexyl]-methyl]-argininamide-diacetate Prepared analogously to Example 1c) from $N^5$-[amino (nitroimino)-methyl]-$N^2$-(diphenylacetyl)-N-[[4-(dimethylamino)phenyl]methyl]-ornithinamide by catalytic hydrogenation in the presence of palladium black and 80% aqueous acetic acid.

The crude product was broken down into two fractions by column chromatography (MN-silica gel 60, Macherey-Nagel, 70–230 mesh ASTM; eluant: butanol/glacial acetic acid/water=4/1/1 (v/v/v)). The product with the higher $R_f$ value was identified as $N^2$-(diphenylacetyl)-N-[[4-(methylamino)cyclohexyl]methyl]-argininamide-diacetate (mixture of diastereomers) and obtained in a yield of 15% of theory.

Colourless amorphous substance, $R_f$ 0.63.

IR (KBr): 1630–1690 $cm^{-1}$ (C=O, C=N)

EI-MS: $(M+H)^+$=493

The main product, N-[[4-(dimethylamino)phenyl]methyl] -$N^2$-(diphenylacetyl)-argininamide-diacetate, was isolated in a yield of 22% of theory.

Colourless amorphous substance, $R_f$ 0.50.

IR (KBr): 1630–1690 $cm^{-1}$ (C=O, C=N)

EI-MS: $(M+H)^+$=501

EXAMPLE 21

(R)-N-([1,1'-Biphenyl]-4-ylmethyl)-$N^2$-(diphenylacetyl)-argininamide-acetate a) (R)-$N^5$-[Amino(nitroimino)methyl]-N-([1,1'-biphenyl]-4-ylmethyl)-$N^2$-(diphenylacetyl)-ornithinamide Prepared analogously to Example 12a) from (R)-$N^5$-[amino(nitroimino)methyl]-$N^2$-(diphenylacetyl)-ornithine, [1,1'-biphenyl]-4-methylamine (prepared from [1,1'-biphenyl]-4-carbonitrile by catalytic hydrogenation in the presence of Raney-nickel and ammonia) and isobutylchlorocarbonate in a yield of 73% of theory.

Colourless crystals, m.p. 100°–102° C. (ethyl acetate/ tert.butylmethylether).

IR (KBr): 1640 $cm^{-1}$ (amide-C=O)

ESI-MS:

$(M+H)^+$=579

$(M+Na)^+$=601 b) (R)-$N^5$-([1,1'-Biphenyl]-4-ylmethyl)-$N^2$-(diphenyl-acetyl)-argininamide-acetate Prepared analogously to Example 1c) from (R)-$N^5$-[amino(nitroimino)methyl]-N-([1,1'-biphenyl]-4-ylmethyl)-$N^2$-(diphenyl-acetyl)-ornithinamide by catalytic hydrogenation in the presence of palladium black and 80% aqueous acetic acid in a yield of 83% of theory.

Colourless amorphous product, $R_f$ 0.76.

IR ($CH_2Cl_2$): 1660 $cm^{-1}$ (C=O)

ESI-MS: $(M+H)^+$=534

EXAMPLE 22

(R)-$N^2$-(Diphenylacetyl)-N-[[4-(hydroxymethyl) phenyl]-methyl]-argininamide-acetate a) (R)-$N^5$-[Amino(nitroimino)methyl]-$N^2$-(diphenylacetyl)-N-[[4-(hydroxymethyl)phenyl)-methyl]-ornithinamide Prepared analogously to Example 12a) from (R)-$N^5$-[amino(nitroimino)methyl]-$N^2$-(diphenylacetyl)-ornithine, [4-(hydroxymethyl)phenyl]methylamine (m.p.: 75°–77° C., prepared from 4-cyano-benzaldehyde by reduction with lithium aluminium hydride) and isobutylchlorocarbonate in a yield of 77% of theory.

Colourless amorphous substance.

IR (KBr): 1620–1690 $cm^{-1}$ (C═O, C═N)

EI-MS:

$(M+H)^+$=533

$(M+Na)^+$=555 b) (R)-$N^2$-(Diphenylacetyl)-N-[[4-(hydroxymethyl)-phenyl]-methyl]-argininamide-acetate Prepared analogously to Example 14b) from (R)-$N^5$-[amino(nitroimino)methyl-$N^2$-(diphenylacetyl)-N-[[4-hydroxymethyl)phenyl]methyl]-ornithinamide by reduction with tin(II)-chloride-dihydrate in the presence of 60% aqueous formic acid in a yield of 10% of theory.

Colourless amorphous substance, $R_f$ 0.62.

IR (KBr): 1630–1690 $cm^{-1}$ (C═O, C═N)

ESI-MS: $(M+H)^+$=488

EXAMPLE 23

(R)-$N^2$-(Diphenylacetyl)-N-[4-(1-oxoethyl)phenyl]methyl]-argininamide-hydrochloride a) (R)-N-[[4-(1-Oxoethyl)phenyl]methyl]-$N^5$-[amino-(nitroimino)methyl]-$N^2$-(tert.-butoxycarbonyl)-ornithinamide Prepared analogously to Example 5d) from Boc-D-Arg($NO_2$)-OH, [4-(1-oxoethyl)phenyl]methylamine-hydrochloride (W. Korytnyk, N. Angelino, C. Dave and L. Caballas, J. Med. Chem. 21: 507–513 [1978]) and TBTU in a yield of 79% of theory.

Colourless amorphous substance.

IR ($CH_2Cl_2$): 1680 $cm^{-1}$ (C═N, C═O)

Shoulder at 1715 $cm^1$ (ester-C═O)

b) (R)-$N^5$-[Amino(nitroimino)methyl]-N-[[4-(1-oxoethyl)-phenyl]methyl]-ornithinamide Prepared analogously to Example 5e) from (R)-$N^5$-[amino(nitroimino)methyl]-$N^2$-(tert.-butoxycarbonyl)-N-[[4-(1-oxoethyl)-phenyl]methyl]-ornithinamide by treating with trifluoroacetic acid in dichloromethane. The salt thus obtained was dissolved in water, this solution was made ammoniacal and the desired base was finally precipitated from the aqueous solution by saturating with common salt. The product obtained was dried in vacuo in diphosphorus pentoxide and used in the following stage without any further purification.

c) (R)-$N^5$-[Amino(nitroimino)methyl]-$N^2$-(diphenylacetyl)-N-[[4-(1-oxoethyl)phenyl]methyl]-ornithinamide Prepared analogously to Example 5f) from (R)-$N^5$-[amino(nitroimino)methyl]-N-[[4-(1-oxoethyl)phenyl]-methyl]-ornithinamide, diphenylacetic acid and TBTU in a yield of 48% of theory.

Colourless crystals, mp. 208°–210° C. (Decomp.).

IR (KBr): 1640, 1660, 1680 $cm^{-1}$ (C═O, C═N)

d) (R)-$N^2$-(Diphenylacetyl)-N-[[4-(1-oxoethyl)phenyl]-methyl]-argininamide-hydrochloride Prepared analogously to Example 14b) from (R)-$N^5$-[amino(nitroimino)methyl]-$N^2$-(diphenylacetyl)-N-[[4-(1-oxoethyl)phenyl]methyl]-ornithinamide by reduction with tin(II)-chloride-dihydrate in the presence of 60% aqueous formic acid in a yield of 23% of theory.

Colourless amorphous substance, $R_f$ 0.67.

IR (KBr): 1630–1700 $cm^{-1}$ (C═O, C═N)

EI-MS: $(M+H)^+$=500

EXAMPLE 24

(R)-N-[(4-Chlorophenyl)methyl]-$N^2$-(diphenylacetyl)-argininamide-hydrochloride a) (R)-N-[(4-Chlorophenyl)methyl]-$N^5$-[amino(nitroimino)methyl]-$N^2$-(tert.-butoxycarbonyl)-ornithinamide Prepared analogously to Example 5d) from Boc-D-Arg($NO_2$)-OH, (4-chlorophenyl)methylamine and TBTU in a yield of 87% of theory.

Colourless amorphous substance.

IR ($CH_2Cl_2$):

1630 (C═O), 1675 (C═O or C═N), 1715 (shoulder, ester-C═O) $cm^{-1}$ b) (R)-$N^5$-[Amino(nitroimino)methyl]-N-[(4-chlorophenyl)-methyl]-ornithinamide Prepared analogously to Example 23b) from (R)-$N^5$-[amino(nitroimino)methyl]-$N^2$-(tert.-butoxycarbonyl)-N-[(4-chlorophenyl)-methyl]-ornithinamide by treating with trifluoroacetic acid in dichloromethane.

Yield: 83% of theory.

Colourless amorphous compound which was further processed without total purification.

c) (R)-$N^5$-[Amino(nitroimino)methyl]-N-[(4-chlorophenyl)-methyl]-$N^2$-(diphenylacetyl)-ornithinamide Prepared analogously to Example 5f) from (R)-$N^5$-[amino(nitroimino)methyl]-N-[(4-chlorophenyl)methyl]-ornithinamide, diphenylacetic acid and TBTU in a yield of 64% of theory.

Colourless crystals, mp. 212°–215° C. (ethyl acetate).

IR (KBr): 1645 $cm^{-1}$ (C═O)

d) (R)-N-[(4-Chlorophenyl)methyl]-$N^2$-(diphenylacetyl)argininamide-hydrochloride Prepared analogously to Example 14b) from (R)-$N^5$-[amino(nitroimino)methyl]-N-[(4-chlorophenyl)methyl]-$N^2$-(diphenylacetyl)-ornithinamide by reduction with tin(II)-chloride-dihydrate in the presence of 60% aqueous formic acid in a yield of 72% of theory.

Colourless amorphous substance, $R_f$ 0.74.

IR (KBr): 1620–1690 $cm^{-1}$ (C═O, C═N)

ESI-MS: $(M+H)^+$=492/494 (Cl)

EXAMPLE 25

(R)-$N^2$-(Diphenylacetyl)-N-[4-(hydroxymethyl)phenyl]-argininamide-hydrochloride-hydrate a) (R)-$N^5$-[Amino(nitroimino)methyl]-$N^2$-(diphenylacetyl)-N-[4-(hydroxymethyl)phenyl]-ornithinamide Prepared analogously to Example 12a) from (R)-$N^5$-[amino(nitroimino)methyl]-$N^2$-(diphenylacetyl)-ornithine, (4-aminophenyl)methanol and isobutylchlorocarbonate in a yield of 86% of theory.

Colourless crystals, mp. 239°–240° C. and $R_f$ 0.32 (Macherey-Nagel, Polygram® SIL G/$UV_{254}$, ready-made films for TLC; eluant: dichloromethane/methanol/cyclohexane/ethyl acetate/conc. aqueous ammonia=66/13/13/6/2, (v/v/v/v/v)).

b) (R)-$N^2$-(Diphenylacetyl)-N-[4-(hydroxymethyl)phenyl]-argininamide-hydrochloride-hydrate A mixture of 1.2 g (2.34 mMol) of (R)-$N^5$-[amino(nitroimino)methyl]-$N^2$-(diphenylacetyl)-N-[4-(hydroxymethyl)-phenyl]-ornithinamide, 200 ml of methanol and 1.6 g of 10% palladium on animal charcoal was hydrogenated at 40° C. under 5 bar of hydrogen pressure until the uptake of hydrogen had ceased. The catalyst was filtered off, the filtrate was evaporated down in vacuo, the residue was taken up in water and suction filtered. The jelly-like filter residue was suspended in 30 ml of water once more, acidified with 2N hydrochloride acid and stirred for 1 hour after the addition of a further 30 ml of water. The precipitate formed in the meantime was collected and recrystallised from acetonitrile. 0.2 g (16% of theory) of colourless crystals were obtained, mp. 138°–141° C. and $R_f$ 0.62.

R (KBr): 1655 $cm^{-1}$ (C═O)

EI-MS: $(M+H)^+$=474

EXAMPLE 26

(R)-$N^2$-(Diphenylacetyl)-N-(4-hydroxy-2-butyn-1-yl)-argininamide-acetate-hydrate a) (R)-$N^5$-[Amino(nitroimino)methyl]-$N^2$-(diphenylacetyl)-N-(4-hydroxy-2-butyn-1-yl)-ornithinamide Prepared analogously to Example 12a) from (R)-$N^5$-[amino(nitroimino)methyl ]-$N^2$-(diphenylacetyl)-ornithine and 4-amino-2-butyn-1-ol (mp.: 167°–169° C., prepared by reacting 4-chloro-2-butyn-1-ol with conc. aqueous ammonia at 100° C.) in the presence of isobutylchlorocarbonate in a yield of 17% of theory.

Colourless crystals, mp. 151°–153° C. (acetonitrile).

IR (KBr): 3390, 3290 (NH), 1645 (C═O) $cm^{-1}$

ESI-MS:

$(M+H)^+$=481

$(M+Na)^+$=503

$(M+K)^+$=519 b) (R)-$N^2$-(Diphenylacetyl)-N-(4-hydroxy-2-butyn-1-yl)-argininamide-acetate-hydrate Prepared analogously to Example 14b) from (R)-$N^5$-[amino(nitroimino)methyl]-$N^2$-(diphenylacetyl)-N-(4-hydroxy-2-butyn-1-yl)-ornithinamide by reduction with tin (II)-chloride-dihydrate in the presence of 60% aqueous formic acid in a yield of 9% of theory.

Colourless amorphous substance, $R_f$ 0.54.

IR (KBr): 1655 $cm^{-1}$ (C═O)

ESI-MS: $(M+H)^+$=436

EXAMPLE 27

(R,S)-$N^2$-(Diphenylacetyl)-$N^6$-[ethylamino (ethylimino)-methyl]-N-[(4-hydroxyphenyl)methyl]-lysinamide-dihydroiodide a) (R,S)-$N^2$-(Diphenylacetyl)-$N^6$-[(phenylmethoxy)-carbonyl]-lysine Prepared analogously to Example 1a) from diphenylacetylchloride and racemic $N^6$-(phenylmethoxycarbonyl)-lysine in the presence of sodium hydroxide solution. 81% of theory of colourless crystals were obtained, mp. 98°–100° C. (diisopropylether).

IR (KBr): 3235 (NH), 1735 (ester-C═O), 1715 (acid-C═O), 1650 (amide-C═O) $cm^{-1}$ b) (R,S)-$N^2$-(Diphenylacetyl)-N-[(4-hydroxyphenyl)-methyl]-$N^6$-[(phenylmethoxy)carbonyl]-lysinamide Prepared analogously to Example 8a) from (R,S)-$N^2$-(diphenylacetyl)-$N^6$-[(phenylmethoxy)carbonyl]-lysine and (4-hydroxyphenyl)-methylamine in the presence of TBTU in a yield of 88% of theory.

Colourless crystals, mp. 86°–92° C.

(dichloromethane/methanol=95/5 (v/v)) and $R_f$ 0.78 (Macherey-Nagel, Polygram® SIL G/$UV_{254}$, ready-made films for TLC; eluant: dichloromethane/methanol/cyclohexane/conc. aqueous ammonia=68/15/15/2 (v/v/v/v)).

IR (KBr): 1695, 1645 $cm^{-1}$ (C═N, C═O)

c) (R,S)-$N^2$-(Diphenylacetyl)-N-[(4-hydroxyphenyl)-methyl]-lysine-acetate 3.0 g (5.175 mMol) of (R,S)-$N^2$-(diphenylacetyl)-N-[(4-hydroxyphenyl)methyl]-$N^6$-[(phenylmethoxy)carbonyl]-lysinamide were suspended in a mixture of 70 ml of methanol, 30 ml of glacial acetic acid and 10 ml of water and after the addition of 0.8 g of 10% palladium on animal charcoal at ambient temperature the mixture was hydrogenated under a pressure of 5 bar until the uptake of hydrogen had ceased. After removal of the catalyst and solvents the residue remaining was recrystallised from a little diisopropylether. 2.0 g (76% of theory) of colourless crystals were obtained, mp. 113°–116° C. and $R_f$ 0.24 (test conditions as in Example 27b)).

IR (KBr): 1640 $cm^{-1}$ (amide-C═O)

MS: $M^{+\bullet}$445 d) (R,S)-$N^2$-(Diphenylacetyl)-$N^6$-[ethylamino-(ethylimino)-methyl]-N-[(4-hydroxyphenyl)methyl)-lysinamide-dihydroiodide A mixture of 1.2 g (2.373 mMol) of (R,S)-$N^2$-(diphenylacetyl)-N-[(4-hydroxyphenyl)methyl]-lysine-acetate, 0.8 g (3.052 mMol) of N,N'-diethyl-S-methyl-thiuroniumiodide, 0.91 g (8.58 mMol) of anhydrous sodium carbonate and 12 ml of dimethylformamide was heated to 65° C. for 12 hours with stirring and then to 80° C. for a further 2 hours. The mixture was then cooled with ice water and filtered and the filter cake was thoroughly washed with dimethylformamide. The filtrates were evaporated down in vacuo and the residue remaining was purified by column chromatography on silica gel (Macherey-Nagel, 35–70 mesh ASTM; mobile phase: ethyl acetate/methanol/glacial acetic acid =50/25/0.5 (v/v/v)). 0.7 g (37% of theory) of a colourless amorphous substance were obtained, $R_f$ 0.73.

IR (KBr): 1622, 1659 $cm^{-1}$ (C═O, C═N)

EI-MS: $(M+H)^+$=544

EXAMPLE 28

(R)-$N^2$-(Diphenylacetyl)-N-[[4-(hydroxymethyl)phenyl]-methyl]-argininamide-hydrate a) (R)-$N^5$-[Amino(nitroimino)methyl]-$N^2$-(tert.-butoxycarbonyl)-N-[(4-(hydroxymethyl)phenyl]-methyl]-ornithinamide Prepared analogously to Example 5d) from Boc-D-Arg($NO_2$)-OH, [4-hydroxymethyl)phenyl]methylamine and TBTU in a yield of 80% of theory.

Colourless amorphous substance.

IR (KBr): 1715, 1695, 1655, 1630 (C═O, C═N)

ESI-MS:

$(M+Na)^+$=461

$(M+K)^+$=477

$(2M+Na)^+$=899 b) (R)-$N^5$-(Amino(nitroimino)methyl]-N-[[4-(hydroxy-methyl)-phenyl]methyl]-ornithinamide Prepared analogously to Example 23b) from (R)-$N^5$-[amino(nitroimino)methyl]-$N^2$-(tert.-butoxycarbonyl)-N-[[4-(hydroxymethyl)phenyl]methyl]-ornithinamide by the action of trifluoroacetic acid in a yield of 83% of theory.

Colourless amorphous substance which was further processed without total purification.

c) (R)-$N^5$-[Amino(nitroimino)methyl]-$N^2$-(diphenylacetyl)-N-[[4-(hydroxymethyl)-phenyl]methyl]-ornithinamide Prepared analogously to Example 5f) from (R)-$N^5$-[amino (nitroimino)methyl]-N-[[4-(hydroxymethyl)-phenyl [methyl]-ornithinamide, diphenylacetic acid and TBTU in a yield of 79% of theory.

Colourless amorphous substance which is totally identical, in terms of its thin layer chromatographic behaviour, with a preparation prepared according to Example 22a).

d) (R)-$N^2$-(Diphenylacetyl)-N-[4-(hydroxymethyl)-phenyl]-methyl]-argininamide-hydrate Prepared totally analogously to Example 22b; however, the substance obtained was subsequently additionally purified by column chromatography (silica gel, Macherey-Nagel, Type 60, 70–230 mesh ASTM; mobile phase: ethyl acetate/methanol/glacial acetic acid=70/30/1 (v/v/v)); the suitable eluates were evaporated down in vacuo, the residue was taken up in a little water and made alkaline with 1N NaOH. The crystals precipitated were suction filtered, washed thoroughly with water and dried over diphosphorus pentoxide in vacuo.

Yield: 13% of theory.

Colourless crystals mp. 140°–142° C. and $R_f$ 0.62.

IR (KBr): 1641 $cm^{-1}$ (C═O)

ESI-MS: $(M+H)^+$=488

EXAMPLE 29

(R,S)-α-[(Diphenylacetyl)amino]-N-[(4-hydroxyphenyl)-methyl]-1H-imidazole-4-propanamide a) (R,S)-α-Amino-N-[(4-hydroxyphenyl)methyl]-1-(phenyl-methyl)-1H-imidazole-4-propanamide Prepared analogously to Example 23b) from (R,S)-α-[(tert.-butoxycarbonyl)amino]-N-[(4-hydroxyphenyl)methyl]-1-(phenylmethyl)-1H-imidazole-4-propanamide by the action of trifluoroacetic acid in a yield of 100% of theory. The product was reacted without any further purification.

b) (R,S)-α-[(Diphenylacetyl)amino]-N-[(4-hydroxyphenyl)-methyl]-1-(phenylmethyl)-1H-imidazole-4-propanamide and (R,S)-α-[(diphenylacetyl)amino]-N-[[4-(diphenylacetoxy)-phenyl]methyl]-1-(phenylmethyl)-1H-imidazole-4-propanamide The crude mixture obtained under the reaction conditions of Example 5f) from (R,S)-α-amino-N-[(4-hydroxyphenyl)methyl)-1-(phenylmethyl)-1H-imidazole-4-propanamide, diphenylacetic acid and TBTU was separated into two products by column chromatography (silica gel MN 60, Macherey-Nagel, 70–230 mesh ASTM; mobile phase: ethyl acetate/methanol =9/1 (v/v)).

b1) (R,S)-α-[(Diphenylacetyl)amino]-N-[[4-(diphenylacetoxy)-phenyl]methyl]-1H-imidazole-4-propanamide Yield: 30% of theory;

colourless crystals, mp. 168° C. and $R_f$ 0.44 (Merck-ready-made TLC plates, silica gel 60 $F_{254}$, layer thickness 0.25 mm; eluant: ethyl acetate/methanol 9/1 (v/v)).

IR (KBr): 1747 (ester-C═O), 1643 (amide-C═O) $cm^{-1}$

MS: $M^+$=738 b2) (R,S)-α-[(Diphenylacetyl)amino]-N-[(4-hydroxyphenyl)-methyl]-1-(phenylmethyl)-1H-imidazole-4-propanamide Yield: 8% of theory;

Colourless crystals mp. 212°–214° C. and $R_f$ 0.34 (test conditions as hereinbefore).

IR (KBr): 1643 $cm^{-1}$ (amide-C═O)

ESI-MS:

$(M+H)^+$=545

$(M+Na)^+$=567 c) (R,S)-α-[(Diphenylacetyl)amino]-N-[(4-hydroxyphenyl)-methyl]-1H-imidazole-4-propanamide 1.0 g (1,836 mMol) of (R,S)-α-[(diphenylacetyl)amino]-N-[(4-hydroxyphenyl)methyl]-1-(phenylmethyl)-1H-imidazole-4-propanamide were dissolved in 100 ml of methanol and hydrogenated in the presence of 500 mg of 10% palladium/charcoal and 2 ml of 1N hydrochloric acid at 50° C. under a hydrogen pressure of 5 bar. The catalyst was filtered off, the filtrate was evaporated down, the residue was taken up in water, made alkaline with potash and extracted exhaustively with ethyl acetate. The combined ethyl acetate extracts dried over sodium sulphate were freed from solvent in vacuo and purified by column chromatography (silica gel MN 60, Macherey-Nagel, 70–230 mesh ASTM; mobile phase: ethyl acetate/methanol/conc. aqueous ammonia =90/10/1 (v/v/v)). 0.2 g (24% of theory) of a colourless amorphous substance were obtained, $R_f$ 0.65.

IR (KBr): 1647 $cm^{-1}$ (amide-C═O)

MS: $M^+$=454

EXAMPLE 30

(R)-$N^2$-(Diphenylacetyl)-N-[[4-[(methylaminocarbonyl)-amino]phenyl]methyl]-argininamide-diacetate a) (R)-$N^5$-[Amino(nitroimino)methyl]-$N^2$-(diphenylacetyl)-N-[[4-[(methylaminocarbonyl)-amino]phenyl]methyl]-ornithinamide Prepared analogously to Example 5d), but using N,N-diisopropyl-ethylamine (Hunig-Base) instead of triethylamine, from (R)-$N^2$-(diphenylacetyl)-$N^5$-[amino(nitroimino)methyl]-ornithine and N-methyl-N'-[4-(aminomethyl)-phenyl]-urea (mp.: 144°–145° C., prepared from N-methyl-N'-(4-cyanophenyl)-urea by catalytic hydrogenation in the presence of Raney-nickel and ammonia) in the presence of TBTU.

Yield: 61% of theory.

Colourless amorphous substance, $R_f$ 0.29 (test conditions as in Example 29b).

IR (KBr): 1639 $cm^{-1}$ (carboxamide-C═O)

ESI-MS:

$(M+H)^+$=575

$(M+Na)^+$=597 b) (R)-$N^2$-(Diphenylacetyl)-N-[[4-((methylamino-carbonyl)-amino]phenyl]methyl]-argininamide-diacetate Prepared analogously to Example 1c) from (R)-$N^5$-[amino(nitroimino)methyl]-$N^2$-(diphenylacetyl)-N-[[4-[(methylaminocarbonyl)amino]phenyl]methyl]-ornithinamide by catalytic hydrogenation in the presence of palladium black and 80% aqueous acetic acid in a yield of 83% of theory.

Colourless amorphous substance, $R_f$ 0.58.

IR (KBr): 1647 $cm^{-1}$ (amide-C═O)

ESI-MS: $(M+H)^{+=530}$

EXAMPLE 31

(R,S)-$N^2$-(Diphenylacetyl)-N-[(4-hydroxyphenyl)methyl]-$N^5$-methyl-$N^5$-(phenylmethyl)-ornithinamide a) Diethyl α-(acetylamino)-α-[3-[(phenylmethyl)-methylamino]-propyl]-malonate A sodium ethoxide solution freshly prepared from 5.8 g (0.252 Mol) of sodium and 250 ml of anhydrous ethanol was added dropwise, at ambient temperature and within about 15 minutes, to a mixture obtained from 49.4 g (0.25 Mol) of 3-chloro-N-methyl-N-(phenylmethyl)-propylamine, 60 g (0.268 Mol) of 97% diethyl acetamidomalonate, 11.3 g (0.075 Mol) of sodium iodide and 800 ml of dry dioxane. The mixture was stirred at ambient temperature for 30 minutes and then refluxed for 5 hours. It was left to stand overnight at ambient temperature, the insoluble matter was filtered off, the filtrate was freed from solvent and the residue remaining was distributed between ethyl acetate and water. The ethyl acetate phase was dried over sodium sulphate and evaporated down and the oil obtained was finally purified by column chromatography (silica gel MN 60, Macherey-Nagel, 70–230 mesh ASTM; mobile phase: dichloromethane/methanol/conc. aqueous ammonia=90/10/0.25 (v/v/v)). 53 g (56% of theory) of a colourless viscous oil were obtained.

IR (KBr): 1741.6 (ester-C═O), 1683.8 (amide-C═O) $cm^{-1}$ b) (R,S)-$N^5$-Methyl-$N^5$-(phenylmethyl)-ornithine-dihydrochloride 20.4 g (0.0539 Mol) of diethyl α-(acetylamino)-α-[3-[(phenylmethyl)-methylamino]propyl]-malonate were dissolved in 50 ml of glacial acetic acid and after the addition of 100 ml of 3N aqueous hydrochloric acid the mixture was refluxed for 6 hours. The highly viscous, pale yellow mass obtained in a quantitative yield and remaining after the evaporation of the solvent was reacted further without any more purification.

c) (R,S)-$N^2$-(Diphenylacetyl)-$N^5$-methyl-$N^5$-(phenylmethyl)-ornithine-hydrochloride Diphenylacetylchloride and (R,S)-$N^5$-methyl-$N^5$-(phenylmethyl)-ornithine-dihydrochloride were reacted analogously to Example 1a). The mixture obtained was evaporated down in a water jet vacuum until the tetrahydrofuran used as solvent had been removed, then made acidic with 3N aqueous hydrochloric acid and carefully extracted with diethylether. The aqueous phase was then evaporated down under reduced pressure at a bath temperature of not more than +40° C. The yield of colourless crystals, mp. 125°–130° C., which were used in the next stage without purification, was 27% of theory.

IR (KBr): 1715 (carboxylic acid-C═O), 1664 (amide-C═O) $cm^{-1}$ d) (R,S)-$N^2$-(Diphenylacetyl)-N-[(4-hydroxyphenyl)methyl]-$N^5$-methyl-$N^5$-(phenylmethyl)-ornithinamide Prepared analogously to Example 8a) from (R,S)-$N^2$-(diphenylacetyl)-$N^5$-methyl-$N^5$-(phenylmethyl)-ornithine-hydrochloride, (4-hydroxyphenyl)methylamine and TBTU in a yield of 28% of theory.

Colourless crystals, mp. 160°–162° C. (ethyl acetate) and $R_f$ 0.75.

IR (KBr): 1679.9 and 1633.6 (amide-C═O) $cm^{-1}$

EXAMPLE 32

(R)-$N^2$-(Diphenylacetyl)-N-[(4-hydroxycyclohexyl)methyl]-argininamide-acetate (mixture of diastereomers)

a) (4-Hydroxycyclohexyl)methylamine (cis/trans-mixture)

A solution of 1.0 g (8.12 mmol) of (4-hydroxyphenyl)methylamine in an alkaline solution prepared from 0.34 g (8.50 mmol) of sodium hydroxide and 10 ml of water was hydrogenated for 20 hours at 70° C. under a hydrogen pressure of 50 psi after the addition of 0.3 g of 5% rhodium/animal charcoal. The catalyst was filtered off and the filtrate was evaporated down in vacuo. The residue remaining was dissolved in a little water, this solution was adjusted to pH 14 with a few drops of 40% sodium hydroxide solution, saturated with common salt and extracted with diethylether using a rotary perforator for 3 days. The diethylether extracts were dried with sodium sulphate and freed from solvent and yielded 0.24 g (23% of theory) of a colourless viscous oil.

IR ($CH_2Cl_2$): 3610 $cm^{-1}$ (OH)

b) (R)-$N^5$-[Amino(nitroimino)methyl]-$N^2$-[(tert.-butyloxy)-carbonyl]-N-[(4-hydroxycyclohexyl)-methyl]-ornithinamide (mixture of diastereomers)

Prepared analogously to Example 8a) from Boc-D-Arg ($NO_2$)-OH and (4-hydroxycyclohexyl)methylamine in the presence of TBTU in a yield of 41% of theory.

Colourless amorphous substance.

IR (KBr): 1650 (amide-C═O), 1700 (ester-C═O) $cm^{-1}$

EI-MS:

$(M+H)^+$=431

$(M+Na)^+$=453

$(2M+H)^+$=861

$(2M+Na)^+$=883 c) (R)-$N^5$-[Amino(nitroimino)methyl]-N-[(4-hydroxycyclohexyl)methyl]-ornithinamide (mixture of diastereomers)

Prepared analogously to Example 23b) from (R)-$N^5$-[amino(nitroimino)methyl]-$N^2$-(tert.-butyloxycarbonyl)-N-[(4-hydroxycyclohexyl)methyl]-ornithinamide (mixture of diastereomers) by the action of trifluoroacetic acid in a yield of 71% of theory.

Colourless amorphous substance.

IR (KBr): 1681.8 (C═O) $cm^{-1}$ d) (R)-$N^5$-[Amino(nitroimino)methyl]-$N^2$-(diphenylacetyl)-N-[(4-hydroxycyclohexyl)methyl]-ornithinamide (mixture of diastereomers)

To a solution of 1.6 g (4.84 mMol) of (R)-$N^5$-[amino(nitroimino)methyl]-N-[(4-hydroxycyclohexyl)-methyl]-ornithinamide (mixture of diastereomers) in 20 ml of anhydrous tetrahydrofuran were added dropwise, first of all, 1.5 g (14.8 mMol) of triethylamine, then a solution of 0.7 g (3.034 mMol) diphenylacetylchloride, dissolved in 5 ml of dry tetrahydrofuran. After 20 minutes stirring at ambient temperature the mixture was evaporated down in vacuo, the residue was distributed between water and ethyl acetate and the ethyl acetate phase was dried over sodium sulphate and evaporated down. The residue was purified by column chromatography on silica gel (Macherey-Nagel, 70–230 mesh ASTM using dichloromethane/methanol/conc. aqueous ammonia=90/10/0.25 (v/v/v)). 0.15 g (9% of theory) of a colourless amorphous product were obtained.

IR (KBr): 1649 $cm^{-1}$ (amide-C═O)

ESI-MS: $(M-H)^-$=523 e) (R)-$N^2$-(Diphenylacetyl)-N-[(4-hydroxycyclohexyl)-methyl]-argininamide-acetate (mixture of diastereomers)

Prepared analogously to Example 1c) from (R)-$N^5$-[amino(nitroimino)methyl]-$N^2$-(diphenylacetyl)-N-[(4-hydroxycyclohexyl)-methyl]-ornithinamide (mixture of diastereomers) by catalytic hydrogenation in the presence of palladium black and 80% aqueous acetic acid.

Yield: 84% of theory.

Colourless amorphous, water-soluble substance, $R_f$ 0.63.

IR (KBr): 1652.9 $cm^{-1}$ (amide-C═O)

ESI-MS: $(M+H)^+$=480

EXAMPLE 33

(R,S)-$N^5$,$N^5$-Dimethyl-$N^2$-(diphenylacetyl)-N-[(4-hydroxy-phenyl)methyl]-ornithinamide a) Diethyl α-(acetylamino)-α-(3-(dimethylamino)propyl]-malonate Prepared analogously to Example 31a) from diethyl acetamidomalonate and 3-chloro-N,N-dimethyl-propylamine in the presence of sodium ethoxide.

Yield: 27% of theory.

Colourless viscous oil.

IR (KBr): 1741.6 (ester-C═O), 1679.9 (amide-C═O) $cm^{-1}$ b) (R,S)-$N^5$,$N^5$-Dimethyl-ornithine-dihydrochloride Prepared analogously to Example 31b) from diethyl α-(acetylamino)-α-[3-(dimethylamino)propyl]-malonate and hydrochloric acid in a yield of 100% of theory. Colourless highly viscous substance which was used in the next stage without purification c) (R,S)-$N^5$,$N^5$-Dimethyl-$N^2$-(diphenylacetyl)-ornithine-hydrochloride Prepared analogously to Example 31c) from (R,S)-$N^5$,$N^5$-dimethyl-ornithine-dihydrochloride and diphenylacetylchloride in a yield of 3% of theory. Colourless crystals which were reacted in the next step without purification.

d) (R,S)-$N^5$,$N^5$-Dimethyl-$N^2$-(diphenylacetyl)-N-[(4-hydroxyphenyl)methyl]-ornithinamide Prepared analogously to Example 8a) from (R,S)-$N^5$,$N^5$-dimethyl-$N^2$-(diphenylacetyl)-ornithine-hydrochloride, (4-hydroxyphenyl)-methylamine and TBTU in a yield of 33% of theory.

Colourless amorphous substance.

MS: $M^+$=459

IR (KBr): 1652.9 $cm^{-1}$ (amide-C═O)

EXAMPLE 34

(R,S)-$N^2$-(Diphenylacetyl)-$N^5$-[ethylamino (ethylimino)-methyl]-N-[(4-hydroxyphenyl5methyl]-ornithinamide-acetate-hydroiodide a) (R,S)-$N^2$-(Diphenylacetyl)-$N^5$-[(phenylmethoxy)-carbonyl]-ornithine Prepared analogously to Example 1a) from diphenyacetylchloride and D,L-$N^5$-[(phenylmethoxy)-carbonyl]-ornithine in the presence of sodium hydroxide solution. 96% of theory of colourless crystals were obtained mp. 120°–122° C.

IR (KBr): 3320 (NH), 1715, 1685, 1665, 1645 $cm^{-1}$ (C═O)

b) (R,S)-$N^2$-(Diphenylacetyl)-N-[(4-hydroxyphenyl)-methyl]-$N^5$-[(phenylmethoxy)carbonyl]-ornithinamide Prepared analogously to Example 8a) from (R,S)-$N^2$-(diphenylacetyl)-$N^5$-[(phenylmethoxy)carbonyl]-ornithine and 4-hydroxybenzylmethylamine in the presence of TBTU in a yield of 50% of theory.

Colourless crystals, mp. 118°–121° C. (ethyl acetate).

IR (KBr): 1740 (ester-C═O), 1695, 1645 $cm^{-1}$ (amide-C═O).

MS: M:$^+$=565 c) (R,S)-$N^2$-(Diphenylacetyl)-N-[(4-hydroxyphenyl)-methyl]ornithinamide-acetate Prepared analogously to Example 27c) from (R,S)-$N^2$-(diphenylacetyl)-N-[(4-hydroxyphenyl)methyl]-$N^5$-[(phenylmethoxy)carbonyl]-ornithinamide by catalytic hydrogenation in the presence of palladium/animal charcoal.

Yield of 95% of theory.

Colourless crystals, mp. 185°–186° C. and $R_f$ 0.42 (Macherey-Nagel, Polygram® SIL G/$UV_{254}$, ready-made films for TLC; eluant: ethyl acetate/methanol/glacial acetic acid=50/50/1 (v/v/v)).

IR (KBr): 1640 $cm^{-1}$ (amide-C═O).

ESI-MS: $(M+H)^+$=432 d) (R,S)-$N^2$-(Diphenylacetyl)-$N^5$-[ethylamino-(ethylimino)-methyl]-N-[(4-hydroxyphenyl)methyl]-ornithinamide-acetate-hydroiodide Prepared analogously to Example 27d) from (R,S)-$N^2$-(diphenyl-acetyl)-N-[(4-hydroxyphenyl)methyl]-ornithine-acetate and N,N'-diethyl-S-methyl-thiuroniumiodide (mp.: 73°–74° C., prepared from N,N'-diethylthiourea and methyliodide) in a yield of 47% of theory.

Colourless amorphous substance, $R_f$ 0.70.

IR (KBr): 1654.8, 1627.8 $cm^{-1}$ (C═O, C═N).

EI-MS: $(M+H)^+$=530

EXAMPLE 35

(R)-N-[(4-Amino-3,5-dichlorophenyl)methyl]-$N^2$-(diphenylacetyl)-argininamide a) (R)-N-[(4-Amino-3,5-dichlorophenyl)methyl]-$N^5$-[amino (nitroimino)methyl]-$N^2$-(diphenylacetyl)-ornithinamide Prepared analogously to Example 5f) but using N-ethyl-diisopropylamine instead of triethylamine, from (R)-N-[(4-amino-3,5-dichlorophenyl)methyl]-$N^5$-[amino-(nitroimino) methyl]-ornithinamide, diphenylacetic acid and TBTU in a yield of 71% of theory.

Colourless crystals mp. 224°–225° C. (ethanol).

IR (KBr): 1633.6 $cm^{-1}$ (C═O)

b) (R)-N-[(4-Amino-3,5-dichlorophenyl)methyl]-$N^2$-(diphenylacetyl)-argininamide Prepared analogously to Example 14b) from (R)-N-[(4-amino-3,5-dichlorophenyl)methyl]-$N^5$-[amino(nitroimino)-methyl-$N^2$-(diphenylacetyl)-ornithinamide by reduction with tin(II)-chloride-dihydrate in the presence of 60% aqueous formic acid.

Yield: 65% of theory.

Colourless crystals, mp. 148°–152° C. and $R_f$ 0.62.

IR (KBr): 1656.8 $cm^{-1}$ (amide-C═O)

EI-MS: $(M+H)^+$=541/543/545 ($Cl_2$)

According to MS and NMR investigation the substance is contaminated with (R)-$N^2$-(diphenylacetyl)-N-[(3,5-dichloro-4-(formylamino)phenyl)methyl]-argininamide.

EXAMPLE 36

(R)-N-[(4-Amino-3,5-dichlorophenyl)methyl]-$N^2$-(3,3-diphenyl-1-oxopropyl)-argininamide-acetate-hydrochloride a) (R)-N-[(4-Amino-3,5-dichlorophenyl)methyl]-$N^5$-[amino (nitroimino)methyl]-$N^2$-[(tert.-butyloxy)carbonyl]-ornithinamide To a mixture of 21.7 g (0.068 Mol) of Boc-D-Arg($NO_2$) -OH, 12.2 ml (0.07 Mol) of N,N-diisopropyl-ethylamine and 13.0 g (0.068 Mol) of (4-amino-3,5-dichlorophenyl)-methylamine (prepared from 4-amino-3,5-dichlorobenzaldehyde and α-aminoisobutyric acid analogously to G. P. Rizzi, J. Org. Chem. 36: 1710–1711 (1971)) in 225 ml of anhydrous dimethylformamide were added, with stirring and external cooling with ice water, 22.4 g (0.0698 Mol) of TBTU and the mixture was then kept at ambient temperature for 2 hours. The mixture was stirred into copious amounts of water then extracted exhaustively with ethyl acetate. The combined ethyl acetate extracts were washed successively with 10% aqueous citric acid, water, saturated aqueous sodium hydrogen carbonate solution and water, dried over magnesium sulphate and evaporated down. 27.9 g (83% of theory) of colourless crystals were obtained, mp. 105°–107° C.

IR (KBr): 1630, 1660, 1700 $cm^{-1}$ (C═O)

b) (R)-N-[(4-Amino-3,5-dichlorophenyl)methyl]-$N^5$-[amino(nitroimino)methyl]-ornithinamide A solution of 27.9 g (0.0567 Mol) of (R)-N-[(4-amino-3,5-dichlorophenyl)methyl)-$N^5$-[amino(nitroimino)-methyl]-$N^2$-[(tert.-butyloxy)carbonyl]-ornithinamide in 200 ml of anhydrous methanol was added dropwise to 150 ml of a solution of dry hydrogen chloride in absolute methanol. After the development of gas had ceased (after about 30 minutes) the solvent was eliminated in vacuo, the residue was taken up in water, the mixture was filtered and the filtrate was made ammoniacal. It was extracted with ethyl acetate, the combined extracts were dried over magnesium sulphate and evaporated down in vacuo. 20.0 g (90% of theory) of a colourless oil were obtained which solidified in crystalline form after a few days.

IR (KBr): 1624.0 $cm^{-1}$ (C═O)

c) (R)-N-[(4-Amino-3,5-dichlorophenyl)methyl]-$N^5$-[amino (nitroimino)methyl]-$N^2$-(3,3-diphenyl-1-oxopropyl)-ornithinamide Prepared analogously to Example 35a) from 3,3-diphenylpropanoic acid, (R)-N-[(4-amino-3,5- dichlorophenyl)methyl]-$N^5$-[amino(nitroimino)methyl]-ornithinamide and TBTU in a yield of 58% of theory.

Colourless crystals, mp. 218°–219° C. (ethyl acetate).

IR (KBr): 1631.7 $cm^{-1}$ (C═O)

d) (R)-N-[(4-Amino-3,5-dichlorophenyl)methyl]-$N^2$-(3,3-diphenyl-1-oxopropyl)-argininamide-acetate-hydrochloride Prepared analogously to Example 14b) from (R)-N-[(4-amino-3,5-dichlorophenyl)methyl]-$N^5$-[amino(nitroimino)-methyl]-$N^2$-(3,3-diphenyl-1-oxopropyl)-ornithinamide by reduction with tin(II)-chloride-dihydrate in the presence of 60% aqueous formic acid in a yield of 40% of theory.

Colourless amorphous substance, $R_f$ 0.62.

IR (KBr): 1656.8 $cm^{-1}$ (carboxamide-C═O)

ESI-MS: $(M+H)^+$=555/556/559 ($Cl_2$)

According to MS and NMR investigations the substance is contaminated with (R)-N-[[3,5-dichloro-4-(formylamino)-phenyl)methyl]-$N^2$-(3,3-diphenyl-1-oxopropyl)-argininamide or a salt thereof.

EXAMPLE 37

(R)-N-[(4-Aminophenyl)methyl]-argininamide-acetate-dihydrochloride

Prepared analogously to Example 1c) from (R)-N-[(4-amino-3,5-dichlorophenyl)methyl]-$N^5$-[amino(nitroimino) methyl]-ornithinamide by catalytic hydrogenation in the presence of palladium black and 80% aqueous acetic acid.

Yield 57% of theory.

Colourless amorphous substance, $R_f$ 0.07.

IR (KBr): 1668.3 $cm^{-1}$ (amide-C═O)

ESI-MS: $(M+H)^+$=279

EXAMPLE 38

(R)-$N^2$-[(4-Amino-3,5-dichlorophenyl)sulphonyl)-N-[(4-hydroxyphenyl)methyl]-argininamide-hydrochloride a) (R)-$N^2$-[(4-Amino-3,5-dichlorophenyl)sulphonyl]-$N^5$-[amino(nitroimino)methyl]-ornithine A suspension of 2.6 g (10.55 mMol) of 4-amino-3,5-dichlorobenzenesulphonylchloride in 31 ml of water was combined successively with 2.6 g of sodium hydrogen carbonate and a solution of 2.02 g (9.2 mMol) of H-D-Arg ($NO_2$)-OH in 15 ml of acetone and the mixture was then maintained at pH 10.5–10.8 by dropwise addition of 40% sodium hydroxide solution. After about 45 minutes the pH of the mixture had stabilised, the mixture was stirred for a further hour at ambient temperature, then adjusted to pH 3 with dilute hydrochloric acid and finally mixed with 3 g of solid citric acid. The mixture was extracted exhaustively with ethyl acetate and the extracts were dried over sodium sulphate and evaporated down. The residue was triturated with diethylether and yielded 3.0 g (74% of theory) of colourless crystals, mp. 196°–200° C.

IR (KBr):

1728.1 $cm^{-1}$ (carboxylic acid-C═O), 1625.9

(amide-C═O), 1340 and 1170 ($SO_2N$) $cm^{-1}$ b) (R)-$N^2$-[(4-Amino-3,5-dichlorophenyl)sulphonyl]-$N^5$-[amino(nitroimino)methyl]-N-[(4-hydroxyphenyl)-methyl]-ornithinamine Prepared analogously to Example 8a) but using N,N-diisopropyl-ethylamine instead of triethylamine, from (R)-$N^2$-[(4-amino-3,5-dichlorophenyl)sulphonyl]-$N^5$-[amino (nitroimino)methyl]-ornithine and (4-hydroxyphenyl) methylamine and TBTU in a yield of 58% of theory.

Colourless crystals, mp. 241°–242° C.

IR (KBr): 1639.4 (amide-C═O), 1336.6 and 1159.2 ($SO_2N$) $cm^{-1}$.

C) (R)-$N^2$-[(4-Amino-3,5-dichlorophenyl)sulphonyl]-N-[(4-hydroxyphenyl)methyl]-argininamide-hydrochloride Prepared analogously to Example 14b) from (R)-$N^2$-[(4-amino-3,5-dichlorophenyl)sulphonyl]-$N^5$-[amino (nitroimino)methyl]-N-[(4-hydroxyphenyl)methyl)-ornithinamide by reduction with tin(II)-chloride-dihydrate in the presence of 60% aqueous formic acid.

Yield: 80% of theory.

Colourless crystals, mp. 245°–249° C. and $R_f$ 0.65.

IR (KBr): 1662.5, 1639.4 (C═O, C═N) $cm^{-1}$ 1334.7, 1159.2 ($SO_2N$) $cm^1$.

ESI-MS: $(M+H)^+$=503/505/507 ($Cl_2$)

EXAMPLE 39

(R)-N-[(4-Amino-3,5-dichlorophenyl)methyl]-$N^2$-benzoyl-argininamide-hydrochloride a) (R)-N-[(4-Amino-3,5-dichlorophenyl)methyl]-$N^5$-[amino (nitroimino)methyl]-$N^2$-benzoyl-ornithinamide Prepared analogously to Example 38b) from benzoic acid and (R)-N-[(4-amino-3,5-dichlorophenyl)methyl]-$N^5$-[amino(nitroimino)methyl]-ornithinamide and TBTU in a yield of 91% of theory.

Colourless crystals, mp. 235°–237° C.

IR (KBr): 1625.9 $cm^{31\ 1}$ (amide-C═O)

b) (R)-N-[(4-Amino-3,5-dichlorophenyl)methyl]-$N^2$-benzoyl-argininamide-hydrochloride Prepared analogously to Example 14b) from (R)-N-[(4-amino- 3,5-dichlorophenyl)methyl]-$N^5$-[amino(nitroimino) methyl]-$N^2$-benzoyl-ornithinamide by reduction with tin(II) -chloride-dihydrate in the presence of 60% aqueous formic acid.

Yield: 46% of theory.

Colourless crystals, mp. 212°–214° C. (diisopropylether) and $R_f$ 0.65.

IR (KBr): 1652.9 $cm^{-1}$ (amide-C═O).

ESI-MS: $(M+H)^+$=451/453/455 ($Cl_2$)

EXAMPLE 40

(R)-N-[(4-Amino-3,5-dichlorophenyl)methyl]-$N^2$-(2,2-diphenyl-1-oxopropyl)-argininamide-hydrochloride a) (R)-N-[(4-Amino-3,5-dichlorophenyl)methyl]-$N^5$-[amino (nitroimino)methyl]-$N^2$-(2,2-diphenyl-1-oxopropyl)-ornithinamide Prepared analogously to Example 38b) from 2,2-diphenyl-propanoic acid and (R)-N-[(4-amino-3,5-dichlorophenyl)methyl]-$N^5$-[amino(nitroimino)methyl]-ornithinamide and TBTU in a yield of 75% of theory.

Colourless crystals, mp. 221°–223° C.

IR (KBr): 1624.0, 1666.4 $cm^{-1}$ (C═O, C═N)

b) (R)-N-[(4-Amino-3,5-dichlorophenyl)methyl]-$N^2$-(2,2-diphenyl-1-oxopropyl)-argininamide-hydrochloride Prepared analogously to Example 14b) from (R)-N-[(4-amino-3,5-dichlorophenyl)methyl]-$N^5$-[amino(nitroimino)-methyl]-$N^2$-(2,2-diphenyl-1-oxopropyl)-ornithinamide by reduction with tin(II)-chloride-dihydrate in the presence of 60% aqueous formic acid.

Yield: 95% of theory.

Colourless amorphous substance, $R_f$ 0.63.

IR (KBr): 1652.9 $cm^{-1}$ (amide-C═O).

ESI-MS: $(M+H)^+$=555/557/559 ($Cl_2$)

According to MS and NMR investigation the substance is contaminated with (R)-N-[[3,5-dichloro-4-(formylamino) phenyl]methyl]-$N^2$-(2,2-diphenyl-1-oxopropyl)-argininamide or a salt thereof.

EXAMPLE 41

(R)-N-[(4-Amino-3,5-dichlorophenyl)methyl]-$N^2$-(3,4-dichlorobenzoyl)-argininamide-hydrochloride-hydrate a) (R)-N-[(4-Amino-3,5-dichlorophenyl)methyl]-$N^5$-[amino(nitroimino)methyl]-$N^2$-(3,4-dichlorobenzoyl)-ornithinamide Prepared analogously to Example 38b) from 3,4-dichlorobenzoic acid and (R)-N-[(4-amino-3,5-dichlorophenyl)methyl]-$N^5$-[amino(nitroimino)methyl]-ornithine and TBTU in a yield of 88% of theory.

Colourless crystals, mp. >260° C.

IR (KBr): 1668.3, 1627.8 $cm^{-1}$ (C═O)

b) (R)-N-[(4-Amino-3,5-dichlorophenyl)methyl]-$N^2$-(3,4-dichlorobenzoyl)-argininamide-hydrochloride-hydrate Prepared analogously to Example 14b) from (R)-N-[(4-amino-3,5-dichlorophenyl)methyl]-$N^5$-[amino(nitroimino)methyl]-$N^2$-(3,4-dichlorobenzoyl)-ornithinamide by reduction with tin(II)-chloride-dihydrate in the presence of 60% aqueous formic acid.

Yield: 90% of theory.

Colourless crystals, mp. 252°–255° C. and $R_f$ 0.69.

IR (KBr): 1691.5, 1649.0 $cm^{-1}$ (C═O)

ESI-MS: $(M+H)^+$=519/521/523/525/527 ($Cl_4$)

According to MS and NMR investigation the substance is contaminated with (R)-N-[3,5-dichloro-4-(formylamino)phenyl]methyl]-$N^2$-(3,4-dichlorobenzoyl)-argininamide or the salts thereof.

EXAMPLE 42

(R,S)-$N^6$-(Aminoiminomethyl)-$N^2$-(diphenylacetyl)-N-[[3-[(1,2-dihydro-3,5(4H)dioxo-1,2-diphenyl-3H-1,2,4-triazol-4-yl)-methyl]phenyl ]methyl]-lysinamide a) 1,2-Dihydro-1,2-diphenyl-3H-1,2,4-triazol-3,5(4H)-dione 50 g (0.378 Mol) of ethylallophanate and 76.6 g (0.416 Mol) of 1,2-diphenylhydrazine were suspended in 100 ml of anhydrous xylene and refluxed for 6 hours with stirring, during which time ammonia was released. The solvent was distilled off, the residue was mixed with 150 ml of xylene once more and refluxed for 1 hour. The mixture was left to cool, the reaction product was suction filtered, and thoroughly washed with cold xylene. After drying in vacuo, 60.0 g (63% of theory) of colourless crystals were obtained, mp. 216°–217° C.

b) 3-[(1,2-Dihydro-3,5(4H)-dioxo-1,2-diphenyl-3H-1,2,4-triazol-4-yl)methyl]-benzonitrile To a solution of 10.5 g (41.5 mMol) of 1,2-dihydro-1,2-diphenyl-3H-1,2,4-triazol-3,5(4H)-dione in 40 ml of anhydrous dimethylformamide were added, with external cooling with ice, 4.5 g (40.1 mMol) of potassium tert.-butoxide and, after half an hours' stirring at this temperature, a solution of 8.0 g (40.8 mMol) of 3-(bromomethyl)-benzonitrile in 10 ml of absolute dimethylformamide and the mixture was then left to warm up to ambient temperature overnight. Finally it was heated to 70° C. for 1 hour, the solvent was eliminated in vacuo, the residue remaining was taken up in water and suction filtered. After washing with diethylether and drying in the air, 13.6 g (92% of theory) of colourless crystals were obtained.

c) 3-[(1,2-Dihydro-3,5(4H)-dioxo-1,2-diphenyl-3H-1,2,4-triazol-4-yl)methyl]-benzenemethylamine 12.0 g (32.6 mmol) of 3-[(1,2-dihydro-3,5(4H)-dioxo-1,2-diphenyl-3H-1,2,4-triazol-4-yl)methyl]-benzonitrile were dissolved in 500 ml of ammonia-saturated methanol and after the addition of 3 g of Raney-Nickel the mixture was hydrogenated at ambient temperature under 5 bar of hydrogen pressure until the uptake of hydrogen had ceased. After working up 8.0 g (66% of theory) of a colourless crystalline substance were obtained.

d) (R,S)-$N^2$-(Diphenylacetyl)-$N^6$-[(phenylmethoxy)-carbonyl]-lysine

Prepared analogously to Example 1a) from diphenylacetylchloride and (R,S)-$N^6$-[(phenylmethoxy)carbonyl]-lysine in a yield of 84% of theory.

Colourless crystals, mp. 99°–100° C.

IR (KBr): 1735 (ester-C═O), 1715 (acid-C═O), 1650 (amide-C═O) $cm^{-1}$ e) (R,S)-$N^2$-(Diphenylacetyl)-N-[[3-[(1,2-dihydro-3,5(4H)-dioxo-1,2-diphenyl-3H-1,2,4-triazol-4-yl)methyl]phenyl]-methyl]-$N^6$-[(phenylmethoxy)-carbonyl]-lysinamide Prepared analogously to Example 5d) from (R,S)-$N^2$-(diphenylacetyl)-$N^6$-[(phenylmethoxy)carbonyl]-lysine and 3-[(1,2-dihydro-3,5(4H)-dioxo-1,2-diphenyl-3H-1,2,4-triazol-4-yl)methyl]-benzenemethylamine and TBTU in a yield 91% of theory.

Colourless crystals.

IR (KBr): 1720, 1685, 1640 $cm^{-1}$ (C═O).

ESI-MS: $(M+Na)^+$=851 f) (R,S)-$N^2$-(Diphenylacetyl)-N-[[3-[(1,2-dihydro-3,5(4H)-dioxo-1,2-diphenyl-3H-1,2,4-triazol-4-yl)methyl]phenyl]methyl]-lysinamide A mixture of 3.0 g (3.619 mMol) of (R,S)-$N^2$-(diphenylacetyl)-N-[[3-[(1,2-dihydro-3,5(4H)-dioxo-1,2-diphenyl-3H-1,2,4-triazol-4-yl)methyl]phenyl]methyl]-$N^6$-[(phenylmethoxy)carbonyl]-lysinamide, 50 ml of methanol, 40 ml of tetrahydrofuran, 0.5 ml of trifluoroacetic acid and 0.3 g of 10% palladium/animal charcoal was shaken in a Parr apparatus for 72 hours at ambient temperature under a pressure of 50 psi. The residue remaining after the elimination of the catalyst and solvents was purified by column chromatography (silica gel Baker 30–60 μm; mobile phase: ethyl acetate/methanol/cyclohexane/conc. aqueous ammonia=8/1/1/0.1 (v/v/v/v)). 1.2 g (40% of theory) of a colourless, highly viscous, amorphous substance were obtained.

g) (R,S)-$N^6$-(Aminoiminomethyl)-$N^2$-(diphenylacetyl)-N-[[3-[(1,2-dihydro-3,5(4H)-dioxo-1,2-diphenyl-3H-1,2,4-triazol-4-yl)methyl]phenyl]methyl]-lysinamide A mixture of 1.1 g (1.583 mMol) of (R,S)-$N^2$-(diphenylacetyl)-N-[[3-[(1,2-dihydro-3,5(4H)-dioxo-1,2-diphenyl-3H-1,2,4-triazol-4-yl)methyl]phenyl]methyl]-lysinamide, 600 mg (2.982 mmol) of 3,5-dimethylpyrazole-1-carboxylic acid amidinium nitrate, 0.8 ml (5.74 mMol) of triethylamine and 25 ml of tetrahydrofuran was stirred at ambient temperature for 30 hours and then poured into copious amounts of water. The oil remaining after the aqueous phase was decanted off was purified by column chromatography (Baker silica gel 30–60 μm) using initially ethyl acetate, followed by methanol, and finally methanol/glacial acetic acid=95/5 (v/v). The suitable eluates were combined, evaporated down in vacuo, taken up in methanol and made alkaline with sodium hydroxide. 800 mg (69% of theory) of a colourless amorphous substance were obtained, $R_f$ 0.75.

IR (KBr): 1620–1690 $cm^{-1}$ (C═O).

ESI-MS: $(M+H)^+$=737

EXAMPLE 43

$N^2$-(Diphenylacetyl)-N-(3,3-diphenylpropyl)-argininamide a) $N^5$-[Amino(nitroimino)methyl]-$N^2$-(diphenylacetyl)-N-(3,3-diphenylpropyl)-ornithinamide Prepared analogously to Example 5d) from (R)-$N^5$-[amino(nitroimino)methyl]-$N^2$-(diphenylacetyl)-ornithine, 3,3-diphenyl-propylamine and TBTU in a yield of 52% of theory.

Colourless crystalline substance.

IR ($CH_2Cl_2$): 1620, 1655 $cm^{-1}$ (C═O, C═N)

b) $N^2$-(Diphenylacetyl)-N-(3,3-diphenylpropyl)-argininamide

Prepared analogously to Example 1c) from $N^5$-[amino(nitroimino)methyl]-$N^2$-(diphenylacetyl)-N-(3,3-diphenylpropyl)-ornithinamide by catalytic hydrogenation in the presence of palladium black and 80% aqueous acetic acid in a yield of 53% of theory.

Colourless amorphous substance, $R_f$ 0.72.

IR ($CH_2Cl_2$): 1630–1690 $cm^{-1}$ (C═O, C═N)

EI-MS: $(M+H)^+$=562

EXAMPLE 44

$N^2$-(Diphenylacetyl)-N-(2,2-diphenylethyl)-argininamide a) $N^5$-[Amino(nitroimino)methyl]-$N^2$-(diphenylacetyl)-N-(2,2-diphenylethyl)-ornithinamide Prepared analogously to Example 5d) from (R)-$N^5$-[amino(nitroimino)methyl]-$N^2$-(diphenylacetyl)-ornithine, 2,2-diphenyl-ethanamine and TBTU in a yield of 98% of theory.

Colourless amorphous substance.

IR (KBr): 1635 $cm^{-1}$ (C═O)

b) $N^2$-(Diphenylacetyl)-N-(2,2-diphenylethyl)-argininamide

Prepared analogously to Example 1c) from $N^5$-[[amino(nitroimino)methyl]-$N^2$-(diphenylacetyl)-N-(2,2-diphenylethyl)-ornithinamide by catalytic hydrogenation in the presence of palladium black and 80% aqueous acetic acid in a yield of 100% of theory.

Colourless amorphous substance, $R_f$ 0.77.

IR ($CH_2Cl_2$): 1630–1690 $cm^{-1}$ (C═O)

ESI-MS: $(M+H)^+$=548

EXAMPLE 45

$N^2$-(Diphenylacetyl)-N-[2-(5-methoxy-1H-indol-3-yl)-ethyl]-argininamide a) $N^5$-[Amino(nitroimino)methyl]-$N^2$-(diphenylacetyl)-N-[2-(5-methoxy-1H-indol-3-yl)ethyl]-ornithinamide Prepared analogously to Example 5d) from (R)-$N^5$-[amino(nitroimino)methyl]-$N^2$-(diphenylacetyl)-ornithine, 5-methoxytryptamine and TBTU in a yield of 36% of theory.

Colourless crystals.

b) $N^2$-(Diphenylacetyl)-N-[2-(5-methoxy-1H-indol-3-yl)-ethyl]-argininamide

Prepared analogously to Example 1c) from $N^5$-[amino(nitroimino)methyl]-$N^2$-(diphenylacetyl)-N-[2-(5-methoxy-1H-indol-3-yl)-ethyl]-ornithinamide by catalytic hydrogenation in the presence of palladium black and 80% aqueous acetic acid in a yield of 68% of theory.

Colourless amorphous substance, $R_f$ 0.70.

IR (KBr): 1620–1690 $cm^{-1}$ (C═O)

EI-MS: $(M+H)^+$=541

EXAMPLE 46

N-[[2,3-Dihydro-2-[(diphenylamino)carbonyl]-1H-isoindol-5-yl]methyl]-$N^2$-(diphenylacetyl)-argininamide a) $N^5$-[Amino(nitroimino)methyl]-N-[[2,3-dihydro-2-[(diphenylamino)carbonyl]-1H-isoindol-5-yl)methyl]-$N^2$-(diphenylacetyl)-ornithinamide Prepared analogously to Example 5d) from (R)-$N^5$-[amino(nitroimino)methyl]-$N^2$-(diphenylacetyl)-ornithine, 2,3-dihydro-2-[(diphenylamino)carbonyl]-1H-isoindol-5-methylamine (mp.: 129°–130° C.; prepared from methyl 3,4-dimethylbenzoate via methyl 3,4-bis(bromomethyl)-benzoate[N-bromosuccinimide/azoisobutyronitrile]; methyl 2,3-dihydro-2-(phenylmethyl)-1H-isoindol-5-carboxylate [benzenemethanamine], mp.: 72° C. (tert.-butylmethylether); 2,3-dihydro-2-(phenylmethyl)-1H-isoindole-5-carboxylic acid[aqueous-ethanolic sodium hydroxide solution]; 2,3-dihydro-2-(phenylmethyl)-1H-isoindole-5-carboxylic acid chloride-hydrochloride [thionylchloride], mp.: 226°–228° C. (decomp.); 2,3-dihydro- 2-(phenylmethyl)-1H-isoindole-5-carboxamide [conc. aqueous ammonia]; 2,3-dihydro-2-(phenylmethyl)-1H-isoindole-5-methanamine[lithium aluminium hydride]; N-[(tert.-butyloxy)carbonyl]-2,3-dihydro-2-(phenylmethyl)-1H-isoindole-5-methanamine (di-tert.-butylpyrocarbonate], mp.: 114°–115° C.; N-[(tert.-butyloxy)carbonyl]-2,3-dihydro-1H-isoindole-5-methanamine [hydrogen/palladium/animal charcoal], mp.: 114°–115°; N-[(tert.-butyloxy)carbonyl]-2,3-dihydro-2-[(diphenylamino)carbonyl]-1H-isoindole-5-methanamine [diphenylcarbamoylchloride], and finally by reacting with methanolic hydrogen chloride solution and then with sodium hydroxide solution) and TBTU in a yield of 34% of theory.

Colourless crystals.

IR ($CH_2Cl_2$): 1630, 1655 $cm^{-1}$ (C═O)

b) N-[[2,3-Dihydro-2-[(diphenylamino)carbonyl]-1H-isoindol-5-yl]methyl]-$N^2$-(diphenylacetyl)-argininamide Prepared analogously to Example 1c) from $N^5$-[amino(nitroimino)methyl]-N-[(2,3-dihydro-2-[(diphenylamino)carbonyl]-1H-isoindol-5-yl]methyl]-$N^2$-(diphenylacetyl)-ornithinamide by catalytic hydrogenation in the presence of palladium black and 80% aqueous acetic acid in a yield of 60% of theory.

Colourless amorphous substance, $R_f$ 0.68.

IR (KBr): 1630–1690 $cm^{-1}$ (C═O)

EI-MS: $(M+H)^+$=694

EXAMPLE 47

$N^2$-(Diphenylacetyl)-N-[3-[1-[2-[5,11-dihydro-6(6H)-oxopyrido[2,3-b][1,4]benzodiazepin-5-yl]-2-oxoethyl]-4-piperidinyl]propyl)-argininamide a) $N^5$-[Amino(nitroimino)methyl]-$N^2$-(diphenylacetyl)-N-[3-[1-[2-[5,11-dihydro-6(6H)oxo-pyrido[2,3-b]-[1,4]benzodiazepin-5-yl]-2-oxoethyl]4-piperidinyl]-propyl]-ornithinamide Prepared analogously to Example 8a) from (R)-$N^5$-[amino(nitroimino)methyl)-$N^2$-(diphenylacetyl)-ornithine, [3-[1-[2-[5,11-dihydro-6(6H)oxo-pyrido[2,3-b][1,4]-benzodiazepin-5-yl]-2-oxoethyl]-4-piperidinyl]-propanamine (mp.: 232°–234° C.; prepared from 2-bromo-N-[(tert.-butyloxy)carbonyl]-ethanamine via N-[(tert.-butyloxy)carbonyl]-3-(4-pyridinyl)-propanamine[4-picolin/n-butyllithium]; N-[(tert.-butyloxy)carbonyl]-3-(4-piperidinyl)propanamine-3-[1-[2-[5,11-dihydro-6(6H)oxo-pyrido[2,3-b][1,4]benzodiazepin-5-yl]-2-oxoethyl]-4-piperidinyl]-propanamine[11-(chloroacetyl)-5,11-dihydro-6H-pyrido[2,3-b][1,4]benzodiazepin-6-one] and treatment with a solution of hydrogen bromide in glacial acetic acid) and TBTU in a yield of 53% of theory.

Colourless amorphous substance which was further processed in its crude state.

b) $N^2$-(Diphenylacetyl)-N-[3-[1-[2-[5,11-dihydro-6(6H)-oxopyrido[2,3-b][1,4]benzodiazepin-5-yl]-2-oxoethyl]-4-piperidinyl]propyl]-argininamide Prepared analogously to Example 1c) from $N^5$-[amino (nitroimino)-methyl]-$N^2$-(diphenylacetyl)-N-[3-[1-[2-[5,11-dihydro-6(6H)-oxo-pyrido[2,3-b][1,4]-benzodiazepin-5-yl]-2-oxoethyl]-4-piperidinyl]propyl]-ornithinamide by catalytic hydrogenation in the presence of palladium black and 80% aqueous acetic acid in a yield of 60% of theory.

Colourless crystals, mp. 172°–174° C. and $R_f$ 0.23.

IR (KBr): 1630–1690 $cm^{-1}$ (C═O)

ESI-MS: $(M+H)^+$=744

EXAMPLE 48

N-[(1,1'-Biphenyl)-2-ylmethyl]-$N^2$-(diphenylacetyl)-argininamide-acetate a) $N^5$-[Amino(nitroimino)methyl]-N-([1,1'-biphenyl]-2-yl-methyl)-$N^2$-(diphenylacetyl)-ornithinamide Prepared analogously to Example 5d) from (R)-$N^5$-[amino(nitroimino)methyl]-$N^2$-(diphenylacetyl)-ornithine, [1,1-biphenyl]-2-methanamine and TBTU in a yield of 42% of theory.

Colourless crystals, mp. 205°–207° C.

IR (KBr): 1635, 1655, 1680 $cm^{-1}$ (c═O, C═N)

ESI-MS:

$(M+H)^+$=579

$(M+Na)^+$=601

$(2M+Na)^+$=1179 b) N-([1,1'-Biphenyl]-2-ylmethyl)-$N^2$-(diphenylacetyl)-argininamide-acetate

Prepared analogously to Example 1c) from $N^5$-[amino (nitroimino)methyl]-N-([1,1'-biphenyl]-2-ylmethyl)-$N^2$-(diphenylacetyl)-ornithinamide by catalytic hydrogenation in the presence of palladium black and 80% aqueous acetic acid in a yield of 89% of theory.

Colourless crystals, mp. 106°–108° C. and $R_f$ 0.75.

IR ($CH_2Cl_2$): 1630–1690 $cm^{-1}$ (C═O)

EI-MS: $(M+H)^+$=534

EXAMPLE 49

$N^2$-(Diphenylacetyl)-N-[(4-hydroxy-3-methoxyphenyl)-methyl]argininamide-acetate a) $N^5$-[Amino(nitroimino)methyl]-$N^2$-(diphenylacetyl)-N-[(4-hydroxy-3-methoxyphenyl)methyl3-ornithinamide Prepared analogously to Example 5d) from (R)-$N^5$-[amino(nitroimino)methyl]-$N^2$-(diphenylacetyl)-ornithine, 4-hydroxy-3-methoxybenzenmethanamine and TBTU in a yield of 14% of theory.

Colourless crystals, mp. 197°–198° C. (ethyl acetate).

b) $N^2$-(Diphenylacetyl)-N-[(4-hydroxy-3-methoxyphenyl)-methyl]-argininamide-acetate Prepared analogously to Example 1c) from $N^5$-[amino (nitroimino)methyl]-$N^2$-(diphenylacetyl)-N-[(4-hydroxy-3-methoxyphenyl)-methyl]-ornithinamide by catalytic hydrogenation in the presence of palladium black and 80% aqueous acetic acid in a yield of 97% of theory.

Colourless amorphous substance, $R_f$ 0.65.

EI-MS: $(M+H)^+$=504

EXAMPLE 50

N-[(3,4-Dimethoxyphenyl)methyl]-$N^2$-(diphenylacetyl)-argininamide a) $N^5$-[Amino(nitroimino)methyl]-N-[(3,4-dimethoxyphenyl)-methyl]-$N^2$-(diphenylacetyl)-ornithinamide Prepared analogously to Example 5d) from (R)-$N^5$-[amino(nitroimino)methyl]-$N^2$-(diphenylacetyl)-ornithine, 3,4-dimethoxybenzenmethanamine and TBTU in a yield of 68% of theory.

Colourless crystals, mp. 135°–137° C. (methanol).

IR (KBr): 1640 $cm^{-1}$ (C═O)

ESI-MS:

$(M+H)^+$=563

$(M+Na)^+$=585

$(M+K)^+$=601 b) N-[(3,4-Dimethoxyphenyl)methyl]-$N^2$-(diphenylacetyl)-argininamide

Prepared analogously to Example 1c) from $N^5$-[amino (nitroimino)methyl)-N-[(3,4-dimethoxyphenyl)-methyl]-$N^2$-(diphenylacetyl)-ornithinamide by catalytic hydrogenation in the presence of palladium black and 80% aqueous acetic acid in a yield of 58% of theory. Colourless amorphous substance $R_f$ 0.62.

ESI-MS: $(M+H)^+$=518

EXAMPLE 51

N-(Diphenylacetyl)-N-[(3-hydroxy-4-methoxyphenyl)-methyl]-argininamide-acetate a) $N^5$-[Amino(nitroimino)methyl]-$N^2$-(diphenylacetyl)-N-[(3-hydroxy-4-methoxyphenyl)methyl]-ornithinamide Prepared analogously to Example 5d) from (R)-$N^5$-[amino(nitroimino)methyl]-$N^2$-(diphenylacetyl)-ornithine, 3-hydroxy-4-methoxybenzenmethanamine (mp.: 162°–163° C. [methanol], prepared from 3-hydroxy-4-methoxybenzaldehyde by catalytic hydrogenation in the presence of ammonia and Raney-Nickel) and TBTU in a yield of 66% of theory.

Colourless crystals, mp. 183°–185° C. (ethyl acetate).

IR (KBr): 1675, 1655, 1630 $cm^{-1}$ (C═O, C═N)

ESI-MS:

$(M+H)^+$=549

$(M+Na)^+$=571

$(M+K)^+$=587

$(2M+Na)^+$=1119 b) $N^2$-(Diphenylacetyl)-N-[(3-hydroxy-4-methoxyphenyl)-methyl]-argininamide-acetate Prepared analogously to Example 1c) from $N^5$-[amino (nitroimino)methyl]-$N^2$-(diphenylacetyl)-N-[(3-hydroxy-4-methoxyphenyl)methyl)-ornithinamide by catalytic hydrogenation in the presence of palladium black and 80% aqueous acetic acid in a yield of 90% of theory.

Colourless crystals mp. 152° C. and $R_f$ 0.67.

IR (KBr): 1620–1690 $cm^{-1}$ (C═O)

ESI-MS: $(M+H)^+$=504

EXAMPLE 52

(R,S)-N-[(4-Amino-3,5-dibromophenyl)methyl]-$N^6$-(aminoiminomethyl)-$N^2$-(diphenylacetyl)-lysinamide a) (R,S)-$N^2$-(Diphenylacetyl)-lysine Prepared analogously to Example 27c) from (R,S)-$N^2$-(diphenylacetyl)-$N^6$-[(phenylmethoxy)carbonyl]-lysine by catalytic hydrogenation in the presence of palladium/animal charcoal.

Yield: 68% of theory.

Colourless crystals.

IR (KBr): 1660 $cm^{-1}$ (C═O)

b) (R,S)-$N^6$-[(tert.-Butyloxy)carbonyl]-$N^2$-(diphenylacetyl) -lysine

To a solution of 1.0 g (2.938 mMol) of (R,S)-$N^2$-(diphenylacetyl)-lysine in 6 ml (6 mMol) of 1N sodium hydroxide solution and 10 ml of tetrahydrofuran were added 0.66 g (3.024 mmol) of di-tert.-butyl-dicarbonate and the mixture was then stirred for 1 hour at ambient temperature. It was diluted with 20 ml of water, extracted once with 30 ml of tert.-butyl-methylether and the aqueous phase was then freed from organic solvents by distillation in vacuo. The aqueous phase was then acidified with 20% aqueous citric acid solution, whereupon the precipitate was separated off by decanting and the residue was taken up in acetone. The acetone solution was dried over sodium sulphate and evaporated down in vacuo. 1.1 g (85% of theory) of a substance which slowly crystallised after some days was obtained.

IR ($CH_2Cl_2$): 1715 (ester-C═O), 1675 (amide-C═O) $cm^{-1}$ c) (R,S)-N-[(4-Amino-3,5-dibromophenyl)methyl]-$N^6$-[(tert.-butyloxy)carbonyl]-$N^2$-(diphenylacetyl)-lysinamide To a solution of 0.75 g (1.7 mMol) of (R,S)-$N^6$-[(tert.-butyloxy)carbonyl]-$N^2$-(diphenylacetyl)-lysine in 10 ml of tetrahydrofuran were added first 0.325 g (2.0 mMol) of N,N'-carbonyldiiiaidazole, and then, after 30 minutes' stirring at 40° C., 0.56 g (2.0 mMol) of 4-amino-3,5-dibromobenzylmethylamine and the mixture was stirred for a further hour without external heating. The reaction mixture was poured into 30 ml of water, 15 ml of tert.-butylmethylether were added and the water-insoluble mass was stirred until it had crystallised. It was suction filtered, the precipitate was washed thoroughly with water and tert.-butyl-methylether, dried in vacuo and 0.8 g (67% of theory) of colourless crystals were obtained, mp. 169°–171° C.

IR (KBr): 1685, 1640 $cm^{-1}$ (C═O)

d) (R,S)-N-[(4-Amino-3,5-dibromophenyl)methyl]-$N^2$-(diphenylacetyl)-lysinamide Prepared analogously to Example 36b) from (R,S)-N-[(4-amino-3,5-dibromophenyl)methyl]-$N^6$-[(tert.-butyloxy)carbonyl]-$N^2$-(diphenylacetyl)-lysinamide by treatment with methanolic hydrochloric acid solution in a yield of 99% of theory.

Colourless crystals mp. 162°–163° C.

IR (KBr): 1640 $cm^{-1}$ (C═O).

MS: $M^+$=600/602/604 ($Br_2$)

e) (R,S)-N-[(4-Amino-3,5-dibromophenyl)methyl]-$N^6$-(aminoiminomethyl)-$N^2$-(diphenylacetyl)-lysinamide Prepared analogously to Example 42g) from (R,S)-N-[(4-amino-3,5-dibromophenyl)methyl]-$N^2$-(diphenylacetyl)-lysinamide and 3,5-dimethylpyrazole-1-carboxylic acid amidinium nitrate in a yield of 78% of theory.

Colourless crystals mp. 139°–140° C. (acetone).

IR (KBr): 1640 $cm^{-1}$

ESI-MS: $(M+H)^+$=643/645/647 ($Br_2$)

EXAMPLE 53

$N^2$-(Diphenylacetyl)-N-[2-(4-imidazolyl)ethyl]-argininamide a) $N^5$-[Amino(nitroimino)methyl]-$N^2$-(diphenylacetyl)-N-[2-(4-imidazolyl)ethyl]-ornithinamide Prepared analogously to Example 5d) from (R)-$N^5$-[amino(nitroimino)methyl]-$N^2$-(diphenylacetyl)-ornithine, histamine and TBTU in a yield of 45% of theory.

Colourless amorphous substance, $R_f$ 0.45 (Merck ready-made TLC plates, silica gel 60 $F_{254}$; eluant: ethyl acetate).

b) $N^2$-(Diphenylacetyl)-N-[2-(4-imidazolyl)ethyl]-argininamide

Prepared analogously to Example 1c) from $N^5$-[amino(nitroimino)methyl]-$N^2$-(diphenylacetyl)-N-[2-(4-imidazolyl)ethyl]-ornithinamide by catalytic hydrogenation in the presence of palladium black and 80% aqueous acetic acid in a yield of 88% of theory.

Colourless amorphous substance, $R_f$ 0.34.

IR (KBr): 1630–1690 $cm^{-1}$ (C═O)

ESI-MS:

$(M+H)^+$=462

$(M+2H)^{++}$=231

EXAMPLE 54

(R,S)-$N^2$-(Diphenylacetyl)-N-[(4-hydroxyphenyl)methyl]-phenylalaninamide a) (R,S)-$N^2$-(Diphenylacetyl)-phenylalanine Prepared analogously to Example 1a) from diphenylacetyl-chloride and (R,S)-phenylalanine in a yield of 70% of theory.

Colourless crystals, mp. 154° C. (methanol/water=4/1 (v/v)).

IR (KBr): 1710 (carboxylic acid-C═O), 1660 (amide-C═O) $cm^{-1}$ b) (R,S)-$N^2$-(Diphenylacetyl)-N-[(4-hydroxyphenyl)-methyl]phenylalaninamide Prepared analogously to Example 8a) from (R,S)-$N^2$-(diphenylacetyl)-phenylalanine, 4-hydroxybenzenemethanamine and TBTU in a yield of 43% of theory.

Colourless crystals, mp. 117°–119° C. and $R_f$ 0.95.

IR (KBr): 1645, 1630 $cm^{-1}$ (C═O)

EXAMPLE 55

N-[(3,5-Dimethyl-4-hydroxyphenyl)methyl)-$N^2$-(diphenylacetyl)-argininamide-acetate a) $N^5$-[Amino(nitroimino)methyl]-N-[(3,5-dimethyl-4-hydroxyphenyl)methyl]-$N^2$-(diphenylacetyl)-ornithinamide Prepared analogously to Example 8a) from (R)-$N^5$-[amino(nitroimino)methyl]-$N^2$-(diphenylacetyl)-ornithine, 3,5-dimethyl-4-hydroxybenzenemethanamine (prepared from 3,5-dimethyl-4-hydroxybenzaldehyde and ammonia by catalytic hydrogenation in the presence of Raney-nickel) and TBTU.

Yield: 50% of theory,

Colourless crystals, mp. 194° C. (ethyl acetate).

ESI-MS:

$(M+H)^+$=547

$(M+Na)^+$=569

$(2M+Na)^+$=1115

$(M+K)^+$=585 b) N-[(3,5-Dimethyl-4-hydroxyphenyl)methyl]-$N^2$-(diphenylacetyl)-argininamide-acetate Prepared analogously to Example 1c) from $N^5$-[amino(nitroimino)methyl]-N-[(3,5-dimethyl-4-hydroxyphenyl)methyl]-$N^2$-(diphenylacetyl)-ornithinamide by catalytic hydrogenation in the presence of palladium black and 80% aqueous acetic acid in a yield of 90% of theory.

Colourless amorphous substance, $R_f$ 0.75.

IR (KBr): 1620–1690 $cm^{-1}$ (C═O)

ESI-MS: $(M+H)^+$=502

EXAMPLE 56

N-[(1H-Benzimidazol-5-yl)methyl]-$N^2$-(diphenylacetyl)-argininamide a) $N^5$-[Amino(nitroimino)methyl]-N-[(1H-benzimidazol-5-yl)-methyl]-$N^2$-(diphenylacetyl)-ornithinamide Prepared analogously to Example 8a) from (R)-$N^5$-[amino(nitroimino)methyl]-$N^2$-(diphenylacetyl)-ornithine, 1H-benzimidazole-5-methanamine (mp.: 134° C.; prepared from 1H-benzimidazole-5-carboxylic acid via 1H-benzimidazole-5-carbonamide [ammonium carbonate], mp.: 266° C.; 1H-benzimidazol-5-carbonitrile [phosphorus oxychloride/piperidine], mp.: 230°–231C; then catalytic hydrogenation in the presence of ammonia and Raney-nickel) and TBTU.

Yield: 36% of theory,

Colourless crystals, mp. 158°–160° C.

IR (KBr): 1635 $cm^{-1}$ (C═O)

ESI-MS:

$(M+H)^+$=543

$(M+Na)^+$=565 b) N-[(1H-Benzimidazol-5-yl)methyl]-$N^2$-(diphenylacetyl)-argininamide

Prepared analogously to Example 1c) from $N^5$-[amino (nitroimino)methyl]-N-[(1H-benzimidazol-1-yl)-methyl]-$N^2$-(diphenylacetyl)-ornithinamide by catalytic hydrogenation in the presence of palladium black and 80% aqueous acetic acid in a yield of 21% of theory.

Colourless amorphous substance, $R_f$ 0.45.

IR (KBr): 1620–1690 $cm^{-1}$ (C═O)

ESI-MS: $(M+H)^+$=498

EXAMPLE 57

$N^2$-(Diphenylacetyl)-N-[(4-hydroxy-3-methylphenyl)-methyl]argininamide-acetate a) $N^5$-[Amino(nitroimino)methyl]-$N^2$-(diphenylacetyl)-N-[(4-hydroxy-3-methylphenyl)methyl]-ornithinamide Prepared analogously to Example 8a) from (R)-$N^5$-[amino(nitroimino)methyl]-$N^2$-(diphenylacetyl)-ornithine, 4-hydroxy-3-methylbenzenemethanamine (mp.: 108° C.; prepared from 4-hydroxy-3-methylbenzaldehyde and ammonia by catalytic hydrogenation in the presence of Raney-nickel) and TBTU in a yield of 71% of theory.

Colourless amorphous substance.

IR (KBr): 1620–1690 $cm^{-1}$ (C═O).

ESI-MS:

$(M+H)^+$=533

$(M+Na)^+$=555 b) $N^2$-(Diphenylacetyl)-N-[(4-hydroxy-3-methylphenyl) methyl]-argininamide-acetate Prepared analogously to Example 1c) from $N^5$-[amino (nitroimino)methyl]-$N^2$-(diphenylacetyl)-N-[(4-hydroxy-3-methylphenyl)methyl]-ornithinamide by catalytic hydrogenation in the presence of palladium black and 80% aqueous acetic acid in a yield of 83% of theory.

Colourless amorphous substance, $R_f$ 0.72.

IR (KBr): 1620–1690 $cm^{-1}$ (C═O)

ESI-MS: $(M+H)^+$=488

EXAMPLE 58

N-[[4-(Aminocarbonyl)phenyl]methyl]-$N^2$-(diphenylacetyl)-argininamide-acetate a) N-[[4-(Aminocarbonyl)phenyl]methyl]-$N^5$-[amino (nitroimino)methyl]-$N^2$-(diphenylacetyl)-ornithinamide Prepared analogously to Example 8a) from (R)-$N^5$-[amino(nitroimino)methyl]-$N^2$-(diphenylacetyl)-ornithine, 4-(aminocarbonyl)-benzenemethanamine (mp.: 146° C.; prepared from 4-cyanobenzoylchloride via 4-cyanobenzamide (mp.: 227°) by catalytic hydrogenation in the presence of ammonia and Raney-nickel) and TBTU in a yield of 76% of theory.

Colourless crystals, mp.: 215°–216° C. (decomp.) (ethyl acetate).

IR (KBr): 1665, 1640 $cm^{-1}$ (C═O, C═N).

b) N-[[4-(Aminocarbonyl)phenyl]methyl]-$N^2$-(diphenylacetyl)-argininamide-acetate Prepared analogously to Example 1c) from N-[[4-(aminocarbonyl)phenyl]methyl]-$N^5$-[amino-(nitroimino) methyl]-$N^2$-(diphenylacetyl)-ornithinamide by catalytic hydrogenation in the presence of palladium black and 80% aqueous acetic acid in a yield of 85% of theory.

Colourless amorphous substance, $R_f$ 0.60.

IR (KBr): 1630–1690 $cm^{-1}$ (C═O)

ESI-MS: $(M+H)^+$=501

EXAMPLE 59

(R,S)-$N^6$-(Aminoiminomethyl)-N-[(3,5-dibromo-4-hydroxyphenyl)methyl]-$N^2$-(diphenylacetyl)-lysinamide a) (R,S)-$N^6$-[(tert.-Butyloxy)carbonyl]-N-[(3,5-dibromo-4-hydroxyphenyl)methyl]-$N^2$-(diphenylacetyl)-lysinamide Prepared analogously to Example 52c) from (R,S)-$N^6$-[(tert.-butyloxy)carbonyl]-$N^2$-(diphenylacetyl)-lysine, N,N'-carbonyl-diimidazole and 3,5-dibromo-4-hydroxybenzenemethanamine (Mp.: 179°–181° C.; prepared from 3,5-dibromo-4-hydroxybenzonitrile by reduction with lithium aluminium hydride) in a yield of 67% of theory.

Colourless crystals.

IR (KBr): 1690, 1635 $cm^{-1}$ (C═O)

b) (R,S)-N-[(3,5-Dibromo-4-hydroxyphenyl)methyl]-$N^2$-(diphenylacetyl)-lysinamide Prepared analogously to Example 23b) from (R,S)-$N^6$-[(tert.-butyloxy)carbonyl]-N-[(3,5-dibromo-4-hydroxyphenyl)methyl]-$N^2$-(diphenylacetyl)-lysinamide by the action of trifluoroacetic acid in a yield of 73% of theory (mp.: 244°–246° C.).

IR (KBr): 1680, 1640 $cm^{-1}$ (C═O)

MS: $M^+$=601/603/605 ($Br_2$)

c) (R,S)-$N^6$-(Aminoiminomethyl)-N-[(3,5-dibromo-4-hydroxyphenyl)methyl]-$N^2$-(diphenylacetyl)-lysinamide Prepared analogously to Example 42g), but using dimethylformamide as solvent instead of tetrahydrofuran, from (R,S)-N-[(3,5-dibromo-4-hydroxyphenyl)methyl]-$N^2$-(diphenylacetyl)-lysinamide and 3,5-dimethylpyrazole-1-carboxylic acid amidinium nitrate in a yield of 47% of theory.

Colourless crystals, mp. 186–188° C. and $R_f$ 0.72.

IR (KBr): 1655 $cm^{-1}$ (C═O)

EI-MS: $(M+H)^+$=644/646/648 ($Br_2$)

EXAMPLE 60

(R,S)-$N^6$-(Aminoiminomethyl)-$N^2$-(diphenylacetyl)-N-[(4-hydroxyphenyl)methyl]-lysinamide a) (R,S)-$N^6$-[(tert.-Butyloxy)carbonyl]-$N^2$-(diphenylacetyl) -N-[(4-hydroxyphenyl)methyl]-lysinamide Prepared analogously to Example 8a) from (R,S)-$N^6$-[(tert.-butyloxy)carbonyl]-$N^2$-(diphenylacetyl)-lysine, 4-hydroxybenzenemethanamine and TBTU in a yield of 51% of theory.

Colourless crystals, mp. 161°–162° C.

IR (KBr):

3280 (OH, NH), 1695, 1680, 1635 (C═O), 1520 (amide-II) $cm^{-1}$ b) (R,S)-$N^2$-(Diphenylacetyl)-N-[(4-hydroxyphenyl)-methyl]-lysinamide Prepared analogously to Example 23b) from (R,S)-$N^6$-[(tert.-butyloxy)carbonyl]-$N^2$-(diphenylacetyl)-N-[(4-hydroxyphenyl)methyl]lysinamide by the action of trifluoroacetic acid in a yield of 78% of theory.

Colourless crystals, mp. 198°–200° C. (acetone).

IR (KBr): 1650, 1680 $cm^{-1}$ (C═O)

c) (R,S)-$N^6$-(Aminoiminomethyl)-$N^2$-(diphenylacetyl)-N-[(4-hydroxyphenyl)methyl]-lysinamide Prepared analogously to Example 59c) from (R,S)-$N^2$-diphenylacetyl)-N-[(4-hydroxyphenyl)methyl]-lysinamide and 3,5-dimethylpyrazole-1-carboxylic acid amidinium nitrate in a yield of 37% of theory.

Colourless crystals, mp. 194°–197° C. and $R_f$ 0.72.

IR (KBr): 1640 $cm^{-1}$ (C═O).

EI-MS: $(M+H)^+$=488

EXAMPLE 61

(R,S)-$N^6$-(Aminoiminomethyl)-$N^2$-(diphenylacetyl)-N-[(4-methoxyphenyl)methyl)-lysinamide a) (R,S)-$N^6$-[(tert.-Butyloxy)carbonyl]-$N^2$-(diphenylacetyl)-N-[(4-methoxyphenyl)methyl]-lysinamide Prepared analogously to Example 8a) from (R,S)-$N^6$-[(tert.-butyloxy)carbonyl]-$N^2$-(diphenylacetyl)-lysine, 4-methoxybenzenemethanamine and TBTU in a yield of 54% of theory.

Colourless crystals, mp. 130°–131° C. (acetonitrile/diethylether)

IR ($CH_2Cl_2$): 3430, 3310 $cm^{-1}$ (NH), 1710, 1665 $cm^{-1}$ (C═O), 1510 $cm^{-1}$ (amide-II).

b) (R,S)-$N^2$-(Diphenylacetyl)-N-[(4-methoxyphenyl)-methyl]lysinamide-trifluoroacetate Prepared analogously to Example 5e) from (R,S)-$N^6$-[(tert.-butyloxy)carbonyl]-$N^2$-(diphenylacetyl)-N-[(4-methoxyphenyl)methyl]-lysinamide by the action of trifluoroacetic acid in a yield of 87% of theory.

Colourless crystals, mp. 193° C. (ethyl acetate).

IR (KBr):

3280 $cm^{-1}$ (NH)

1685, 1670, 1640 $cm^{-1}$ (C═O)

c) (R,S)-$N^6$-(Aminoiminomethyl)-$N^2$-(diphenylacetyl)-N-[(4-methoxyphenyl)methyl]-lysinamide Prepared analogously to Example 59c) from (R,S)-$N^2$-diphenylacetyl)-N-[( 4-methoxyphenyl)methyl]-lysinamide-trifluoroacetate and 3,5-dimethylpyrazole-1-carboxylic acid amidinium nitrate in a yield of 66% of theory.

Colourless crystals, mp. 140°–143° C. and $R_f$ 0.62.

IR (KBr): 1645 $cm^{-1}$ (C═O).

ESI-MS: $(M+H)^+$=502

EXAMPLE 62

(R)-N-[(4-Hydroxyphenyl)methyl]-$N^2$-(phenylacetyl)-argininamide-acetate a) (R)-$N^5$-(Amino(nitroimino)methyl]-N-[(4-hydroxyphenyl)methyl]-$N^2$-(phenylacetyl)-ornithinamide Prepared analogously to Example 5f) from (R)-$N^5$-[amino(nitroimino)methyl]-N-[(4-hydroxyphenyl)methyl)-ornithinamide, phenylacetic acid and TBTU in a yield of 61% of theory. It was further processed without purification.

b) (R)-N-[(4-Hydroxyphenyl)methyl]-$N^2$-(phenylacetyl)-argininamide-acetate

Prepared analogously to Example 1c) from (R)-$N^5$-[amino(nitroimino)methyl]-N-[(4-hydroxyphenyl)methyl]-$N^2$-(phenylacetyl)-ornithinamide by catalytic hydrogenation in the presence of palladium black and 80% aqueous acetic acid in a yield of 76% of theory.

Colourless amorphous substance, $R_f$ 0.65.

IR (KBr): 1650 $cm^{-1}$ (C═O)

ESI-MS: $(M+H)^+$=398

EXAMPLE 63

(R)-$N^2$-Acetyl-N-[(4-hydroxyphenyl)methyl]-argininamide-acetate a) (R)-$N^2$-Acetyl-$N^5$-[amino(nitroimino)methyl]-N-[(4-hydroxyphenyl)methyl]-ornithinamide 0.3 g (0.925 mMol) of (R)-$N^5$-[amino(nitroimino)methyl]-N-[(4-hydroxyphenyl)methyl]-ornithinamide were dissolved in 3 ml of glacial acetic acid and after the addition of 3 ml (0.032 Mol) of acetic anhydride the mixture was heated to a reaction temperature of 50° C. for 30 minutes. The product remaining after the volatile components had evaporated off was further processed without purification.

b) (R)-$N^2$-Acetyl-N-[(4-hydroxyphenyl)methyl]-argininamide-acetate

Prepared analogously to Example 1c) from (R)-$N^2$-acetyl-$N^5$-[amino(nitroimino)methyl]-N-[(4-hydroxyphenyl)methyl]-ornithinamide by catalytic hydrogenation in the presence of palladium black and 80% aqueous acetic acid in a yield of 65% of theory.

Colourless amorphous substance, $R_f$ 0.45.

IR (KBr): 1655 $cm^{-1}$ (C═O)

ESI-MS: $(M+H)^+$=322

EXAMPLE 64

$N^2$-[Diphenylacetyl)-N-[(1H-indol-5-yl)methyl]-argininamide-acetate a) $N^5$-[Amino(nitroimino)methyl]-$N^2$-(diphenylacetyl)-N-[(1H-indol-5-yl)methyl]-ornithinamide Prepared analogously to Example 5d) from (R)-$N^5$-[amino(nitroimino)methyl]-$N^2$-(diphenylacetyl)-ornithine, 1H-indole-5-methanamine (mp.: 123°–124° C.; obtained from 1H-indole-5-carbonitrile by catalytic hydrogenation in the presence of Raney nickel and ammonia) and TBTU in a yield of 62% of theory.

Colourless crystals, mp. 203°–204° C.

IR (KBr): 1640 $cm^{-1}$ (C═O)

b) $N^2$-(Diphenylacetyl)-N-[(1H-indol-5-yl)methyl]-argininamide-acetate

Prepared analogously to Example 1c) from $N^5$-[amino(nitroimino)methyl]-$N^2$-(diphenylacetyl)-N-[(1H-indol-5-yl)methyl]-ornithinamide by catalytic hydrogenation in the presence of palladium black and 80% aqueous acetic acid in a yield of 54% of theory.

Colourless amorphous substance, $R_f$ 0.74.

ESI-MS: $(M+H)^+$=497

EXAMPLE 65

(R)-N-[[4-(Aminosulphonyl)phenyl]methyl]-$N^2$-(diphenylacetyl)-argininamide a) (R)-$N^5$-[Amino(nitroimino)methyl]-N-[[4-(aminosulphonyl)phenyl]methyl]-$N^2$-(diphenylacetyl)-ornithinamide Prepared analogously to Example 1b) from (R)-$N^5$-[amino(nitroimino)methyl]-$N^2$-(diphenylacetyl)-ornithine, 4-(aminosulphonyl)benzenemethanamine and isobutylchlorocarbonate in a yield of 30% of theory.

Colourless crystals, mp. 162° C. (ethanol).

IR (KBr): 1685, 1645 $cm^{-1}$ (C═O)

ES-MS:

$(M+H)^+$=582

$(M+Na)^+$=604

$(M+K)^+$=620 b) (R)-N-[[4-(Aminosulphonyl)phenyl]methyl]-$N^2$-(diphenylacetyl)-argininamide

Prepared analogously to Example 1c) from (R)-$N^5$-[amino(nitroimino)methyl]-N-[[4-(aminosulphonyl)-phenyl]methyl]-$N^2$-(diphenylacetyl)-ornithinamide by catalytic hydrogenation in the presence of palladium black and 80% aqueous acetic acid in a yield of 30% of theory.

Colourless amorphous substance, $R_f$ 0.60.

IR (KBr) 1630–1690 $cm^{-1}$ (C═O)
ESI-MS: $(M+H)^+$=537

EXAMPLE 66

N-[[4-[(Dimethylamino)carbonyl]phenyl]methyl]-$N^2$-(diphenylacetyl)-argininamide-acetate a) $N^5$-[Amino(nitroimino)methyl]-N-[[4-[(dimethylamino)-carbonyl]phenyl]methyl]-$N^2$-(diphenylacetyl)-ornithinamide Prepared analogously to Example 5d) from (R)-$N^5$-[amino(nitroimino)methyl]-$N^2$-(diphenylacetyl)-ornithine, 4-(dimethylaminocarbonyl)benzenemethylamine and TBTU in a yield of 36% of theory.

Colourless crystals, mp. 192° C.
IR (KBr): 1680, 1640 $cm^{-1}$ (C═O)

b) N-[[4-[(Dimethylamino)carbonyl]phenyl]methyl]-$N^2$-(diphenylacetyl)-argininamide-acetate Prepared analogously to Example 1c) from $N^5$-[amino(nitroimino)methyl]-N-[[4-[(dimethylamino)-carbonyl]phenyl]methyl]-$N^2$-(diphenylacetyl)-ornithinamide by catalytic hydrogenation in the presence of palladium black and 80% aqueous acetic acid in a yield of 97% of theory.

Colourless amorphous substance, $R_f$ 0.55.
IR (KBr): 1660 $cm^{-1}$ (C═O)
ESI-MS: $(M+H)^+$=529

EXAMPLE 67

(R)-$N^2$-(Diphenylacetyl)-N-[[4-(methoxycarbonyl)phenyl]-methyl]-argininamide-acetate a) (R)-$N^5$-[Amino(nitroimino)methyl]-$N^2$-(diphenylacetyl)-N-[[4-(methoxycarbonyl)phenyl]-methyl]-ornithinamide To a mixture of 2.1 g (5.08 mMol) of (R)-$N^5$-[amino(nitroimino)methyl-$N^2$-(diphenylacetyl)-ornithine, 1.61 g (5.014 mMol) of TBTU and 0.7 g (5.18 mMol) of HOBt in 50 ml of anhydrous dimethylformamide was added, with stirring and external cooling with ice water, a mixture of 2.6 ml (14.9 mMol) of N,N-diisopropyl-ethylamine and 1.1 g (5.45 mMol) of 4-(methoxycarbonyl)-benzenemethylamine (prepared from 4-(methoxycarbonyl)-benzonitrile by catalytic hydrogenation using palladium/animal charcoal as catalyst and in the presence of methanolic hydrochloric acid), the mixture was allowed to come up to ambient temperature and then stirred for 1 hour under these conditions. The reaction mixture was stirred into 500 ml of ice water, covered with 200 ml of tert.-butyl-methylether and stirred overnight. The mixture was suction filtered, the precipitate was washed thoroughly with water and dried in air. The product was dissolved while hot in tetrahydrofuran/methanol mixture (1/1 (v/v)), the solution was filtered while warm and the filtrate was concentrated by evaporation in vacuo. 2.1 g (73% of theory) of a colourless crystalline substance were obtained.

IR (KBr): 1724.3 (ester-C═O), 1639.4 (amide-C═O) $cm^{-1}$ b) (R)-$N^2$-(Diphenylacetyl)-N-[[4-(methoxycarbonyl)-phenyl]methyl]-argininamide-acetate Prepared analogously to Example 1c) from (R)-$N^5$-[amino(nitroimino)methyl]-$N^2$-(diphenylacetyl)-N-[[4-(methoxycarbonyl)phenyl]methyl]-ornithinamide by catalytic hydrogenation in the presence of palladium black and 80% aqueous acetic acid in a yield of 67% of theory.

Colourless amorphous substance, $R_f$ 0.68.
IR ($CH_2Cl_2$): 1720, 1665 $cm^{-1}$ (C═O)
ESI-MS: $(M+H)^+$=516

EXAMPLE 68

(R)-$N^2$-(Diphenylacetyl)-N-[(4-pyridinyl)methyl]-argininamide-formate a) (R)-$N^5$-[Amino(nitroimino)methyl]-$N^2$-(diphenylacetyl)-N-[(4-pyridinyl)methyl]-ornithinamide Prepared analogously to Example 1b) from (R)-$N^5$-[amino(nitroimino)methyl]-$N^2$-(diphenylacetyl)-ornithine, 4-pyridine-methylamine and isobutylchlorocarbonate in a yield of 70% of theory.

Colourless crystals.
IR (KBr): 1665, 1655, 1630, 1610 $cm^{-1}$ (C═O, C═N)
ESI-MS:
$(M+H)^+$=504
$(M+Na)^+$=526 b) (R)-$N^2$-(Diphenylacetyl)-N-[(4-pyridinyl)methyl]-argininamide-formate

Prepared analogously to Example 14b) from (R)-$N^5$-[amino(nitroimino)methyl]-$N^2$-(diphenylacetyl)-N-[(4-pyridinyl)methyl]-ornithinamide by reduction with tin(II)-chloride-dihydrate in the presence of 60% aqueous formic acid in a yield of 91% of theory.

Colourless amorphous substance, $R_f$ 0.39.
IR (KBr): 1650 $cm^{-1}$ (C═O)
ESI-MS: $(M+H)^+$=459

EXAMPLE 69

(R)-N-[(4-Amino-3,5-dibromophenyl)methyl]-$N^2$-(diphenylacetyl)-argininamide-hydrochloride a) (R)-N-[(4-Amino-3,5-dibromophenyl)methyl]-$N^5$-[amino(nitroimino)methyl]-$N^2$-[(tert.-butyloxy)carbonyl]-ornithinamide Prepared analogously to Example 1b) from (R)-$N^5$-[amino(nitroimino)methyl]-$N^2$-[(tert.-butyloxy)carbonyl]-ornithine, 4-amino-3,5-dibromobenzenemethylamine and isobutylchlorocarbonate in a yield of 80% of theory.

Colourless amorphous substance.
IR (KBr): 1700, 1660, 1625 $cm^{-1}$ (C═O, C═N)

b) (R)-N-[(4-Amino-3,5-dibromophenyl)methyl]-$N^5$-[amino(nitroimino)methyl]-ornithinamide-hydrochloride Prepared analogously to Example 36b) from (R)-N-[(4-amino-3,5-dibromophenyl)methyl]-$N^5$-[amino(nitroimino)methyl]-$N^2$-[(tert.-butyloxy)carbonyl]-ornithinamide by treating with methanolic hydrochloric acid in a quantitative yield.

Colourless amorphous substance which was further processed without purification.

c) (R)-[(4-Amino-3,5-dibromophenyl)methyl]-$N^5$-[amino(nitroimino)methyl]-$N^2$-(diphenylacetyl)-ornithinamide To an ice cold solution of 2.518 g (5 mMol) of (R)-N-[(4-amino-3,5-dibromophenyl)methyl]-$N^5$-[amino(nitroimino)methyl]-ornithinamide-hydrochloride and 2.8 ml (20.1 mMol) of triethylamine in a mixture of 80 ml tetrahydrofuran and 50 ml dimethylformamide was added dropwise a solution of 1.3 g (5.64 mmol) of diphenylacetylchloride in 20 ml of tetrahydrofuran and then, with the cooling removed, the mixture was stirred for 2 hours at a reaction temperature of 40°–50° C. After conventional working up 2.3 g (68% of theory) of a colourless amorphous substance were obtained.

d) (R)-N-[(4-Amino-3,5-dibromophenyl)methyl]-$N^2$-(diphenylacetyl)-argininamide-hydrochloride Prepared analogously to Example 14b) from (R)-[(4-amino-3,5-dibromophenyl)methyl)-$N^5$-[amino(nitroimino)methyl]-$N^2$-(diphenylacetyl)-ornithinamide by reduction with tin(II)-chloride-dihydrate in the presence of 60% aqueous formic acid in a yield of 17% of theory.

Colourless crystals, $R_f$ 0.65.
IR (KBr): 1645 $cm^{-1}$ (C═O)
EI-MS: $(M+H)^+$=629/631/633 ($Br_2$)

EXAMPLE 70

(R,S)-3-[4-[(Aminoiminomethyl)amino]phenyl]-$N^2$-(diphenylacetyl)-N-[(4-methoxyphenyl)methyl]-alaninamide-hydrochloride a) (R,S)-$N^2$-(Diphenylacetyl)-3-(4-nitrophenyl)-alanine Prepared analogously to Example 1a) from diphenylacetylchloride and (R,S)-3-(4-nitrophenyl)-alanine in the presence of sodium hydroxide solution in a yield of 100%. Colourless crystals which were reacted with any further purification.

b) (R,S)-$N^2$-(Diphenylacetyl)-N-[(4-methoxyphenyl)-methyl]-3-(4-nitrophenyl)-alaninamide Prepared analogously to Example 52c) from (R,S)-$N^2$-(diphenylacetyl)-3-(4-nitrophenyl)-alanine, 4-methoxybenzenemethylamine and N,N'-carbonyldiimidazole in a yield of 34% of theory.

Colourless crystals, mp. 220°–222° C.

IR (KBr): 3310 (N—H), 1640 (C═O) $cm^{-1}$

MS: $M^+$=523 c) (R,S)-3-(4-Aminophenyl)-$N^2$-(diphenylacetyl)-N-[(4-methoxyphenyl)methyl]-alaninamide Prepared analogously to Example 25b) from (R,S)-$N^2$-(diphenylacetyl)-N-[(4-methoxyphenyl)methyl]-3-(4-nitrophenyl)-alaninamide by catalytic hydrogenation in the presence of palladium/animal charcoal in a yield of 95% of theory.

Colourless crystals, mp. 206°–207° C.

IR (KBr): 3470, 3380, 3300 $cm^{-1}$ (N—H, $NH_2$) 1680, 1635 $cm^{-1}$ (C═O)

MS: $M^+$=493 d) (R,S)-3-[4-[(Aminoiminomethyl)amino]phenyl]-$N^2$-(diphenylacetyl)-N-[(4-methoxyphenyl)methyl]-alaninamide-hydrochloride 2.0 g (4.05 mMol) of (R,S)-3-(4-aminophenyl)-$N^2$-(diphenylacetyl)-N-[(4-methoxyphenyl)methyl]-alaninamide were dissolved in a mixture of 50 ml of methanol and 50 ml of dioxane and mixed with 4 ml of 1N aqueous hydrochloric acid. The mixture obtained was evaporated down in vacuo and the residue remaining was freed from any water still contained therein by azeotropic distillation carried out twice using toluene as an entrainer. The hydrochloride thus obtained was suspended in 50 ml of dioxane, whereupon sufficient methanol (approx. 50 ml) was added to make the substance go totally into solution in the warm (about 60° C.). 0.42 g (10 mMol) of cyanamide were added and the mixture was refluxed for 3 hours. After 1.0 g (23.8 mMol) of cyanamide had been added once more the mixture was refluxed for a further 15 hours. The reaction mixture was freed from solvents in vacuo, the residue was suspended in a little water and mixed with tetrahydrofuran until completely dissolved. Then it was saturated with common salt, the tetrahydrofuran phase was separated off and evaporated down in vacuo, the residue was purified by chromatography on silica gel (200–500 $\mu$m) using initially dichloromethane/methanol=9/1 (v/v), followed by dichloromethane/methanol/conc. aqueous ammonia=8/2/0.3 (v/v/v). 100 mg (4.3% of theory) of colourless crystals were obtained, mp. 149°–150° C. and $R_f$ 0.77.

IR (KBr): 1660, 1640 $cm^{-1}$ (C═O)

ESI-MS: $(M+H)^+$=536

EXAMPLE 71

(R,S)-3-[4-[[(Cyanoimino)methyl)amino]phenyl]-$N^2$-(diphenylacetyl)-N-[(4-methoxyphenyl)methyl]-alaninamide 10.0 g (20.25 mMol) of (R,S)-3-(4-aminophenyl)-$N^2$-(diphenylacetyl)-N-[(4-methoxyphenyl)methyl]-alaninamide were dissolved in a mixture of 50 ml of methanol and 250 ml of tetrahydrofuran with heating. After the addition of 4 g (40.77 mMol) of ethyl N-cyano-formimidate the mixture was stirred for 15 hours at ambient temperature. The residue remaining after the solvents had been distilled off was purified by chromatography on silica gel (200–500 $\mu$m; mobile phase: dichloromethane/methanol=9/1 (v/v)). 6.6 g (60% of theory) of colourless crystals were obtained, $R_f$ 0.9.

IR (KBr): 1685, 1665, 1645 $cm^{-1}$ (C═O, C═N)

ESI-MS: $(M+H)^+$=546

EXAMPLE 72

(R,S)-$N^2$-(Diphenylacetyl)-N-[(4-methoxyphenyl)methyl]-3-[4-[[(methylamino)methylidene]amino]phenyl]-alaninamide 1.0 g (1.834 mMol) of (R,S)-3-[4-[[(cyanoimino)methyl]amino]phenyl]-$N^2$-(diphenylacetyl)-N-[(4-methoxyphenyl)methyl]alaninamide was dissolved in 20 ml of dimethylformamide, mixed with 1.7 ml (0.6 g=18 mMol) of an aqueous 40% methylamine solution and stirred for 2 days at ambient temperature. The reaction mixture was stirred into plenty of water, the solid obtained was suction filtered and purified by chromatography on silica gel (200–500 $\mu$m; mobile phase: dichloromethane/methanol=9/1 (v/v)). 25 mg (2.5% of theory) of colourless crystals were obtained, $R_f$ 0.9.

IR (KBr): 1690, 1660, 1640 $cm^{-1}$ (C═O, C═N)

ESI-MS: $(M+H)^+$=535

EXAMPLE 73

(R)-$N^2$-(Diphenylacetyl)-N-[(2-thienyl)methyl]-argininamide-acetate a) (R)-$N^5$-[Amino(nitroimino)methyl]-N-[(2-thienyl)-methyl]-ornithinamide First of all Boc-Arg($NO_2$)-OH was reacted with thiophene-2-methanamine and TBTU as in Example 8a). The resulting (R)-$N^5$-[amino(nitroimino)methyl]-$N^2$-[(tert.-butyloxy)carbonyl]-N-[(2-thienyl)methyl]-ornithinamide was then reacted, without purification, with trifluoroacetic acid as in Example 23b). The crude product obtained in a quantitative yield was further processed without purification.

b) (R)-$N^5$-[Amino(nitroimino)methyl]-$N^2$-(diphenylacetyl)-N-[(2-thienyl)methyl]-ornithinamide Prepared analogously to Example 69c) from (R)-$N^5$-[amino(nitroimino)methyl]-N-[(2-thienyl)methyl]-ornithinamide and diphenylacetylchloride in a yield of 50% of theory.

Colourless crystals, mp. 192° C.

IR (KBr):

3430, 3300 $cm^{-1}$ (NH)

1640 $cm^{-1}$ (C═O)

c) (R)-$N^2$-(Diphenylacetyl)-N-[(2-thienyl)methyl]-argininamide-acetate

Prepared analogously to Example 1c) from (R)-$N^5$-[amino(nitroimino)methyl]-$N^2$-(diphenylacetyl)-N-[(2-thienyl)methyl]ornithinamide by catalytic hydrogenation in the presence of palladium black and 80% aqueous acetic acid in a yield of 12% of theory. Colourless amorphous substance, $R_f$ 0.72.

IR (KBr): 1660 $cm^{-1}$ (C═O)

EI-MS: $(M+H)^+$=464

EXAMPLE 74

(R)-N-[(4-Hydroxyphenyl)methyl]-$N^2$-(1-oxo-2-propylpentyl)-argininamide-acetate a) (R)-$N^5$-[Amino(nitroimino)methyl]-N-[(4-hydroxyphenyl)methyl]-$N^2$-(1-oxo-2-propylpentyl)-ornithinamide Prepared analogously to Example 5d), but using tetrahydrofuran instead of acetonitrile, from (R)-$N^5$-[amino(nitroimino)methyl]-N-[(4-hydroxyphenyl)methyl]-ornithinamide, 2-propyl-pentanoic acid and TBTU in a yield of 65% of theory. Colourless crystalline substance which was further processed without purification.

b) (R)-N-[(4-Hydroxyphenyl)methyl]-$N^2$-(1-oxo-2-propylpentyl)-argininamide-acetate Prepared analogously to Example 1c) from (R)-$N^5$-[amino(nitroimino)methyl]-N-[(4-hydroxyphenyl)methyl]-$N^2$-(1-oxo-2-propylpentyl)-ornithinamide by catalytic hydrogenation in the presence of palladium black and 80% aqueous acetic acid in a yield of 10% of theory.

Colourless amorphous substance, $R_f$ 0.7.

IR (KBr): 1650 $cm^{-1}$ (C═O)

EI-MS: $(M+H)^+$=406

EXAMPLE 75

(R,S)-$N^6$-(Iminomethyl)-$N^2$-(diphenylacetyl)-N-[(4-methoxy-phenyl)methyl]-lysinamide-hydrochloride A mixture of 0.69 g (1.2 mMol) of (R,S)-$N^2$-(diphenylacetyl)-N-[(4-methoxyphenyl)methyl]-lysinamide-trifluoroacetate, 40 ml of acetonitrile and 0.2 g (1.826 mMol) of ethyl formimidate-hydrochloride was stirred at ambient temperature for 3 days. Undissolved parts were filtered off and the filtrate was evaporated down in vacuo and the residue was purified by chromatography on silica gel (J. T. Baker, silica gel for flash chromatography, 30–60 $\mu$m, mobile phase: ethyl acetate/methanol/glacial acetic acid=7/3/0.3 (v/v/v)). 0.15 g (24% of theory) of a colourless amorphous substance, $R_f$ 0.68, was obtained.

IR (KBr): 1640 $cm^{-1}$ (C═O)

EXAMPLE 76

(R,S)-3-[3-[(Aminoiminomethyl)amino]phenyl]-$N^2$-(diphenylacetyl)-N-[(4-methoxyphenyl)methyl]-alaninamide-hydrochloride a) (R,S)-$N^2$-(Diphenylacetyl)-3-(3-nitrophenyl)-alanine Prepared analogously to Example 1a) from diphenylacetylchloride and (R,S)-3-(3-nitrophenyl)-alanine-hydrochloride (mp.: 251°–252° C.; obtained from 3-nitrobenzylchloride via diethyl α-acetamido-α-(3-nitrobenzyl)malonate [acetamidomalonic ester/sodium ethoxide], mp.: 153°–154° C., finally boiling with a mixture of glacial acetic acid and 6N aqueous hydrochloric acid) in the presence of sodium hydroxide solution in a yield of 58% of theory.

Colourless crystals mp. 157°–158° C.

IR (KBr): 1650, 1715, 1740 $cm^{-1}$ (C═O)

b) (R,S)-$N^2$-(Diphenylacetyl)-N-[(4-methoxyphenyl)-methyl]-3-(3-nitrophenyl)alaninamide Prepared analogously to Example 1b) from (R,S)-$N^2$-(diphenylacetyl)-3-(3-nitrophenyl)-alanine, 4-methoxybenzenemethylamine and isobutylchlorocarbonate in a yield of 93% of theory.

Colourless crystals, mp. 220°–222° C.

IR (KBr):

1676, 1637.5 $cm^{-1}$ (C═O)

1352, 1527.5 $cm^{-1}$ ($NO_2$)

c) (R,S)-3-(3-Aminophenyl)-$N^2$-(diphenylacetyl)-N-[(4-methoxyphenyl)methyl]-alaninamide Prepared analogously to Example 25b) from (R,S)-$N^2$-(diphenylacetyl)-N-[(4-methoxyphenyl)methyl]-3-(3-nitrophenyl)-alaninamide by catalytic hydrogenation in the presence of palladium/animal charcoal in a yield of 82% of theory.

Colourless crystals, mp. 184°–185° C.

IR (KBr): 1641.3 $cm^{-1}$ (C═O)

d) (R,S)-3-[3-[(Aminoiminomethyl)amino]-phenyl]-$N^2$-(diphenylacetyl)-N-[(4-methoxyphenyl)methyl]-alaninamide-hydrochloride-dihydrate Prepared analogously to Example 70d) from (R,S)-3-(3-aminophenyl)-$N^2$-(diphenylacetyl)-N-[(4-methoxyphenyl)methyl]-alaninamide and cyanamide in a yield of 84% of theory.

Colourless crystals, mp. 127°–128° C. (Decomp.) and $R_f$ 0.8.

IR (KBr): 1660.6 $cm^{-1}$ (C═O)

EI-MS: $(M+H)^+$=536

EXAMPLE 77

(R,S)-$N^2$-(Diphenylacetyl)-N-[(4-methoxyphenyl)methyl]-3-[3-[[(methylamino)methylidene]amino]phenyl]-alaninamide a) (R,S)-3-[3-[[(Cyanimino)methyl]amino]phenyl]-$N^2$-(diphenylacetyl)-N-[(4-methoxyphenyl)methyl]-alaninamide Prepared analogously to Example 71 from (R,S)-3-(3-aminophenyl)-$N^2$-(diphenylacetyl)-N-[(4-methoxyphenyl)methyl]-alaninamide and ethyl N-cyano-formimidate in a yield of 86% of theory.

Colourless amorphous substance which was further processed without purification.

b) (R,S)-$N^2$-(Diphenylacetyl)-N-[(4-methoxyphenyl)-methyl]-3-[3-[[(methylamino)methylidene]-amino]phenyl]-alaninamide Prepared analogously to Example 72 from (R,S)-3-[3-[[(cyanimino)-methyl]amino]phenyl]-$N^2$-(diphenylacetyl)-N-[( 4-methoxyphenyl)methyl]-alaninamide and methylamine in a yield of 26% of theory.

Colourless amorphous substance, $R_f$ 0.95.

IR (KBr): 1643.3 $cm^{-1}$ (C═O)

MS: $M^+$=534

EXAMPLE 78

(R,S)-$N^2$-(Diphenylacetyl)-$N^5$-(iminomethyl)-N-[(4-methoxyphenyl)methyl]-ornithinamide-hydrochloride a) (R,S)-$N^2$-(Diphenylacetyl)-N-[(4-methoxyphenyl)-methyl]-$N^5$-[(phenylmethoxy)carbonyl]-ornithinamide Prepared analogously to Example 5d) from (R,S)-$N^2$-(diphenylacetyl)-$N^5$-[(phenylmethoxy)carbonyl]-ornithine and 4-methoxybenzenemethylamine in the presence of TBTU in a quantitative yield.

Colourless crystals which were further processed without purification.

b) (R,S)-$N^2$-(Diphenylacetyl)-N-[(4-methoxyphenyl)-methyl]-ornithinamide-acetate Prepared analogously to Example 27c) from (R,S)-$N^2$-(diphenylacetyl)-N-[(4-methoxyphenyl)methyl]-$N^5$-[(phenylmethoxy)carbonyl]-ornithinamide by catalytic hydrogenation in the presence of palladium/animal charcoal. Yield: 75% of theory.

Colourless crystals, mp. 141°–143° C.

IR (KBr): 1649.0 $cm^{-1}$ (C═O)

c) (R,S)-$N^2$-(Diphenylacetyl)-$N^5$-(iminomethyl)-N-[(4-methoxyphenyl)methyl]-ornithinamide-hydrochloride Prepared analogously to Example 75 from (R,S)-$N^2$-(diphenylacetyl)-N-[(4-methoxyphenyl)methyl]-ornithinamide-acetate and ethyl formimidate-hydrochloride in the presence 4-methylmorpholine.

Colourless crystals, mp. 145°–147° C. and $R_f$ 0.65. Yield: 20% of theory.

IR (KBr): 1714.6, 1652.9 $cm^{-1}$ (C═N, C═O)

EXAMPLE 79

(R,S)-3-[3-(Aminoiminomethyl)phenyl]-$N^2$-[(diphenylamino)-carbonyl]-N-[(4-hydroxyphenyl)methyl]-alaninamide-hydrochloride a) (R,S)-3-(3-Cyanophenyl)-alaninemethylester-hydrochloride A mixture of 33.0 g (0.146 Mol) of 3-(3-cyanophenyl)-alanine-hydrochloride, 1 liter of anhydrous methanol and 37.5 g (0.345 Mol) of chlorotrimethylsilane was stirred for 3 days at ambient temperature. The residue remaining after the solvent had been distilled off was taken up in 200 ml of dichloromethane and washed thoroughly with 10% aqueous sodium hydrogen carbonate solution. The oily product remaining after the dichloromethane solution had been dried and evaporated down was taken up in dry ethyl acetate and converted into the hydrochloride with ethereal hydrochloric acid solution. 23.0 g (65% of theory) of colourless crystals, mp. 157°–159° C., were obtained.

IR (KBr):

1733.9 $cm^{-1}$ (ester-C═O)

2229.6 $cm^{-1}$ (C≡N)

b) (R,S)-2-(3-Cyanophenyl)-1-(methoxycarbonyl)-ethylisocyanate

To a mixture of 9.2 g (0.038 Mol) of (R,S)-3-(3-cyanophenyl)-alaninemethylester-hydrochloride, 150 ml of anhydrous dichloromethane and 14.7 ml (0.182 Mol) of dry pyridine was added dropwise, at a reaction temperature of 0° to 5° C. and with stirring, 30 ml (0.0585 Mol) of a 1.95M solution of phosgene in toluene. The mixture was stirred for a further 2 hours at 0° C., filtered to remove the salty precipitate and the filtrate was evaporated down in vacuo. The oily residue remaining was dissolved in 150 ml of dry dichloromethane. Aliquot portions thereof were used in the following reactions without being purified.

c) (R,S)-3-(3-Cyanophenyl)-$N^2$-[(diphenylamino)carbonyl]-alanine methylester

A mixture of 50 ml (0.0127 Mol) of the above-mentioned solution of (R,S)-2-(3-cyanophenyl)-1-(methoxycarbonyl)-ethylisocyanate in dichloromethane was refluxed for 2 hours with 3.0 g (0.0177 Mol) of diphenylamine and 1.8 g (0.0147 Mol) of 4-dimethylaminopyridine. The mixture was diluted with a further 50 ml of dichloromethane and the organic phase was washed twice with 5% aqueous hydrochloric acid and once with water, dried with magnesium sulphate and evaporated down in vacuo. The oily residue (1.5 g, i.e. 30% of theory) was used in the next stage without further purification.

MS: $M^+$=399 d) (R,S)-3-(3-Cyanophenyl)-$N^2$-[(diphenylamino)-carbonyl]-alanine

To a solution of 5.78 g (0.0145 Mol) of (R,S)-3-(3-cyanophenyl)-$N^2$-[(diphenylamino)carbonyl]-alaninemethylester in 60 ml of tetrahydrofuran was added dropwise, with stirring, a solution of 2.5 g (0.60 Mol) of lithium hydroxide-hydrate in 10 ml of water. After one hour the tetrahydrofuran was distilled off in vacuo and the residue was distributed between ether and water. The ethereal phase was discarded, the aqueous phase was acidified with dilute hydrochloric acid and extracted exhaustively with ethyl acetate. After working up in the usual way the combined ethyl acetate extracts yielded 5.4 g (97% of theory) of a colourless slowly crystallising oil which was reacted in the following steps without further purification.

IR (KBr):

2229.6 $cm^{-1}$ (C≡N)

1733.9, 1672.2 $cm^{-1}$ (C═O)

e) (R,S)-3-(3-Cyanophenyl)-$N^2$-[(diphenylamino)-carbonyl]-N-[(4-hydroxyphenyl)methyl]-alaninamide Prepared analogously to Example 8a) from (R,S)-3-(3-cyanophenyl)-$N^2$-[(diphenylamino)-carbonyl]-alanine, 4-hydroxybenzene-methylamine and TBTU in a yield of 53% of theory.

Colourless amorphous substance which was further processed without purification.

f) (R,S)-3-[3-(Aminoiminomethyl)phenyl]-$N^2$-[(diphenylamino)carbonyl]-N-[(4-hydroxyphenyl)-methyl]-alaninamide-hydrochloride 3.9 g (7.95 mMol) of (R,S)-3-(3-cyanophenyl)-$N^2$-[(diphenylamino)carbonyl]-N-[(4-hydroxyphenyl)methyl]-alaninamide were dissolved in 40 ml of anhydrous ethanol saturated with dry hydrogen chloride and stirred for 24 hours at ambient temperature. The solvent was distilled off in vacuo at a bath temperature below 30° C., the residue was taken up in 30 ml of absolute ethanol and 5 g (52 mmol) of ammonium carbonate were added. After a further 24 hours' stirring at ambient temperature the undissolved fractions were filtered off, the filtrate was evaporated down in vacuo and the residue was distributed between water and ethyl acetate. The aqueous phase was evaporated down in vacuo and the residue was triturated several times with a little water and methanol and finally with diethylether. 2.1 g (49% of theory) of a colourless amorphous substance were obtained, $R_f$ 0.75.

IR (KBr): 1652.9 $cm^{-1}$ (C═O)

ESI-MS: $(M+H)^+$=508

EXAMPLE 80

(R)-N-[(4-Amino-3,5-dichlorophenyl)methyl]-$N^2$-(2-naphthoyl)-argininamide-acetate a) (R)-N-[(4-Amino-3,5-dichlorophenyl)methyl]-$N^5$-[amino(nitroimino)methyl]-$N^2$-(2-naphthoyl)-ornithinamide Prepared analogously to Example 38b) from (R)-N-[(4-amino-3,5-dichlorophenyl)methyl]-$N^5$-[amino(nitroimino)-methyl]-ornithinamide, 2-naphthoic acid and TBTU in a yield of 59% of theory.

Colourless crystals, mp. 232°–233° C. (methanol).

IR (KBr): 1662.5, 1633.6 $cm^{-1}$ (C═O)

b) (R)-N-[(4-Amino-3,5-dichlorophenyl)methyl]-$N^2$-(2-naphthoyl)-argininamide-acetate Prepared analogously to Example 14b) from (R)-N-[(4-amino-3,5-dichlorophenyl)methyl]-$N^5$-[amino(nitroimino)-methyl]-$N^2$-(2-naphthoyl)-ornithinamide by reduction with tin(II)-chloride-dihydrate in 60% aqueous formic acid in a yield of 62% of theory.

Colourless amorphous substance, $R_f$ 0.65.

IR (KBr): 1652.9 $cm^{-1}$ (C═O)

ESI-MS: $(M+H)^+$=501/503/505 ($Cl_2$)

According to MS and NMR investigation the substance is contaminated with (R)-N-[(3,5-dichloro-4-(formylamino)-phenyl]methyl]-$N^2$-(2-naphthyl)-argininamide-acetate.

EXAMPLE 81

(R)-$N^2$-(Diphenylacetyl)-N-[[4-[(methylamino)carbonyl]-phenyl]methyl]-argininamide-acetate a) (R)-$N^5$-[Amino(nitroimino)methyl]-$N^2$-(diphenylacetyl)-N-[[4-[(methylamino)carbonyl]-phenyl]methyl]-ornithinamide Prepared, analogously to Example 67a) but using acetonitrile as solvent instead of dimethylformamide, from (R)-$N^5$-[amino(nitroimino)methyl]-$N^2$-(diphenylacetyl)- ornithine, 4-[(methylamino)carbonyl]-benzenemethylamine (prepared from 4-cyano-N-methylbenzamide by catalytic hydrogenation in the presence of palladium/animal charcoal) and TBTU in a yield of 22% of theory.

Colourless amorphous substance which was further processed without purification.

b) (R)-$N^2$-(Diphenylacetyl)-N-[[4-[(methylamino)-carbonyl]phenyl]methyl]-argininamide-acetate Prepared analogously to Example 1c) from (R)-$N^5$-[amino(nitroimino)methyl]-$N^2$-(diphenylacetyl)-N-[[4-[(methylamino)carbonyl]phenyl]methyl]-ornithinamide by catalytic hydrogenation in the presence of palladium black and 80% aqueous acetic acid in a yield of 32% of theory.

Colourless amorphous substance, $R_f$ 0.73.

IR (KBr): 1652.9 $cm^{-1}$ (C═O)

ESI-MS: $(M+H)^+$=515

EXAMPLE 82

(R)-N-[[4-[(Butylamino)carbonyl]phenyl]methyl]-$N^2$-diphenylacetyl)-argininamide-acetate a) (R)-$N^5$-[Amino(nitroimino)methyl]-N-[[4-[(butylamino) carbonyl[phenyl]methyl]-$N^2$-(diphenylacetyl)-ornithinamide Prepared analogously to Example 81a) from (R)-$N^5$-[amino(nitroimino)methyl]-$N^2$-(diphenylacetyl)-ornithine, 4-[(butylamino)carbonyl]-benzenemethylamine and TBTU in a yield of 62% of theory.

Colourless crystals, mp. 182° C. (Decomp.).

IR (KBr):

3377.2, 3273.0 $cm^{-1}$ (NH)

1668.3, 1631.7 $cm^{-1}$ (C═O)

b) (R)-N-[[4-[(Butylamino)carbonyl]phenyl]methyl]-$N^2$-(diphenylacetyl)-argininamide-acetate Prepared analogously to Example 1c) from (R)-$N^5$-[amino(nitroimino)methyl]-N-[[4-[(butylamino)carbonyl]-phenyl]methyl]-$N^2$-(diphenylacetyl)-ornithinamide by catalytic hydrogenation in the presence of palladium black and 80% aqueous acetic acid in a yield of 45% of theory.

Colourless amorphous substance, $R_f$ 0.80.

IR (KBr): 1649 $cm^{-1}$ (C═O)

ESI-MS: $(M+H)^+$=557

EXAMPLE 83

(R,S)-$N^5$-(4,5-Dihydro-1H-imidazol-2-yl)-$N^2$-(diphenylacetyl)-N-[(4-hydroxyphenyl)methyl]-ornithinamide A mixture of 0.5 g (1.159 mMol) of (R,S)-$N^2$-(diphenylacetyl)-N-[(4-hydroxyphenyl)methyl]-ornithinamide, 317.3 mg (1.3 mMol) of 2-(methylmercapto)-2-imidazoline-hydroiodide, 0.43 ml (2.47 mMol) of N,N-diisopropyl-ethylamine and 20 ml of anhydrous ethanol was refluxed for 5 hours. The reaction mixture was divided between ethyl acetate and plenty of water, the organic-phase was dried over sodium sulphate, treated with activated charcoal and evaporated down in vacuo. Chromatographic purification (neutral aluminium oxide, activity stage IV [made by ICN Biomedicals]; mobile phase: dichloromethane/methanol=9/1 (v/v)) yielded 50 mg (6.3% of theory) of a colourless amorphous substance.

MS: $M^+$=499

EXAMPLE 84

(R)-$N^2$-(Diphenylacetyl)-N-[[4-(hydroxycarbonyl) phenyl]-methyl]-argininamide a) (R)-$N^5$-[Amino(nitroimino)methyl]-$N^2$-(diphenylacetyl)-N-[[4-(hydroxycarbonyl)phenyl]-methyl]-ornithinamide Prepared analogously to Example 79d) but using methanol as solvent instead of tetrahydrofuran, from (R)-$N^5$-[amino(nitroimino)methyl]-$N^2$-(diphenylacetyl)-N-[[4-(methoxy)carbonyl]phenyl]-methyl]-ornithinamide and lithium hydroxide-hydrate in a yield of 17% of theory.

Colourless crystals, mp. 157°–158° C. (Decomp.)

IR (KBr): 1637.5 $cm^{-1}$ (C═O)

b) (R)-$N^2$-(Diphenylacetyl)-N-[[4-(hydroxycarbonyl) phenyl]-methyl]-argininamide Prepared analogously to Example 1c) from (R)-$N^5$-[amino(nitroimino)methyl]-$N^2$-(diphenylacetyl)-N-[[4-(hydroxycarbonyl)phenyl]methyl]-argininamide by catalytic hydrogenation in the presence of palladium black and 80% aqueous acetic acid in a yield of 58% of theory.

Colourless crystals, mp. 164°–165° C.

IR (KBr): 1652.9 $cm^{-1}$ (C═O)

ESI-MS:

$(M+H)^+$=502

$(M+Na)^+$=524

EXAMPLE 85

(R,S)-$N^2$-(Diphenylacetyl)-N-[(4-hydroxyphenyl) methyl]-$N^5$-(1H-imidazol-2-yl)-ornithinamide A mixture of 1.0 g (2.317 mMol) of (R,S)-$N^2$-(diphenylacetyl)-N-[(4-hydroxyphenyl)methyl]-ornithinamide, 1.9 g (5.685 mMol) of N-[(2,2-diethoxy) ethyl]-S-methylthiuronium-iodide, 1 ml (7.17 mMol) of triethylamine and 20 ml of ethanol was refluxed for 2 hours, during which methanethiol was released. The reaction mixture was evaporated down in vacuo, the residue was taken up in 5 ml of methanol, 5 ml of concentrated hydrochloric acid were added and the mixture was stirred for one hour at ambient temperature. Then the methanol was eliminated in vacuo, the aqueous phase was extracted once with ethyl acetate (20 ml) and then made distinctly ammoniacal. It was stirred vigorously for 15 minutes, the crystals formed were suction filtered and recrystallised once from the required amount of dioxane/methanol (9/1 (v/v)) and tetrahydrofuran/methanol (9/1 (v/v)) and 430 mg (37% of theory) of colourless crystals were obtained, mp. 244°–245° C. (Decomp.).

IR (KBr): 1647.1 $cm^{-1}$ (C═O)

MS: $M^+$=497

EXAMPLE 86

(R,S)-3-[3-(Aminoiminomethyl)phenyl]-$N^2$-[(hexahydro-1H-azepin-1-yl)carbonyl]-N-[(4-hydroxyphenyl)methyl]-alaninamide-hydrochloride a) (R,S)-3-(3-Cyanophenyl)-$N^2$-[(hexahydro-1H-azepin-1-yl)-carbonyl]-alanine-methylester Prepared analogously to Example 79c) from (R,S)-2-(3-cyanophenyl)-1-(methoxycarbonyl)ethylisocyanate and hexamethyleneimine in a yield of 100% of theory.

Colourless crystals, mp. 111°–112° C. (dichloromethane).

IR (KBr):

2227.5 $cm^{-1}$ (C≡N)

1743.5 $cm^{-1}$ (ester-C═O)

1624.0 $cm^{-1}$ (amide-C═O)

b) (R,S)-3-(3-Cyanophenyl)-$N^2$-[(hexahydro-1H-azepin-1-yl)-carbonyl]-alanine

Prepared analogously to Example 79d) from (R,S)-3-(3-cyanophenyl)-$N^2$-[(hexahydro-1H-azepin-1-yl)-carbonyl]-alanine-methylester and lithium hydroxide-hydrate in a yield of 67% of theory.

Colourless crystals which were further processed without purification.

c) (R,S)-3-(3-Cyanophenyl)-$N^2$-[(hexahydro-1H-azepin-1-yl)-carbonyl]-N-[(4-hydroxyphenyl)methyl]-alaninamide Prepared analogously to Example 8a) from (R,S)-3-(3-cyanophenyl)-$N^2$-[(hexahydro-1H-azepin-1-yl)-carbonyl]-N-[(4-hydroxyphenyl)methyl]-alanine, 4-hydroxybenzenemethylamine and TBTU in a yield of 64% of theory.

Colourless crystals, mp. 155°–157° C.

IR (KBr):

3294.2 $cm^{-1}$ (NH)

2227.7 $cm^{-1}$ (C≡N)

1664.5 $cm^{-1}$ (amide-C═O)

d) (R,S)-3-[3-(Aminoiminomethyl)phenyl]-$N^2$-[(hexahydro-1H-azepin-1-yl)carbonyl]-N-[(4-hydroxyphenyl)-methyl]-alaninamide-hydrochloride Prepared analogously to Example 79f) from (R,S)-3-(3-cyanophenyl)-$N^2$-[(hexahydro-1H-azepin-1-yl)-carbonyl]-N-[(4-hydroxyphenyl)methyl]-alaninamide using first ethanolic hydrogen chloride solution and then ammonium carbonate.

Yield: 11% of theory.

Colourless crystals, mp. 164°–166° C.

ESI-MS: $(M+H)^+$=438

EXAMPLE 87

(R)-N-[(4-Amino-3,5-dichlorophenyl)methyl]-$N^2$-[(4-amino-3,5-dichlorophenyl)sulphonyl]-argininamide a) (R)-N-[(4-Amino-3,5-dichlorophenyl)methyl]-$N^2$-[(4-amino-3,5-dichlorophenyl)sulphonyl]-$N^5$-[amino(nitroimino)methyl]-ornithinamide Prepared, analogously to Example 8a) but using 4-methylmorpholine instead of triethylamine from (R)-$N^2$-[(4-amino-3,5-dichlorophenyl)sulphonyl]-$N^5$-[[amino(nitroimino)methyl]-ornithine and 4-amino-3,5-dichlorobenzenemethylamine in a yield of 67% of theory.

Colourless crystals, mp. 186°–188° C.

IR (KBr):

1643.3, 1621.4 $cm^{-1}$ (amide-C═O, $NO_2$)

1336.6, 1161.1 $cm^{-1}$ ($SO_2$—N)

b) (R)-N-[(4-Amino-3,5-dichlorophenyl)methyl]-$N^2$-[(4-amino-3,5-dichlorophenyl)sulphonyl]-argininamide Prepared analogously to Example 14b) from (R)-N-[(4-amino-3,5-dichlorophenyl)methyl]-$N^2$-[(4-amino-3,5-dichlorophenyl)-sulphonyl]-$N^5$-[amino(nitroimino)methyl] ornithinamide by reduction with tin(II)-chloride-dihydrate in the presence of 60% aqueous formic acid in a yield of 67% of theory.

Colourless crystals, mp. 254°–256° C. and $R_f$ 0.78.

IR (KBr):

1672.2, 1625.9 $cm^{-1}$ (C═O)

1342.4, 1137.9 $cm^{-1}$ ($SO_2$—N)

ESI-MS: $(M+H)^+$=570/572/574/576/578 ($Cl_4$)

EXAMPLE 88

(R)-N-[[3-[(1,2-Dihydro-3,5(4H)-dioxo-1,2-diphenyl-3H-1,2,4-triazol-4-yl)methyl]phenyl]methyl]-$N^2$-(diphenylacetyl)-argininamide a) (R)-$N^5$-[Amino(nitroimino)methyl]-$N^2$-[(tert.-butyloxy)-carbonyl]-N-[[3-[(1,2-dihydro-3,5(4H)-dioxo-1,2-diphenyl-3H-1,2,4-triazol-4-yl)methyl]-phenyl]methyl]-ornithinamide Prepared, analogously to Example 13a) but using a mixture of tetrahydrofuran/dimethylformamide (1/1 (v/v)) as solvent instead of tetrahydrofuran, from Boc-D-Arg($NO_2$)-OH and 3-[(1,2-dihydro-3,5(4H)-dioxo-1,2-diphenyl-3H-1,2,4-triazol-4-yl)methyl]-benzenemethylamine in a yield of 28% of theory.

Colourless amorphous substance.

IR (KBr):

1785 $cm^{-1}$ (five-membered ring C═O)

1725 $cm^{-1}$ (ester-C═O)

1660, 1630 $cm^{-1}$ (amide-C═O)

ESI-MS:

$(M+H)^+$=674

$(M+Na)^+$=696

$(M+K)^+$=712 b) (R)-$N^5$-[Amino(nitroimino)methyl]-N-[[3-[(1,2-dihydro-3,5-(4H)-dioxo-1,2-diphenyl-3H-1,2,4-triazol-4-yl)methyl]phenyl]methyl]-ornithinamide Prepared, analogously to Example 23b) but using saturated aqueous sodium carbonate solution instead of ammonia, from (R)-$N^5$-[amino(nitroimino)methyl]-$N^2$-[(tert.-butyloxy)carbonyl-N-[[3-[(1,2-dihydro-3,5(4H)-dioxo-1,2-diphenyl-3H-1,2,4-triazol-4-yl)methyl]-phenyl]methyl]-ornithinamide by the action of trifluoroacetic acid in a yield of 80% of theory.

Colourless amorphous substance which was further processed without purification.

c) (R)-$N^5$-[Amino(nitroimino)methyl]-N-[[3-[(1,2-dihydro-3,5-(4H)-dioxo-1,2-diphenyl-3H-1,2,4-triazol-4-yl)methyl]phenyl]methyl]-$N^2$-(diphenylacetyl)-ornithinamide Prepared, analogously to Example 69c) but using 4-methylmorpholine instead of triethylamine and tetrahydrofuran as solvent instead of dimethylformamide, from (R)-$N^5$-[amino(nitroimino)methyl]-N-[[3-[(1,2-dihydro-3,5(4H)-dioxo-1,2-diphenyl-3H-1,2,4-triazol-4-yl)methyl]phenyl]methyl]-ornithinamide and diphenylacetylchloride in a yield of 40% of theory.

Colourless amorphous substance which was further processed without purification.

IR (KBr):

1785 $cm^{-1}$ (triazolidindione)

1725 $cm^{-1}$ (triazolidindione)

1650 $cm^{-1}$ (amide-C═O)

ESI-MS:

$(M+H)^+$=768

$(M+Na)^+$=790

$(M+K)^+$=806 d) (R)-N-[[3-(1,2-Dihydro-3,5(4H)-dioxo-1,2-diphenyl-3H-1,2,4-triazol-4-yl)methyl]phenyl]methyl]-$N^2$-(diphenylacetyl)-argininamide Prepared analogously to Example 1c) from (R)-$N^5$-[amino(nitroimino)methyl]-N-[[3-[(1,2-dihydro-3,5(4H)-dioxo-1,2-diphenyl-3H-1,2,4-triazol-4-yl)methyl]phenyl]methyl]-$N^2$-(diphenylacetyl)-ornithinamide by catalytic hydrogenation in the presence of palladium black and 80% aqueous acetic acid in a yield of 48% of theory.

Colourless amorphous substance, $R_f$ 0.78.

EXAMPLE 89

(R,S)-N-[[3-[(1,2-Dihydro-3,5(4H)-dioxo-1,2-diphenyl-3H-1,2,4-triazol-4-yl)methyl]phenyl]methyl]-$N^2$-(diphenylacetyl)-2-methyl-argininamide a) (R,S)-2-(2-Cyanoethyl)-$N^2$-(phenylmethylene)-alanine methylester To a solution of 10.0 g (0.052 Mol) of (R,S)-$N^2$-(phenylmethylene)-alanine methylester (prepared from benzaldehyde and D,L-alanine methylester) in 200 ml of acetonitrile were added, one after the other, 14 g (0.101 Mol) of potassium carbonate, 1.1 g (0.00483 Mol) of benzyltriethylammoniumchloride and 3.3 ml (0.05 Mol) of acrylonitrile and the mixture was then stirred for 4 hours at ambient temperature. The mixture was freed from solvent, the residue was distributed between water and petroleum ether/ethyl acetate (1/1 (v/v)), the organic phase was dried, treated with activated charcoal and evaporated down. The colourless oil obtained in a yield of 10.0 g (82% of theory) was further processed without purification.

IR ($CH_2Cl_2$):

1735 $cm^{-1}$ (ester-C═O)

2240 $cm^{-1}$ (C≡)

MS: $M^+$=244 b) (R,S)-2-(2-Cyanoethyl)-alaninemethylester-hydrochloride

A mixture of 10.0 g (0.041 Mol) of (R,S)-2-(2-cyanoethyl)-$N^2$-(phenylmethylene)-alaninemethylester, 25 ml of methanol and 30 ml of 1N aqueous hydrochloric acid was stirred for 1 hour at ambient temperature. After the addition of 15 ml of 4N hydrochloric acid and covering with 100 ml of diethylether the mixture was stirred for another 14 hours. The ether phase was extracted once more with 20 ml of 1N hydrochloric acid, the aqueous phases were then combined and evaporated down in vacuo. The viscous slurry remaining was taken up in 50 ml of methanol and evaporated down again and this procedure was repeated once more. 6.5 g (82% of theory) of a colourless crystalline product were obtained which was further processed without purification.

c) (R,S)-2-(2-Cyanoethyl)-$N^2$-(diphenylacetyl)-alanine methylester

Prepared, analogously to Example 69c) but using 4-methylmorpholine instead of triethylamine and acetonitrile as solvent instead of dimethylformamide, from diphenylacetylchloride and (R,S)-2-(2-cyanoethyl)-alanine methylester-hydrochloride in a yield of 42% of theory.

Colourless crystals, mp. 177°–179° C.

IR ($CH_2Cl_2$):

2240 $cm^{-1}$ (C≡N)

1740 $cm^{-1}$ (ester-C═O)

1680 $cm^{-1}$ (amide-C═O)

MS: $M^+$=350 d) (R,S)-2-(2-Cyanoethyl)-$N^2$-(diphenylacetyl)-alanine

Prepared analogously to Example 79d) from (R,S)-2-(2-cyanoethyl)-$N^2$-(diphenylacetyl)-alanine methylester and lithiumhydroxide-hydrate in a yield of 73% of theory.

Colourless crystals, mp. 167°–169° C. (acetone).

IR (KBr):

2250 $cm^{-1}$ (C≡N)

1750, 1715 $cm^{-1}$ (carboxylic acid-C═O)

1645 $cm^{-1}$ (amide-C═O)

e) (R,S)-2-(2-Cyanoethyl)-N-[[3-[(1,2-dihydro-3,5(4H)-dioxo-1,2-diphenyl-3H-1,2,4-triazol-4-yl)methyl]-phenyl] methyl]-$N^2$-(diphenylacetyl)-alaninamide Prepared analogously to Example 1b) from (R,S)-2-(2-cyanoethyl)-$N^2$-(diphenylacetyl)-alanine, 3-[(1,2-dihydro-3,5(4H)-dioxo-1,2-diphenyl-3H-1,2,4-triazol-4-yl)methyl]-benzenemethylamine and isobutyl chlorocarbonate in a yield of 48% of theory, Colourless amorphous substance which was further processed without purification.

IR (KBr):

3440, 3270 $cm^{-1}$ (NH, partly associated)

2250 $cm^{-1}$ (C≡N)

1780, 1720 $cm^{-1}$ (triazolidinedione-C═O)

1680 $cm^{-1}$ (amide-C═O)

MS: $M^+$=690 f) (R,S)-N-[[3-[(1,2-Dihydro-3,5(4H)-dioxo-1,2-diphenyl-3H-1,2,4-triazol-4-yl)methyl]phenyl]-methyl]-$N^2$-(diphenylacetyl)-2-methyl-ornithinamide 0.69 g (1 mMol) of (R,S)-2-(2-cyanoethyl)-N-[[3-[(1,2-dihydro-3,5(4H)-dioxo-1,2-diphenyl-3H-1,2,4-triazol-4-yl) methyl]phenyl]methyl]-$N^2$-(diphenylacetyl)-alaninamide were dissolved in a mixture of 10 ml of tetrahydrofuran and 50 ml of methanol saturated with ammonia and after the addition of 0.6 g of Raney nickel the mixture was hydrogenated under a pressure of 5 bar and at ambient temperature until the uptake of hydrogen had ceased. After working up in the usual way 0.5 g (72% of theory) of a colourless amorphous substance were obtained which was further processed without purification.

IR ($CH_2Cl_2$): 1680, 1630 $cm^{-1}$ (amide-C═O)

MS: $M^+$=694 g) (R,S)-N-[[3-[(1,2-Dihydro-3,5(4H)-dioxo-1,2-diphenyl-3H-1,2,4-triazol-4-yl)methyl]phenyl]-methyl]-$N^2$-(diphenylacetyl)-2-methyl-argininamide Prepared analogously to Example 42g) from (R,S)-N-[[3-](1,2-dihydro-3,5(4H)-dioxo-1,2-diphenyl-3H-1,2,4-triazol-4-yl)methyl]phenyl]methyl]-$N^2$-(diphenylacetyl)-2-methyl-ornithinamide and 3,5-dimethylpyrazol-1-carboxylic acid amidinium nitrate in a yield of 41% of theory.

Colourless amorphous substance, $R_f$ 0.75.

IR (KBr): 1685, 1630 $cm^{-1}$ (amide-C═O)

EI-MS: $(M+H)^+$=737

EXAMPLE 90

$N^5$-[Amino(nitroimino)methyl]-$N^2$-(diphenylacetyl)-N-[(4-hydroxyphenyl)methyl]-ornithinamide Prepared analogously to Example 8a) from (R)-$N^5$-[amino(nitroimino)methyl]-$N^2$-(diphenylacetyl)-ornithine, 4-hydroxybenzenemethylamine and TBTU in a yield of 45% of theory.

Colourless crystals, mp. 172°–175° C. (acetone/diethylether).

IR (KBr):

3600 $cm^{-1}$ (O—H)

1645 $cm^{-1}$ (amide-C═O)

1550, 1275 $cm^{-1}$ (N—$NO_2$)

ESI-MS:

$(M+H)^+$=519

$(M+Na)^+$=541

EXAMPLE 91

$N^2$-(Diphenylacetyl)-N-[(3-hydroxyphenyl)methyl]-argininamide-acetate a) $N^5$-(Amino(nitroimino)methyl]-$N^2$-(diphenylacetyl)-N-[(3-hydroxyphenyl)methyl]-ornithinamide Prepared analogously to Example 8a) from (R)-$N^5$-[amino(nitroimino)methyl]-$N^2$-(diphenylacetyl)-ornithine, 3-hydroxybenzenemethanamine and TBTU in a yield of 38% of theory.

Colourless amorphous substance.

IR (KBr):

1645 $cm^{-1}$ (amide-C═O)

1550, 1275 $cm^{-1}$ (N—$NO_2$)

ESI-MS:

$(M+H)^+$=519

$(M+NH_4)^+=536$ $(M+Na)^+=541$ $(M+K)^+=557$ b) $N^2$-(Diphenylacetyl)-N-[(3-hydroxyphenyl)methyl]-argininamide-acetate Prepared analogously to Example 1c) from $N^5$-[amino(nitroimino)-methyl]-$N^2$-(diphenylacetyl)-N-[(3-hydroxyphenyl)methyl]-ornithinamide by catalytic hydrogenation in the presence of palladium black and 80 aqueous acetic acid in a yield of 79% of theory.

Colourless amorphous substance, $R_f$ 0.75.

IR (KBr): 1635–1670 $cm^{-1}$ (C═O)

ESI-MS: $(M+H)^+=474$

EXAMPLE 92

(R)-N-[[3-[(4,5-Dihydro-2,4(3H)-dioxo-5,5-diphenyl-1H-imidazol-3-yl)methyl]phenyl]methyl]-$N^2$-(diphenylacetyl)-argininamide-acetate a) 3-[(3-Cyanophenyl)methyl]-4,5-dihydro-5,5-diphenyl-1H-imidazol-2,4(3H)-dione Prepared by reacting 25.5 g (0.101 Mol) of 5,5-diphenylhydantoin with 21.15 g (0.108 Mol) of 3-(bromomethyl)-benzonitrile in the presence of 12.0 g (0.107 Mol) of potassium tert.-butoxide and 200 ml of anhydrous dimethylformamide. After conventional working up 34.0 g (92% of theory) of colourless crystals were obtained, mp. 160°–164° C.

IR ($CH_2Cl_2$):

3330 $cm^{-1}$ (N—H)

2220 $cm^{-1}$ (C≡N)

1780, 1720 $cm^{-1}$ (imidazolidindione-C═O)

MS: $M^+=367$ b) 3-[(4,5-Dihydro-2,4(3H)-dioxo-5,5-diphenyl-1H-imidazol-3-yl)methyl]benzenemethanamine Prepared analogously to Example 89f) from 3-[(3-cyanophenyl)-methyl]-4,5-dihydro-5,5-diphenyl-1H-imidazol-2,4(3H)-dione by catalytic hydrogenation in the presence of Raney nickel and ammonia in a yield of 100% of theory.

Colourless crystals.

IR ($CH_2Cl_2$):

3430 $cm^{-1}$ (NH)

1780, 1720 $cm^{-1}$ (imidazolidindione-C═O)

MS: $M^+=371$ c) (R)-$N^5$-[Amino(nitroimino)methyl]-$N^2$-[(tert.-butyloxy)-carbonyl]-N-[[3-[(4,5-dihydro-2,4(3H)-dioxo-5,5-diphenyl-1H-imidazol-3-yl)methyl]phenyl]methyl]-ornithinamide Prepared analogously to Example 8a) from Boc-D-Arg $(NO_2)$-OH, 3-[(4,5-dihydro-2,4(3H)-dioxo-5,5-diphenyl-1H-imidazol-3-yl)-methyl]-benzenemethanamine and TBTU in a yield of 65% of theory.

Colourless crystals which were further processed without purification.

d) (R)-$N^5$-[Amino(nitroimino)methyl]-N-[[3-[(4,5-dihydro-2,4(3H)-dioxo-5,5-diphenyl-1H-imidazol-3-yl)methyl]phenyl]methyl]-ornithinamide-trifluoroacetate Prepared analogously to Example 5e) from (R)-$N^5$-[amino(nitroimino)methyl]-$N^2$-[(tert.-butyloxy)carbonyl]-N-[[3-[(4,5-dihydro-2,4(3H)-dioxo-5,5-diphenyl-1H-imidazol-3-yl)methyl]-phenyl]methyl]-ornithinamide by the action of trifluoroacetic acid in a yield of 100%.

Colourless amorphous substance which was further processed without purification.

e) (R)-$N^5$-[Amino(nitroimino)methyl]-N-[[3-[(4,5-dihydro-2,4(3H)-dioxo-5,5-diphenyl-1H-imidazol-3-yl)methyl]-phenyl]methyl]-$N^2$-(diphenylacetyl)-ornithinamide Prepared analogously to Example 69c) from (R)-$N^5$-[amino(nitroimino)methyl]-N-[[3-[(4,5-dihydro-2,4(3H)-dioxo-5,5-diphenyl-1H-imidazol-3-yl)methyl]phenyl]-methyl]-ornithinamide-trifluoroacetate and diphenylacetylchloride in a yield 55% of theory.

Colourless crystals, mp. 218°–220° C. (diisopropylether/ethyl acetate=1/1 (v/v)).

IR (KBr):

3430, 3310, 3240 $cm^{-1}$ (NH)

1770, 1710 $cm^{-1}$ (imidazolidindione-C═O)

1670, 1660, 1615 $cm^{-1}$ (C═O, C═N)

ESI-MS:

$(M+H)^+=767$ $(M-H)^-=765$ f) R-N-[[3-[(4,5-Dihydro-2,4(3H)-dioxo-5,5-diphenyl-1H-imidazol-3-yl)methyl]phenyl]methyl]-$N^2$-(diphenylacetyl)-argininamide-acetate Prepared analogously to Example 1c) from (R)-$N^5$-[amino(nitroimino)methyl]-N-[[3-[(4,5-dihydro-2,4(3H)-dioxo-5,5-diphenyl-1H-imidazol-3-yl)methyl]phenyl]-methyl]-$N^2$-(diphenylacetyl)-ornithinamide by catalytic hydrogenation in the presence of palladium black and 80% aqueous acetic acid in a yield of 93% of theory.

Colourless amorphous substance.

IR ($CH_2Cl_2$):

1770, 1715 $cm^{-1}$ (imidazolidindione-C═O)

1660 $cm^{-1}$ (amide-C═O)

ESI-MS: $(M+H)^+=722$

EXAMPLE 93

(R)-$N^2$-(Diphenylacetyl)-N-[(4-hydroxyphenyl)methyl]-argininamide-acetate

Prepared analogously to Example 1c) from (R)-$N^5$-[amino(nitroimino)methyl]-$N^2$-(diphenylacetyl)-N-[(4-hydroxyphenyl)-methyl]-ornithinamide by catalytic hydrogenation in the presence of palladium black and 80% aqueous acetic acid in a yield of 81% of theory.

Colourless crystals, mp. 223°–225° C. (methyl acetate/methanol=98/2 (v/v)).

$R_f$ 0.73.

IR (KBr): 1680, 1665 $cm^{-1}$ (amide-C═O)

ESI-MS: $(M+H)^+=474$

The base melts at mp.: 152°–154° C. (acetone).

EXAMPLE 94

(R,S)-3-(3-Cyanophenyl)-N-[[3-[(4,5-dihydro-2,4(3H)-dioxo-5,5-diphenyl-1H-imidazol-3-yl)methyl]phenyl]-methyl]-$N^2$-(diphenylacetyl)alaninamide a) (R,S)-$N^2$-[(tert.-Butyloxy)carbonyl]-3-(3-cyanophenyl)-alanine Prepared analogously to Example 52b) from 3-(3-cyanophenyl)-alanine-hydrochloride, di-tert.-butyl-dicarbonate and sodium hydroxide solution in a yield of 28% of theory.

Colourless crystals.

IR ($CH_2Cl_2$):

3430 $cm^{-1}$ (NH, partly associated)

2230 $cm^{-1}$ (C≡N)

ESI-MS: $(M-H)^-=289$ b) (R,S)-$N^2$-[(tert.-Butyloxy)carbonyl]-3-(3-cyanophenyl)-N-[[3-[(4,5-dihydro-2,4(3H)dioxo-5,5-diphenyl-1H-imidazol-3-yl)methyl]phenyl]methyl]-alaninamide Prepared analogously to Example 8a) from (R,S)-$N^2$-[(tert.-butyloxy)carbonyl]-3-(3-cyanophenyl)-alanine, 3-[(4,5-dihydro-2,4(3H)-dioxo-5,5-diphenyl-1H-imidazol-3-yl)methyl]-benzenemethanamine and TBTU in a yield of 49% of theory.

Colourless crystals, mp. 185°–187° C. (Decomp.).

IR (KBr):

2235 $cm^{-1}$ (C≡N)

1780, 1725, 1715 $cm^{-1}$ (ester-C=O, imidazolidindione-C=O)

1655 $cm^{-1}$ (amide-C=O)

c) (R,S)-3-(3-Cyanophenyl)-N-[[3-[(4,5-dihydro-2,4(3H)-dioxo-5,5-diphenyl-1H-imidazol-3-yl)methyl]phenyl]methyl]-alaninamide-trifluoroacetate Prepared analogously to Example 5e) from (R,S)-$N^2$-[(tert.-butyloxy)carbonyl]-3-(3-cyanophenyl)-N-[[3-[(4,5-dihydro-2,4(3H)-dioxo-5,5-diphenyl-1H-imidazol-3-yl)methyl]phenyl]methyl]-alaninamide by the action of trifluoroacetic acid in a yield of 100%.

Colourless crystals were further processed without purification.

IR ($CH_2Cl_2$):

2230 $cm^{-1}$ (C≡N)

1775, 1715 $cm^{-1}$ (imidazolidindione-C=O)

1675 $cm^{-1}$ (amide-C=O)

d) (R,S)-3-(3-Cyanophenyl)-N-[[3-[(4,5-dihydro-2,4(3H)-dioxo-5,5-diphenyl-1H-imidazol-3-yl)methyl]phenyl]methyl]-$N^2$-(diphenylacetyl)-alaninamide Prepared analogously to Example 69c) from (R,S)-3-(3-cyanophenyl)-N-[[3-[(4,5-dihydro-2,4(3H)-dioxo-5,5-diphenyl-1H-imidazol-3-yl)-methyl]phenyl]methyl]-alaninamide-trifluoroacetate and diphenylacetylchloride in a yield of 45% of theory.

Colourless crystals, mp. 211°–213° C. (ethyl acetate).

IR (KBr):

3290 $cm^{-1}$ (NH)

2230 $cm^{-1}$ (C≡N)

1770, 1715 $cm^{-1}$ (imidazolidindione-C=O)

1645 $cm^{-1}$ (amide-C=O)

MS: $M^+$=737

EXAMPLE 95

$N^2$-(Diphenylacetyl)-N-[2-(4-hydroxyphenyl)ethyl]-argininamide-acetate a) $N^5$-[Amino(nitroimino)methyl]-$N^2$-(diphenylacetyl)-N-[2-(4-hydroxyphenyl)ethyl]-ornithinamide Prepared analogously to Example 5d) from (R)-$N^5$-[amino(nitroimino)methyl]-$N^2$-(diphenylacetyl)-ornithine, 2-(4-hydroxyphenyl)ethanamine and TBTU in a yield of 44% of theory.

Colourless crystals, mp. 144°–145° C.

IR (KBr): 1645 $cm^{-1}$ (amide-C=O)

ESI-MS:

$(M+H)^+$=533

$(M+Na)^+$=555 b) $N^2$-(Diphenylacetyl)-N-[2-(4-hydroxyphenyl)ethyl]-argininamide-acetate

Prepared analogously to Example 1c) from $N^5$-[amino(nitroimino)methyl]-$N^2$-(diphenylacetyl)-N-[2-(4-hydroxyphenyl)-ethyl]-ornithinamide by catalytic hydrogenation in the presence of palladium black and 80% aqueous acetic acid in a yield of 51% of theory.

Colourless amorphous substance, $R_f$ 0.75.

IR (KBr): 1655 $cm^{-1}$ (amide-C=O)

ESI-MS: $(M+H)^+$=488

EXAMPLE 96

$N^2$-(Diphenylacetyl)-N-[(4'-hydroxy)-[1,1'-biphenyl]-4-yl)-methyl]-argininamide-acetate a) $N^5$-[Amino(nitroimino)methyl]-$N^2$-(diphenylacetyl)-N-[(4'-hydroxy-[1,1'-biphenyl]-4-yl)methyl]-ornithinamide Prepared analogously to Example 5d) from (R)-$N^5$-[amino(nitroimino)methyl]-$N^2$-(diphenylacetyl)-ornithine, 4'-hydroxy-[1,1'-biphenyl]-4-methanamine and TBTU in a yield of 48% of theory.

Colourless amorphous substance which was further processed without purification.

IR (KBr):

1640 $cm^{-1}$ (amide-C=O)

1575, 1265 $cm^{-1}$ (N—$NO_2$)

1505 $cm^{-1}$ (Amid-II)

ESI-MS:

$(M-H)^-$=593

$(M+Na)^+$=617 b) $N^2$-(Diphenylacetyl)-N-[(4'-hydroxy-[1,1'-biphenyl]-4-yl)methyl]-argininamide-acetate Prepared analogously to Example 1c) from $N^5$-[amino(nitroimino)-methyl]-$N^2$-(diphenylacetyl)-N-[(4'-hydroxy-[1,1'-biphenyl]-4-yl)methyl]-ornithinamide by catalytic hydrogenation in the presence of palladium black and 80% aqueous acetic acid in a yield of 48% of theory.

Colourless amorphous substance, $R_f$ 0.76.

IR (KBr):

1655 $cm^{-1}$ (amide-C=O)

1505 $cm^{-1}$ (amide-II)

ESI-MS: $(M+H)^+$=550

EXAMPLE 97

N-[[4-[(1,2-Dihydro-3,5(4H)-dioxo-1,2-diphenyl-3H-1,2,4-triazol-4-yl)methyl]phenyl]methyl]-$N^2$-(diphenylacetyl)-argininamide-acetate a) $N^5$-[Amino(nitroimino)methyl]-N-[[4-[(1,2-dihydro-3,5(4H)-dioxo-1,2-diphenyl-3H-1,2,4-triazol-4-yl)methyl]-phenyl]methyl]-$N^2$-(diphenylacetyl)-ornithinamide Prepared analogously to Example 5d) from (R)-$N^5$-[amino(nitroimino)methyl]-$N^2$-(diphenylacetyl)-ornithine, 4-[(1,2-dihydro-3,5(4H)-dioxo-1,2-diphenyl-3H-1,2,4-triazol-4-yl)methyl]-benzenemethanamine and TBTU in a yield of 28% of theory, Colourless amorphous substance which was further processed without purification.

IR (KBr):

1755, 1725 $cm^{-1}$ (tiazolidindione-C=O)

1645 $cm^{-1}$ (amide-C=O)

1505 $cm^{-1}$ (Amid-II)

ESI-MS:

$(M+H)^+$=768

$(M+H)^+$=790 b) N-[[4-[(1,2-Dihydro-3,5(4H)-dioxo-1,2-diphenyl-3H-1,2,4-triazol-4-yl)methyl]phenyl]methyl]-$N^2$-(diphenylacetyl)-argininamide-acetate Prepared analogously to Example 1c) from $N^5$-[amino(nitroimino)-methyl]-N-[[4-[(1,2-dihydro-3,5(4H)-dioxo-1,2-diphenyl-3H-1,2,4-triazol-4-yl)methyl]phenyl]methyl]-$N^2$-(diphenylacetyl)-ornithinamide by catalytic hydrogenation in the presence of palladium black and 80% aqueous acetic acid in a yield of 21% of theory.

Colourless amorphous substance, $R_f$ 0.73.

IR (KBr):

1780, 1730 $cm^{-1}$ (triazolidindione-C═O)

1660 $cm^{-1}$ (amide-C═O)

ESI-MS: $(M+H)^+$=723

EXAMPLE 98

(R,S)-$N^5$-(Aminocarbonyl)-$N^2$-(diphenylacetyl)-N-[(4-hydroxyphenyl)methyl]-ornithinamide Prepared analogously to Example 5d) from (R,S)-$N^5$-(aminocarbonyl)-$N^2$-(diphenylacetyl)-ornithine (obtained according to Example 1a) from diphenylacetylchloride and (R,S)-citrullin) and 4-hydroxybenzenemethanamine and TBTU in a yield of 34% of theory.

Colourless crystals, mp. 217°–220° C. and $R_f$ 0.89.

IR (KBr): 1640 $cm^{-1}$ (amide-C═O)

ESI-MS:

$(M+H)^+$=475

$(M+Na)^+$=497

$(M-H)^-$=473

EXAMPLE 99

$N^2$-(Diphenylacetyl)-N-[(4-methoxyphenyl)methyl]-argininamide-acetate a) $N^5$-[Amino(nitroimino)methyl]-$N^2$-(diphenylacetyl)-N-[(4-methoxyphenyl)methyl]-ornithinamide Prepared analogously to Example 8a) from (R)-$N^5$-[amino(nitroimino)methyl]-$N^2$-(diphenylacetyl)-ornithine, 4-methoxybenzenemethanamine and TBTU in a yield of 37% of theory.

IR (KBr):

1635 $cm^{-1}$ (amide-C═O)

1515 $cm^{-1}$ (amide-II)

ESI-MS:

$(M+H)^+$=533

$(M+Na)^+$=555

$(M+K)^+$=571 b) $N^2$-(Diphenylacetyl)-N-[(4-methoxyphenyl)methyl]-argininamide-acetate

Prepared analogously to Example 1c) from $N^5$-[amino(nitroimino)-methyl]-$N^2$-(diphenylacetyl)-N-[(4-methoxyphenyl)methyl]-ornithinamide by catalytic hydrogenation in the presence of palladium black and 80% acetic acid in a yield of 85% of theory.

Colourless amorphous substance, $R_f$ 0.72.

IR (KBr): 1660 $cm^{-1}$ (amide-C═O)

EI-MS:

$(M+H)^+$=488

$(2M+H)^+$=975

EXAMPLE 100

$N^2$-(Diphenylacetyl)-N-[2-(4-methoxyphenyl)ethyl]-argininamide-acetate a) $N^5$-[Amino(nitroimino)methyl]-$N^2$-(diphenylacetyl)-N-[2-(4-methoxyphenyl)ethyl]-ornithinamide Prepared analogously to Example 8a) from (R)-$N^5$-[amino(nitroimino)methyl]-$N^2$-(diphenylacetyl)-ornithine, 4-methoxybenzenethanamine and TBTU in a yield of 47% of theory.

Colourless crystals which were further processed without purification.

IR (KBr): 1670, 1655, 1630 $cm^{-1}$ (C═O, C═N)

EI-MS:

$(M+H)^+$=547

$(M+Na)^+$=569 b) $N^2$-(Diphenylacetyl)-N-[2-(4-methoxyphenyl)ethyl]-argininamide-acetate

Prepared analogously to Example 1c) from $N^5$-[amino(nitroimino)-methyl]-$N^2$-(diphenylacetyl)-N-[2-(4-methoxyphenyl)ethyl]-ornithinamide by catalytic hydrogenation in the presence of palladium black and 80% aqueous acetic acid in a yield of 43% of theory.

Colourless amorphous substance, $R_f$ 0.72.

IR (KBr): 1655, 1630 $cm^{-1}$ (amide-C═O)

EI-MS: $(M+H)^+$=502

EXAMPLE 101

$N^2$-(Diphenylacetyl)-N-[(2-methoxyphenyl)methyl]-argininamide-acetate a) $N^5$-[Amino(nitroimino)methyl]-$N^2$-(diphenylacetyl)-N-[2-methoxyphenyl)methyl]-ornithinamide Prepared analogously to Example 8a) from (R)-$N^5$-[amino(nitroimino)methyl]-$N^2$-(diphenylacetyl)-ornithine, 2-methoxybenzenemethanamine and TBTU in a yield of 29% of theory.

Colourless crystals, mp. 182°–185° C.

EI-MS:

$(M+H)^+$=533

$(M+Na)^+$=555

$(M+K)^+$=571 b) $N^2$-(Diphenylacetyl)-N-[(2-methoxyphenyl)methyl]-argininamide-acetate

Prepared analogously to Example 1c) from $N^5$-[amino(nitroimino)-methyl]-$N^2$-(diphenylacetyl)-N-[(2-methoxyphenyl)methyl]-ornithinamide by catalytic hydrogenation in the presence of palladium black and 80% acetic acid in a yield of 65% of theory.

Colourless amorphous substance, $R_f$ 0.70.

IR (KBr): 1650 $cm^{-1}$ (amide-C═O)

EI-MS: $(M+H)^+$=488

EXAMPLE 102

$N^2$-(Diphenylacetyl)-N-[2-(3-methoxyphenyl)ethyl]-argininamide-acetate a) $N^5$-[Amino(nitroimino)methyl]-$N^2$-(diphenylacetyl)-N-[2-(3-methoxyphenyl)ethyl]-ornithinamide Prepared analogously to Example 8a) from (R)-$N^5$-[amino(nitroimino)methyl]-$N^2$-(diphenylacetyl)-ornithine, 3-methoxybenzeneethanamine and TBTU in a yield of 28% of theory.

Colourless crystals, mp. 200°–203° C. (ethyl acetate).

IR (KBr): 1670, 1655, 1635 $cm^{-1}$ (C═O, C═N)

ESI-MS:

$(M+H)^+$=547

$(M+Na)^+$=569

$(M+K)^+$=585 b) $N^2$-(Diphenylacetyl)-N-[2-(3-methoxyphenyl)ethyl]-argininamide-acetate

Prepared analogously to Example 1c) from $N^5$-[amino(nitroimino)-methyl]-$N^2$-(diphenylacetyl)-N-[2-(3-methoxyphenyl)ethyl]-ornithinamide by catalytic hydrogenation in the presence of palladium black and 80% aqueous acetic acid in a yield of 63% of theory.

Colourless amorphous substance, $R_f$ 0.76.

IR ($CH_2Cl_2$): 1660 $cm^{-1}$ (amide-C═O)

ESI-MS: $(M+H)^+$=502

EXAMPLE 103

$N^2$-[$N^2$-(Diphenylacetyl)-D-arginyl]-L-tyrosinamide a) $N^2$-[$N^5$-[Amino(nitroimino)methyl]-$N^2$-(diphenylacetyl)-D-ornithyl]-L-tyrosinamide Prepared analogously to Example 8a) from (R)-$N^5$-[amino(nitroimino)methyl]-$N^2$-(diphenylacetyl)-ornithine, L-tyrosinamide and TBTU in a yield of 47% of theory.

Colourless amorphous substance.

IR (KBr):

1660 $cm^{-1}$ (amide-C═O)

1515 $cm^{-1}$ (amide-II)

b) $N^2$-[$N^2$-(Diphenylacetyl)-D-arginyl]-L-tyrosinamide

Prepared analogously to Example 1c) from $N^2$-[$N^5$-[amino(nitroimino)methyl]-$N^2$-(diphenylacetyl)-D-ornithyl]-L-tyrosinamide by catalytic hydrogenation in the presence of palladium black and 80% aqueous acetic acid.

Colourless amorphous substance, $R_f$ 0.70.

IR (KBr):

1660 $cm^{-1}$ (amide-C═O)

1515 $cm^{-1}$ (amide-II)

ESI-MS: $(M+H)^+$=531

EXAMPLE 104

$N^2$-(Diphenylacetyl)-N-[(3-methoxyphenyl)methyl]-argininamide-acetate a) $N^5$-[Amino(nitroimino)methyl]-$N^2$-(diphenylacetyl)-N-[(3-methoxyphenyl)methyl]-ornithinamide Prepared analogously to Example 8a) from (R)-$N^5$-[amino(nitroimino)methyl]-$N^2$-(diphenylacetyl)-ornithine, 3-methoxybenzenemethanamine and TBTU in a yield of 55% of theory.

IR (KBr):

1670, 1655, 1635 $cm^{-1}$ (amide-C═O, C═N)

1495 $cm^{-1}$ (amide-II)

ESI-MS:

$(M+H)^+$=533

$(M+Na)^+$=555 b) $N^2$-(Diphenylacetyl)-N-[(3-methoxyphenyl)methyl]-argininamide-acetate

Prepared analogously to Example 1c) from $N^5$-[amino(nitroimino)methyl]-$N^2$-(diphenylacetyl)-N-[(3-methoxyphenyl)methyl]-ornithinamide by catalytic hydrogenation in the presence of palladium black and 80% aqueous acetic acid in a yield of 93% of theory.

Colourless amorphous substance, $R_f$ 0.73.

IR ($CH_2Cl_2$):

1660 $cm^{-1}$ (C═O)

1495 $cm^{-1}$ (amide-II)

ESI-MS: $(M+H)^+$=488

EXAMPLE 105

(R,S)-3-[4-(Aminoiminomethyl)phenyl]-$N^2$-(diphenylacetyl)-N-[(4-methoxyphenyl)methyl]-alaninamide-hydrochloride a) (R,S)-3-(4-Cyanophenyl)-alanine-hydrochloride A mixture of 235 g (0.707 Mol) of diethyl α-(acetamido)-α-[(4-cyanophenyl)methyl]-malonate (mp.: 163°–165° C.; prepared from diethyl α-acetamido-malonate and 4-(bromomethyl)-benzonitrile in the presence of sodium ethoxide), 1.28 liters (3.84 Mol) of 3N aqueous hydrochloric acid and 0.64 liters of glacial acetic acid was refluxed for 7 hours. The mixture cooled to +5° C. was filtered and the filtrate was evaporated down in vacuo. The residue was intensively washed with isopropanol and then dried in vacuo. 92.9 g (58% of theory) of colourless crystals were obtained, mp. 219° C. (Decomp.).

b) (R,S)-3-4-Cyanophenyl)-$N^2$-(diphenylacetyl)-alanine

Prepared analogously to Example 1a) from (R,S)-3-(4-cyanophenyl)-alanine-hydrochloride and diphenylacetyl-chloride in the presence of sodium hydroxide solution in a yield of 82% of theory.

Colourless crystals, mp. 110° C. (Decomp.).

IR ($CH_2Cl_2$):

2225 $cm^{-1}$ (C≡N)

1655 $cm^{-1}$ (amide-C═O)

c) (R,S)-3-(4-Cyanophenyl)-$N^2$-(diphenylacetyl)-N-[(4-methoxyphenyl)methyl]-alaninamide Prepared analogously to Example 8a) from (R,S)-3-(4-cyanophenyl)-$N^2$-(diphenylacetyl)-alanine, 4-methoxybenzenemethanamine and TBTU in a yield of 61% of theory.

Colourles crystals, mp. 213°–215° C. (Isopropanol).

IR (KBr):

1645 $cm^{-1}$ (amide-C═O)

2230 $cm^{-1}$ (C≡N)

3270 $cm^{-1}$ (N—H)

2840 $cm^{-1}$ ($OCH_3$)

1515 $cm^{-1}$ (Amid-II)

ESI-MS: $M^+$=503 d) (R,S)-3-[4-(Aminoiminomethyl)phenyl]-$N^2$-(diphenylacetyl)-N-[(4-methoxyphenyl)methyl]-alaninamide-hydrochloride Prepared, analogously to Example 79f) but using methanol instead of ethanol, from (R,S)-3-(4-cyanophenyl)-$N^2$-(diphenlacetyo-N-[(4-methoxyphenyl)methyl]-alaninamide and hydrogen chloride, then later ammonium carbonate, in a yield of 82% theory.

Colourless crystals, mp. 161°–166° C. and $R_f$ 0.77.

IR (KBr): 1665, 1645 $cm^{-1}$ (C═O, C═N)

ESI-MS: $(M+H)^+$=521

EXAMPLE 106

(R,S)-3-[4-(Aminoiminomethyl)phenyl]-$N^2$-(diphenylacetyl)-N-[(4-hydroxyphenyl)methyl]-alaninamide-hydrochloride a) (R,S)-3-(4-Cyanophenyl)-$N^2$-(diphenylacetyl)-N-[(4-hydroxyphenyl)methyl]-alaninamide Prepared analogously to Example 8a) from (R,S)-3-(4-cyanophenyl)-$N^2$-(diphenylacetyl)-alanine, 4-hydroxybenzenemethanamine and TBTU in a yield of 58% of theory.

Colourless crystals, mp. 190°–194° C. (Decomp.).

IR (KBr):

2230 $cm^{-1}$ (C≡N)

1645 $cm^{-1}$ (amide-C═O)

1515 $cm^{-1}$ (amide-II)

MS: $M^+$=489 b) (R,S)-3-(4-Aminoiminomethyl)phenyl]-$N^2$-(diphenylacetyl)-N-[(4-hydroxyphenyl)methyl]-alaninamide-hydrochloride Prepared analogously to Example 105d) from (R,S)-3-(4-cyanophenyl]-$N^2$-(diphenylacetyl)-N-[(4-hydroxyphenyl)methyl]-alaninamide using hydrogen chloride and then ammonium carbonate in a yield of 67% of theory.

Colourless crystals, mp. 136° C. (Decomp.) and $R_f$ 0.78.

IR (KBr):

1655 cm$^{-1}$ (amide-C═O)

1515 cm$^{-1}$ (amide-II)

ESI-MS: $(M+H)^+$=507

EXAMPLE 107

(R,S)-3-(3-Cyanophenyl)-N$^2$-(diphenylacetyl)-N-[(4-hydroxyphenyl)methyl]-alaninamide a) (R,S)-3-(3-Cyanophenyl)-alanine-hydrochloride Prepared analogously to Example 105a) from diethyl α-(acetamido)-α-[(3-cyanophenyl)methyl]malonate (mp.: 139°–141° C.), hydrochloric acid and glacial acetic acid in a yield of 69% of theory.

Colourless crystals, mp. 206° C. (Decomp.).

b) (R,S)-3-(3-Cyanophenyl)-N$^2$-(diphenylacetyl)-alanine

Prepared analogously to Example 1a) from (R,S)-3-(3-cyanophenyl)-alanine-hydrochloride and diphenylacetylchloride in the presence of sodium hydroxide solution in a yield of 58% of theory.

Colourless crystals, mp. 145°–147° C. (ethyl acetate).

IR (KBr):

3380 cm$^{-1}$ (N—H)

2230 cm$^{-1}$ (C≡N)

1725 cm$^{-1}$ (carboxylic acid-C═O)

1665 cm$^{-1}$ (amide-C═O)

1515 cm$^{-1}$ (amide-II)

c) (R,S)-3-(3-Cyanophenyl)-N$^2$-(diphenylacetyl)-N-[(4-hydroxyphenyl)methyl]-alaninamide Prepared analogously to Example 8a) from (R,S)-3-(3-cyanophenyl)-N$^2$-(diphenylacetyl)-alanine, 4-hydroxybenzenemethylamine and TBTU in a yield of 58% of theory.

Colourless crystals, mp. 115°–118° C. (Decomp.) (isopropanol) and $R_f$ 0.96.

IR (KBr):

2230 cm$^{-1}$ (C≡N)

1645 cm$^{-1}$ (amide-C═O)

MS: $M^+$=489

EXAMPLE 108

(R)-N,N-Diethyl-N$^2$-(diphenylacetyl)-argininamide-acetate a) (R)-N$^5$-[Amino(nitroimino)methyl]-N,N-diethyl-N$^2$-(diphenylacetyl)-ornithinamide Prepared analogously to Example 1b) from (R)-N$^5$-[amino(nitroimino)methyl]-N$^2$-(diphenylacetyl)-ornithine, N,N-diethylamine and isobutyl chlorocarbonate in a yield of 37% of theory.

Colourless crystals, mp. 141°–144° C. (ethyl acetate/isopropanol=1/1 (v/v)).

IR ($CH_2Cl_2$): 1635, 1660 cm$^{-1}$ (amide-C═O)

ESI-MS:

$(M+H)^+$=469

$(M+Na)^+$=491

$(M+K)^+$=507

$(M+NH_4)^+$=486 b) (R)-N,N-Diethyl-N$^2$-(diphenylacetyl)-argininamide-acetate

Prepared analogously to Example 1c) from (R)-N$^5$-[amino(nitroimino)methyl]-N,N-diethyl-N$^2$-(diphenylacetyl)-ornithinamide by catalytic hydrogenation in the presence of palladium black and 80% aqueous acetic acid in a yield of 64% of theory.

Colourless amorphous substance, $R_f$ 0.63.

IR (KBr): 1680, 1620 cm$^{-1}$ (amide-C═O)

ESI-MS: $(M+H)^+$=424

EXAMPLE 109

(R)-N$^2$-(Diphenylacetyl)-N-[[4-[[[(2,2-diphenylethyl)-amino]carbonyl]amino]phenyl]methyl]-argininamide-acetate a) (R)-N$^5$-[Amino(nitroimino)methyl]-N$^2$-(diphenylacetyl)-N-[[4-[[[(2,2-diphenylethyl)-amino]carbonyl]amino]phenyl]-methyl]-ornithinamide Prepared, analogously to Example 13a) but using dichloromethane as solvent instead of tetrahydrofuran and without using triethylamine, from 4-[[[(2,2-diphenylethyl)amino]carbonyl]amino]benzenemethylamine (mp.: 161°–163° C.; obtained from 4-cyanophenylisocyanate and 2,2-diphenylethylamine via N-(4-cyanophenyl-N'-(2,2-diphenylethyl)-urea, mp.: 235°–237° C., and finally by catalytic hydrogenation in the presence of Raney nickel and ammonia), (R)-N$^5$-[amino(nitroimino)methyl]-N$^2$-(diphenylacetyl)-ornithine, DCC and HOBt in a yield of 48% of theory.

Colourless crystals, mp. 274°–276° C. (isopropanol).

IR (KBr): 1640 cm$^{-1}$ (carboxamide-C═O)

ESI-MS:

$(M+H)^+$=741

$(M+Na)^+$=763

$(M-H)^-$=739 b) (R)-N$^2$-(Diphenylacetyl)-N-[[4-[[[(2,2-diphenylethyl)amino]carbonyl]amino]phenyl]methyl]-argininamide-acetate Prepared analogously to Example 1c) from (R)-N$^5$-[amino(nitroimino)methyl]-N$^2$-(diphenylacetyl)-N-[[4-[[[(2,2-diphenylethyl)amino]carbonyl]amino]phenyl]-methyl]-ornithinamide by catalytic hydrogenation in the presence of palladium black and 80% aqueous acetic acid in a yield of 90% of theory.

Colourless crystals, mp. 125°–128° C. and $R_f$ 0.80.

IR (KBr): 1655 cm$^{-1}$ (C═O)

ESI-MS:

$(M+H)^+$=696

$(2M+H)^+$=1391

EXAMPLE 110

(R)-N-(Diphenylmethyl)-N$^2$-[(4-methoxyphenyl)acetyl)-argininamide-acetate a) (R)-N$^5$-[Amino(nitroimino)methyl]-N$^2$-[(tert.-butyloxy)-carbonyl]-N-(diphenylmethyl)-ornithinamide Prepared, analogously to Example 5d) but using dichloromethane as solvent instead of acetonitrile, from Boc-D-Arg($NO_2$)-OH, 1,1-diphenylmethylamine and TBTU in a yield of 83% of theory.

Colourless crystals, mp. 125°–127° C. (ethyl acetate/diisopropylether=1/9 (v/v)).

b) (R)-N$^5$-[Amino (nitroimino)methyl]-N-(diphenylmethyl)-ornithinamide-trifluoroacetate Prepared analogously to Example 5e) from (R)-N$^5$-[amino(nitroimino),methyl]-N$^2$-[(tert.-butyloxy)carbonyl]-N-(diphenylmethyl)-ornithinamide by the action of trifluoroacetic acid in a yield of 95% of theory.

Colourless crystals, mp. 130°–133° C.

c) (R)-N$^5$-[Amino(nitroimino)methyl]-N-(diphenylmethyl)-N$^2$-[(4-methoxyphenyl)acetyl]-ornithinamide Prepared analogously to Example 110a) from (R)-N$^5$-[amino(nitroimino)methyl]-N-(diphenylmethyl)-ornithinamide-trifluoroacetate, 4-methoxybenzylethanoic acid and TBTU in a yield of 47% of theory.

Colourless crystals, mp. 185°–187° C. (methanol).

IR (KBr):

1675, 1655, 1630 $cm^{-1}$ (C═O, C═N)

1515 $cm^{-1}$ (amide-II)

ESI-MS:

$(M+H)^+$=533

$(M+Na)^+$=555 d) (R)-N-(Diphenylmethyl)-$N^2$-[(4-methoxyphenyl)acetyl]-argininamide-acetate

Prepared analogously to Example 1c) from (R)-$N^5$-[amino(nitroimino)methyl]-N-(diphenylmethyl)-$N^2$-[(4-methoxyphenyl)acetyl]-ornithinamide by catalytic hydrogenation in the presence of palladium/animal charcoal and 80% aqueous acetic acid.

Colourless crystals, mp. 150°–160° C. (Decomp.) and $R_f$ 0.71

IR ($CH_2Cl_2$):

1660 $cm^{-1}$ (amide-C═O)

1515 $cm^{-1}$ (amide-II)

ESI-MS: $(M+H)^+$=488

EXAMPLE 111

(R)-N-(Diphenylmethyl)-$N^2$-(phenylacetyl)-argininamide-acetate a) (R)-$N^5$-[Amino(nitroimino)methyl]-N-(diphenylmethyl)-$N^2$-(phenylacetyl)-ornithinamide Prepared analogously to Example 110a) from benzylethanoic acid, R-$N^5$-[amino(nitroimino)methyl]-N-(diphenylmethyl)-ornithine-amide-trifluoroacetate and TBTU in a yield of 45% of theory.

Colourless crystals, mp. 207°–209° C. (methanol).

IR (KBr):

1640 $cm^{-1}$ (amide-C═O)

3430, 3290 $cm^{-1}$ (NH)

ESI-MS:

$(M+H)^+$=503

$(M+Na)^+$=525

$(M+K)^+$=541 b) (R)-N-(Diphenylmethyl)-$N^2$-(phenylacetyl)-argininamide-acetate

Prepared analogously to Example 1c) from (R)-$N^5$-[amino(nitroimino)methyl]-N-(diphenylmethyl)-$N^2$-(phenylacetyl)-ornithinamide by catalytic hydrogenation in the presence of palladium black and 80% aqueous acetic acid.

Colourless crystals, mp. 150°–160° C. (Decomp.) and $R_f$ 0.71.

IR (KBr): 1645 $cm^{-1}$ (C═O)

ESI-MS: $(M+H)^+$=458

EXAMPLE 112

(R)-N-(Diphenylmethyl)-$N^2$-[(4-hydroxyphenyl)acetyl]-argininamide-acetate a) (R)-$N^5$-[Amino(nitroimino)methyl]-N-(diphenylmethyl)-$N^2$-[(4-hydroxyphenyl)acetyl]-ornithinamide Prepared analogously to Example 110a) from 4-hydroxybenzylethanoic acid and (R)-$N^5$-[amino(nitroimino)methyl]-N-(diphenylmethyl)-ornithinamide-trifluoroacetate and TBTU in a yield of 48% of theory.

Colourless crystals, mp. 253°–255° C. (methanol).

IR (KBr):

1675, 1635, 1615 $cm^{-1}$ (C═O, C═N)

1515 $cm^{-1}$ (amide-II)

ESI-MS:

$(M+Na)^+$=541

$(M+K)^+$=557 b) (R)-N-(Diphenylmethyl)-$N^2$-[(4-hydroxyphenyl) acetyl]-argininamide-acetate

Prepared analogously to Example 1c) from (R)-$N^5$-[amino(nitroimino)methyl]-N-(diphenylmethyl)-$N^2$-[(4-hydroxyphenyl)acetyl]-ornithinamide by catalytic hydrogenation in the presence of palladium black and 80% aqueous acetic acid in a yield of 75% of theory.

Colourless crystals, mp. 150°–160° C. (Decomp.) and $R_f$ 0.72.

IR (KBr):

1650 $cm^{-1}$ (amide-C═O)

1515 $cm^{-1}$ (amide-II)

ESI-MS: $(M+H)^+$=474

EXAMPLE 113

$N^2$-(Diphenylacetyl)-N-[4-(4-methoxyphenyl)butyl]-argininamide-acetate a) $N^5$-[Amino(nitroimino)methyl]-$N^2$-(diphenylacetyl)-N-[(4-methoxyphenyl)butyl]-ornithinamide Prepared analogously to Example 8a) from (R)-$N^5$-[amino(nitroimino)methyl]-$N^2$-(diphenylacetyl)-ornithine, 4-(4-methoxyphenyl)-butylamine and TBTU in a yield of 34% of theory.

Colourless crystals, mp. 161°–164° C. (methanol).

IR (KBr):

1670, 1655, 1635 $cm^{-1}$ (C═O, C═N)

1515 $cm^{-1}$ (amide-II)

ESI-MS:

$(M+H)^+$=575

$(M+Na)^+$=597

$(M+K)^+$=613 b) $N^2$-(Diphenylacetyl)-N-[4-(4-methoxyphenyl)butyl]-argininamide-acetate

Prepared analogously to Example 1c) from $N^5$-[amino(nitroimino)methyl]-$N^2$-(diphenylacetyl)-N-[4-(4-methoxyphenyl)butyl]-ornithinamide by catalytic hydrogenation in the presence of palladium black and 80% aqueous acetic acid.

Colourless amorphous substance, $R_f$ 0.74.

IR ($CH_2Cl_2$): 1660 $cm^{-1}$ (amide-C═O)

ESI-MS: $(M+H)^+$=530

EXAMPLE 114

(R,S)-3-[3-(Aminoiminomethyl)phenyl]-$N^2$-(diphenylacetyl)-N-[(4-methoxyphenyl)methyl]-alaninamide-hydrochloride a) (R,S)-3-(3-Cyanophenyl)-$N^2$-(diphenylacetyl)-N-[(4-methoxyphenyl)methyl]-alaninamide Prepared analogously to Example 8a) from (R,S)-3-(3-cyanophenyl)-$N^2$-(diphenylacetyl)-alanine, 4-methoxybenzenemethylamine and TBTU in a yield of 46% of theory.

Colourless crystals, mp. 208°–210° C. (isopropanol).

IR (KBr):

3270 $cm^{-1}$ (NH)

2830 $cm^{-1}$ (C≡N)

1675, 1655, 1640 $cm^{-1}$ (C═O, C═N)

ESI-MS: $M^+$=503 b) (R,S)-3-[3-(Aminoiminomethyl)phenyl]-$N^2$-(diphenylacetyl)-N-[(4-methoxyphenyl)methyl]-alaninamide-hydrochloride Prepared analogously to Example 105d) from (R,S)-3-(3-cyanophenyl)-$N^2$-(diphenylacetyl)-N-[(4-methoxyphenyl)

methyl]-alaninamide by the action of first hydrogen chloride and then ammonium carbonate, in a yield of 98% of theory.

Colourless amorphous substance, $R_f$ 0.78.

IR (KBr): 1655 $cm^{-1}$ (C═O)

ESI-MS: $M^+$=521

EXAMPLE 115

(R,S)-3-[3-(Aminoiminomethyl)phenyl]-$N^2$-(diphenylacetyl)-N-[(4-hydroxyphenyl)methyl]-alaninamide-hydrochloride a) (R,S)-3-(3-Cyanophenyl)-$N^2$-(diphenylacetyl)-N-[(4-hydroxyphenyl)methyl]-alaninamide Prepared analogously to Example 8a) from (R,S)-3-(3-cyanophenyl)-$N^2$-(diphenylacetyl)-alanine, 4-hydroxybenzenemethylamine and TBTU in a yield of 58% of theory.

Colourless crystals, mp. 115°–1180° C. (Decomp.) (isopropanol).

IR (KBr):

2230 $cm^{-1}$ (C≡N)

1645 $cm^{-1}$ (amide-C═O)

1520 $cm^{-1}$ (amide-II)

$M^+$489 b) (R,S)-3-[3-(Aminoiminomethyl)phenyl]-$N^2$-(diphenylacetyl)-N-[(4-hydroxyphenyl)methyl]-alaninamide-hydrochloride Prepared analogously to Example 105d) from (R,S)-3-(3-cyanophenyl)-$N^2$-(diphenylacetyl)-N-[(4-hydroxyphenyl)methyl]-alaninamide by the action of first hydrogen chloride and then ammonium carbonate, in a yield of 97% of theory.

Colourless crystals, mp. 205° C. (Decomp.) (ethanol/diisopropylether=1/9 (v/v)).

IR (KBr):

1655 $cm^{-1}$ (C═O)

1518 $cm^{-1}$ (amide-II)

ESI-MS: $(M+H)^+$=507

EXAMPLE 116

(R,S)-3-[3-(Aminoiminomethyl)phenyl]-$N^2$-(diphenylacetyl)-N-[[3-[(1,2-dihydro-3,5(4H)-dioxo-1,2-diphenyl-3H-1,2,4-triazol-4-yl)methyl]phenyl]methyl]-alaninamide-hydrochloride a) (R,S)-$N^2$-[(tert.-Butyloxy)carbonyl]-3-(3-cyanophenyl)-N-[[3-[(1,2-dihydro-3,5(4H)-dioxo-1,2-diphenyl-3H-1,2,4-triazol-4-yl)methyl]phenyl]-methyl]-alaninamide Prepared analogously to Example 8a) from (R,S)-$N^2$-[(tert.-butyloxy)carbonyl]-3-(3-cyanophenyl)-alanine, 3-[(1,2-dihydro-3,5(4H)-dioxo-1,2-diphenyl-3H-1,2,4-triazol-4-yl)methyl]-benzenemethylamine and TBTU in a yield of 70% theory.

Colourless crystals, mp. 148°–151° C. (methanol).

IR ($CH_2Cl_2$):

3430 $cm^{-1}$ (NH)

2230 $cm^{-1}$ (C≡N)

1780, 1730 $cm^{-1}$ (triazolidindione-C═O)

1685 $cm^{-1}$ (amide-C═O)

ESI-MS:

$(M+H)^+$=645

$(M+NH_4)^+$=662

$(M+Na)^+$=667

$(M+K)^+$=683

$(M-H)^-$=643

$(2M+H)^+$=1289 b) (R,S)-3-(3-Cyanophenyl)-N-[[3-[(1,2-dihydro-3,5(4H)-dioxo-1,2-diphenyl-3H-1,2,4-triazol-4-yl)methyl]phenyl]methyl]-alaninamide-trifluoroacetate Prepared analogously to Example 5e) from (R,S)-$N^2$-[(tert.-butyloxy)carbonyl]-3-(3-cyanophenyl)-N-[[3-[(1,2-dihydro-3,5(4H)-dioxo-1,2-diphenyl-3H-1,2,4-triazol- 4-yl)methyl]phenyl]methyl]-alaninamide by the action of trifluoroacetic acid in quantitative yield.

IR ($CH_2Cl_2$):

2230 $cm^{-1}$ (C≡N)

1780, 1725 $cm^{-1}$ (triazolidindione-C═O)

1685 $cm^{-1}$ (amide-C═O)

MS: $M^+$=544 c) (R,S)-3-(3-Cyanophenyl)-$N^2$-(diphenylacetyl)-N-[[3-[(1,2-dihydro-3,5(4H)-dioxo-1,2-diphenyl-3H-1,2,4-triazol-4-yl)-methyl]phenyl]methyl]-alaninamide Prepared, analogously to Example 69c) but using only dimethylformamide as solvent, from (R,S)-3-(3-cyanophenyl)-N-[[3-[(1,2-dihydro-3,5(4H)-dioxo-1,2-diphenyl-3H-1,2,4-triazol-4-yl)methyl]phenyl]methyl]-alaninamide-trifluoroacetate and diphenylacetylchloride in a yield of 78% of theory.

Colourless crystals, mp. 186–190° C. (ethyl acetate/diisopropylether=1/1 (v/v)).

IR ($CH_2Cl_2$):

3420 $cm^{-1}$ (NH)

2230 $cm^{-1}$ (C≡N)

1780, 1725 $cm^{-1}$ (triazolidindione-C═O)

1675 $cm^{-1}$ (amide-C═O)

MS: $M^+$=738 d) (R,S)-3-[3-(Aminoiminomethyl)phenyl]-$N^2$-(diphenylacetyl)-N-[[3-[(1,2-dihydro-3,5(4H)-dioxo-1,2-diphenyl-3H-1,2,4-triazol-4-yl)methyl]phenyl]-methyl]-alaninamide-hydrochloride Prepared analogously to Example 105d) from (R,S)-3-(3-cyanophenyl)-$N^2$-(diphenylacetyl)-N-[[3-[(1,2-dihydro-3,5(4H)-dioxo-1,2-diphenyl-3H-1,2,4-triazol-4-yl)methyl)phenyl]methyl]-alaninamide by the action of first hydrogen chloride and then ammonium carbonate in a yield of 98% of theory.

Colourless crystals, mp. 225° C. (Decomp.) and $R_f$ 0.85.

IR ($CH_2Cl_2$):

1780, 1725 $cm^{-1}$ (triazolidindione-C═O)

1675 $cm^{-1}$ (amidinium, amide-C═O)

ESI-MS: $(M+H)^+$=756

EXAMPLE 117

(R)-$N^5$-[Amino(nitroimino)methyl)-$N^2$-[[bis-(4-bromophenyl)]acetyl]-N-[(4-hydroxyphenyl)methyl]-ornithinamide To a solution of 0.9 g (2.775 mmol) of (R)-$N^5$-[amino(nitroimino)methyl]-N-(4-hydroxyphenyl)methyl]-ornithinamide in 50 ml of tetrahydrofuran were added first a solution of 0.8 g (7.55 mMol) of sodium carbonate in 10 ml of water, then, dropwise, a solution of 1.259 g (3.32 Mol) of (bis-(4-bromophenyl)]acetylchloride in 50 ml of tetrahydrofuran and the resulting mixture was then stirred for 60 minutes at a reaction temperature of 30° C. The solvent was distilled off in vacuo, the residue was taken up in water and made slightly acidic with acetic acid. It was extracted exhaustively with ethyl acetate, the combined ethyl acetate extracts were dried over sodium sulphate and evaporated down. The residue was purified by column chromatography on silica gel (Baker, silica gel for flash chromatography, 30–60 $\mu$m) using ethyl acetate as the mobile phase. 1.0 g (53% of theory) of colourless crystals were obtained, mp. 163°–167° C. (acetone/diethylether) and $R_f$ 0.96.

IR (KBr): 1660, 1630 $cm^{-1}$ (amide-C═O)

EI-MS: $(M-H)^-$=673/675/677 ($Br_2$)

EXAMPLE 118

(R)-$N^2$-[[Bis-(4-bromophenyl)]acetyl]-N-[(4-hydroxyphenyl)-methyl]-argininamide-formate Prepared analogously to Example 14b) by reduction of (R)-$N^5$-[amino(nitroimino)methyl]-$N^2$-[[bis(4-bromophenyl)]acetyl]-N-[( 4-hydroxyphenyl)methyl)-ornithinamide with tin(II)-chloride-dihydrate in the presence of 60% aqueous formic acid.

Colourless amorphous substance, $R_f$ 0.80.

IR (KBr): 1655 $cm^{-1}$ (C═O)

ESI-MS: $(M+H)^+$=630/632/634 ($Br_2$)

EXAMPLE 119

(R,S)-3-[[(Aminoiminomethyl)amino]methyl]-$N^2$-(diphenyl-acetyl)-N-[(4-methoxyphenyl)methyl]-alaninamide-hydrochloride a) (R,S)-$N^2$-(Diphenylacetyl)-serine-methylester Prepared, analogously to Example 1a) but using sodium carbonate instead of sodium hydroxide, from diphenylacetylchloride and serine-methylester-hydrochloride in a yield of 85% of theory.

Colourless crystals, mp. 156°–158° C.

IR (KBr):

1745 $cm^{-1}$ (ester-C═O)

1655 $cm^{-1}$ (amide-C═O)

2850 $cm^{-1}$ ($OCH_3$)

b) (R,S)-$N^2$-(Diphenylacetyl)-O-(methylsulfonyl) serine-methylester

To a mixture of 12.11 g (0.0386 Mol) of (R,S)-$N^2$-(diphenylacetyl)-serine-methylester, 3.32 ml (0.0429 Mol) methanesulphonic acid chloride and 250 ml of dry tetrahydrofuran was added dropwise a solution of 6.0 ml (0.043 Mol) of triethylamine in 50 ml of dry tetrahydrofuran, taking care that the reaction temperature did not exceed +40° C. The mixture was stirred for a further hour at ambient temperature and filtered and the filtrate was evaporated down in vacuo. The residue was crystallised by triturating with diisopropylether and recrystallised once more from hot ethyl acetate/diisopropylether (3/7 (v/v)).

Mp.: 117°–119° C.

Yield: 11.87 g (79% of theory).

c) (R,S)-3-Cyano-$N^2$-(diphenylacetyl)-alanine-methylester

To a solution of 1.91 g (0.039 Mol) of sodium cyanide in 150 ml of dimethylsulphoxide was added, in batches, 15.5 g (0.0396 Mol) of (R,S)-$N^2$-(diphenylacetyl)-O-(methylsulphonyl)-serine-methylester and the mixture was then heated to 60° C. for 90 minutes. After cooling, the mixture was stirred into 1 liter of water and extracted exhaustively with a total of 1liter of a mixture of ethyl acetate/petroleum ether (1/1 (v/v)). The organic extracts were combined, dried over sodium sulphate and freed from solvent. The residue was triturated with diisopropylether and crystallised. 10.11 g (80% of theory) of colourless crystals were obtained, mp. 126°–129° C.

d) (R,S)-3-Cyano-$N^2$-(diphenylacetyl)-alanine

Prepared analogously to Example 79d) from (R,S)-3-cyano-$N^2$-(diphenylacetyl)-alanine-methylester and lithium hydroxide-hydrate in a yield of 83% of theory.

Colourless crystals, mp. 149°–154° C. (ethyl acetate and diisopropylether).

e) (R,S)-3-Cyano-$N^2$-(diphenylacetyl)-N-[(4-methoxyphenyl)-methyl]-alaninamide Prepared analogously to Example 8a) from (R,S)-3-cyano-$N^2$-(diphenylacetyl)-alanine and 4-methoxybenzene-methylamine and TBTU in a yield of 59% of theory.

Colourless crystals, mp. 183°–187° C. (ethanol).

IR (KBr):

3310, 3210 $cm^{-1}$ (NH)

2840 $cm^{-1}$ ($OCH_3$)

2250 $cm^{-1}$ (C≡N, weak)

1675, 1670, 1660, 1645 $cm^{-1}$ (amide-C═O)

1515 $cm^{-1}$ (amide-II)

MS: $M^+$=427 f) (R,S)-3-(Aminomethyl)-$N^2$-(diphenylacetyl)-N-[(4-methoxyphenyl)methyl]-alaninamide-hydrochloride Prepared analogously to Example 29c) from (R,S)-3-cyano-$N^2$-(diphenylacetyl)-N-[(4-methoxyphenyl)methyl]-alaninamide by catalytic hydrogenation in the presence of palladium/animal charcoal and hydrochloric acid in a yield of 30% of theory.

IR ($CH_2Cl_2$):

1680, 1655 $cm^{-1}$ (amide-C═O)

2840 $cm^{-1}$ ($OCH_3$)

1515 $cm^{-1}$ (amide II)

g) (R,S)-3-[[(Aminoiminomethyl)amino]methyl]-$N^2$-(diphenylacetyl)-N-[(4-methoxyphenyl)methyl]-alaninamide-hydrochloride Prepared analogously to Example 42 g) from (R,S)-3-(aminomethyl)-$N^2$-(diphenylacetyl)-N-[(4-methoxyphenyl) methyl]-alaninamide-hydrochloride, 3,5-dimethylpyrazole-1-carboxylic acid amidinium nitrate and triethylamine in a yield of 20% of theory.

Colourless amorphous substance, $R_f$ 0.73.

IR (KBr):

2840 $cm^{-1}$ ($OCH_3$)

1695, 1675, 1655, 1630 $cm^{-1}$ (C═O, amidinium)

1515 $cm^{-1}$ (amide II)

EI-MS:

$(M+H)^+$=474

$(2M+H)^+$=947

EXAMPLE 120

(R)-$N^2$-(Diphenylacetyl)-N-[(4-ethoxyphenyl) methyl]-argininamide-acetate a) (R)-$N^5$-[Amino(nitroimino)methyl]-$N^2$-[(tert.-butyloxy)-carbonyl]-N-[(4-ethoxyphenyl)methyl]-ornithinamide Prepared analogously to Example 8a) from Boc-D-Arg-($NO_2$)-OH, 4-ethoxybenzenemethylamine-hydrochloride (mp.: 262°–264° C.; from 4-ethoxybenzonitrile by catalytic hydrogenation in the presence of palladium/animal charcoal and aqueous hydrochloric acid), triethylamine and TBTU in a yield of 77% of theory.

IR ($CH_2Cl_2$):

1730 $cm^{-1}$ (ester-C═O)

1675 $cm^{-1}$ (amide C═O)

1510 $cm^{-1}$ (amide II)

b) (R)-$N^5$-[Amino(nitroimino)methyl]-N-[(4-ethoxyphenyl) -methyl]-ornithinamide-trifluoroacetate Prepared analogously to Example 5e) from (R)-$N^5$-[amino(nitroimino)methyl]-$N^2$-[(tert.-butyloxy) carbonyl]-N-[(4-ethoxyphenyl)methyl]-ornithinamide by the action of trifluoroacetic acid in a yield of 70% of theory. The base liberated from the salt by treatment with 1N sodium hydroxide solution melted at 182°–184° C. (ethyl acetate).

ESI-MS:

$(M+H)^+$=547

$(M+Na)^+$=569

$(M+K)^+$=585 c) (R)-$N^5$-[Amino(nitroimino)methyl]-$N^2$-(diphenylacetyl)-N-[(4-ethoxyphenyl)methyl]-ornithinamide Prepared analogously to Example 69c) from (R)-$N^5$-[amino(nitroimino)methyl]-N-((4-ethoxyphenyl)methyl]-ornithinamide and diphenylacetylchloride in a yield of 62% of theory.

Colourless crystals, mp. 182°–184° C. (ethyl acetate/methanol=1/1 (v/v)).

ESI-MS:

$(M+H)^+$=547

$(M+Na)^+$=569

$(M+K)^+$=585 d) (R)-$N^2$-(Diphenylacetyl)-N-[(4-ethoxyphenyl)methyl]-argininamide-acetate

Prepared analogously to Example 1c) from (R)-$N^5$-[amino(nitroimino)methyl]-$N^2$-(diphenylacetyl)-N-[(4-ethoxyphenyl)-methyl]-ornithinamide by catalytic hydrogenation in the presence of palladium black and 80% aqueous acetic acid in a yield of 97% of theory.

Colourless crystals, mp. 97°–100° C. and $R_f$ 0.75.

IR ($CH_2Cl_2$):

1665 $cm^{-1}$ (C═O)

1515 $cm^{-1}$ (amide-II)

ESI-MS: $(M+H)^+$=502

EXAMPLE 121

(R)-$N^2$-(Diphenylacetyl)-N-[(4-hydroxyphenyl) methyl]-N-methyl-argininamide a) (R)-$N^5$-[Amino(nitroimino)methyl]-$N^2$-[(tert.-butyloxy) carbonyl]-N-[(4-hydroxyphenyl)methyl)-N-methyl]-ornithinamide Prepared analogously to Example 8a) from Boc-D-Arg ($NO_2$)-OH, N-methyl-4-hydroxybenzenemethylamine (the hydrochloride melts at 190°–192° C. [ethanol]) and TBTU in a yield of 80% of theory.

Colourless crystals, mp. 78°–81° C.

IR (KBr):

1705 $cm^{-1}$ (ester-C═O)

1635 $cm^{-1}$ (C═O, C═N)

1520 $cm^{-1}$ (amide-II)

ESI-MS:

$(M+Na)^+$=461

$(M+K)^+$=477

$(2M+Na)^+$=899 b) (R)-$N^5$-[Amino(nitroimino)methyl]-N-[(4-hydroxyphenyl)-methyl]-N-methyl-ornithinamide-trifluoroacetate Prepared analogously to Example 5e) from (R)-$N^5$-[amino(nitroimino)methyl]-$N^2$-[(tert.-butyloxy)carbonyl]-N-[(4-hydroxyphenyl)methyl]-N-methyl-ornithinamide by the action of trifluoroacetic acid in a yield of 93% of theory.

Colourless crystals, mp. 114° C.

IR (KBr): 1650 $cm^{-1}$ (C═O)

ESI-MS:

$(M+H)^+$=339

$(M+Na)^+$=361

$(2M+H)^+$=677 c) (R)-$N^5$-[Amino(nitroimino)methyl]-$N^2$-(diphenylacetyl)-N-[(4-hydroxyphenyl)methyl]-N-methyl-ornithinamide Prepared analogously to Example 69c) from (R)-$N^5$-[amino(nitroimino)methyl]-N-[(4-hydroxyphenyl)methyl]-N-methyl-ornithinamide and diphenylacetylchloride in a yield of 85% of theory.

Colourless amorphous substance which was further processed without purification.

d) (R)-$N^2$-(Diphenylacetyl)-N-[(4-hydroxyphenyl)methyl]-N-methyl-argininamide

Prepared analogously to Example 1c) from (R)-$N^5$-[amino(nitroimino)methyl]-$N^2$-(diphenylacetyl)-N-[(4-hydroxyphenyl)methyl]-N-methyl-ornithinamide by catalytic hydrogenation in the presence of palladium black and 80% aqueous acetic acid in a yield of 84% of theory.

Colourless amorphous substance, $R_f$ 0.73.

IR (KBr): 1635.5 $cm^{-1}$ (amide-C═O)

ESI-MS: $(M+H)^+$=488

EXAMPLE 122

(R,S)-3-[3-(Aminomethyl)phenyl]-$N^2$-(diphenylacetyl)-N-[(4-hydroxyphenyl)methyl]-alaninamide 0.48 g (0.98 mMol) of (R,S)-3-(3-cyanophenyl)-$N^2$-(diphenylacetyl)-N-[(4-hydroxyphenyl)methyl]-alaninamide were dissolved in a mixture of 200 ml of methanol and 5 ml of glacial acetic acid and after the addition of 2.0 g of 10% palladium/animal charcoal the mixture was hydrogenated at ambient temperature under a pressure of 5 bar until the hydrogen uptake had ended. The catalyst was separated off, the filtrate was freed from solvent in vacuo, the residue was taken up in 50 ml of dichloromethane and washed successively with water, saturated sodium carbonate solution and water. The residue remaining from the dichloromethane solution after evaporation of the solvent was crystallised with a mixture of diethylether/diisopropylether/methanol (49/49/2 (v/v/v)) by trituration. Colourless crystals were obtained in a yield of 0.47 g (97% of theory), mp. 208° C. and $R_f$ 0.78.

IR (KBr): 1643.3 $cm^{-1}$ (amide-C═O)

MS: $M^+$=493

EXAMPLE 123

(R,S)-N-[(4-Amino-3,5-dibromophenyl)methyl]-3-[3-(aminoiminomethyl)phenyl]-$N^2$-(diphenylacetyl)-alaninamide-hydrochloride a) (R,S)-3-(3-Cyanophenyl)-$N^2$-(diphenylacetyl)-alanine Prepared analogously to Example 1a) from diphenylacetylchloride, 3-(3-cyanophenyl)-alanine-hydrochloride and sodium hydroxide solution in a yield of 58% of theory.

Colourless crystals, mp. 145°–147° C. (ethyl acetate).

b) (R,S)-N-[(4-Amino-3,5-dibromophenyl)methyl]-3-(3-cyanophenyl)-$N^2$-(diphenylacetyl)-alaninamide Prepared analogously to Example 5d) from (R,S)-3-(3-cyanophenyl)-$N^2$-(diphenylacetyl)-alanine, 4-amino-3,5-dibromobenzenemethylamine and TBTU in a yield of 38% of theory.

Colourless amorphous substance.

IR (KBr):

2230 $cm^{-1}$ (C≡N)

1640 $cm^{-1}$ (amide-C═O)

c) (R,S)-N-[(4-Amino-3,5-dibromphenyl)methyl]-3-[3-(aminoiminomethyl)phenyl]-$N^2$-(diphenylacetyl)-alaninamide-hydrochloride Prepared analogously to Example 105d) from (R,S)-N-[(4-amino-3,5-dibromophenyl)methyl]-3-(3-cyanophenyl)-$N^2$-(diphenylacetyl)-alaninamide by the action of first hydrogen chloride and then ammonium carbonate in a yield of 57% of theory.

Colourless amorphous substance, $R_f$ 0.84.

IR (KBr):

1654.8 $cm^{-1}$ (amidinium, amide-C═O)

1520 $cm^{-1}$ (amide-II).

ESI-MS: $(M+H)^+$=662/664/666 ($Br_2$)

EXAMPLE 124

(R)-$N^2$-[(rac.-5,11-Dihydro-6-oxo-6H-dibenz [b,e] azepin-11-yl) carbonyl]-N-[(4-ethoxyphenyl)methyl] -argininamide-acetate a) (R)-$N^5$-[Amino(nitroimino)methyl]-$N^2$-[(rac.-5,11-dihydro-6-oxo-6H-dibenz [b,e]azepin-11-yl) carbonyl]-N-[(4-ethoxyphenyl)methyl]-ornithinamide Prepared, analogously to Example 69c) but using N,N-diisopropylethylamine instead of triethylamine, from rac.11-(chlorocarbonyl)-5,11-dihydro-6H-dibenz[b,e]azepin-6-one and (R)-$N^5$-[amino-(nitroimino)methyl]-N-[(4-ethoxyphenyl)methyl]-ornithinamide-trifluoroacetate in a yield of 85% of theory.

Colourless crystalline substance decomposing at about 140° C.

IR (KBr): 1654.8 $cm^{-1}$ (C═O)

ESI-MS:

$(M+H)^+$=588

$(M+Na)^+$=610

$(M+NH_4)^+$=605

$(M+K)^+$=626 b) (R)-$N^2$-[(rac.-5,11-Dihydro-6-oxo-6H-dibenz[b,e] azepin-11-yl)carbonyl]-N-[(4-ethoxyphenyl)methyl]-argininamide-acetate Prepared analogously to Example 1c) from (R)-$N^5$-[amino(nitroimino)methyl]-$N^2$-[(rac.-5,11-dihydro-6-oxo-6H-dibenz[b,e]azepin-11-yl)carbonyl]-N-[(4-ethoxyphenyl) methyl]-ornithinamide by catalytic hydrogenation in the presence of palladium black and 80% aqueous acetic acid in a yield of 90% of theory.

Colourless crystals, mp. 135° C. (diisopropylether/isopropanol 95/5 (v/v)) and $R_f$ 0.66.

IR (KBr):

1654.8 $cm^{-1}$ (amidinium, amide-C═O)

1510 $cm^{-1}$ (amide-II)

ESI-MS: $(M+H)^+$=543

EXAMPLE 125

(R)-N-[[4-[(Dimethylamino)sulfonyloxy]phenyl] methyl]-$N^2$-(diphenylacetyl)-argininamide-acetate a) (R)-$N^5$-[Amino(nitroimino)methyl]-$N^2$-[(tert.-butyloxy)-carbonyl]-N-[[4-[(dimethylamino)-sulphonyloxy]phenyl]-methyl]-ornithinamide Prepared analogously to Example 8a) from Boc-D-Arg ($NO_2$)-OH, 4-[(dimethylamino)sulphonyloxy]-benzenemethylamine-hydrochloride (mp.: 215°–218° C.; obtained from commercial 4-[(dimethylamino)-sulphonyloxy]benzonitrile by catalytic hydrogenation in the presence of palladium/animal charcoal and 1N aqueous hydrochloric acid), triethylamine and TBTU in a yield of 48% of theory.

Colourless crystals, mp. 82°–84° C. (Decomp.).

IR ($CH_2Cl_2$):

1715 $cm^{-1}$ (ester-C═O)

1675, 1630 $cm^{-1}$ (amide-C═O; C═N)

1505 $cm^{-1}$ (amide-II)

1370, 1150 $cm^{-1}$ ($SO_2$)

ESI-MS:

$(M+H)^+$=532

$(M+Na)^+$=554

$(M+K)^+$=570 b) (R)-$N^5$-[Amino(nitroimino)methyl]-N-[[4-[(dimethylamino)-sulphonyloxy]phenyl]methyl]-ornithinamide-trifluoroacetate Prepared, analogously to Example 5e) but using tetrahydrofuran as solvent instead of dichloromethane, from (R)-$N^5$-[amino(nitroimino)methyl]-$N^2$-[(tert.-butyloxy) carbonyl]-N-[[4-[(dimethylamino)-sulphonyloxy]phenyl]-methyl]-ornithinamide by the action of trifluoroacetic acid in a yield of 92% of theory.

Colourless crystals, mp. 150°–160° C.

IR (KBr):

1678 $cm^{-1}$ (C═O, C═N)

1369.4, 1149.5 $cm^{-1}$ ($SO_2$)

c) (R)-$N^5$-[Amino(nitroimino)methyl]-$N^2$-(diphenylacetyl)-N-[[4-[(dimethylamino)-sulphonyloxy]phenyl]methyl]-ornithinamide Prepared, analogously to Example 5f) but using dichloromethane as solvent instead of acetonitrile, from (R)-$N^5$-[amino(nitroimino)methyl]-N-[[4-[(dimethylamino)-sulphonyloxy]phenyl]methyl]-ornithinamide-trifluoroacetate, diphenylacetic acid and TBTU in a yield of 80% of theory.

Colourless crystals, mp. 150°–160° C.

IR (KBr):

1651.0 $cm^{-1}$ (C═O, C═N)

1510 $cm^{-1}$ (amide-II)

1371.3, 1149.5 $cm^{-1}$, ($SO_2$)

d) (R)-N-[[4-[(Dimethylamino)sulphonyloxy]phenyl]-methyl]-$N^2$-(diphenylacetyl)-argininamide-acetate Prepared analogously to Example 1c) from (R)-$N^5$-[amino(nitroimino)methyl]-$N^2$-(diphenylacetyl)-N-[[4-(dimethylamino)-sulphonyloxy]phenyl]methyl)-ornithinamide by catalytic hydrogenation in the presence of palladium black and 80% aqueous acetic acid in a yield of 66% of theory.

Colourless crystals, mp. 97°–105° C. and $R_f$ 0.67.

IR (KBr):

1656.8 $cm^{-1}$ (amidinium, amide-C═O)

1369.4, 1149.5 $cm^{-1}$, ($SO_2$)

ESI-MS: $(M+H)^+$=581

EXAMPLE 126

(R)-$N^2$-(Diphenylacetyl)-N-[(2-hydroxyphenyl) methyl]-argininamide-acetate a) (R)-$N^5$-[Amino(nitroimino)methyl]-$N^2$-(diphenylacetyl)-N-[(2-hydroxyphenyl)[methyl]-ornithinamide Prepared analogously to Example 12a) from (R)-$N^5$-[amino(nitroimino)methyl]-$N^2$-(diphenylacetyl)-ornithine, 2-hydroxybenzenemethylamine and isobutyl chlorocarbonate in a yield of 40% of theory.

Colourless crystals.

IR (KBr): 1635 $cm^{-1}$ (C═O, C═N)

EI-MS: $(M-H)^-$=517 b) (R)-$N^2$-(Diphenylacetyl)-N-[(2-hydroxyphenyl)methyl]-argininamide-acetate

Prepared analogously to Example 1c) from (R)-$N^5$-[amino(nitroimino)methyl]-$N^2$-diphenylacetyl-N-[(2-hydroxyphenyl)-methyl]-ornithinamide by catalytic hydrogenation in the presence of palladium black and 80% aqueous acetic acid in a yield of 77% of theory.

Colourless amorphous substance, $R_f$ 0.78.

IR (KBr): 1652.9 $cm^{-1}$ (amide-C═O)

EI-MS: $(M+H)^+$=474

EXAMPLE 127

(R)-N-[(4-Hydroxyphenyl)methyl]-$N^2$-[(2-naphthyl)-sulphonyl]-argininamide-acetate a) (R)-$N^5$-[Amino(nitroimino)methyl]-N-[(4-hydroxyphenyl)-methyl]-$N^2$-[(2-naphthyl) sulphonyl]-ornithinamide Prepared, analogously to Example 88c) but using N,N-diisopropylethylamine instead of 4-methylmorpholine, from 2-naphthalenesulphonic acid chloride and (R)-$N^5$-[amino-(nitroimino)methyl]-N-[(4-hydroxyphenyl)methyl]-ornithinamide in a yield of 26% of theory.

Colourless, highly viscous oil, $R_f$ 0.19 (Polygram® SIL G/$UV_{254}$, ready-made films for TLC; Macherey-Nagel, Art. 805021; eluant: dichloromethane/ethyl acetate/methanol/cyclohexane/conc. aqueous ammonia=59/25/7.5/7.5/1 (v/v/v/v/v)).

IR (KBr):

1639.4 $cm^{-1}$ (amide-C═O, N—$NO_2$)

1330.8, 1159.2 $cm^{-1}$ (N—$SO_2$)

b) (R)-N-[(4-Hydroxyphenyl)methyl]-$N^2$-[(2-naphthyl) sulphonyl]-argininamide-acetate Prepared analogously to EXAMPLE 1c) from (R)-$N^5$-[amino(nitroimino)methyl]-N-[(4-hydroxyphenyl)methyl]-$N^2$-[(2-naphthyl)sulphonyl]-ornithinamide by catalytic hydrogenation in a yield of 63% of theory. Colourless amorphous substance, $R_f$ 0.70.

IR (KBr):

1663.2 $cm^{-1}$ (amide-C═O, amidinium)

1323.1, 1159.2 $cm^{-1}$ (N—$SO_2$)

ESI-MS: $(M+H)^+$=470

EXAMPLE 128

(R)-N-[[4-(Aminomethyl)phenyl]methyl]-$N^2$-(diphenylacetyl)-argininamide-bis-(trifluoroacetate)

a) (R)-$N^2$-(9-Fluorenylmethoxycarbonyl)-$N^5$-[[(2,2,5,7,8-pentamethylchromane-6-sulphonyl)amino](imino)-methyl]-N-[[4-[[(phenylmethoxycarbonyl)amino]-methyl]phenyl] methyl]-ornithinamide Prepared, analogously to Example 109a) but using tetrahydrofuran instead of dichloromethane, from Fmoc-D-Arg (Pmc)-OH and 4-[[(phenylmethoxycarbonyl)-amino] methyl]-benzenemethylamine (R. Epton et al., Polymer 21: 481–482 (1980); C.A. 93, 168654k (1980)) in a yield of 88% of theory.

Colourless crystals, mp. 132°–136° C.

IR (KBr):

3323.2 $cm^{-1}$ (N—H)

1693.4 $cm^{-1}$ (carboxyl-C═O, ester C═O)

ESI-MS:

$(M+H)^+$=915

$(M+Na)^+$=937 b) (R)-$N^5$-[[(2,2,5,7,8-Pentamethylchromane-6-sulphonyl)-amino](imino)methyl]-N-[[4-[[(phenylmethoxycarbonyl) amino]methyl]phenyl]-methyl]-ornithinamide A solution of 14.41 g (15.75 mMol) of (R)-$N^2$-(9-fluorenyl-methoxycarbonyl)-$N^5$-[[(2,2,5,7,8-pentamethylchromane-6-sulphonyl)amino](imino)methyl]-N-[[4-[[(phenyl-methoxycarbonyl)-amino]methyl]phenyl] methyl]-ornithinamide in 86 ml of dimethylformamide was mixed with 19 ml (13.5 g; 184.6 mMol) of diethylamine and stirred overnight at ambient temperature. The solvent was distilled off in vacuo, the residue remaining was taken up in 200 ml of ethyl acetate and filtered through glass fibre filter No. 8 (Schleicher & Schüll). The filtrate was washed with 50 ml of water, dried over sodium sulphate and evaporated down in vacuo. The glassy phase thus obtained was purified by chromatography on silica gel (Macherey-Nagel, 70–230 mesh ASTM; dichloromethane/methanol/conc. aqueous ammonia (90/10/0.25)) and yielded 9.8 g (90% of theory) of a uniform, highly viscous, non-crystallising substance.

IR (KBr): 1714.6, 1620.1 $cm^{-1}$ (C═O)

c) (R)-$N^2$-(Diphenylacetyl)-$N^5$-[[(2,2, 5,7,8-pentamethyl-chromane-6-sulphonyl)amino](imino)methyl]-N-[[4-[[(phenylmethoxycarbonyl)amino]methyl]phenyl]-methyl]-ornithinamide Prepared analogously to Example 128a) from diphenylacetic acid, (R)-$N^5$-[[(2,2,5,7,8-pentamethylchromane-6-sulphonyl)amino]-(imino)methyl]-N-[[4-[[(phenylmethoxycarbonyl)amino]-methyl]-phenyl]methyl]-ornithinamide and dicyclohexylcarbodiimide in a yield of 96% of theory.

Colourless crystals, mp. 118°–121° C.

IR (KBr):

3442.7, 3307.7 $cm^{-1}$ (N—H)

1693.4, 1643.3 $cm^{-1}$ (C═O)

d) (R)-N-[[4-(Aminomethyl)phenyl]methyl]-$N^2$-(diphenyl-acetyl)-$N^5$-[[(2,2,5,7,8-pentamethylchromane-6-sulphonyl)-amino](imino)methyl]-ornithinamide Prepared, analogously to Example 27c) but using methanol as solvent, by catalytic hydrogenation of (R)-$N^2$-(diphenylacetyl)-$N^5$-[[(2,2,5,7,8-pentamethylchromane-6-sulfonyl)amino](imino)methyl]-N-[[4-[[(phenylmethoxy-carbonyl)amino]methyl]phenyl]methyl]-ornithinamide in the presence of 10% palladium/animal charcoal in a yield of 79% of theory.

Colourless amorphous substance.

IR (KBr):

1652.9 $cm^{-1}$ (amide-C═O)

1298.0, 1166.9 $cm^{-1}$ (N—$SO_2$)

e) (R)-[[4-(Aminomethyl)phenyl]methyl]-$N^2$-(diphenylacetyl)-argininamide-bis-(trifluoroacetate)

With external cooling using a mixture of crushed ice and methanol, 1.0 g (1.328 mmol) of (R)-N-[[4-(aminomethyl) phenyl]methyl]-$N^2$-(diphenylacetyl)-$N^5$-[[(2,2,5,7,8-pentamethylchromane-6-sulphonyl)amino]-(imino)methyl]-ornithinamide was added to a solution consisting of 9.3 ml of trifluoroacetic acid, 0.3 ml of anisole and 0.2 ml of 1,2-ethanedithiol, with stirring, and the mixture was maintained at ambient temperature for 14 hours after the cooling had been removed. The precipitate formed was filtered off, and after the addition of 5 ml of diethylether the filtrate was filtered again. The resulting filtrate was evaporated down in vacuo at ambient temperature and the viscous residue remaining was triturated with 50 ml of diethylether. It was suction filtered and 0.50 g (53% of theory) of colourless crystals were obtained, mp. 98°–103° C. and $R_f$ 0.32, which were readily soluble in water, methanol, dimethylsulphoxide and dichloromethane.

IR (KBr): 1670.3 $cm^{-1}$ (amide-C═O, guanidinium)

ESI-MS:

$(M+H)^+$=487

$(2M+H)^+$=973

EXAMPLE 129

(R,S)-$N^2$-(Diphenylacetyl)-N-[(4-hydroxyphenyl) methyl]-$N^5$-methyl -ornithinamide Prepared analogously to Example 128d) from (R,S)-$N^2$-(diphenylacetyl)-N-[(4-hydroxyphenyl)methyl]-$N^5$-methyl-$N^5$-(phenylmethyl)-ornithinamide by catalytic hydrogenation in the presence of palladium hydroxide/activated charcoal (Pearlman's catalyst) in a yield of 75% of theory.

Colourless crystals, mp. 118°–130° C. (dichloromethane) and $R_f$ 0,52.

IR (KBr):

3290 $cm^{-1}$ (N—H, O—H)

1635.5 $cm^{-1}$ (amide-C═O)

MS: $M^+$=445

EXAMPLE 130

(R)-N-[[4-(Aminosulphonylamino)phenyl]methyl]-$N^2$-(diphenylacetyl)-argininamide a) (R)-$N^5$-[Amino(nitroimino)methyl]-N-[[4-(aminosulphonylamino)phenyl]methyl]-$N^2$-(diphenylacetyl)-ornithinamide Prepared analogously to Example 36a) from (R)-$N^5$-[amino(nitroimino)methyl]-$N^2$-(diphenylacetyl)-ornithine, 4-(aminosulphonylamino)-benzenemethylamine (mp. >250° C.; prepared from 4-aminobenzonitrile via N-(tert.butyl)-N'-(4-cyanophenyl)-sulphamide (mp. 162°–163° C.) [N-(tert.butyl)-sulphamoylchloride]; 4-(aminosulphonylamino) -benzonitrile mp. 163°–165° C. [trifluoroacetic acid] and finally catalytic hydrogenation in the presence of Raney nickel and ammonia) and TBTU in a yield of 29% of theory.

Colourless crystals.

IR (KBr):

3379.1, 3307.9, 3263.4 $cm^{-1}$ (N—H; $NH_2$)

1641.3 $cm^{-1}$ (amide-C═O)

ESI-MS:

$(M+Na)^+$=619

$(M-H)^-$=595 b) (R)-N-[[4-(Aminosulphonylamino)phenyl]methyl]-$N^2$-(diphenylacetyl)-argininamide Prepared analogously to Example 1c) from (R)-$N^5$-amino (nitroimino)methyl]-N-[[4-(aminosulphonylamino)-phenyl] methyl]-N $^2$-(diphenylacetyl)-ornithinamide by catalytic hydrogenation in the presence of palladium black and 80% aqueous acetic acid in a yield of 83% of theory.

Colourless crystals, mp. 165°–167° C. and $R_f$ 0.62.

IR (KBr): 1639.4 $cm^{-1}$ (amide-C═O)

ES-MS: $(M+H)^+$=552

EXAMPLE 131

(R)-N-[(4-Aminophenyl)methyl]-$N^2$-(diphenylacetyl)-argininamide-dihydrochloride (a) (R)-$N^5$-[Amino(nitroimino)methyl]-$N^2$-(diphenylacetyl) -N-[(4-nitrophenyl)methyl]-ornithinamide Prepared, analogously to Example 74a) but using N,N-diisopropylethylamine as base instead of triethylamine, from (R)-$N^5$-[amino(nitroimino)methyl]-$N^2$-(diphenylacetyl)-ornithine, 4-nitrobenzenemethylamine-hydrochloride and TBTU in a yield of 61% of theory.

Colourless crystals, mp. 110°–112° C.

IR (KBr):

3290.4 $cm^{-1}$ (N—H)

1641.3 $cm^{-1}$ (amide-C═O)

1517.9, 1346.2 $cm^{-1}$ ($NO_2$)

ESI-MS:

$(M+Na)^+$=570

$(2M+Na)^+$=1117 b) (R)-N-[(4-Aminophenyl)methyl]-$N^2$-(diphenylacetyl)-argininamide-dihydrochloride Prepared analogously to Example 29c) from (R)-$N^5$-[amino(nitroimino)methyl]-$N^2$-(diphenylacetyl)-N-[(4-nitrophenyl)methyl]-ornithinamide by catalytic hydrogenation in the presence of palladium black in a yield of 81% of theory.

Colourless amorphous substance, $R_f$ 0.48.

IR (KBr): 1649.0 $cm^{-1}$ (amide-C═O)

ESI-MS:

$(M+H)^+$=473

$(2M+H)^+$=945

EXAMPLE 132

(R)-N-[(6-Quinolinyl)methyl]-$N^2$-(diphenylacetyl)-argininamide-acetate a) (R)-$N^5$-[Amino(nitroimino)methyl]-N-[(6-quinolinyl) methyl]-$N^2$-(diphenylacetyl)-ornithinamide Prepared analogously to Example 87a) from (R)-$N^5$-[amino(nitroimino)methyl]-$N^2$-(diphenylacetyl)-ornithine, 6-quinoline-methanamine (prepared from 6-methylquinoline via 6-quinoline-carboxaldehyde [selenium dioxide] and reductive amination thereof [ammonium acetate/sodium cyanoborohydride]) and TBTU in a yield of 40% of theory.

Colourless crystals, mp. 222°–224° C.

IR (KBr): 1637.5 $cm^{-1}$ (amide-C═O)

b) (R)-N-[(6-Quinolinyl)methyl]-$N^2$-(diphenylacetyl)-argininamide-acetate

Prepared analogously to Example 14b) from (R)-$N^5$-[amino(nitroimino)methyl]-N-[(6-quinolinyl)methyl]-$N^2$-(diphenylacetyl)-ornithinamide by reduction with tin(II)-chloride-dihydrate in the presence of 60% aqueous formic acid in a yield of 29% of theory.

Colourless amorphous substance, $R_f$ 0.42.

IR (KBr): 1645.2 $cm^{-1}$ (amide-C═O)

ESI-MS:

$(M+H)^+$=509

$(M+2H)^{++}$=255

EXAMPLE 133

(R,S)-$N^5$-(5-Amino-1H-1,2,4-triazol-3-yl)-$N^2$-(diphenyl-acetyl)-N-[(4-hydroxyphenyl)methyl]-ornithinamide a) (R,S)-$N^2$-(Diphenylacetyl)-N-[(4-hydroxyphenyl)-methyl]-$N^5$-[phenoxy(cyanoimino)methyl]-ornithinamide A mixture of 0.75 g (1.74 mMol) of (R,S)-$N^2$-(diphenylacetyl)-N-[(4-hydroxyphenyl)methyl]-ornithinamide, 0.41 g (1.74 mMol) of N-cyanodiphenoxyimidocarbonate and 36 ml of isopropanol was stirred for 15 hours at ambient temperature. The crystal slurry obtained was suction filtered, washed twice with 5 ml of isopropanol and dried in vacuo. 0.7 g (70% of theory) of colourless crystals were obtained, mp. 140°–142° C.

IR (KBr):

2189.1 $cm^{-1}$ (C═N—CN)

1639.4 $cm^{-1}$ (amide-C═O)

b) (R,S)-$N^5$-(5-Amino-1H-1,2,4-triazol-3-yl)-$N^2$-(diphenylacetyl)-N-[(4-hydroxyphenyl)methyl]-ornithinamide To a suspension of 0.4 g (0.695 mMol) of (R,S)-$N^2$-(diphenylacetyl)-N-[(4-hydroxyphenyl)methyl]-$N^5$-[phenoxy(cyanoimino)methyl]-ornithinamide in 16 ml of methanol was added 0.19 ml (3.13 mMol) of 80% hydrazine hydrate and the mixture was then stirred for 3 hours at ambient temperature. The resulting mixture was evaporated to dryness in vacuo, the residue was taken up in anhydrous ethanol and stored overnight in a refrigerator (approx. +7° C.). The colourless crystals obtained were suction filtered, washed thoroughly with 3 ml of ice cold ethanol and dried in vacuo. 0.2 g (56% of theory) of colourless crystals were obtained, mp. 133°–136° C. and $R_f$ 0.83.

IR (KBr): 1641.3 $cm^{-1}$ (amide-C═O)

MS: $M^+$=513

EXAMPLE 134

(R)-$N^2$-[2-(3,4-Dichlorophenyl)-1-oxoethyl]-N-[(4-hydroxyphenyl)methyl)-argininamide-acetate a) (R)-$N^5$-[Amino(nitroimino)methyl]-$N^2$-[2-(3,4-dichlorophenyl)-1-oxoethyl]-N-[(4-hydroxyphenyl)methyl]-ornithinamide Prepared analogously to Example 12a) from 3,4-dichlorobenzene acetic acid, (R)-$N^5$-[amino(nitroimino)methyl]-N-[(4-hydroxyphenyl)methyl]-ornithinamide and TBTU in a yield of 39% of theory.

Colourless amorphous substance, $R_f$ 0.59 (Polygram® SIL G/$UV_{254}$, ready-made TLC films; Macherey-Nagel, Art. 805021; eluant: dichloromethane/methanol/cyclohexane/conc. aqueous ammonia=68/15/15/2 (v/v/v/v)).

IR (KBr): 1652.9 $cm^{-1}$ (amide-C═O)

b) (R)-$N^2$-[2-(3,4-Dichlorophenyl)-1-oxoethyl]-N-[(4-hydroxyphenyl)methyl]-argininamide-acetate Prepared analogously to Example 1c) from (R)-$N^5$-[amino(nitroimino)methyl]-$N^2$-[2-(3,4-dichlorophenyl)-1-oxoethyl]-N-[(4-hydroxyphenyl)methyl]-ornithinamide by catalytic hydrogenation in the presence of palladium/animal charcoal and 80% aqueous acetic acid in a yield of 88% of theory.

Colourless amorphous substance, $R_f$ 0.65.

IR (KBr): 1652.9 $cm^{-1}$ (amide-C═O)

ESI-MS: $(M+H)^+$=466/468/470 ($Cl_2$)

EXAMPLE 135

(R)-$N^2$-(Diphenylacetyl)-N-[[4-(2-hydroxyethyl)phenyl]-methyl]-argininamide a) (R)-$N^5$-[Amino(nitroimino)methyl]-$N^2$-(diphenylacetyl)-N-[[4-(2-hydroxyethyl)-phenyl]methyl]-ornithinamide Prepared analogously to Example 87a) from (R)-$N^5$-[amino(nitroimino)methyl]-$N^2$-(diphenylacetyl)-ornithine, 4-(2-hydroxyethyl)-benzenemethylamine (prepared from 4-cyanophenylacetonitrile via 4-cyanophenyl acetic acid, mp. 152°–154° C. [conc. hydrochloric acid], and finally reduction with lithium aluminium hydride) and TBTU in a yield of 52% of theory.

Colourless crystals, mp. 168°–170° C. (acetone).

IR (KBr): 1641.3 $cm^{-1}$ (amide-C═O)

b) (R)-$N^2$-(Diphenylacetyl)-N-[[4-(2-hydroxyethyl)-phenyl]methyl]-argininamide Prepared analogously to Example 1c) from (R)-$N^5$-[Amino(nitroimino)methyl]-$N^2$-(diphenylacetyl)-N-[[4-(2-hydroxyethyl)-phenyl]methyl]-ornithinamide by catalytic hydrogenation in the presence of palladium black and 80% aqueous acetic acid.

Colourless amorphous substance, $R_f$ 0.65.

ESI-MS: $(M+H)^+$=502

EXAMPLE 136

(R,S)-$N^5$-(3-Amino-1,2,4-oxadiazol-5-yl)-$N^2$-(diphenyl-acetyl)-N-[(4-hydroxyphenyl)methyl]-ornithinamide and (R,S)-$N^5$-(5-Amino-1,2,4-oxadiazol-3-yl)-$N^2$-(diphenyl-acetyl)-N-[(4-hydroxyphenyl)methyl]-ornithinamide To a suspension of 0.3 g (0.521 mMol) of (R,S)-$N^2$-(diphenylacetyl)-N-[( 4-hydroxyphenyl)methyl]-$N^5$-[phenoxy(cyanoimino)methyl]-ornithinamide in 14 ml of methanol was added a solution of 46.2 mg (1.4 mmol) of hydroxylamine in 0.5 ml of water and the resulting mixture was stirred for 24 hours at ambient temperature. The precipitate formed was filtered off, the filtrate was evaporated to dryness in vacuo, the residue was stirred with 15 ml of absolute ethanol and filtered once more. The filtrate thus obtained was separated by chromatography (silica gel Baker, 30–60 μm; dichloromethane/ethyl acetate/methanol/cyclohexane/conc. aqueous ammonia=59/25/7.5/7.5/1 (v/v/v/v/v)) into two structurally isomeric products:

A.: Colourless crystals, mp. 92°–96° C. and $R_f$ 0.95 and 0.20 respectively (Polygram® SIL G/$UV_{254}$, ready-made TLC films, Macherey-Nagel, Art. 805021; eluant: dichloromethane/ethyl acetate/methanol/cyclohexane/conc. aqueous ammonia=59/25/7.5/7.5/1 (v/v/v/v/v)).

Yield: 30 mg (11% of theory).

ESI-MS:

$(M+H)^+$=515

$(M+Na)^+$=537

$(M+Na)^+$=1051

B: Colourless crystals, mp. 70°–73° C. and $R_f$ 0.95 and 0.17 respectively, (test conditions as in A).

Yield: 30 mg (11% of theory).

ESI-MS:

$(M+H)^+$=515

$(M+Na)^+$=537

$(2M+H)^+$=1029

$(2M+Na)^+$=1051

We have provisionally assigned Compound A the structure of (R,S)-$N^5$-(5-amino-1,2,4-oxadiazol-3-yl)-$N^2$-(diphenylacetyl)-N-[(4-hydroxyphenyl)methyl]-ornithinamide, and compound B the structure of (R,S)-$N^5$-(3-amino-1,2,4-oxadiazol-5-yl)-$N^2$-(diphenylacetyl)-N-[(4-hydroxyphenyl)methyl]-ornithinamide; whether this classification might not have to be reversed at some stage cannot be stated beyond all doubt in the light of the spectroscopic data available at present.

EXAMPLE 137

(R)-N-[(4-Hydroxyphenyl)methyl]-$N^2$-(1-naphthoyl)-argininamide-acetate a) (R)-$N^5$-[Amino(nitroimino)methyl]-N-[(4-hydroxyphenyl)-methyl]-$N^2$-(1-naphthoyl)-ornithinamide Prepared analogously to Example 116c) from 1-naphthoylchloride and (R)-$N^5$-[amino(nitroimino)methyl]-N-[(4-hydroxyphenyl)methyl]-ornithinamide-hydrochloride in a yield of 49% of theory.

Colourless crystals.

IR (KBr): 1668.3, 1622.0 $cm^{-1}$ (C═O, C═N)

b) (R)-N-[(4-Hydroxyphenyl)methyl]-$N^2$-(1-naphthoyl)-argininamide-acetate

Prepared analogously to Example 1c) from (R)-$N^5$-[amino(nitroimino)methyl]-N-[(4-hydroxyphenyl)methyl]-$N^2$-(1-naphthoyl)-ornithinamide by catalytic hydrogenation in the presence of palladium black and 80% aqueous acetic acid in a yield of 30% of theory.

Colourless amorphous substance, $R_f$ 0.70.

IR (KBr): 1637.5 $cm^{-1}$ (amide-C═O)

ESI-MS:

$(M+H)^+$=434

$(2M+H)^+$=867

EXAMPLE 138

(R)-N-[(4-Hydroxyphenyl)methyl]-$N^2$-(2-naphthoyl)-argininamide-acetate a) (R)-$N^5$-[Amino(nitroimino)methyl]-N-[(4-hydroxyphenyl)-methyl]-$N^2$-(2-naphthoyl)-ornithinamide Prepared analogously to Example 36a) from (R)-$N^5$-[amino(nitroimino)methyl]-$N^2$-(2-naphthoyl)-ornithine (obtained analogously to Example 1a) from 2-naphthoylchloride and H-D-Arg ($NO_2$)-OH), 4-hydroxybenzenemethylamine and TBTU in a yield of 36% of theory.

Colourless amorphous substance.

IR (KBr): 1639.4, 1626.7 $cm^{-1}$ (C═O, C═N)

ESI-MS:

$(M+Na)^+$=501

$(M-H)^-$=477 b) (R)-N-[(4-Hydroxyphenyl)methyl]-$N^2$-(2-naphthoyl)-argininamide-acetate

Prepared analogously to Example 1c) from (R)-$N^5$-[amino(nitroimino)methyl]-N-[(4-hydroxyphenyl)methyl]-$N^2$-(2-naphthoyl)-ornithinamide by catalytic hydrogenation in the presence of palladium black and 80% aqueous acetic acid in a yield of 63% of theory.

Colourless amorphous substance, $R_f$ 0.68.

IR (KBr): 1652.9 $cm^{-1}$ (amide-C═O)

ESI-MS:

$(M+H)^+$=434

$(2M+H)^+$=867

EXAMPLE 139

(R)-$N^2$-(2,2-Diphenyl-2-hydroxy-1-oxoethyl)-N-[(4-hydroxyphenyl)methyl]-argininamide-acetate a) (R)-$N^5$-[Amino(nitroimino)methyl]-$N^2$-(2,2-diphenyl-2-hydroxy-1-oxoethyl)-N-[(4-hydroxyphenyl)methyl]-ornithinamide 0.01 Mol of the crude reaction product obtained analogously to Example 124a) from 2-chloro-2,2-diphenyl-acetylchloride and (R)-$N^5$-[amino(nitroimino)methyl]-N-[(4-hydroxyphenyl)methyl]-ornithinamide-hydrochloride was dissolved in 50 ml of 80% aqueous acetic acid and heated to 80° C. for 30 minutes after the addition of 5 g of sodium acetate. The reaction product was divided between water and ethyl acetate, the ethyl acetate extracts were dried over magnesium sulphate and evaporated down in vacuo. The residue remaining was purified by chromatography on aluminium oxide (Activity stage IV) using ethyl acetate/methanol=99/1 (v/v) as eluant. After the appropriate fractions had been worked up, 2.4 g (45% of theory) of an amorphous substance were obtained which was used without further purification in the next step.

IR (KBr): 1649.0 $cm^{-1}$ (amide-C═O)

ESI-MS:

$(M+H)^+$=535

$(M+Na)^+$=557

$(2M+Na)^+$=1091 b) (R)-$N^2$-(2,2-Diphenyl-2-hydroxy-1-oxoethyl)-N-[(4-hydroxyphenyl)methyl]-argininamide-acetate Prepared analogously to Example 1c) from (R)-$N^5$-[amino(nitroimino)methyl]]-$N^2$-(2,2-diphenyl-2-hydroxy-1-oxoethyl)-N-[(4-hydroxyphenyl)methyl]-ornithinamide by catalytic hydrogenation in the presence of palladium black and 80% aqueous acetic acid in a yield of 80% of theory.

Colourless amorphous substance, $R_f$ 0.60.

IR (KBr): 1652.9 $cm^{-1}$ (amide-C═O, guanidinium)

ESI-MS:

$(M+H)^+$=490

$(2M+H)^+$=979

EXAMPLE 140

(R,S)-$N^2$-(Diphenylacetyl)-$N^5$-(1H-imidazol-2-yl)-N-[(4-methoxyphenyl)methyl]-ornithinamide Prepared analogously to Example 85 from (R,S)-$N^2$-(diphenylacetyl)-N-[(4-methoxyphenyl)methyl]-ornithinamide and N-[(2,2-diethoxy)ethyl]-S-methyl-thiuroniumiodide in a yield of 12% of theory.

Colourless crystals, mp. 200° C. (Decomp.) and $R_f$ 0.74.

MS: $M^+$=511

EXAMPLE 141

(R,S)-3-[3-(Aminoiminomethyl)phenyl]-$N^2$-[[(diphenylmethyl)-amino]carbonyl]-N-[(4-hydroxyphenyl)methyl]-alaninamide-acetate a) (R,S)-3-(3-Cyanophenyl)-$N^2$-[[(diphenylmethyl)-amino]carbonyl]-alanine methylester Prepared analogously to Example 79c) from (R,S)-2-(3-cyanophenyl)-1-(methoxycarbonyl)-ethylisocyanate and α-phenyl-benzenemethylamine in a yield of 61% of theory.

Colourless crystals, mp. 192°–193° C.

IR (KBr):

2229.6 $cm^{-1}$ (C≡N)

1732.0 $cm^{-1}$ (ester-C═O)

1624.6 $cm^{-1}$ (urea-C═O)

b) (R,S)-3-(3-Cyanophenyl)-$N^2$-[[(diphenylmethyl)-amino]carbonyl]-alanine

Prepared analogously to Example 79d) from (R,S)-3-(3-cyanophenyl)-$N^2$-[[(diphenylmethyl)amino]carbonyl]-alanine-methylester and lithium hydroxide-hydrate in a yield of 41% of theory.

Colourless crystals.

IR (KBr):

3377.2 $cm^{-1}$ (N—H)

2229.6 $cm^{-1}$ (C≡N)

1714.6 $cm^{-1}$ (carboxylic acid-C═O)

1633.6 $cm^{-1}$ (urea-C═O)

ESI-MS:

$(M+H)^+$=400

$(2M+H)^+$=799

$(M+Na)^+$=422

$(2M+Na)^+$=821 c) (R,S)-3-(3-Cyanophenyl)-$N^2$-[[(diphenylmethyl)-amino]carbonyl]-N-[(4-hydroxyphenyl)methyl]-alaninamide Prepared analogously to Example 36a) from (R,S)-3-(3-cyanophenyl)-$N^2$-[[(diphenylmethyl)amino]carbonyl]-alanine, 4-hydroxybenzenemethylamine and TBTU in a yield of 82% of theory.

Colourless amorphous substance.

IR (KBr): 1629.8 $cm^{-1}$ (C═O)

d) (R,S)-3-[3-[Amino(hydroxyimino)methyl]phenyl]-$N^2$-[[(diphenylmethyl)amino]carbonyl]-N-[(hydroxyphenyl)methyl]-alaninamide A mixture of 2.6 g (5.15 mMol) of (R,S)-3-(3-cyanophenyl)-$N^2$-[(diphenylmethyl)amino]carbonyl]-N-[(4-hydroxyphenyl)-methyl]-alaninamide, 1.0 g (14.4 mMol) of hydroxylamine-hydrochloride, 1.53 g (14,4 mMol) of sodium carbonate, 30 ml methanol and 5 ml water was refluxed for 1.5 hours. After cooling, the mixture was diluted with 100 ml of water, then covered with 100 ml of diethylether and finally the colourless precipitate formed was suction filtered. The product was washed successively with 5 ml of methanol, acetonitrile and diethylether and dried in vacuo.

Colourless crystals mp. 175°–177° C. and $R_f$ 0.41 were obtained in a yield of 0.7 g (25% of theory) (silica gel 60 $F_{254}$ for TLC, Merck (Darmstadt); dichloromethane/cyclohexan/methanol/conc. aqueous ammonia 68/15/15/2 (v/v/v/v)).

e) (R,S)-3-[3-(Aminoiminomethyl)phenyl]-$N^2$-[[(diphenylmethyl)amino]carbonyl]-N-[(4-hydroxyphenyl)methyl]-alaninamide-acetate Prepared analogously to Example 27c) from (R,S)-3-[3-[amino(hydroxyimino)methyl)phenyl]-$N^2$-[[(diphenylmethyl)amino]carbonyl]-N-[(4-hydroxyphenyl) methyl]-alaninamide by catalytic hydrogenation in the presence of palladium/animal charcoal and glacial acetic acid in a yield of 20% of theory.

Colourless amorphous substance, $R_f$ 0.80.

IR (KBr): 1658.8 $cm^{-1}$ (amide-C═O, amidinium)

ESI-MS:

$(M+H)^+$=522

$(2M+H)^+$=1043

EXAMPLE 142

(R,S)-$N^2$-(Diphenylacetyl)-$N^5$-(1H-imidazol-2-yl)-N-(phenylmethyl)-ornithinamide a) (R,S)-$N^5$-(Phenylmethoxycarbonyl)-N-(phenylmethyl)-ornithinamide With external cooling and maintaining a reaction temperature of 5°–10° C., a solution of 12.2 ml (11.99 g; 0.112 Mol) of benzenemethylamine in 50 ml tetrahydrofuran was added dropwise to a solution of 5.0 g (17.1 mMol of $N^2$-carboxy-$N^5$-(phenylmethoxycarbonyl)-ornithine-anhydride (M. Bodanszky, "Principles of Peptide Synthesis", Springer-Verlag, 1984, page 124) in 100 ml of tetrahydrofuran. The mixture was maintained at the specified temperature for a further hour and then the resulting suspension was evaporated down in vacuo at a bath temperature of +50° C. the resulting product was stirred with 10 ml of diisopropylether at +40° C. The crystal slurry obtained was cooled completely and suction filtered, the crystals were washed once more with 10 ml of diisopropylether and dried at 60° C. in vacuo.

Yield: 4.90 g (81% of theory).

Colorless crystals, mp. 87° C.

IR (KBr):

3330.9 $cm^{-1}$ (N—H)

1693.4 $cm^{-1}$ (urethane-C═O)

16433 $cm^{-1}$ (amide-C═O)

MS: $M^+$=355 b) (R,S)-$N^2$-(Diphenylacetyl)-$N^5$-(phenylmethoxycarbonyl)-N-(phenylmethyl)-ornithinamide Prepared analogously to Example 32d) from (R,S)-$N^5$-(phenylmethoxycarbonyl)-N-(phenylmethyl)-ornithinamide and diphenylacetylchloride in a yield of 75% of theory.

Colorless crystals, mp. 167°–170° C.

c) (R,S)-$N^2$-(Diphenylacetyl)-N-(phenylmethyl)-ornithinamide-acetate

Prepared analogously to Example 27c), but using methanol/water/glacial acetic acid=7/3/1 (v/v/v) as solvent, by catalytic hydrogenation of (R,S)-$N^2$-(diphenylacetyl)-$N^5$-(phenylmethoxycarbonyl)-N-(phenylmethyl) ornithinamide in the presence of palladium/animal charcoal as catalyst in a yield of 70% of theory.

Colourless crystals, mp. 159°–160° C.

d) (R,S)-$N^2$-(Diphenylacetyl)-$N^5$-(1H-imidazol-2-yl)-N-(phenylmethyl)-ornithinamide Prepared analogously to Example 85) from (R,S)-$N^2$-(diphenylacetyl)-N-(phenylmethyl)-ornithinamide-acetate and N-(2,2-diethoxy)ethyl]-S-methylthiuroniumiodide in a yield of 25% of theory.

Colourless crystals, mp. 195° C. (Decomp.) and $R_f$ 0.74.

IR (KBr):

3309.7, 3240.2 $cm^{-1}$ (N—H)

1639.4, 1666.4 $cm^{-1}$ (amide-C═O)

MS: $M^+$481

EXAMPLE 143

(R)-$N^2$-(2,2-Diphenylethyl)-N-[(4-hydroxyphenyl) methyl]-argininamide-hydrochloride a) (R)-$N^5$-[Amino(nitroimino)methyl]-$N^2$-(2,2-diphenylethyl)-N-[(4-hydroxyphenyl)methyl]-ornithinamide-hydrochloride A mixture of 1.8 g (5.0 mMol) of (R)-$N^5$-[amino (nitroimino)methyl]-N-[(4-hydroxyphenyl)methyl]-ornithinamide-hydrochloride, 1.0 g (5.096 mMol) of diphenylacetaldehyde, 0.75 g (11.94 mMol) of sodium cyanoborohydride and 100 ml of anhydrous methanol was stirred for 24 hours at ambient temperature. The solvent was distilled off in vacuo, the residue was divided between water and ethyl acetate, the ethyl acetate phase was mixed with 5 ml of 1N hydrochloric acid, the precipitate formed was suction filtered and washed successively with water and ethyl acetate, then dried in vacuo.

Yield: 1.4 g (52% of theory).

Colourless crystals, mp. 244°–247° C.

IR (KBr):

3394.5 $cm^{-1}$ (N—H)

1681.8, 1672.2, 1639.4 $cm^{-1}$ (C═O, C═N)

ESI-MS:

$(M+H)^+$=505

$(M+Na)^+$=527

$(2M+H)^+$=1009 b) (R)-$N^2$-(2,2-Diphenylethyl)-N-[(4-hydroxyphenyl) methyl]-argininamide-hydrochloride Prepared analogously to Example 1c) from (R)-$N^5$-[amino(nitroimino)methyl]-$N^2$-(2,2-diphenylethyl)-N-[(4-hydroxyphenyl)-methyl]-ornithinamide-hydrochloride by catalytic hydrogenation in the presence of palladium black and 80% aqueous acetic acid in a yield of 78% of theory.

Colourless amorphous substance, $R_f$ 0.55.

IR (KBr): 1652.9 $cm^{-1}$ (amide-C═O, guanidinium)

ESI-MS: $(M+H)^+$=460

EXAMPLE 144

(R,S)-N-[(4-Amino-3,5-dichlorophenyl)methyl]-$N^2$-(diphenylacetyl)-$N^5$-(1H-imidazol-2-yl)-ornithinamide a) (R,S)-$N^2$-(Diphenylacetyl)-$N^5$-(phenylmethoxycarbonyl)-ornithine Prepared analogously to Example 1a) from diphenylacetylchloride and (R,S)-$N^5$-(phenylmethoxycarbonyl)-ornithine in the presence of sodium hydroxide solution in a yield of 100% of theory.

Colourless crystals, mp. 128°–130° C.

b) (R,S)-$N^2$-(Diphenylacetyl)-ornithine

Prepared analogously to Example 142c) from (R,S)-$N^2$-(diphenylacetyl)-$N^5$-(phenylmethoxycarbonyl)-ornithine by catalytic hydrogenation in the presence of palladium/animal charcoal in a yield of 81% of theory.

Colourless crystals, mp. 170°–172° C.

c) (R,S)-$N^5$-(tert.Butyloxycarbonyl)-$N^2$-(diphenylacetyl)-ornithine

Prepared analogously to Example 52b) from (R,S)-$N^2$-(diphenylacetyl)-ornithine and di-tert.-butyl dicarbonate in the presence of sodium hydroxide solution in a yield of 99% of theory.

Colourless crystalline substance which was further processed without purification.

d) (R,S)-N-[(4-Amino-3,5-dichlorophenyl)methyl]-$N^5$-(tert.-butyloxycarbonyl)-$N^2$-(diphenylacetyl)-ornithinamide Prepared analogously to Example 67a) from (R,S)-$N^5$-(tert.butyloxycarbonyl)-$N^2$-(diphenylacetyl)-ornithine, 4-amino-3,5-dichlorobenzenemethylamine and TBTU in a yield of 97% of theory.

Colourless crystals, mp. 123° C.

IR (KBr):

3444.7, 3280.7 $cm^{-1}$ (N—H)

1685.7 $cm^{-1}$ (urethane-C═O)

1639.4 $cm^{-1}$ (amide-C═O)

e) (R,S)-N-[(4-Amino-3,5-dichlorophenyl)methyl]-$N^2$-(diphenylacetyl)-$N^5$-(1H-imidazol-2-yl)-ornithinamide The (R,S)-N-[(4-amino-3,5-dichlorophenyl)methyl]-$N^2$-(diphenylacetyl)-ornithinamide obtained analogously to Example 36b) from (R,S)-N-[(4-amino-3,5-dichlorophenyl)-methyl]-$N^5$-(tert.-butyloxycarbonyl)-$N^2$-(diphenylacetyl)-ornithinamide by treating with methanolic hydrochloric acid solution was reacted as the crude product directly, according to Example 85, with N-[(2,2-diethoxy)ethyl]-S-methylthiuroniumiodide, and then with hydrochloric acid.

Yield: 4% of theory.

Colourless crystals, mp. 184°–186° C. and $R_f$ 0.78.

IR (KBr):

3384.9, 3307.7 $cm^{-1}$ (N—H)

1651.0, 1635.5 $cm^{-1}$ (amide-C═O)

MS: $M^+$=564/566 ($Cl_2$)

EXAMPLE 145

(R,S)-N-[(4-Amino-3-fluorophenyl)methyl]-$N^2$-(diphenylacetyl)-$N^5$-(1H-imidazol-2-yl)-ornithinamide a) (R,S)-N-[(4-Amino-3-fluorophenyl)methyl]-$N^5$-(tert.-butyloxycarbonyl)-$N^2$-(diphenylacetyl)-ornithinamide Prepared analogously to Example 67a) from (R,S)-$N^5$-(tert.butyloxycarbonyl)-$N^2$-(diphenylacetyl)-ornithine,4-amino-3-fluorobenzenemethylamine and TBTU in a yield of 60% of theory.

Colourless crystals, mp. 168°–170° C.

IR (KBr):

3446.6, 3555.9, 3261.4 $cm^{-1}$ (N—H)

1695.3 $cm^{-1}$ (urethane-C═O)

1645.2 $cm^{-1}$ (amide-C═O)

b) (R,S)-N-[(4-Amino-3-fluorophenyl)methyl]-$N^2$-(diphenylacetyl)-$N^5$-(1H-imidazol-2-yl)-ornithinamide Prepared analogously to Example 144e) from (R,S)-N-[(4-amino-3-fluorophenyl)methyl]-$N^5$-(tert.-butyloxycarbonyl)-$N^2$-(diphenylacetyl)-ornithinamide by successively treating with methanolic hydrogen chloride solution, then N-[(2,2-diethoxy)ethyl]-S-methyl-thiuroniumiodide, and finally with hydrochloric acid in a yield of 23% of theory.

Colourless crystals, mp. 162° C. and $R_f$ 0.69.

IR (KBr): 1639.4 $cm^{-1}$ (amide-C═O)

MS: $M^+$=514

EXAMPLE 146

(R,S)-N-[(4-Hydroxyphenyl)methyl]-$N^5$-(1H-imidazol-2-yl)-$N^2$-(2-naphthoyl)-ornithinamide-hydrochloride a) (R,S)-N-[(4-Hydroxyphenyl)methyl]-$N^5$-(phenylmethoxycarbonyl)-ornithinamide Prepared analogously to Example 142a) from (R,S)-4-[3-[(phenylmethoxycarbonyl)amino]propyl]-4,5-dihydro-1,3-oxazol-2,5-dione and 4-hydroxybenzenemethanamine in a yield of 86% of theory.

Colourless crystals, mp. 162° C. (ethyl acetate).

IR (KBr): 1689.5 $cm^{-1}$ (urethane-C═O)

ESI-MS:

$(M+H)^+$=372

$(2M+H)^+$=743

$(M+Na)^+$=394

$(2M+Na)^+$=765 b) (R,S)-N-[(4-Hydroxyphenyl)methyl]-$N^2$-(2-naphthoyl)-$N^5$-(phenylmethoxycarbonyl)-ornithinamide Prepared analogously to Example 36a) from 2-naphthoic acid, (R,S)-N-[(4-hydroxyphenyl)methyl]-$N^5$-(phenylmethoxycarbonyl)-ornithinamide and TBTU in a yield of 100% of theory.

Colourless crystals, mp. 168°–170° C.

IR (KBr): 1687.6 $cm^{-1}$ (urethane-C═O)

c) (R,S)-N-[(4-Hydroxyphenyl)methyl]-$N^2$-(2-naphthoyl)-ornithinamide-acetate

Prepared analogously to Example 142c) from (R,S)-N-[(4-hydroxyphenyl)methyl]-$N^2$-(2-naphthoyl)-$N^5$-(phenylmethoxycarbonyl)-ornithinamide by catalytic hydrogenation in the presence of palladium/animal charcoal (10%) in a yield of 100% of theory.

Colourless crystals.

IR (KBr): 1635.5 $cm^{-1}$ (amide-C═O)

1517.9 $cm^{-1}$ (amide-II)

d) (R,S)-N-[(4-Hydroxyphenyl)methyl]-$N^5$-(1H-imidazol-2-yl)-$N^2$-(2-naphthoyl)-ornithinamide-hydrochloride Prepared analogously to Example 85 from (R,S)-N-[(4-hydroxyphenyl)methyl]-$N^2$-(2-naphthoyl)-ornithinamide-acetate and N-[(2,2-diethoxy)ethyl]-S-methylthiuroniumchloride in a yield of 44% of theory.

Colourless crystals, mp. 197° C. and $R_f$ 0.76.

IR (KBr): 1670.3 $cm^{-1}$ (amide-C═O)

ESI-MS: $(M+H)^+$458

EXAMPLE 147

(R,S)-$N^2$-[[(Diphenylmethyl)amino]carbonyl]-N-[(4-hydroxy-phenyl)methyl]-$N^5$-(1H-imidazol-2-yl)-ornithinamide a) Methyl (R,S)-2-isocyanato-5-[[(phenylmethoxy)-carbonyl]amino]-pentanoate As a dichloromethane solution prepared analogously to Example 79b) from $N^5$-[(phenylmethoxy)carbonyl]-ornithine-methylester-hydrochloride and phosgene. Aliquot portions thereof were used without purification in the following reactions.

b) (R,S)-$N^2$-[[(Diphenylmethyl) amino]carbonyl]-$N^5$-[(phenylmethoxy)carbonyl)-ornithine-methylester Prepared analogously to Example 79c) from methyl (R,S)-2-isocyanato-4-[[(phenylmethoxy)carbonyl]amino]-pentanoate and α-phenyl-benzenemethanamine in a yield of 69% of theory.

Colourless crystals, mp. 104°–105° C.

IR (KBr):

3398.4 $cm^{-1}$ (N—H)

1749.3 $cm^{-1}$ (ester-C═O)

1689.5 $cm^{-1}$ (urethane-C═O)

1627.8 $cm^{-1}$ (urea-C═O)

C) (R,S)-$N^2$-[[(Diphenylmethyl)amino]carbonyl]-$N^5$-[(phenylmethoxy)carbonyl)-ornithine Prepared analogously to Example 79d) from (R,S)-$N^2$-[[(diphenylmethyl)amino)carbonyl]-$N^5$-[(phenylmethoxy)carbonyl]-ornithine-methylester by saponification with lithium hydroxide-hydrate in a yield of 54% of theory.

Colourless crystals, mp. 172°–173° C.

IR (KBr):

1718.5 $cm^{-1}$ (carboxyl-C═O)

1674.1 $cm^{-1}$ (urethane-C═O)

ESI-MS:

$(M+Na)^+$=498

$(M-H)^-$=474 d) (R,S)-$N^2$-[[(Diphenylmethyl)amino]carbonyl]-N-[(4-hydroxyphenyl)methyl]-$N^5$-[(phenylmethoxy)carbonyl]-ornithinamide Prepared analogously to Example 67a) from (R,S)-$N^2$-[[(diphenylmethyl)amino]carbonyl]-$N^5$-[(phenylmethoxy)-carbonyl]-ornithine, 4-hydroxybenzenemethanamine and TBTU in a yield of 54% of theory.

Colourless crystals, mp. 128°–130° C.

IR (KBr):

1687.6 $cm^{-1}$ (urethane-C═O)

1625.9 $cm^{-1}$ (urea-C═O)

ESI-MS:

$(M+H)^+$=581

$(M+Na)^+$=603

$(2M+Na)^+$=1183 e) (R,S)-$N^2$-[[(Diphenylmethyl)amino]carbonyl)-N-[(4-hydroxyphenyl)methyl]-ornithinamide-acetate Prepared analogously to Example 142c) from (R,S)-$N^2$-[[(diphenylmethyl)amino]carbonyl]-N-[(4-hydroxyphenyl)methyl]-$N^5$-[(phenylmethoxy)carbonyl]-ornithinamide by catalytic hydrogenation in the presence of 10% palladium/animal charcoal (10%) in a quantitative yield.

Colourless crystals.

IR (KBr): 1649.0, 1554.5 $cm^{-1}$(C═O)

f) (R,S)-$N^2$-[[(Diphenylmethyl)amino]carbonyl]-N-[(4-hydroxyphenyl)methyl]-$N^5$-(1H-imidazol-1-yl)-ornithinamide Prepared analogously to Example 85 from (R,S)-$N^2$-[[(diphenylmethyl)amino]carbonyl]-N-[(4-hydroxyphenyl)-methyl]-ornithinamide-acetate and N-[(2,2-diethoxy)ethyl]-S-methylthiuronium-chloride in a yield of 8% of theory.

Colourless crystals, $R_f$ 0.77

ESI-MS: $(M+H)^+$=513

EXAMPLE 148

(R,S)-N-[(4-Hydroxyphenyl)methyl]-$N^5$-(1H-imidazol-2-yl)-$N^2$-[2-(2-naphthyl)-1-oxoethyl]-ornithinamide a) (R,S)-N-[(4-Hydroxyphenyl)methyl]-$N^5$-[(phenylmethoxy)-carbonyl]-ornithinamide Prepared analogously to Example 142a) from (R,S)-3,4-dihydro-4-[3-[[(phenylmethoxy)carbonyl)amino]propyl]-1,3-oxazol-2,5-dione and 4-hydroxybenzenemethanamine in a yield of 87% of theory.

Colourless crystals, mp. 162°–163° C.

IR (KBr): 1691.5 (urethane-C═O)

b) (R,S)-N-[(4-Hydroxyphenyl)methyl]-$N^2$-[2-(2-naphthyl)-1-oxoethyl)-$N^5$-[(phenylmethoxy)carbonyl]-ornithinamide Prepared, analogously to Example 67a) but using triethylamine as base instead of N,N-diisopropyl-ethylamine and tetrahydrofuran/dimethylformamide=5/2 (v/v) as solvent instead of dimethylformamide, from (R,S)-N-[(4-hydroxyphenyl)-methyl]-$N^5$-[(phenylmethoxy)carbonyl]-ornithinamide, 4-hydroxybenzenemethanamine and TBTU in a yield of 75% of theory.

Colourless crystals, mp. 120°–125° C.

MS: $M^+$=539 c) (R,S)-N-[(4-Hydroxyphenyl)methyl]-$N^2$-[2-(2-naphthyl)-1-oxoethyl]-ornithinamide-acetate Prepared analogously to Example 142c) from (R,S)-N-[(4-hydroxyphenyl)methyl]-$N^2$-[2-(2-naphthyl)-1-oxoethyl]-$N^5$-[(phenylmethoxy)carbonyl)-ornithinamide by catalytic hydrogenation in the presence of 10% palladium/activated charcoal in a yield of 86% of theory.

Colourless crystals, mp. 160°–162° C.

MS: $M^+$=405 d) (R,S)-N-[(4-Hydroxyphenyl)methyl]-$N^5$-(1H-imidazol-2-yl)-$N^2$-[2-(2-naphthyl)-1-oxoethyl]-ornithinamide Prepared analogously to Example 85 from (R,S)-N-[(4-hydroxyphenyl)methyl]-$N^2$-[2-(2-naphthyl)-1-oxoethyl]-ornithinamide-acetate and N-[(2,2-diethoxy)ethyl]-S-methylthiuroniumchloride in a yield of 33% of theory.

Colourless crystals, $R_f$ 0.70.

IR (KBr): 1645.2 $cm^{-1}$ (amide-C═O)

ESI-MS: $(M+H)^+$=472

EXAMPLE 149

(R,S)-N-[(4-Hydroxyphenyl)methyl]-$N^5$-(1H-imidazol-2-yl)-$N^2$-[[(2-naphthyl)amino]carbonyl)-ornithinamide a) (R,S)-$N^2$-[[(2-Naphthyl)amino]carbonyl]-$N^5$-[(phenylmethoxy)carbonyl]-ornithine-methylester Prepared analogously to Example 79c) from methyl (R,S)-2-isocyanato-5-[(phenylmethoxy)carbonyl]amino]-pentanoate and 2-naphthylamine in a yield of 93% of theory.

Colourless crystals.

IR (KBr): 1720.4 $cm^{-1}$ (ester-C═O)

b) (R,S)-$N^2$-[(2-Naphthyl)amino]carbonyl]-$N^5$-[(phenylmethoxy)carbonyl)-ornithine A mixture of 4.7 g (10.46 mMol) of (R,S)-$N^2$-[[(2-naphthyl)-amino)carbonyl]-$N^5$-[(phenylmethoxy) carbonyl]-ornithine-methylester, 0.42 g (10.5 mMol) of sodium hydroxide, 50 ml of ethanol and 10 ml of water was refluxed for one hour. After cooling, the mixture was diluted with 200 ml of water and acidified to pH 3 with 5% aqueous hydrochloric acid. It was extracted exhaustively with ethyl acetate, the combined ethyl acetate extracts were dried over sodium sulphate, clarified with activated charcoal and evaporated down in vacuo. The crystals obtained were further processed without any further purification.

Yield: 3.8 g (83% of theory).

IR (KBr):

1687.6 $cm^{-1}$ (urethane-C═O)

1677.1 $cm^{-1}$ (C═O)

c) (R,S)-N-[(4-Hydroxyphenyl)methyl]-$N^2$-[[(2-naphthyl)-amino]carbonyl]-$N^5$-[(phenylmethoxy)carbonyl]-ornithinamide Prepared analogously to Example 67a) from (R,S)-$N^2$-[[(2-naphthyl)amino]carbonyl]-$N^5$-[(phenylmethoxy)carbonyl]-ornithine, 4-hydroxybenzenemethanamine and TBTU in a quantitative yield.

Colourless crystals, mp. 145°–146° C. (ethyl acetate).

IR (KBr):

1685.7 $cm^{-1}$ (urethane-C═O)

1635.5 $cm^{-1}$ (C═O)

d) (R,S)-N-[(4-Hydroxyphenyl)methyl]-$N^2$-[[(2-naphthyl)-amino)carbonyl]-ornithinamide-acetate Prepared analogously to Example 142c) from (R,S)-N-[(4-hydroxyphenyl)methyl]-$N^2$-[[(2-naphthyl)amino]carbonyl]-$N^5$-[(phenylmethoxy)carbonyl]-ornithinamide by catalytic hydrogenation in the presence of (10%) palladium/activated charcoal in a yield of 70% of theory.

Colourless crystals.

IR (KBr): 1637.5 $cm^{-1}$ (C═O)

e) (R,S)-N-[(4-Hydroxyphenyl)methyl]-$N^5$-(1H-imidazol-2-yl)-$N^2$[[(2-naphthyl)amino]carbonyl]-ornithinamide Prepared analogously to Example 85 from (R,S)-N-[(4-hydroxyphenyl)methyl]-$N^2$-[[(2-naphthyl) amino]carbonyl]

-ornithinamide-acetate and N-[(2,2-diethoxy)ethyl]-S-methylthiuronium-iodide in a yield of 6% of theory.

Colourless crystals, $R_f$ 0.75.

IR (KBr): 1670.3 $cm^{-1}$ (amide-C═O)

ESI-MS: $(M+H)^+$=473

EXAMPLE 150

(R,S)-$N^2$-(Diphenylacetyl)-N-[(4-hydroxyphenyl) methyl]-3-[(4-piperidinyl)methyl]-alaninamide-hydrochloride a) Ethyl (R,S)-2-(acetylamino)-4-(4-pyridinyl)-butanoate Prepared, analogously to Example 31a) but using potassium ethoxide instead of sodium ethoxide and anhydrous ethanol as solvent instead of dioxane, from diethyl acetamidomalonate and 4-vinylpyridine in a yield of 39% of theory:

Colourless viscous oil.

IR (KBr):

1741.6 $cm^{-1}$ (ester-C═O)

1658.7 $cm^{-1}$ (amide-C═O)

MS: $M^+$=250 b) (R,S)-3-[(4-Pyridinyl)methyl]-alanine-hydrochloride

A mixture of 9.0 g (0.036 Mol) of ethyl (R,S)-2-(acetylamino)-4-(4-pyridinyl)-butanoate and 50 ml of conc. hydrochloric acid was refluxed for 5 hours. The reaction mixture was evaporated to dryness in vacuo, the residue was taken up in methanol and again evaporated down in vacuo. On trituration with isopropanol, crystallisation began. The crystals were suction filtered, the filter contents were washed thoroughly with diethylether and then dried in air. 7.5 g (96% of theory) of colourless crystals were obtained, Mp. 208°–210° C.

IR (KBr): 1741.6 $cm^{-1}$

MS: m/e=135, m/e=118, m/e=93 c) (R,S)-$N^2$-(Diphenylacetyl)-3-[(4-pyridinyl)methyl]-alanine

Prepared analogously to Example 1a) from (R,S)-3-[(4-pyridinyl)-methyl]-alanine-hydrochloride and diphenylacetylchloride in the presence of sodium hydroxide solution in a yield of 62% of theory.

Colourless crystals.

IR (KBr):

3300.0 $cm^{-1}$ (N—H, O—H)

1703.0 $cm^{-1}$ (carboxyl-C═O)

1635.5 $cm^{-1}$ (amide-C═O)

MS: $M^+$=374 d) (R,S)-$N^2$-(Diphenylacetyl)-N-[(4-hydroxyphenyl)-methyl]-3-[(4-pyridinyl)methyl]-alaninamide-hydrochloride Prepared analogously to Example 67a) from (R,S)-$N^2$-(diphenylacetyl)-3-[(4-pyridinyl)methyl]-alanine, 4-hydroxybenzenemethanamine and TBTU in a yield of 26% of theory.

Colourless crystals, mp. >250° C. and $R_f$ 0.55 (silica gel 60 $F_{254}$ for TLC, Merck Darmstadt; dichloromethane/methanol/cyclohexane/conc. aqueous ammonia=68/15/15/2 (v/v/v/v)).

IR (KBr): 1645.2 $cm^{-1}$ (amide-C═O)

MS: $M^+$=479 e) (R,S)-$N^2$-(Diphenylacetyl)-N-[(4-hydroxyphenyl)-methyl]-3-[(4-piperidinyl)methyl]-alaninamide-hydrochloride A solution of 1.4 g (2.713 mMol) of (R,S)-$N^2$-(diphenylacetyl)-N-[(4-hydroxyphenyl)methyl]-3-[(4-pyridinyl)methyl]-alaninamide-hydrochloride in 50 ml of methanol was combined with 0.2 g platinum(IV)-oxide and 10 ml of 1N hydrochloric acid and then hydrogenated at ambient temperature under 3 bars of hydrogen pressure until the uptake of hydrogen had ended. The catalyst was filtered off, the filtrate was evaporated down in vacuo and the residue was crystallised from isopropanol. After washing with tert.-butylmethylether and drying in vacuo, colourless crystals were obtained, mp. 234°–235° C. and $R_f$ 0.57, in a yield of 0.7 g (49% of theory).

IR (KBr): 1643.3 $cm^{-1}$ (amide-C═O)

MS: $M^+$=485

EXAMPLE 151

(R,S)-$N^2$-[(2-Quinolinyl)carbonyl]-N-[(4-hydroxyphenyl)methyl]-$N^5$-(1H-imidazol-2-yl)-ornithinamide and diastereomers of N-[(4-hydroxyphenyl)methyl]-$N^5$-(1H-imidazol-2-yl)-$N^2$-[(1,2,3,4-tetrahydro-2-quinolinyl)carbonyl]-ornithinamide a) (R,S)-$N^2$-[(2-Quinolinyl)carbonyl]-N-[(4-hydroxyphenyl)-methyl]-$N^5$-[(phenylmethoxy)carbonyl]-ornithinamide Prepared analogously to Example 148b) from quinoline-2-carboxylic acid, (R,S)-N-[(4-hydroxyphenyl)methyl]-$N^5$-[(phenylmethoxy)carbonyl]-ornithinamide and TBTU in a yield of 88% of theory.

Colourless crystals, mp. 189°–192° C.

ESI-MS:

$(M+Na)^+$=549

$(M+K)^+$=565 b) Mixture of (R,S)-$N^2$-((2-quinolinyl)carbonyl]-N-[(4-hydroxyphenyl)methyl]-ornithinamide and diastereomers of N-[(4-hydroxyphenyl)methyl]-$N^2$-[(1,2,3,4-tetrahydroquinolinyl)carbonyl]-ornithinamide Prepared analogously to Example 142c) from (R,S)-$N^2$-[(2-quinolinyl)carbonyl]-N-[(4-hydroxyphenyl)methyl]-$N^5$-[(phenylmethoxy)carbonyl]-ornithinamide by catalytic hydrogenation in the presence of 10% palladium/activated charcoal in a yield of 74% of theory.

IR (KBr): 1643 $cm^{-1}$ (amide-C═O)

ESI-MS:

$(M_1+H)^+$=393

$(M_2+H)^+$=397

The mixture was used, unseparated, for the following step.

c) (R,S)-$N^2$-[(2-Quinolinyl)carbonyl]-N-[(4-hydroxyphenyl)-methyl]-$N^5$-(1H-imidazol-2-yl)-ornithinamide and diastereomers of N-[(4-hydroxyphenyl) methyl]-$N^5$-(1H-imidazol-2-yl)-$N^2$-[(1,2,3,4-tetrahydro-2-quinolinyl)carbonyl]-ornithinamide The mixture of products obtained analogously to Example 85 from a mixture of (R,S)-$N^2$-[(2-quinolinyl)carbonyl)-N-[(4-hydroxyphenyl)methyl]-ornithinamide and the two diastereomers of N-[(4-hydroxyphenyl)methyl]-$N^2$-[(1,2,3,4-tetrahydro-2-quinolinyl)carbonyl]-ornithinamide by reacting first with N-[(2,2-diethoxy)-ethyl]-S-methylthiuroniumiodide, and then with hydrochloric acid was separated by chromatography on silica gel (Baker, 30–60 μm) using ethyl acetate/cyclohexan/methanol/conc. aqueous ammonia=10/2/1/0.1 (v/v/v/v) as mobile phase and then crystallised from diisopropylether. The following were obtained:

I. $N^2$-[(2-Quinolinyl)carbonyl]-N-[(4-hydroxyphenyl) methyl]-$N^5$-(1H-imidazol-2-yl)-ornithinamide, Yield: 1% of theory.

Colourless crystals, $R_f$ 0.70

ESI-MS: $(M+H)^+$=459

II. N-[(4-Hydroxyphenyl)methyl]-$N^5$-(1H-imidazol-2-yl)-$N^2$-[(1,2,3,4-tetrahydro-2-quinolinyl)carbonyl]-ornithinamide (Diastereomer A),
Yield: 3% of theory.
Colourless crystals, $R_f$ 0.69
ESI-MS: $(M+H)^+$=463

III. N-[(4-Hydroxyphenyl)methyl]-$N^5$-(1H-imidazol-2-yl)-$N^2$-[(1,2,3,4-tetrahydro-2-quinolinyl)carbonyl]-ornithinamide (Diastereomer B),
Yield: 1% of theory.
Colourless crystals, $R_f$ 0.62
ESI-MS: $(M+H)^+$=463

EXAMPLE 152

Diastereomers of N-[(4-hydroxyphenyl)methyl]-$N^5$-(1H-imidazol-2-yl)-$N^2$-[(1,2,3,4-tetrahydro-3-quinolinyl)carbonyl]-ornithinamide a) (R,S)-$N^2$-[(3-Quinolinyl)carbonyl]-N-[(4-hydroxyphenyl)-methyl]-$N^5$-[(phenylmethoxy) carbonyl]-ornithinamide Prepared analogously to Example 148b) from quinoline-3-carboxylic acid, (R,S)-N-[(4-hydroxyphenyl)methyl]-$N^5$-[(phenylmethoxy)carbonyl]-ornithinamide and TBTU in a yield of 60% of theory.

Colourless crystals, mp. 181°–183° C.
ESI-MS:
$(M+H)^+$=527
$(M+Na)^+$=549
$(M+K)^+$=565 b) Mixture of diastereomers of N-[(4-hydroxyphenyl)-methyl]-$N^2$-[(1,2,3,4-tetrahydro-3-quinolinyl)carbonyl]-ornithinamide-acetate Prepared analogously to Example 142c) from (R,S)-$N^2$-[(3-quinolinyl)carbonyl]-N-[(4-hydroxyphenyl)methyl]-$N^5$-[(phenylmethoxy)carbonyl]-ornithinamide by catalytic hydrogenation in the presence of 10% palladium/activated charcoal in a yield of 70% of theory.

Colourless amorphous product, which was used without separation in the next step.

IR (KBr): 1649.0 $cm^{-1}$ (amide-C═O)

c) Diastereomers of N-[(4-hydroxyphenyl)methyl]-$N^5$-(1H-imidazol-2-yl)-$N^2$-[(1,2,3,4-tetrahydro-3-quinolinyl) carbonyl]-ornithinamide The mixture of products obtained analogously to Example 85 from a mixture of the two diastereomers of N-[(4-hydroxyphenyl)methyl]-$N^2$-[(1,2,3,4-tetrahydro-3-quinolinyl)carbonyl)-ornithinamide-acetate by reacting first with N-[(2,2-dethoxy)ethyl]-S-methylthiuroniumiodide, and then with hydrochloric acid was separated by column chromatography on silica gel (Baker, 15–25 μm) using ethyl acetate/cyclohexane/methanol/conc. aqueous ammonia and was then recrystallised from diisopropylether. The following were obtained:

I. N-[(4-Hydroxyphenyl)methyl]-$N^5$-(1H-imidazol-2-yl)-$N^2$-[(1,2,3,4-tetrahydro-3-quinolinyl)carbonyl]-ornithinamide (Diastereomer A),
Yield: 2% of theory.
Colourless crystals, $R_f$ 0.62
ESI-MS: $(M+H)^+$=463

II. N-[(4-Hydroxyphenyl)methyl]-$N^5$-(1H-imidazol-2-yl)-$N^2$-[(1,2,3,4-tetrahydro-3-quinolinyl)carbonyl]-ornithinamide (Diastereomer B),
Yield: 3% of theory.
Colourless crystals, $R_f$ 0.60
ESI-MS:
$(M+H)^+$=463
$(M+Na)^+$=485
$(M+K)^+$=501

EXAMPLE 153

(R,S)-3-[2-[(Aminoiminomethyl)amino]phenyl]-$N^2$-(diphenylacetyl)-N-[(4-hydroxyphenyl)methyl]-alaninamide-hydrochloride a) Diethyl α-(acetylamino)-α-[(2-nitrophenyl)methyl]-malonate Prepared analogously to Example 31a) from diethyl acetamidomalonate and 2-nitrobenzylchloride in a yield of 86% of theory.

Colourless crystals, mp. 108° C.
IR (KBr):
1745.5 $cm^{-1}$ (ester-C═O)
1643.3 $cm^{-1}$ (amide-C═O)
1527.5 $cm^{-1}$ (amide-II, $NO_2$)
1355.9 $cm^{-1}$ ($NO_2$)

b) (R,S)-3-(2-Nitrophenyl)-alanine-hydrochloride

Prepared analogously to Example 31b) from diethyl α-(acetylamino)-α-[(2-nitrophenyl)methyl]-malonate and aqueous hydrochloric acid in a yield of 47% of theory.

Colourless crystals
IR (KBr):
1730.0 $cm^{-1}$ (carboxylic acid-C═O)
1523.7 $cm^{-1}$ (amide-II, $NO_2$)
1336.6 $cm^{-1}$ ($NO_2$)
ESI-MS:
$(M+H)^+$=211
$(M-H)^-$=209
$(M+Na)^+$=233
(2M+Na)=443
(2M−2H+Na)=441 c) (R,S)-$N^2$-(Diphenylacetyl)-3-(2-nitrophenyl)-alanine

Prepared analogously to Example 1a) from diphenylacetylchloride and (R,S)-3-(2-nitrophenyl)-alanine-hydrochloride in the presence of sodium hydroxide solution in a yield of 97% of theory.

Colourless crystals, mp. 150°–151° C.
IR (KBr):
3320 $cm^{-1}$ (N—H, O—H)
1710.8 $cm^{-1}$ (carboxylic acid-C═O)
1652.9 $cm^{-1}$ (amide-C═O)
1529.5 $cm^{-1}$ (amide-II, $NO_2$)
1344.3 $cm^{-1}$ ($NO_2$)

d) (R,S)-$N^2$-(Diphenylacetyl)-N-[(4-hydroxyphenyl)-methyl]-3-(2-nitrophenyl)-alaninamide Prepared analogously to Example 67a) from (R,S)-$N^2$-(diphenylacetyl)-3-(2-nitrophenyl)-alanine, 4-hydroxybenzenemethanamine and TBTU in a yield of 100% of theory.

Colourless crystals
IR (KBr):
3280 $cm^{-1}$ (N—H, O—H)
1639.4 $cm^{-1}$ (amide-C═O)
ESI-MS:
$(M+H)^+$=510
$(M+Na)^+$=532

$(M+K)^+$=548 e) (R,S)-3-(2-Aminophenyl)-$N^2$-(diphenylacetyl)-N-[(4-hydroxyphenyl)methyl]-alaninamide Prepared, analogously to Example 25b) but using methanol/tetrahydrofuran=1/5 (v/v) as solvent, from(R,S)-$N^2$-(diphenylacetyl)-N-[(4-hydroxyphenyl)methyl]-3-(2-nitrophenyl)-alaninamide by catalytic hydrogenation in the presence of 10% palladium/activated charcoal in a yield of 83% of theory.

Colourless crystals, mp. 194°–195° C.

IR (KBr):

3450.4, 3359.8, 3265.3 $cm^{-1}$ (O—H; N—H)

1649.0 $cm^{-1}$ (amide-C═O)

1616.3 $cm^{-1}$ (amide-II)

MS: $M^+$=479 f) (R,S)-3-[2-((Aminoiminomethyl)amino]phenyl]-$N^2$-(diphenylacetyl)-N-[(4-hydroxyphenyl)methyl]-alaninamide-hydrochloride Prepared analogously to Example 70d) from (R,S)-3-(2-aminophenyl)-$N^2$-(diphenylacetyl)-N-[(4-hydroxyphenyl)-methyl]-alaninamide and cyanamide in a yield of 9% of theory.

Colourless crystals, mp. 175°–176° C. and $R_f$ 0.80.

IR (KBr):

1678.0 $cm^{-1}$ (guanidinium)

1643.3 $cm^{-1}$ (amide-C═O)

ESI-MS:

$(M+H)^+$=522

$(2M+H)^+$=1043

$(2M+Na)^+$=1065

EXAMPLE 154

(R)-$N^2$-[2-(2,4-Dichlorophenoxy)-1-oxoethyl]-N-[(4-hydroxyphenyl)methyl]-argininamide a) (R)-$N^5$-[Amino(nitroimino)methyl]-$N^2$-[2-(2,4-dichlorophenoxy)-1-oxoethyl]-ornithine Prepared analogously to Example 1a) from 2-(2,4-dichlorophenoxy)-acetylchloride and H-D-Arg($NO_2$)-OH in the presence of sodium hydroxide solution in a yield of 56% of theory.

Colourless crystals, mp. 235°–237° C. (methanol/water=1/1 (v/v))

IR (KBr):

3386.8 $cm^{-1}$ (N—H, O—H)

1732 $cm^{-1}$ (carboxylic acid-C═O)

1629.8 $cm^{-1}$ (amide-C═O)

b) (R)-$N^5$-[Amino(nitroimino)methyl]-$N^2$-[2-(2,4-dichlorophenoxy)-1-oxoethyl]-N-[(4-hydroxyphenyl) methyl]-ornithinamide Prepared analogously to Example 67a) from (R)-$N^5$-[amino(nitroimino)methyl]-$N^2$-[2-(2,4-dichlorophenoxy)-1-oxoethyl]-ornithine, 4-hydroxybenzenemethanamine and TBTU in a yield of 66% of theory.

Colourless crystals, mp. 205°–210° C. and $R_f$ 0.50 (silica gel 60 $F_{254}$ for thin layer chromatography, Merck-Darmstadt; eluant: ethyl acetate/methanol/glacial acetic acid 100/10/5=(v/v/v)).

IR (KBr): 1645.2 $cm^{-1}$ (amide-C═O)

c) (R)-$N^2$-(2-(2,4-Dichlorophenoxy)-1-oxoethyl]-N-[(4-hydroxyphenyl)methyl]-argininamide Prepared analogously to Example 1c) from (R)-$N^5$-[amino(nitroimino)methyl]-$N^2$-[2-(2,4-dichlorophenoxy)-1-oxoethyl)-N-[(4-hydroxyphenyl)methyl]-ornithinamide by catalytic hydrogenation in the presence of palladium black and 80% aqueous acetic acid in a yield of 87% of theory.

Colourless amorphous substance, $R_f$ 0.51

IR (KBr): 1652.9 $cm^{-1}$ (amide-C═O)

ESI-MS: $(M+H)^+$=482/484/486 ($Cl_2$)

EXAMPLE 155

(R) $N^2$-[(9-Fluorenyl)carbonyl]-N-[(4-hydroxyphenyl)methyl]-argininamide-acetate a) (R)-$N^5$-[Amino(nitroimino)methyl]-$N^2$-[(9-fluorenyl)-carbonyl]-N-[( 4-hydroxyphenyl)methyl]-ornithinamide Prepared analogously to Example 67a) from 9-fluorenecarboxylic acid, (R)-$N^5$-[amino(nitroimino)-methyl]-N-[(4-hydroxyphenyl)methyl]-ornithinamide-hydrochloride and TBTU in a yield of 9% of theory.

Colourless crystals, mp. 230°–234° C. and $R_f$ 0.36 (silica gel 60 $F_{254}$ for TLC, Merck-Darmstadt; eluant: ethyl acetate/methanol/glacial acetic acid=100/2/1 (v/v/v)).

IR (KBr):

1637.5 $cm^{-1}$ (amide-C═O)

ESI-MS:

$(M+H)^+$=517

$(M+Na)^+$=539

$(M+K)^+$=555

$(M-H)^-$=515 b) (R)-$N^2$-[(9-Fluorenyl)carbonyl]-N-[(hydroxyphenyl) methyl]-argininamide-acetate Prepared analogously to Example 1c) from (R)-$N^5$-[amino(nitroimino)methyl]-$N^2$-[(9-fluorenyl)carbonyl]-N-[(4-hydroxyphenyl)methyl]-ornithinamide by catalytic hydrogenation in the presence of palladium black and 80% aqueous acetic acid in a yield of 40% of theory.

Colourless crystals, mp. 93°–96° C. and $R_f$ 0.52

ESI-MS: $(M+H)^+$=472

EXAMPLE 156

(R)-N-[(4-Hydroxyphenyl)methyl]-$N^2$-(2,2,2-triphenyl-1-oxoethyl)-argininamide a) (R)-$N^5$-[Amino(nitroimino)methyl]-N-[(4-hydroxyphenyl)methyl]-$N^2$-(2,2,2-triphenyl-1-oxoethyl)-ornithinamide Prepared analogously to Example 8a) from 2,2,2-triphenylacetic acid, (R)-$N^5$-[amino(nitroimino)methyl]-N-[(4-hydroxyphenyl)methyl]-ornithinamide and TBTU in a yield of 26% of theory.

Colourless crystals.

IR (KBr): 1645 $cm^{-1}$ (amide-C═O)

b) (R)-N-[(4-Hydroxyphenyl)methyl]-$N^2$-(2,2,2-triphenyl-1-oxoethyl)-argininamide Prepared analogously to Example 1c) from (R)-$N^5$-[amino(nitroimino)methyl]-N-(4-hydroxyphenyl)methyl]-$N^2$-(2,2,2-triphenyl-1-oxoethyl)-ornithinamide by catalytic hydrogenation in the presence of palladium black and 80% aqueous acetic acid in a yield of 50% of theory.

Colourless crystals, $R_f$ 0.54

IR (KBr): 1664.5 $cm^{-1}$ (amide-C═O, amidinium)

ESI-MS: $(M+H)^+$=550

EXAMPLE 157

(R,S)-3-(4-Aminobutyl)-$N^2$-(diphenylacetyl)-N-[(4-hydroxyphenyl)methyl]-alaninamide-hydrochloride a) (R,S)-N-(Diphenylmethylene)-2-(4-cyanobutyl)-glycinemethylester To a solution of 35 g (0.138 Mol) of N-(diphenylmethylene)-glycinemethylester in 300 ml of acetonitrile were added, successively, 26.9 g (0.166 Mol) of 5-bromovaleronitrile, 4.45 g (0.0138 Mol) tetrabutylammoniumbromide and 76.2 g (0.551 Mol) of potassium carbonate and the mixture was refluxed for 3 hours. After a further 5.0 g (0.031 Mol) of 5-bromovaleronitrile had been added the mixture was refluxed for a further 5 hours. The insoluble matter was filtered off and the filtrate was evaporated down in vacuo. The viscous, oily residue obtained in a yield of 46.1 g (100% of theory) was used in the next step without purification.

b) (R,S)-2-(4-Cyanobutyl)-glycinemethylester-hydrochloride

A mixture of 46.1 g (0.138 Mol) of N-(diphenylmethylene)-2-(4-cyanobutyl)-glycinemethylester and 179.5 ml of 1N aqueous hydrochloric acid was stirred for 4 hours at ambient temperature. It was extracted twice with 100 ml of ether and the aqueous phase was evaporated down under reduced pressure. The residue was digested with methanol and freed from solvent once more in vacuo. This procedure was repeated twice more. Then the solid obtained was triturated with tetrahydrofuran and suction filtered. After distillation the filtrate yielded 23.5 g (100% of theory) of an amorphous substance, which was further processed as a crude product.

IR (KBr):

2246.9 $cm^{-1}$ (C≡N)

1749.3 $cm^{-1}$ (ester-C═O)

ESI-MS:

$(M+H)^+$=171

$(2M+H)^+$=341 c) (R,S)-2-(4-Cyanobutyl)-$N^2$-(diphenylacetyl)-glycinemethylester

Prepared, analogously to Example 1a) but using sodium carbonate instead of sodium hydroxide, from diphenylacetylchloride and (R,S)-2-(4-cyanobutyl)-glycinemethylester hydrochloride in a yield of 42% of theory.

Colourless crystals mp. 95°–99° C.

IR (KBr):

3284.6 $cm^{-1}$ (N—H)

2246.9 $cm^{-1}$ (C≡N)

1749.3 $cm^{-1}$ (ester-C═O)

1643.3 $cm^{-1}$ (amide-C═O)

d) (R,S)-2-(4-Cyanobutyl)-$N^2$-(diphenylacetyl)-glycine 3.0 g (8.23 mMol) of (R,S)-2-(4-cyanobutyl)-$N^2$-(diphenylacetyl)-glycinemethylester were dissolved in 50 ml of acetone and after the addition of 7.5 ml (30 mMol) of 4N sodium hydroxide solution the mixture was stirred overnight at ambient temperature. The aqueous phase remaining after the removal of the acetone in vacuo was acidified with 1N hydrochloric acid and extracted exhaustively with ethyl acetate. The combined ethyl acetone extracts were dried over sodium sulphate and evaporated down in vacuo. The residue was triturated with diisopropylether. It was suction filtered and 2.7 g (94% of theory) of colourless crystals were obtained, mp. 131°–133° C.

IR (KBr):

3305.8 $cm^{-1}$ (N—H)

2245.0 $cm^{-1}$ (C≡N)

1716.5 $cm^{-1}$ (carboxylic acid-C═O)

1649.0 $cm^{-1}$ (amide-C═O)

e) (R,S)-2-(4-Cyanobutyl)-$N^2$-(diphenylacetyl)-N-[(4-hydroxyphenyl)methyl)]-glycinamide Prepared, analogously to Example 67a) but using tetrahydrofuran/dimethylformamide=3/1 (v/v/) as solvent instead of pure dimethylformamide, from (R,S)-2-(4-cyanobutyl)-$N^2$-(diphenylacetyl)-glycine, 4-hydroxybenzenemethanamine-hydrochloride and TBTU in a yield of 91% of theory.

Colourless crystals, mp. 158°–160° C. (diisopropylether)

IR (KBr):

3388.7; 3253.7 $cm^{-1}$ (N—H; O—H)

2254.7 $cm^{-1}$ (C≡N)

1643.3 $cm^{-1}$ (amide-C═O)

f) (R,S)-3-(4-Aminobutyl)-$N^2$-(diphenylacetyl)-N-[(4-hydroxyphenyl)methyl]-alaninamide-hydrochloride A solution of 0.7 g (1.537 mMol) of (R,S)-2-(4-cyanobutyl)-$N^2$-(diphenylacetyl)-N-[(4-hydroxyphenyl)-methyl]-glycinamide in 200 ml of methanol was hydrogenated for 2.5 hours at ambient temperature under a hydrogen pressure of 3 bar after the addition of 1 ml of conc. hydrochloric acid and 1.0 g of 10% palladium/activated charcoal catalyst. A further 0.5 g of the catalyst were added and hydrogenation was continued for a further 2.5 hours under the same conditions. The solution freed from catalyst was concentrated by evaporation and the residue was triturated with ice cold ethyl acetate. 0.58 g (76% of theory) of colourless crystals were obtained mp. 210°–211° C. and $R_f$ 0.52.

IR (KBr):

3300 $cm^{-1}$ (N—H, O—H)

1639.4 $cm^{-1}$ (amide-C═O)

MS:

$M^+$=459

EXAMPLE 158

(R,S)-6-(Aminoiminomethyl)-$N^2$-(diphenylacetyl)-N-[(4-hydroxyphenyl)methyl]-norleucinamide-hydrochloride Prepared analogously to Example 79 f) from (R,S)-2-(4-cyanobutyl)-$N^2$-(diphenylacetyl)-N-(4-hydroxyphenyl)-methyl]-glycinamide by reacting first with dry hydrogen chloride in anhydrous ethanol and then with ammonium carbonate. A yield of 60% of theory of colourless crystals were obtained mp. 107° C. and $R_f$ 0.54.

IR (KBr):

1687.6 $cm^{-1}$ (amidinium)

1651.0 $cm^{-1}$ (amide-C═O)

ESI-MS: $(M+H)^+$=473

EXAMPLE 159

(R,S)-3-[4-(4,5-Dihydro-1H-imidazol-2-yl)phenyl]-$N^2$-(diphenylacetyl)-N-[(4-hydroxyphenyl)methyl]-alaninamide-hydrochloride To 60 ml of anhydrous ethanol saturated with dry hydrogen chloride and covered with 30 ml of anhydrous petroleum ether was added, in small portions and whilst maintaining a reaction temperature of 0° to +5° C., a total of 5.2 g (10.62 mMol) of (R,S)-3-(4-cyanophenyl)-$N^2$-(diphenylacetyl)-N-[(4-hydroxyphenyl)methyl]-alaninamide and the mixture was then stirred for 14 hours at the same temperature. The residue remaining after evaporation of the solvent was taken up twice more in 50 ml of anhydrous ethanol and then brought back to dryness in vacuo at a bath temperature of not more than +40° C. The residue in the flask was suspended in 50 ml of dry ethanol and at ambient temperature 3.18 g (52.9 mMol) of 1,2-ethanediamine were added with stirring. After 20 hours the solvent was eliminated in vacuo, the residue was carefully digested with water and suction filtered. After drying in vacuo, 4.6 g (76% of theory) of colourless crystals were obtained, mp. 227°–229° C. and $R_f$ 0.41.

IR (KBr):

3533.4, 3274.9 $cm^{-1}$ (N—H; O—H; $N^+$—H)

1622.0 $cm^{-1}$ (amide-C═O)

MS: $M^+$=532

EXAMPLE 160

(R)-N-[[4-[3-(Dimethylamino)propyloxy)phenyl] methyl]-$N^2$-(diphenylacetyl)-argininamide a) (R)-$N^5$-[Amino(nitroimino)methyl]-N-[[4-[3-(dimethylamino)propyloxy]phenyl]methyl]-$N^2$-(diphenylacetyl)-ornithinamide Prepared analogously to Example 67a) from R)-$N^5$-[amino(nitroimino)methyl]-$N^2$-(diphenylacetyl)-ornithine, 4-[3-(dimethylamino)-propyloxy)-benzene-methylamine and TBTU in a yield of 62% of theory Colourless amorphous substance IR (KBr):

3363.7, 3298.1 $cm^{-1}$ (N—H)

2815.9; 2767.7 $cm^{-1}$ (phenolether; $NCH_3$)

1639.4 $cm^{-1}$ (amide-I)

ESI-MS:

$(M+H)^+$=604

$(M+Na)^+$=626

$(M+K)^+$=642

$(2M+Na)^+$=1229 b) (R)-N-[[4-[3-(Dimethylamino)propyloxy]phenyl]methyl]-$N^2$-(diphenylacetyl)-argininamide Prepared analogously to Example 1c) from (R)-$N^5$-[Amino(nitro-imino)methyl]-N-[[4-[3-(dimethyl-amino)-propyloxy]phenyl]methyl]-$N^2$-(diphenylacetyl)-ornithinamide by catalytic hydrogenation in the presence of palladium black and 80% aqueous acetic acid in a yield of 54% of theory.

Colourless amorphous substance, $R_f$ 0.21.

IR (KBr): 1649 $cm^{-1}$ (amide-C═O)

ESI-MS:

$(M+H)^+$=559

$(2M+H)^+$=1117

EXAMPLE 161

(R,S)-3-[3-[Amino(hydroxyimino)methyl]phenyl]-$N^2$-(diphenyl-acetyl)-N-[(4-hydroxyphenyl)methyl]-alaninamide To a solution of 0.5 g (1.0213 mMol) of (R,S)-3-(3-cyano-phenyl)-$N^2$-(diphenylacetyl)-alaninamide in 10 ml of hot ethanol was added a solution of 0.09 g (1,295 mMol) of hydroxylamine-hydrochloride and 0.08 g (0.755 mMol) of sodium carbonate in 1.5 ml of water and the mixture was refluxed for 2 hours. It was filtered hot, the filtrate was freed from solvent and the residue was taken up in 20 ml of methanol. Water was then added until precipitation had ended. The crystals formed were suction filtered and dried in vacuo over calcium chloride.

Yield: 0.41 g (77% of theory).

Colourless crystals, mp. 157°–160° C. and $R_f$ 0.82.

IR (KBr):

1641.3 $cm^{-1}$ (amide-I)

1514.0 $cm^{-1}$ (amide-II)

ESI-MS:

$(M+H)^+$=523

$(M+Na)^+$=545

$(M+K)^+$=561

EXAMPLE 162

(R,S)-3-[3-(Aminocarbonyl)phenyl]-$N^2$-(diphenylacetyl)-N-[(4-hydroxyphenyl)methyl]-alaninamide A mixture of 0.5 g (1,0213 mMol) of (R,S)-3-(3-cyano-phenyl)-$N^2$-(diphenylacetyl)-N-[(4-hydroxyphenyl)methyl]-alaninamide, 30 ml of methanol saturated with hydrogen chloride and 2 ml of water was stirred for 12 hours at ambient temperature. The mixture was evaporated down in vacuo and the residue was purified by chromatography on silica gel (Baker, 30–60 μm) using dichloromethane/cyclohexane/methanol/conc. aqueous ammonia=350/75/75/10 (v/v/v/v) as an eluant. 56 mg (11% of theory) of colourless crystals, $R_f$ 0.87 were obtained.

MS: m/e=461

EXAMPLE 163

(R)-N-[ (4-Hydroxyphenyl)methyl]-$N^2$-[3-(1-piperidinyl)-1-oxopropyl]-argininamide-dihydrochloride a) (R)-$N^5$-(Amino(nitroimino)methyl]-N-C(4-hydroxyphenyl)-methyl]-$N^2$-(3-(1-piperidinyl)-1-oxopropyl]-ornithinamide-hydrochloride Prepared analogously to Example 67a) from 3-(1-piperidinyl)propanoic acid, (R)-$N^5$-[amino(nitroimino)-methyl]-N-[(4-hydroxy-phenyl)methyl]-ornithinamide-hydrochloride and TBTU in a yield of 14% theory.

Colourless amorphous substance of $R_f$ 0.79 (silica gel plates for thin layer chromatography 60 $F_{254}$, Merck-Darmstadt; eluant: dichloromethane/methanol/conc. aqueous ammonia=30/10/1 (v/v/v)).

IR (KBr): 1649 $cm^{-1}$ (amide-C═O)

ESI-MS:

$(M+H)^+$=464

$(M+Na)^+$=486

$(2M+H)^+$=949

$(2M+Na)^+$=971 b) (R)-N-[(4-Hydroxyphenyl)methyl]-$N^2$-[3-(1-piperidinyl)-1-oxopropyl]-argininamide-dihydrochloride Prepared analogously to Example 1c) from (R)-$N^5$-[amino-(nitroimino)methyl-N-[(4-hydroxyphenyl)methyl]-$N^2$-[3-(1-piperidinyl)-1-oxopropyl]-ornithinamide-hydrochloride in the presence of aqueous palladium black and 80% aqueous acetic acid in a yield of 78% of theory.

Colourless, amorphous crystals, $R_f$ 0.87.

IR (KBr): 1658.7 $cm^{-1}$ (amide-C═O)

ESI-MS:

$(M+H)^+$=419

$(M+2H)^+$=210

$(M+HCl+H)^+$=455/457 (Cl)

EXAMPLE 164

(R,S)-3-[3-(Aminoiminomethyl)phenyl]-$N^2$-(diphenylacetyl)-N-[[4-(ethoxycarbonyloxy)phenyl] methyl]-alaninamide 0.38 g (0,7 mMol) of (R,S)-3-[3-(aminoiminomethyl)-phenyl]-$N^2$-(diphenylacetyl)-N-[(4-hydroxyphenyl)methyl]-alaninamide-hydrochloride were suspended in 500 ml of dichloromethane and, with stirring, 0.2 ml (2.1 mmol) of triethylamine were added thereto, followed by the dropwise addition of a solution of 0.078 ml (0.082 mMol) of ethylchlorocarbonate in 10 ml of dichloromethane. After 2 hours the same amounts of ethylchlorocarbonate and triethylamine were added again and the mixture was stirred for a further two hours at ambient temperature. The solution was washed successively with water, saturated aqueous sodium hydrogen carbonate solution, 5% aqueous citric acid solution and saturated aqueous saline solution, dried over magnesium sulphate and freed from solvent in vacuo. The residue was triturated with a mixture of diisopropylether, petroleum ether and isopropanol=50/50/1 (v/v/v) and after suction filtering and drying in vacuo it yielded 390 mg (96% of theory) of colourless crystals, mp. 117°–120° C. and $R_f$ 0.47.

IR (KBr):

1760.9 $cm^{-1}$ (urethane-C═O)

1652.9 $cm^{-1}$ (amide-C═O)

ESI-MS:

$(M+H)^+$=651

$(M+Na)^+$=673

EXAMPLE 165

(R,S)-N-(2-(1,2-Dihydro-3,5(4H)-dioxo-1,2-diphenyl-3H-1,2,4-triazol-4-yl) ethyl]-$N^2$-(diphenylacetyl)-argininamide-hydrochloride a) (R,S)-$N^5$-[Amino(nitroimino)methyl]-N-[2-(1,2-dihydro-3,5(4H)-dioxo-1,2-diphenyl-3H-1,2,4-triazol-4-yl)ethyl]-$N^2$-(diphenylacetyl)-ornithinamide Prepared analogously to Example 157e) from (R,S)-$N^5$-[amino-(nitroimino)methyl]-$N^2$-(diphenylacetyl)-ornithine, 2-(1,2-dihydro-3,5(4H)-dioxo-1,2-diphenyl-3H-1,2,4-triazole-4-yl)ethanamine and TBTU in a yield of 23% of theory.

Colourless substance, mp. 188°–189° C.

IR (KBr):

3342.4 $cm^{-1}$ (N—H)

1780.2; 1724.3 $cm^{-1}$ (triazolidindione-C═O)

1652.9 $cm^{-1}$ (amide-C═O)

b) (R,S)-N-[2-(1,2-Dihydro-3,5(4H)-dioxo-1,2-diphenyl-3H-1,2,4-triazol-4-yl)ethyl]-$N^2$-(diphenylacetyl)-ornithinamide-hydrochloride Prepared analogously to Example 1c) from (R,S)-$N^5$-[amino-(nitroimino)methyl]-N-(2-(1,2-dihydro-3,5(4H)-dioxo-1,2-diphenyl-3H-1,2,4-triazol-4-yl)ethyl)-$N^2$-(diphenyl-acetyl)-ornithinamide by catalytic hydrogenation in the presence of palladium black and 80% aqueous acetic acid in a yield of 52% of theory.

Colourless crystals mp. 153° C. and $R_f$ 0.53.

IR (KBr):

1768.6 $cm^{-1}$ (five-membered ring-C═O)

1676.0 $cm^{-1}$ (amide-C═O, guanidinium)

ESI-MS: $(M+H)^+$=647

EXAMPLE 166

(R,S)-$N^2$-(Diphenylacetyl)-N-[(4-hydroxyphenyl) methyl]-2-methyl-argininamide a) (R,S)-2-(2-Cyanoethyl)-$N^2$-(phenylmethylene)-alanine-methyl-ester (cis/trans mixture)

Prepared analogously to Example 157a) from $N^2$-(phenylmethylene)alanine-methylester and acrylonitrile in a yield of 78% of theory.

Colourless oil, which was further processed without purification b) (R,S)-2-(2-cyanoethyl)-alanine-methylester-hydrochloride Prepared analogously to Example 157b) from (R,S)-2-(2-cyanoethyl)-$N^2$-(phenylmethylene)-alanine-methylester (cis/trans mixture) and 1N hydrochloric acid in a yield of 92% of theory.

Colourless amorphous substance.

IR (KBr):

2252.7 $cm^{-1}$ (C—N)

1747.4 $cm^{-1}$ (ester-C═O)

ESI-MS:

$(M+H)^+$=157

$(M+Na)^+$=179

$(2M+H)^+$=313

$(2M+Na)^+$=335 c) (R,S)-2-(2-Cyanoethyl)-$N^2$-(diphenylacetyl)-alanine-methyl-ester

Prepared analogously to Example 89c) from diphenylacetyl-chloride and (R,S)-2-(2-cyanoethyl)-alanine-methylester-hydrochloride in the presence of 4-methylmorphine in a yield of 43% of theory.

Colourless crystals, mp. 172°–174° C.

IR (KBr):

3269.2 $cm^{-1}$ (N—H)

2248.9 $cm^{-1}$ (C—N)

1743.5 $cm^{-1}$ (ester-C═O)

1643.3 $cm^{-1}$ (amide-C═O)

d) (R,S)-2-(2-Cyanoethyl)-$N^2$-(diphenylacetyl)-alanine

Prepared analogously to Example 79d) from (R,S)-2-(2-cyanoethyl)-$N^2$-(diphenylacetyl)-alanine-methylester by saponification with lithium hydroxide-hydrate and water in a yield of 86% of theory.

Colourless crystals, mp. 168°–170° C.

IR (KBr):

3269.2 $cm^{-1}$ (N—H)

2252.7 $cm^{-1}$ (C≡N)

1747.4 $cm^{-1}$ (carboxylic acid-C═O)

1643.3 $cm^{-1}$ (amide-C═O)

e) (R,S)-2-(2-Cyanoethyl)-$N^2$-(diphenylacetyl)-N-[(4-hydroxy-phenyl)methyl]-alaninamide Prepared analogously to Example 67a) from (R,S)-2-(2-cyanoethyl)-$N^2$-(diphenylacetyl)-alanine, 4-hydroxybenzene-methanamine-hydrochloride and TBTU in a yield of 85% of theory.

Colourless amorphous substance.

IR (KBr):

3334.7 $cm^{-1}$ (N—H, O—H)

2248.9 $cm^{-1}$ (C≡N)

1654.8 $cm^{-1}$ (amide-I)

1516.0 $cm^{-1}$ (amide-II)

f) (R,S)-$N^2$-(Diphenylacetyl)-N-[(4-hydroxyphenyl)methyl]-2-methyl-ornithinamide-hydrochloride Prepared analogously to Example 157f) from (R,S)-2-(2-cyanoethyl)-$N^2$-(diphenylacetyl)-N-[(4-hydroxyphenyl)-methyl]-alanineamide by catalytic hydrogenation in the presence of hydrochloric acid and 10% palladium/active charcoal in a yield of 21% of theory.

Colourless crystals.

IR (KBr): 1652.9 $cm^{-1}$ (amide-C═O)

MS: $M:^+$=445 g) (R,S)-$N^2$-(Diphenylacetyl)-N-[(4-hydroxyphenyl) methyl]-2-methyl-argininamide Prepared analogously to Example 42g) from (R,S)-$N^2$-(diphenylacetyl)-N-[(4-hydroxyphenyl)methyl]-2-methyl-ornithinamide-hydrochloride and 3,5-dimethylpyrazole-1-carboxylic acid amidinium nitrate in a yield of 15% of theory.

Colourless amorphous substance $R_f$ 0.50.

IR (KBr): 1652.9 $cm^{-1}$ (amide-C═O)

ESI-MS: $(M+H)^+$=488

EXAMPLE 167

(R)-$N^2$-(Diphenylacetyl)-N-methyl-N-(2-phenylethyl)-arginineamide a) (R)-$N^5$-[Amino(nitroimino)methyl]-$N^2$-(diphenylacetyl)-N-methyl-N-(2-phenylethyl)-ornithinamide Prepared analogously to Example 148b) from (R)-$N^5$-[amino-(nitro-imino)methyl]-$N^2$-(diphenylacetyl)-ornithine, N-methyl-2-phenylethanamine by catalytic hydrogenation in the presence of palladium black and 80% aqueous ethyl acetate in a yield of 76% of theory.

Colourless crystals mp. 110° C.

IR (KBr): 1625.9 $cm^{-1}$ (amide-C═O)

ESI-MS: $(M+H)^+$=531

$(M+Na)^+$=553 b) (R)-$N^2$-(Diphenylacetyl)-N-methyl-N-(2-phenylethyl)-argininamid-acetate

Prepared analogously to Example 1c) from (R)-$N^5$-[amino(nitroimino)methyl]-$N^2$-(diphenyl-acetyl)-N-methyl-N-(2-phenyl-ethyl)-ornithinamide by catalytic hydrogenation in the presence of palladium black and 80% aqueous acetic acid in a yield of 90% of theory.

Colourless crystals, mp. $R_f$ 0.52

IR (KBr): 1627.8 $cm^{-1}$ (amide-C═O)

ESI-MS:

$(M+H)^+$=486

$(M+Na)^+$=508

EXAMPLE 168

(R)-N-[[4-[(4,5-Dihydro-5,5-dimethyl-2,4(3H)-dioxo-1H-imidazol-3-yl)methyl]phenyl]methyl]-$N^2$-(diphenyl-acetyl)-argininamide-diacetate a) 3-[(4-Cyanophenyl)methyl]-4,5-dihydro-5,5-dimethyl-1H-imidazol-2,4(3H)-dione Prepared analogously to Example 92a) from 5,5-dimethylhydantoin and 4-(bromomethyl)-benzonitrile in the presence of potassium-tert.-butoxide in a yield of 98% of theory.

Colourless crystals, mp. 173°–175° C.

b) 4-[(4,5-Dihydro-5,5-dimethyl-2,4(3H)-dioxo-1H-imidazol-3-yl)methyl]-benzenemethylamine-hydrochloride Prepared analogously to Example 89f) from 3-[(4-cyanophenyl)methyl]- 4,5-dihydro-5,5-dimethyl-1H-imidazol-2,4(3H)-dione by catalytic hydrogenation in the presence of Raney nickel and ammonia and finally by treatment with ethereal hydrogen chloride solution, in a yield of 73% of theory.

Colourless crystals, mp. >250° C.

c) (R)-$N^5$-[Amino(nitroimino)methyl]-N-[[4-[(4,5-dihydro-5,5-dimethyl-2,4(3H)-dioxo-1H-imidazol-3-yl)methyl]phenyl]methyl]-$N^2$-(diphenylacetyl)-ornithinamide Prepared analogously to Example 81a) from (R)-$N^5$-[amino(nitroimino)methyl]-$N^2$-(diphenylacetyl)-ornithine, 4-[(4,5-dihydro-5,5-dimethyl-2,4(3H)-dioxo-1H-imidazol-3-yl)methyl]benzenemethylamine-hydrochloride and TBTU in a yield of 60% of theory.

Colourless crystals mp. 224°–226° C.

IR (KBr):

1755.1, 1706.9 $cm^{-1}$ (hydantoin-C═O)

1641.3 $cm^{-1}$ (amide-C═O)

d) (R)-N-[[4-[(4,5-Dihydro-5,5-dimethyl-2,4(3H)-dioxo-1H-imidazol-3-yl)methyl]phenyl]methyl]-$N^2$-(diphenyl-acetyl)-argininamide-diacetate Prepared analogously to Example 1c) from (R)-$N^5$-[amino(nitroimino)methyl]-N-[[4-[(4,5-dihydro-5,5-dimethyl-2,4(3H)-dioxo-1H-imidazol-3-yl)methyl]phenyl]methyl]-$N^2$-(diphenylacetyl)-ornithinamide by catalytic hydrogenation in the presence of palladium black and 80% aqueous acetic acid in a yield of 99% of theory.

Colourless amorphous substance, $R_f$ 0.54.

IR (KBr):

1768.6, 1710.8 $cm^{-1}$ (hydantoin-C═O)

1656.8 $cm^{-1}$ (amide-C═O)

ESI-MS:

$(M+H)^+$=598

$(M+Na)^+$=620

EXAMPLE 169

(R)-N-[(4-Hydroxyphenyl)methyl]-$N^2$-(5-phenyl-1-oxopentyl)-argininamid-diacetate a) (R)-$N^5$-[Amino(nitroimino)methyl]-N-[(4-hydroxyphenyl)phenyl)-methyl]-$N^2$-(5-phenyl-1-oxopentyl)-ornithinamide Prepared analogously to Example 67a) from 5-phenylpentanoic acid, (R)-$N^5$-[amino(nitroimino)-methyl]-N-[(4-hydroxy-phenyl)methyl]-ornithinamide-hydrochloride and TBTU in a yield of 52% of theory.

Colourless amorphous substance.

IR (KBr):

3305.8 $cm^{-1}$ (N—H, O—H)

1637.5 $cm^{-1}$ (amide-C═O)

b) (R)-N-[(4-Hydroxyphenyl)methyl]-$N^2$-(5-phenyl-1-oxopentyl)-argininamide-diacetate Prepared analogously to Example 1c) from (R)-$N^5$-[amino(nitroimino)methyl]-N-[(4-hydroxyphenyl)methyl]-$N^2$-(5-phenyl-1-oxopentyl)-ornithinamide by catalytic hydrogenation in the presence of palladium black and 80% aqueous acetic acid in a yield of 66% of theory.

Colourless amorphous substance, $R_f$ 0.58.

IR (KBr): 1652.9 $cm^{-1}$ (amide-C═O)

ESI-MS:

$(M+H)^+$=440

$(2M+H)^+$=879

EXAMPLE 170

(R)-$N^2$-(Diphenylacetyl)-N-[4-(3-hydroxypropyl)phenyl]methyl]-argininamide-acetate a) (R)-$N^5$-[Amino(nitroimino)methyl]-$N^2$-(diphenyl-acetyl)-N-[[4-(3-hydroxypropyl)phenyl]methyl]-ornithinamide Prepared analogously to Example 157e) from (R)-$N^5$-[amino(nitroimino)methyl]-$N^2$-(diphenylacetyl)-ornithine, 4-(3-hydroxypropyl)-benzenemethylamine (mp. 79°–83° C.; prepared from 4-[[[(tert.-butyloxy)carbonyl]-amino]methyl]-benzenepropanoic acid by successive reaction with ethyl chlorocarbonate, sodium borohydride and semi concentrated hydrochloric acid) and TBTU in a yield of 41% of theory.

Colourless crystals, mp. 131°–133° C.

IR (KBr): 1641.3 $cm^{-1}$ (amide-C═O)

ESI-MS:

$(M+H)^+$=561

$(M+Na)^+$=583

$(M+K)^+$=599 b) (R)-$N^2$-(Diphenylacetyl)-N-[[4-(3-hydroxypropyl)phenyl]-methyl]-argininamide-acetate Prepared analogously to Example 1c) from (R)-$N^5$-[amino (nitroimino)methyl]-N -(diphenylacetyl)-N-[[4-(3- hydroxypropyl)-phenyl]methyl]-ornithinamide by catalytic hydrogenation in the presence of palladium black and 80% aqueous acetic acid in a yield of 100% of theory.

Colourless amorphous substance, $R_f$ 0,57.

IR (KBr): 1652.9 $cm^{-1}$ (amide-C=O)

ESI-MS:

$(M+H)^+$=516

$(M+Na)^+$=538

EXAMPLE 171

(R)-N-((4-Hydroxyphenyl)methyl]-$N^2$-(4-phenyl-1-oxobutyl)-argininamide-diacetate a) (R)-$N^5$-[Amino(nitroimino)methyl]-N-[(4-hydroxy-phenyl)-methyl]-$N^2$-(4-phenyl-1-oxobutyl)-ornithin-amide Prepared analogously to Example 67a) from 4-phenyl-butanoic acid, (R)-$N^5$-[amino(nitroimino)methyl]-N-[(4-hydroxyphenyl)methyl]-ornithinamide-hydrochloride and TBTU in a yield of 36% of theory.

Colourless amorphous substance.

IR (KBr): 1639.4 $cm^{-1}$ (amide-C=O)

ESI-MS:

$(M+H)^+$=471

$(M+Na)^+$=493

$(M+K)^+$=509 b) (R)-N-[(4-Hydroxyphenyl)methyl]-$N^2$-(4-phenyl-1-oxobutyl)-argininamide-diacetate Prepared analogously to Example 1c) from (R)-$N^5$-[amino(nitroimino)methyl]-N-(4-hydroxyphenyl)methyl]-$N^2$-(4-phenyl-1-oxobutyl)-ornithinamide by catalytic hydrogenation in the presence of palladium black and 80% aqueous acetic acid in a yield of 89% of theory.

Colourless amorphous substance, $R_f$ 0.57.

IR (KBr): 1652.9 $cm^{-1}$ (amide-C=O)

ESI-MS:

$(M+H)^+$=426

$(M+Na)^+$=448

$(2M+H)^+$=851

EXAMPLE 172

(R)-N-[(4-Hydroxyphenyl)methyl]-$N^2$-(6-phenyl-1-oxohexyl)-argininamide-diacetate a) (R)-$N^5$-[Amino(nitroimino)methyl]-N-[(4-hydroxy-phenyl)-methyl]-$N^2$-(6-phenyl-1-oxohexyl)-ornithinamide Prepared analogously to Example 67a) from 6-phenylhexanoic acid, (R)-$N^5$-[amino(nitroimino)methyl]-N-[4-hydroxyphenyl)methyl]-ornithinamide-hydrochloride and TBTU in a yield of 36% of theory.

Colourless amorphous substance.

IR (KBr): 1639.4 $cm^{-1}$ (amide-C=O)

b) (R)-N-[(4-Hydroxyphenyl)methyl]-$N^2$-(6-phenyl-1-oxohexyl)-argininamide-diacetate Prepared analogously to Example 1c) from (R)-$N^5$-[amino(nitroimino)methyl]-N-[(4-hydroxyphenyl)methyl]-$N^2$-(6-phenyl-1-oxohexyl)-ornithinamide by catalytic hydrogenation in the presence of palladium black and 80% aqueous acetic acid in a yield of 82% of theory.

Colourless amorphous substance, $R_f$ 0.59.

IR (KBr): 1652.9 $cm^{-1}$ (amide-C=O)

ESI-MS:

$(M+H)^+$=454

$(M+Na)^+$=476

EXAMPLE 173

(R,S)-3-[(3-(Aminoiminomethyl)phenyl]-$N^2$-(2,2-diphenylethyl)-N-[(4-hydroxyphenyl)methyl]-alaninamide-hydrochloride a) (R,S)-$N^2$-[(tert.-Butyloxy)carbonyl]-3-(3-cyanophenyl)-alanine Prepared, analogously to Example 52b) but using tert.-butanol instead of tetrahydrofuran as co-solvent, from 3-(3-cyanophenyl)-alanine and di-tert.-butyl dicarbonate in a yield of 78% of theory.

IR (KBr):

2231.5 $cm^{-1}$ (C≡N)

1716.5 $cm^{-1}$ (urethane-C=O)

b) (R,S)-$N^2$-[(tert.-Butyloxy)carbonyl]-3-(3-cyanophenyl)-N-[(4-hydroxyphenyl)methyl]-alaninamide Prepared analogously to Example 67a) from (R,S)-$N^2$-[(tert.-butyloxy)carbonyl]-3-(3-cyanophenyl)-alanine and 4-hydroxy-benzenemethylamine and TBTU in a yield of 77% of theory.

Colourless crystals, mp. 141°–144° C. (decomp.)

IR (KBr):

2233.4 $cm^{-1}$ (C≡N)

1685.7 $cm^{-1}$ (urethane-C=O)

1631.7 $cm^{-1}$ (amide-C=O)

c) (R,S)-3-(3-Cyanophenyl)-N-[(4-hydroxyphenyl)-methyl]-alaninamide

Prepared analogously to Example 5e) from (R,S)-$N^2$-[(tert.- butyloxy)carbonyl]-3-(3-cyanophenyl)-N-[(4-hydroxyphenyl)methyl]-alaninamide by the action of trifluoroacetic acid in a yield of 95% of theory.

IR (KBr):

2229 $cm^{-1}$ (C≡N)

1649.0 $cm^{-1}$ (amide-I)

d) (R,S)-3-(3-Cyanophenyl)-$N^2$-(2,2-diphenylethyl)-N-[(4-hydroxyphenyl)methyl]-alaninamide Prepared analogously to Example 143a) from diphenylacetaldehyde, (R,S)-3-(3-cyanophenyl)-N-[(4-hydroxyphenyl)methyl]-alaninamide and sodium cyanoborohydride in a yield of 60% of theory.

Colourless amorphous substance.

IR (KBr):

2229.6 $cm^{-1}$ (C≡N)

1647.1 $cm^{-1}$ (amide-CO)

e) (R,S)-3-[3-(Aminoiminomethyl)phenyl]-$N^2$-(2,2-diphenyl-ethyl)-N-[(4-hydroxyphenyl)methyl]-alaninamide-hydrochloride Prepared analogously to Example 105d) from (R,S)-3-(cyanophenyl)-$N^2$-(2,2-diphenylethyl)-N-[(4-hydroxyphenyl)methyl]-alaninamide by reacting first with hydrogen chloride in methanol, then with ammonium carbonate, in a quantitative yield.

Colourless crystals, $R_f$ 0,58.

IR (KBr):

1674.1 $cm^{-1}$ (amidinium-C=N)

1652.9 $cm^{-1}$ (amide-CO)

ESI-MS:

$(M+H)^+$=493

$(M+Na)^+$=515

What is claimed is:

1. A compound of the formula $$T—Z—NR^1—(R^2CR^3)—CO—Y—(CH_2)_n—R \quad (I)$$

wherein n denotes the number 0, 1, 2, 3, 4 or 5,

R denotes a phenyl or naphthyl group, a phenyl or naphthyl group which are mono- or disubstituted independently by fluorine, chlorine, bromine or iodine atoms, or by cyano, alkyl, phenyl, hydroxy, alkoxy, dialkylaminoalkoxy, hydroxyphenyl, phenylalkoxy, alkylcarbonyl, amino, alkylamino, dialkylamino, alkylsulphonylamino, alkylcarbonylamino, alkoxycarbonylamino, alkoxycarbonyloxy, carboxy, alkoxycarbonyl, aminocarbonyl, alkylaminocarbonyl, dialkylaminocarbonyl, alkylcarbonyloxy, alkylsulphonyloxy, hydroxymethyl, hydroxyethyl, hydroxypropyl, hydroxybutyl, trifluoromethyl, trifluoromethoxy, trifluoromethylthio, aminoalkyl, alkylaminoalkyl, aminocarbonylaminoalkyl, benzoylamino, alkanoylaminoalkyl, alkoxycarbonylaminoalkyl, benzyloxycarbonylaminoalkyl, aminosulphonyl, alkylaminosulphonyl, dialkylaminosulphonyl, aminosulphonylamino, alkylaminosulphonylamino, dialkylaminosulphonylamino, cyanamino, aminocarbonylamino, alkylaminocarbonylamino, dialkylaminocarbonylamino, aminosulphonylaminoalkyl, alkylaminosulphonylaminoalkyl, carboxyalkyl, alkoxycarbonylalkyl, aminocarbonylalkyl, alkylaminocarbonylalkyl, aminosulphonylalkyl, alkylaminosulphonylalkyl, alkylsulphonyl, aminosulphonyloxy, alkylaminosulphonyloxy, dialkylaminosulphonyloxy or cyanoguanidino groups, an aminophenyl or aminonaphthyl group disubstituted independently by chlorine or bromine atoms, or a hydroxyphenyl or hydroxynaphthyl group, disubstituted independently by chlorine or bromine atoms or alkyl or alkoxy groups, a diphenylmethyl group or a (2,2-diphenylethyl) aminocarbonylaminophenyl group, a phenyl group substituted by a [1,5-dihydro-2,4(3H)-dioxo-imidazol-3-yl]alkyl or [1,2-dihydro-3,5(4H)-dioxo-3H-1,2,4-triazol-4-yl]alkyl group or by a [1,5-dihydro-2,4(3H)-dioxo-imidazol-3-yl]alkyl or [1,2-dihydro-3,5(4H)-dioxo-3H-1,2,4-triazo- 4-yl]alkyl group wherein the imidazole and triazole moiety additionally are substituted by 1 or 2 phenyl groups, $R^1$ denotes a hydrogen atom, a branched or straight-chained $C_{1-10}$-alkyl group, a $C_{3-7}$-cycloalkyl group, a phenyl group, a phenyl group substituted by a hydroxy or hydroxyalkyl group, a phenylmethyl group or a phenylmethyl group substituted in the phenyl moiety by a hydroxy or hydroxyalkyl group, $R^2$ denotes an unbranched $C_{1-5}$-alkyl group which is substituted in the ω-position by a heterocyclic group selected from 2-amino-imidazol-1-yl, (5-amino-4H-1,2,4-triazol-3-yl)amino, (5-amino-4H-1,2,4-triazol-3-yl)methylamino, (3-amino-1,2,4-oxadiazol-5-yl)amino or (5-amino-1,2,4- oxadiazol-3-yl)-amino, imidazol-4-yl, imidazol-2-yl, 1-methyl-imidazol-2-yl, imidazol-2-yl-amino, imidazol-2-yl-methylamino or (4,5-dihydro-1H-imidazol-2-yl)amino, wherein the heterocyclic groups mentioned hereinbefore are meant to encompass said unsubstituted groups and said groups which are substituted at a carbon by one or two methyl groups, or $R^2$ denotes a phenyl or phenylmethyl group or a phenyl or phenylmethyl group substituted in the aromatic ring by a cyano, iminomethylamino, cyaniminomethylamino, (methylamino)methylidenamino, aminoiminomethyl, [amino(hydroxyimino)methyl], [amino-(alkoxyimino) methyl], hydrazinoiminomethyl, [amino(cyanimino) methyl] or guanidino group or by an imidazol-2-yl, 1-methyl-imidazol-2-yl or 4,5-dihydro-1H-imidazol-2-yl group or by an imidazol-2-yl, 1-methyl-imidazol-2-yl or 4,5-dihydro-1H-imidazol-2-yl group substituted at a carbon atom by one or two methyl groups, wherein the aminoiminomethyl, [amino(hydroxyimino)-methyl] and guanidino groups mentioned above in the definition of $R^2$ are meant to encompass said unsubstituted groups and said groups in which one or more hydrogen atoms bound to nitrogen atoms are independently replaced by alkyl groups and wherein the HN<, HN═ or $H_2N$— groups present in the group $R^2$ are unsubstituted or one hydrogen atom in said HN<, HN═ or $H_2N$— groups is replaced by an alkoxycarbonyl group having a total of 2 to 7 carbon atoms, by a phenylalkyloxycarbonyl group having 1 to 6 carbon atoms in the alkyl moiety, by a phenyloxycarbonyl group, or by an $R^{15}$—CO—O—($R^{16}CR^{17}$)—O—CO— or by an ($R^{18}$O)PO(O$R^{19}$)— group, wherein $R^{15}$ denotes a $C_{1-15}$-alkyl group, a $C_{3-7}$-cycloalkyl group, a phenyl group or a phenylalkyl groups having 1 to 3 carbon atoms in the alkyl moiety, $R^{16}$ and $R^{17}$ independently denote hydrogen atoms or $C_{1-6}$-alkyl groups and one of the groups $R^{16}$ or $R^{17}$ additionally denotes a $C_{3-7}$-cycloalkyl group or a phenyl group, $R^{18}$ and $R^{19}$ independently denote hydrogen atoms, $C_{1-4}$-alkyl groups, or benzyl or phenyl groups;

$R^3$ denotes a hydrogen atom, a $C_{1-7}$-alkyl group or a $C_{4-7}$-cycloalkyl group, T denotes the group ($T^1T^2U$)—$(CH_2)_m$—, wherein one of $T^1$ and $T^2$ denotes a hydrogen atom and the other of $T^1$ and $T^2$ denotes a phenyl, 1-naphthyl or 2-naphthyl group or a phenyl, 1-naphthyl or 2-naphthyl group which is independently mono- or disubstituted by fluorine, chlorine, bromine or iodine atoms or by cyano, hydroxy, amino, dimethylamino, diethylamino, N-ethyl-methylamino, trifluoromethyl, trifluoromethoxy, trifluoromethylthio, acetylamino, propionylamino, methanesulphonylamino, methanesulphonyloxy, phenyl, phenylmethoxy, 2-phenylethoxy, alkyl or alkoxy groups, or is trisubstituted by an amino or hydroxy group together with two chlorine or bromine atoms or by a hydroxy group together with two alkyl or alkoxy groups, and the above-mentioned alkyl and alkoxy moieties each contain 1 to 4 carbon atoms, or both of $T^1$ and $T^2$ independently denote phenyl, 1-naphthyl or 2-naphthyl groups or phenyl, 1-naphthyl or 2-naphthyl groups which are independently mono- or disubstituted by fluorine, chlorine, bromine or iodine atoms or by cyano, hydroxy, amino, dimethylamino, diethylamino, N-ethylmethylamino, trifluoromethyl, trifluoromethoxy, trifluoromethylthio, acetylamino, propionylamino, methanesulphonylamino, methanesulphonyloxy, phenyl, phenylmethoxy, 2-phenylethoxy, alkyl or alkoxy groups, or are trisubstituted by an amino or hydroxy group together with two chlorine or bromine atoms or by a hydroxy group together with two alkyl or alkoxy groups, and the above-mentioned alkyl and alkoxy moieties each contain 1 to 4 carbon atoms, U denotes a >CH— group, a >CH— group wherein the hydrogen atom is replaced by an alkyl, phenyl, hydroxy, alkoxy, alkanoyloxy, alkoxycarbonyl or alkanoylamino group, whilst the above-mentioned alkyl and alkoxy moieties each contain 1 to 3 carbon atoms and the above-mentioned alkanoyl moiety each contain 2 or 3 carbon atoms, or U denotes a >$CHCH_2$— group or a nitrogen atom, and m denotes the number 0, 1, 2 or 3, or T denotes a $(T^1T^2U)—(CH_2)_m—$, group wherein $T^1$, $T^2$, U and m are as hereinbefore defined, with the proviso that the phenyl, 1-naphthyl or 2-naphthyl groups mentioned above for $T^1$ and $T^2$ are linked together via a bond or via a $—CH_2—$, $—C(CH_3)_2—$, $—CH_2CH_2—$ or —CH═CH— bridge; or, if Z denotes a carbonyl group, T additionally represents a naphthyl, naphthylmethyl, naphthylamino or diphenylmethyl (amino) group, Y denotes a $—NR^4—$ group, wherein $R^4$ has the meanings given above for $R^1$ and the groups $R^1$ and $R^4$ are identical or different, and Z denotes a single bond, or a —CO— group, and unless otherwise specified the above-mentioned alkyl and alkoxy moieties each contain 1 to 3 carbon atoms, or the compound (R,S)-3-[3-(aminocarbonyl)phenyl]-$N^2$-(diphenylacetyl)-N-[(4-hydroxyphenyl)methyl]-alaninamide, or a tautomer or salt thereof.

2. A compound of the formula I according to claim 1, wherein n, R, $R^1$, $R^3$, T, Y and Z are defined as in claim 1 and $R^2$ denotes an unbranched $C_{1-5}$-alkyl group which is substituted in the ω-position by a heterocyclic group selected from 2-amino-imidazol-1-yl, (5-amino-4H-1,2,4-triazol-3-yl)amino, (5-amino-4H-1,2,4-triazol-3-yl)methylamino, (3-amino-1,2,4-oxadiazol-5-yl)amino or (5-amino-1,2,4-oxadiazol-3-yl)-amino, imidazol-4-yl, imidazol-2-yl, 1-methyl-imidazol-2-yl, imidazol-2-yl-amino, imidazol-2-yl-methylamino or (4,5-dihydro-1H-imidazol-2-yl)amino, wherein the heterocyclic groups mentioned hereinbefore are meant to encompass said unsubstituted groups and said groups which are substituted at a carbon by one or two methyl groups, or $R^2$ denotes a phenyl or phenylmethyl group or a phenyl or phenylmethyl group substituted in the aromatic ring by a cyano, iminomethylamino, cyaniminomethylamino, (methylamino)methylidenamino, aminoiminomethyl, [amino(hydroxyimino)methyl], [amino-(alkoxyimino) methyl], hydrazinoiminomethyl, [amino(cyanimino) methyl] or guanidino group or by an imidazol-2-yl, 1-methyl-imidazol-2-yl or 4,5-dihydro-1H-imidazol-2-yl group or by an imidazol-2-yl, 1-methyl-imidazol-2-yl or 4,5-dihydro-1H-imidazol-2-yl group substituted at a carbon atom by one or two methyl groups, wherein the aminoiminomethyl, [amino(hydroxyimino)-methyl] and guanidino groups mentioned above in the definition of $R^2$ are meant to encompass said unsubstituted groups and said groups in which one or more hydrogen atoms bound to nitrogen atoms are independently replaced by alkyl groups having one to three carbon atoms and wherein the HN<, HN═ or $H_2N—$ groups present in the group $R^2$ are unsubstituted or one hydrogen atom in said HN<, HN═ or $H_2N—$ groups is replaced by an alkoxycarbonyl group having a total of 2 to 7 carbon atoms, by a phenylalkyloxycarbonyl group having 1 to 6 carbon atoms in the alkyl moiety, by a phenyloxycarbonyl group, or the compound (R,S)-3-[3-(aminocarbonyl)phenyl]-$N^2$-(diphenylacetyl)-N-[(4-hydroxy-phenyl)methyl]-alaninamide, or a tautomer or salt thereof.

3. A compound of the formula I according to claim 1, wherein n, R, $R^1$, $R^3$, T, Y and Z are defined as in claim 1 and $R^2$ denotes an unbranched $C_{1-5}$-alkyl group which is substituted in the ω-position by a heterocyclic group selected from 2-amino-imidazol-1-yl, (5-amino-4H-1,2,4-triazol-3-yl)amino, (5-amino-4H-1,2,4-triazol-3-yl)methylamino, (3-amino-1,2,4-oxadiazol-5-yl)amino or (5-amino-1,2,4- oxadiazol-3-yl)-amino, imidazol-4-yl, imidazol-2-yl, 1-methyl-imidazol-2-yl, imidazol-2-yl-amino, imidazol-2-yl-methylamino or (4,5-dihydro-1H-imidazol-2-yl)amino, wherein the heterocyclic groups mentioned hereinbefore are meant to encompass said unsubstituted groups and said groups which are substituted at a carbon by one methyl group, or $R^2$ denotes a phenyl or phenylmethyl group or a phenyl or phenylmethyl group substituted in the aromatic ring by a cyano, iminomethylamino, cyaniminomethylamino, (methylamino)methylidenamino, aminoiminomethyl, [amino(hydroxyimino)methyl] or guanidino group or by an imidazol-2-yl, 1-methyl-imidazol-2-yl or 4,5-dihydro-1H-imidazol-2-yl group, wherein the aminoiminomethyl, [amino(hydroxyimino)-methyl] and guanidino groups mentioned above in the definition of $R^2$ are meant to encompass said unsubstituted groups and said groups in which one atom bound to a nitrogen atom is replaced by an alkyl group having one to three carbon atoms, or the compound (R,S)-3-[3-(aminocarbonyl)phenyl]-$N^2$-(diphenylacetyl)-N-[(4-hydroxyphenyl)methyl]-alaninamide, or a tautomer or salt thereof.

4. A compound of the formula I according to claim 1, wherein n denotes the number 0, 1, 2, 3, 4 or 5, R denotes a phenyl group, a phenyl group substituted by a fluorine, chlorine, bromine or iodine atom, or by an alkyl, phenyl, hydroxy, alkoxy, dialkylaminoalkoxy, hydroxyphenyl, alkylcarbonyl, amino, alkylamino, dialkylamino, alkylsulphonylamino, alkylcarbonylamino, alkoxycarbonylamino, alkoxycarbonyloxy, carboxy, alkoxycarbonyl, aminocarbonyl, alkylaminocarbonyl, dialkylaminocarbonyl, alkylcarbonyloxy, hydroxymethyl, hydroxyethyl, hydroxypropyl, hydroxybutyl, aminoalkyl, alkylaminoalkyl, aminocarbonylaminoalkyl, alkanoylaminoalkyl, alkoxycarbonylaminoalkyl, aminosulphonyl, alkylaminosulphonyl, dialkylaminosulphonyl, aminosulphonylamino, alkylaminosulphonylamino, dialkylaminosulphonylamino, aminocarbonylamino, alkylaminocarbonylamino, dialkylaminocarbonylamino, aminosulphonylaminoalkyl, carboxyalkyl, alkoxycarbonylalkyl, aminocarbonylalkyl, alkylaminocarbonylalkyl, aminosulphonylalkyl or alkylaminosulphonylalkyl group, a phenyl group disubstituted independently by fluorine, amino, hydroxy, methoxy and alkyl, an aminophenyl group disubstituted independently by chlorine or bromine atoms, or a hydroxyphenyl or hydroxynaphthyl group, disubstituted independently by chlorine or bromine atoms or alkyl or alkoxy groups, a diphenylmethyl group or a (2,2-diphenylethyl) aminocarbonylaminophenyl group, a phenyl group substituted by a [1,5-dihydro-2,4(3H)-dioxo-imidazol-3-yl]alkyl or [1,2-dihydro-3,5(4H)-dioxo-3H-1,2,4-triazol-4-yl]alkyl group or by a [1,5-dihydro-2,4(3H)-dioxo-imidazol-3-yl]alkyl or [1,2-dihydro-3,5(4H)-dioxo-3H-1,2,4-triazol-4-yl]alkyl group wherein the imidazole and triazole moiety additionally are substituted by 1 or 2 phenyl groups, $R^1$ denotes a hydrogen atom, a branched or straight-chained $C_{1-5}$-alkyl group, $R^2$ denotes an unbranched $C_{1-5}$-alkyl group which is substituted in the ω-position by a heterocyclic group selected from 2-amino-imidazol-1-yl, (5-amino-4H-1,2,4-triazol-3-yl)amino, (5-amino-4H-1,2,4-triazol-3-yl)methylamino, (3-amino-1,2,4-oxadiazol-5-yl)amino or (5-amino-1,2,4-oxadiazol-3-yl)-amino, imidazol-4-yl, imidazol-2-yl, 1-methyl-imidazol-2-yl, imidazol-2-yl-amino, imidazol-2-yl-methylamino or (4,5-dihydro-1H-imidazol-2-yl)amino, or $R^2$ denotes a phenyl or phenylmethyl group or a phenyl or phenylmethyl group substituted in the aromatic ring by a cyano, iminomethylamino, cyaniminomethylamino, (methylamino)methylidenamino, aminoiminomethyl, [amino(hydroxyimino)methyl] or guanidino group or by an imidazol-2-yl, 1-methyl-imidazol-2-yl or 4,5-dihydro-1H-imidazol-2-yl group, $R^3$ denotes a hydrogen atom or a $C_{1-3}$-alkyl group, T denotes the group $(T^1T^2U)$—$(CH_2)_m$—, wherein one of $T^1$ and $T^2$ denotes a hydrogen atom and the other of $T^1$ and $T^2$ denotes a phenyl, 1-naphthyl or 2-naphthyl group or a phenyl, 1-naphthyl or 2-naphthyl group which is monosubstituted by a chlorine or bromine atom or by a hydroxy, amino, dimethylamino, diethylamino, N-ethylmethylamino, acetylamino, propionylamino, phenyl, phenylmethoxy, 2-phenylethoxy, alkyl or alkoxy group, or is disubstituted by fluorine, chlorine or bromine atoms, or is trisubstituted by an amino or hydroxy group together with two chlorine or bromine atoms or by a hydroxy group together with two alkyl or alkoxy groups, and the above-mentioned alkyl and alkoxy moieties each contain 1 to 4 carbon atoms, or $T^1$ and $T^2$ both independently denote phenyl, 1-naphthyl or 2-naphthyl groups or phenyl, 1-naphthyl or 2-naphthyl groups which are monosubstituted by a chlorine or bromine atom, by a hydroxy, amino, dimethylamino, diethylamino, N-ethyl-methylamino, acetylamino, propionylamino, phenyl, phenylmethoxy, 2-phenylethoxy, alkyl or alkoxy group, or are independently disubstituted by chlorine or bromine atoms or by hydroxy, amino, dimethylamino, diethylamino, N-ethyl-methylamino, acetylamino, propionylamino, phenyl, phenylmethoxy, 2-phenylethoxy, alkyl or alkoxy groups, or trisubstituted by an amino or hydroxy group together with two chlorine or bromine atoms or by a hydroxy group together with two alkyl or alkoxy groups, and the above-mentioned alkyl and alkoxy moieties each contain 1 to 4 carbon atoms, U denotes a >CH— group, a >CH— group wherein the hydrogen atom is replaced by an $C_{1-3}$-alkyl group, or U denotes a $>CHCH_2$— group, and m denotes the number 0, 1, 2 or 3, or T represents a naphthyl, naphthylmethyl, naphthylamino or diphenylmethyl(amino) group, Y denotes a —$NR^4$— group, wherein $R^4$ has the meanings given above for $R^1$ and the groups $R^1$ and $R^4$ are identical or different, and Z denotes a —CO— group, and unless otherwise specified the above-mentioned alkyl and alkoxy moieties each contain 1 to 3 carbon atoms, or the compound (R,S)-3-[3-(aminocarbonyl)phenyl]-$N^2$-(diphenylacetyl)-N-[(4-hydroxyphenyl)methyl]-alaninamide, or a tautomer or salt thereof.

5. A compound of the formula I according to claim 1, wherein n denotes the number 1, R denotes a phenyl group, a phenyl group substituted by a fluorine, chlorine or bromine atom, or by a methyl, hydroxymethyl, hydroxyethyl, hydroxypropyl, hydroxy, methoxy, ethoxy, acetyl, methoxycarbonyl, ethoxycarbonyloxy, aminocarbonyl, aminocarbonylamino, methylaminocarbonylamino, aminosulphonyl or dimethylamino group, a phenyl group disubstituted independently by fluorine, amino, hydroxy, methoxy and alkyl, an aminophenyl group disubstituted independently by chlorine or bromine atoms, or a hydroxyphenyl or hydroxynaphthyl group, disubstituted independently by chlorine or bromine atoms or alkyl or alkoxy groups, a phenyl group substituted by a [1,5-dihydro-2,4(3H)-dioxo-imidazol-3-yl]alkyl or [1,2-dihydro-3,5(4H)-dioxo-3H-1,2,4-triazol-4-yl]alkyl group or by a [1,5-dihydro- 2,4(3H)-dioxo-imidazol-3-yl]alkyl or [1,2-dihydro-3,5(4H)-dioxo-3H-1,2,4-triazol-4-yl]alkyl group wherein the imidazole and triazole moiety additionally are substituted by 1 or 2 phenyl groups, $R^1$ denotes a hydrogen atom, $R^2$ denotes an unbranched $C_{1-3}$-alkyl group which is substituted in the ω-position by a heterocyclic group selected from (5-amino-4H-1,2,4-triazol-3-yl)amino, (5-amino-4H-1,2,4-triazol-3-yl) methylamino, (3-amino-1,2,4-oxadiazol-5-yl)amino, (5-amino-1,2,4- oxadiazol-3-yl)-amino, imidazol-4-yl, imidazol-2-yl, imidazol-2-yl-amino or (4,5-dihydro-1H-imidazol-2-yl)amino, or, $R^2$ denotes a phenyl or phenylmethyl group or a phenyl or phenylmethyl group substituted in the aromatic ring by a cyano, iminomethylamino, cyaniminomethylamino, (methylamino)methylidenamino, aminoiminomethyl, [amino(hydroxyimino)methyl] or guanidino group or by an imidazol-2-yl or 4,5-dihydro-1H-imidazol-2-yl group, $R^3$ denotes a hydrogen atom or a methyl group, T denotes the group $(T^1T^2U)$—$(CH_2)_m$—, wherein one of $T^1$ and $T^2$ denotes a hydrogen atom and the other of $T^1$ and $T^2$ denotes a phenyl, 1-naphthyl or 2-naphthyl group or a phenyl, 1-naphthyl or 2-naphthyl group which is monosubstituted by a chlorine or bromine atom or by a alkyl or alkoxy group, or is disubstituted by chlorine or bromine atoms, and the above-mentioned alkyl and alkoxy moieties each contain 1 to 3 carbon atoms, or $T^1$ and $T^2$ both independently denote phenyl, 1-naphthyl or 2-naphthyl groups or phenyl, 1-naphthyl or 2-naphthyl groups which are mono-substituted by a chlorine or bromine atom or by a alkyl or alkoxy group, or are disubstituted by chlorine or bromine atoms, and the above-mentioned alkyl and alkoxy moieties each contain 1 to 3 carbon atoms, U denotes a >CH— group, and m denotes the number 0, or T represents a naphthyl, naphthylmethyl, naphthylamino or diphenylmethyl(amino) group, Y denotes a —NR$^4$— group, wherein R$^4$ is a hydrogen atom or a methyl group, and Z denotes —CO— group, and unless otherwise specified the above-mentioned alkyl and alkoxy moieties each contain 1 to 3 carbon atoms, or the compound (R,S)-3-[3-(aminocarbonyl)phenyl]-N$^2$-(diphenylacetyl)-N-[(4-hydroxyphenyl)methyl]-alaninamide, or a tautomer or salt thereof.

6. A compound of the formula I according to claim 1, wherein n, R, R$^1$, R$^2$, Y and Z are defined as in claim 5 and R$^3$ denotes a hydrogen atom, T denotes the group (T$^1$T$^2$U)—(CH$_2$)$_m$—, wherein one of T$^1$ and T$^2$ denotes a hydrogen atom and the other of T$^1$ and T$^2$ denotes a phenyl, 1-naphthyl or 2-naphthyl group or a phenyl, 1-naphthyl or 2-naphthyl group which is monosubstituted by a chlorine or bromine atom or by a alkyl or alkoxy group, or is disubstituted by chlorine or bromine atoms, and the above-mentioned alkyl and alkoxy moieties each contain 1 to 3 carbon atoms, or T$^1$ and T$^2$ both independently denote unsubstituted phenyl groups or phenyl groups which are mono-substituted by a chlorine or bromine atom or by a alkyl or alkoxy group, or are disubstituted by chlorine or bromine atoms, and the above-mentioned alkyl and alkoxy moieties each contain 1 to 3 carbon atoms, U denotes a >CH— group, and m denotes the number 0, or T represents a naphthyl, naphthylmethyl, naphthylamino or diphenylmethyl(amino) group, or the compound (R,S)-3-[3-(aminocarbonyl)phenyl]-N$^2$-(diphenylacetyl)-N-[(4-hydroxyphenyl)methyl]-alaninamide, or a tautomer or salt thereof.

7. A compound selected from the group consisting of: (a) (R,S)-α-[(diphenylacetyl)amino]-N-[(4-hydroxyphenyl)-methyl]-1H-imidazole-4-propanamide, (b) (R,S)-N$^2$-(diphenylacetyl)-N-[(4-hydroxyphenyl) methyl]-phenylalaninamide, (c) (R,S)-3-[4-[(aminoiminomethyl)amino]phenyl]-N$^2$-(diphenylacetyl)-N-[(4-methoxyphenyl)methyl]-alaninamide, (d) (R,S)-3-[4-[[(cyanoimino)methyl)amino]phenyl]-N$^2$-(diphenylacetyl)-N-[(4-methoxyphenyl)methyl]-alaninamide, (e) (R,S)-N$^2$-(diphenylacetyl)-N-[(4-methoxyphenyl) methyl]-3-[4-[[(methylamino)-methylidene]amino] phenyl]-alaninamide, (f) (R,S)-3-[3-[(aminoiminomethyl)amino]phenyl]-N$^2$-(diphenylacetyl)-N-[(4-methoxyphenyl)methyl]-alaninamide, (g) (R,S)-N$^2$-(diphenylacetyl)-N-[(4-methoxyphenyl) methyl]-3-[3-[[(methylamino)-methylidene]amino] phenyl]-alaninamide, (h) (R,S)-3-[3-(aminoiminomethyl)phenyl]-N$^2$-[(diphenylamino)-carbonyl]-N-[(4-hydroxyphenyl) methyl]-alaninamide, (i) (R,S)-N$^5$-(4,5-dihydro-1H-imidazol-2-yl)-N$^2$-(diphenylacetyl)-N-[(4-hydroxyphenyl)methyl]-ornithinamide, (j) (R,S)-N$^2$-(diphenylacetyl)-N-[(4-hydroxyphenyl)methyl] -N$^5$-(1H-imidazol-2-yl)-ornithinamide, (k) (R,S)-3-[4-(aminoiminomethyl)phenyl]-N$^2$-(diphenylacetyl)-N-[(4-methoxyphenyl)-methyl]-alaninamide, (l) (R,S)-3-[4-(aminoiminomethyl)phenyl]-N$^2$-(diphenylacetyl)-N-[(4-hydroxyphenyl)-methyl]-alaninamide, (m) (R,S)-3-[3-(aminoiminomethyl)phenyl]-N$^2$-(diphenylacetyl)-N-[(4-methoxyphenyl)-methyl]-alaninamide, (n) (R,S)-3-[3-(aminoiminomethyl)phenyl]-N$^2$-(diphenylacetyl)-N-[(4-hydroxyphenyl)-methyl]-alaninamide, (o) (R,S)-3-[3-(aminoiminomethyl)phenyl]-N$^2$-(diphenylacetyl)-N-[[3-[(1,2-dihydro-3,5(4H)-dioxo-1,2-diphenyl-3H-1,2,4-triazol-4-yl)methyl]phenyl]methyl]-alaninamide, (p) (R,S)-N-[(4-amino-3,5-dibromophenyl)methyl]-3-[3-(aminoiminomethyl)phenyl]-N$^2$-(diphenylacetyl)-alaninamide, (q) (R,S)-3-(3-cyanophenyl)-N$^2$-(diphenylacetyl)-N-[(4-hydroxyphenyl)methyl]-alaninamide, (r) (R,S)-N$^5$-(5-amino-1H-1,2,4-triazol-3-yl)-N$^2$-(diphenylacetyl)-N-[(4-hydroxy-phenyl)methyl]-ornithinamide, (s) (R,S)-N$^5$-(3-amino-1,2,4-oxadiazol-5-yl)-N$^2$-(diphenylacetyl)-N-[(4-hydroxy-phenyl)methyl]-ornithinamide, (t) (R,S)-N$^5$-(5-amino-1,2,4-oxadiazol-3-yl)-N$^2$-(diphenyl-acetyl)-N-[(4-hydroxyphenyl)methyl]-ornithinamide, (u) (R,S)-N$^2$-(diphenylacetyl)-N$^5$-(1H-imidazol-2-yl)-N-[(4-methoxyphenyl)methyl]-ornithinamide, (v) (R,S)-3-[3-(aminoiminomethyl)phenyl]-N$^2$-[[(diphenylmethyl)-amino]carbonyl]-N-[(4-hydroxyphenyl)methyl]-alaninamide, (w) (R,S)-N$^2$-(diphenylacetyl)-N$^5$-(1H-imidazol-2-yl)-N-(phenylmethyl)-ornithinamide, (x) (R,S)-N-[(4-amino-3,5-dichlorophenyl)methyl]-N$^2$-(diphenylacetyl)-N$^5$-(1H-imidazol-2-yl)-ornithinamide, (y) (R,S)-N-[(4-amino-3-fluorophenyl)methyl]-N$^2$-(diphenylacetyl)-N$^5$-(1H-imidazol-2-yl)-ornithinamide, (z) (R,S)-N-[(4-hydroxyphenyl)methyl]-N$^5$-(1H-imidazol-2-yl)-N$^2$-(2-naphthoyl)-ornithinamide, (aa) (R,S)-N$^2$-[[(diphenylmethyl)amino]carbonyl]-N-[(4-hydroxyphenyl)methyl]-N$^5$-(1H-imidazol-2-yl)-ornithinamide, (bb) (R,S)-N-[(4-hydroxyphenyl)methyl]-N$^5$-(1H-imidazol-2-yl)-N$^2$-[2-(2-naphthyl)-1-oxoethyl]-ornithinamide, (cc) (R,S)-N-[(4-hydroxyphenyl)methyl]-N$^5$-(1H-imidazol-2-yl)-N$^2$-[[(2-naphthyl)-amino]carbonyl]-ornithinamide, (dd) (R,S)-3-[2-[(aminoiminomethyl)amino]phenyl]-N$^2$-(diphenylacetyl)-N-[(4-hydroxyphenyl)methyl]-alaninamide, (ee) (R,S)-3-[4-(4,5-dihydro-1H-imidazol-2-yl)phenyl]-N$^2$-(diphenylacetyl)-N-[(4-hydroxyphenyl)methyl]-alaninamide, (ff) (R,S)-3-[3-[amino(hydroxyimino)methyl]phenyl]-N$^2$-(diphenylacetyl)-N-[(4-hydroxyphenyl)methyl]-alaninamide, (gg) (R,S)-3-[3-(aminoiminomethyl)phenyl]-N$^2$-(diphenylacetyl)-N-[[4-(ethoxycarbonyloxy)phenyl] methyl]-alaninamide, (hh) (R,S)-3-[(3-(aminoiminomethyl)phenyl]-$N^2$-(2,2-diphenylethyl)-N-[(4-hydroxyphenyl)methyl]-alaninamide or (ii) (R,S)-3-[3-(aminocarbonyl)phenyl]-$N^2$-(diphenylacetyl)-N-[(4-hydroxyphenyl)methyl]-alaninamide, or a salt thereof.

8. A method for treating obesity which comprises administering to a host in need of such treatment a therapeutic amount of a compound in accordance with claims 1, 2, 3, 4, 5, 6 or 7.

* * * * *